US010584355B2

(12) United States Patent
Sullivan et al.

(10) Patent No.: US 10,584,355 B2
(45) Date of Patent: Mar. 10, 2020

(54) CHIMPANZEE ADENOVIRAL VECTOR-BASED FILOVIRUS VACCINES

(71) Applicants: THE GOVERNMENT OF THE UNITED STATES OF AMERICA AS REPRESENTED BY THE SECRETARY OF THE DEPARTMENT OF HEALTH AND HUMAN SERVICES, Rockville, MD (US); GLAXOSMITHKLINE BIOLOGICALS SA, Rixensart (BE)

(72) Inventors: Nancy J. Sullivan, Kensington, MD (US); Gary J Nabel, Washington, DC (US); Clement Asiedu, Olney, MD (US); Cheng Cheng, Rockville, MD (US); Alfredo Nicosia, Rome (IT); Riccardo Cortese, Rome (IT); Virginia Ammendola, Naples (IT); Stefano Colloca, Rome (IT)

(73) Assignees: THE GOVERNMENT OF THE UNITED STATES OF AMERICA AS REPRESENTED BY THE SECRETARY OF THE DEPARTMENT OF HEALTH AND HUMAN SERVICES, Rockville, MD (US); GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

(21) Appl. No.: 15/339,225

(22) Filed: Oct. 31, 2016

(65) Prior Publication Data

US 2017/0044571 A1    Feb. 16, 2017

Related U.S. Application Data

(62) Division of application No. 13/641,655, filed as application No. PCT/US2011/032682 on Apr. 15, 2011, now Pat. No. 9,526,777.

(60) Provisional application No. 61/325,166, filed on Apr. 16, 2010.

(51) Int. Cl.
| | |
|---|---|
| *C12N 15/86* | (2006.01) |
| *A61K 39/12* | (2006.01) |
| *C07K 14/005* | (2006.01) |
| *C12N 7/00* | (2006.01) |
| *A61K 39/00* | (2006.01) |

(52) U.S. Cl.
CPC ............. *C12N 15/86* (2013.01); *A61K 39/12* (2013.01); *C07K 14/005* (2013.01); *C12N 7/00* (2013.01); *A61K 2039/5254* (2013.01); *A61K 2039/5256* (2013.01); *A61K 2039/545* (2013.01); *C12N 2710/10343* (2013.01); *C12N 2760/14134* (2013.01)

(58) Field of Classification Search
CPC ................................ C12N 15/86; C12N 7/00; C12N 2760/14134; C07K 14/005
See application file for complete search history.

(56) References Cited

U.S. PATENT DOCUMENTS

| | | | |
|---|---|---|---|
| 8,101,739 B2 | 1/2012 | Sullivan et al. | |
| 8,216,834 B2* | 7/2012 | Colloca ................ | C07K 14/005 424/93.1 |
| 9,718,863 B2* | 8/2017 | Colloca ................ | A61K 39/235 |
| 2006/0211115 A1 | 9/2006 | Roy et al. | |
| 2009/0215871 A1 | 8/2009 | Wilson et al. | |
| 2011/0129498 A1 | 6/2011 | Cortese et al. | |

FOREIGN PATENT DOCUMENTS

| | | |
|---|---|---|
| WO | WO 00/00616 A2 | 1/2000 |
| WO | 2006/133911 A2 | 12/2006 |
| WO | 2010/086189 A2 | 8/2010 |

OTHER PUBLICATIONS

Roy, S., et al., 2006, Generation of an adenoviral vaccine vector based on simian adenovirus 21, J. Gen. Virol. 87:2477-2485.*
Yu, Y.-T., and J. L. Manley, 1984, Generational and functional analyses for base-substitution mutants of the adenovirus 2 major late promoter, Nuc. Acids Res. 12(24):9309-9321.*
Jacob, G. A., et al., Nov. 1991, Abortive Initiation is Increased Only for the Weakest Members of a Set of Down Mutants of the Adenovirus 2 Major Late Promoter, J. Biol. Chem. 266(33):22537-22544.*
Brindley, M. A., et al., Jul. 2007, Ebola Virus Glycoprotein 1: Identification of Residues Important for Binding and Postbinding Events, J. Virol. 81(14):7702-7709.*
Martinez, O., et al., Mar. 2013, A Mutation in the Ebola Virus Envelope Glycoprotein Restricts Viral Entry in a Host Species- and Cell-Type-Specific Manner, J. Virol. 87(6):3324-3334.*
Extended European Search Report dated Feb. 2, 2015 for EP Patent Application No. 11769662.5, 12 pages.
Falzarano et al., "Progress in Filovirus Vaccine Development: Evaluating the potential for Clinical Use," Expert Rev. Vaccines, 10(1): 63-77.

(Continued)

*Primary Examiner* — Jeffrey S Parkin
(74) *Attorney, Agent, or Firm* — Birch, Stewart, Kolasch & Birch, LLP

(57) ABSTRACT

This invention provides vaccines for inducing an immune response and protection against filovirus infection for use as a preventative vaccine in humans. In particular, the invention provides chimpanzee adenoviral vectors expressing filovirus proteins from different strains of Ebolavirus (EBOV) or Marburg virus (MARV).

16 Claims, 13 Drawing Sheets

Specification includes a Sequence Listing.

(56) References Cited

OTHER PUBLICATIONS

Hoenen, et al., "Current Ebola Vacines," Expert Opin. Biol. Ther. 12(7): (2012) pp. 859-872.
Hoenen et al., "Ebola Virus: Unraveelling Pathogenis to Combat a Deadly Disease," Trends in Mol. Med., 12(5) May 2006, pp. 206-215.
Kobinger et al., "Chimpanzee adenovirus vaccine protects against Zaire Ebola virus", *Virology*, (346): 394-401 (2006).
Lee et al., "Viral vectors for use in the development of biodefense vaccines", *Advanced Drug Delivery Reviews*, (57): 1293-1314 (2005).
Martin et al., "A DNA Vaccine for Ebola Virus is Safe and Immunogenic in a Phase I Clinical Trial," Clin. Vacc. Immunol. 13(11), Nov. 2006, pp. 1267-1277.
Reed et al., "Status and challenges of filovirus vaccines", *Vaccines*, (25): 1923-1934 (2007).
Reyes-Sandoval, et al., "Prime-Boost Immunization with Adenoviral and Modified Vaccinia Virus Ankara Vectors Enhances the Durability and Polyfunctionality or Protective Malaria CD8+ T-cell Responses," Infect. Immun. 78(1) Jan. 2010, pp. 145-153.
Richardson, et al., "Recent Advances in Ebolavirus Vaccine Development," Human Vaccines, 6(6) Jun. 2010, pp. 439-449.
Roy, S., et al., "Generation of an adenoviral vaccine vector based on simian adenovirus 21," Journal of General Virology, vol. 87, pp. 2477-2485 (2006).
Ledgerwood et al., "Chimpanzee Adenovirus Vector Ebola Vaccine—Preliminary Report," N. Engl. J. Med., Nov. 26, 2014, pp. 1-9.
Stanley et al., "Chimpanzee adenovirus vaccine generates acute and durable protective immunity against ebolavirus challenge," Nat. Med., Oct. 2014; 20(10):1126-9.
Ascenzi et al., "Ebolavirus and Marburgvirus: Insight the Filoviridae Family," Molecular Aspects of Medicine, vol. 29, 2008 pp. 151-185.
Croyle et al., "Nasal Delivery of an Adenovirus-Based Vaccine Bypasses Pre-Existing Immunity to the Vaccine Carrier and Improves the Immune Response in Mice," PLoS One, vol. 3, No. 10, e3548, Published Oct. 29, 2008, pp. 1-9 (10 pages total).
Extended European Search Report, dated Mar. 14, 2019, for European Application No. 18201391.2.
Hevey et al., "Marburg Virus Vaccines Based Upon Alpha Virus Replicons Protect Guinea Pigs and Nonhuman Primates," Virology, vol. 251, 1998, pp. 28-37.
Jones et al., "Live Attenuated Recombinant Vaccine Protects Nonhuman Primates Against Ebola and Marburg Viruses," Nature Medicine, vol. 11, No. 7, Jul. 2005, (published online Jun. 5, 2005), pp. 786-790, XP-002527152.
Ledgerwood et al., "A Replication Defective Recombinant Ad5 Vaccine Expressing Ebola Virus GP is Safe and Immunogenic in Healthy Adults," Vaccine, vol. 29, 2011 (Available online Oct. 27, 2010), pp. 304-313.
Sullivan et al., "Immune Protection of Nonhuman Primates Against Ebola Virus with Single Low-Dose Adenovirus Vectors Encoding Modified GPs," PLoS Medicine, vol. 3, No. 6, e177, Jun. 2006, (Published: May 16, 2006), pp. 0865-0873.
Swenson et al., "Vaccine to Confer to Nonhuman Primates Complete Protection Against Multistrain Ebola and Marburg Virus Infections," Clinical and Vaccine Immunology, vol. 15, No. 3, Mar. 2008 (Published ahead of print, Jan. 23, 2008), pp. 460-467.
Tapia et al., "Use of ChAd3-EBO-Z Ebola Virus Vaccine in Malian and US Adults, and Boosting of Malian Adults with MVA-BN-Filo: A Phase 1, Single-Blind, Randomised Trial, a Phase 1b, Open-label and Double-blind . . ." Lancet Infectious Diseases, Published online Nov. 3, 2015, pp. 1-12.
Wang et al., "Complex Adenovirus-vectored Vaccine Protects Guinea Pigs from Three Strains of Marburg Virus Challenges," Virology, vol. 353, 2006, (Available online Jul. 3, 2006), pp. 324-332.
Wang et al., "De novo Syntheses of Marburg Virus Antigens from Adenovirus Vectors Induce Potent Humoral and Cellular Immune Responses," Vaccine, vol. 24, 2006 (Available online Dec. 9, 2005), pp. 2975-2986.

\* cited by examiner

Figure 1A pCMV Ebola GP          Ad5 E4orf6

-E1                    -E4

| Dosage: | 0 | rAd5 | | | ChAd63 | | | ChAd3 | | |
|---|---|---|---|---|---|---|---|---|---|---|
| | | $10^1$ | $10^2$ | $10^3$ | $10^1$ | $10^2$ | $10^3$ | $10^1$ | $10^2$ | $10^3$ |
| 150kD | | | | | | | | | | | ← EB(Z) |
| 150kD | | | | | | | | | | | ← EB(SG) |

Figure 1B

Figure 6A
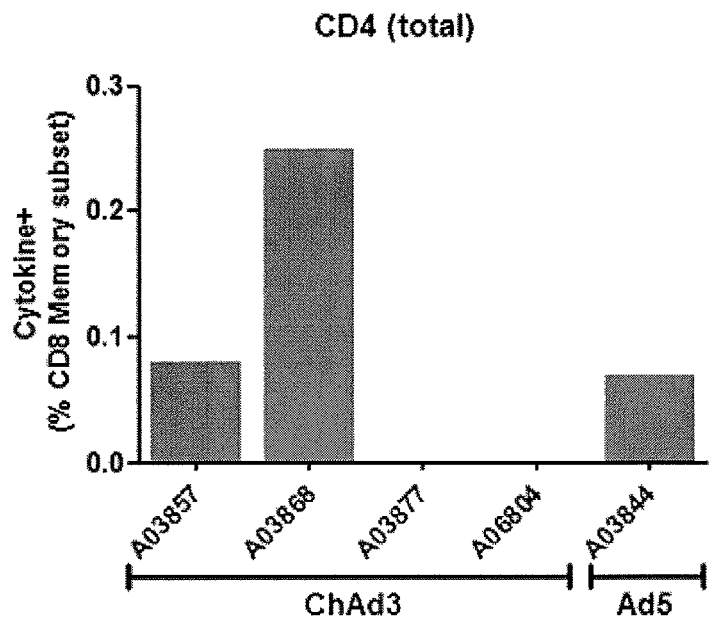
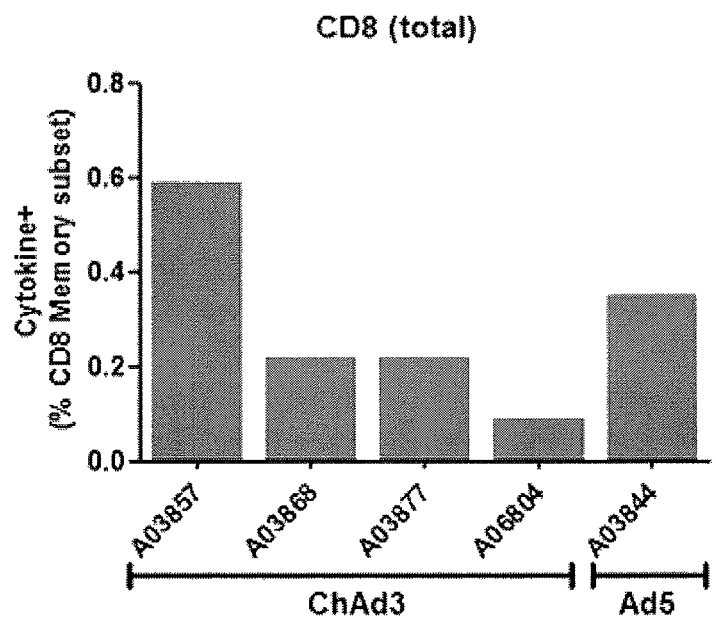
Figure 6B

Figure 7

| Vaccine | N | Survival |
|---|---|---|
| ChAd3-EBOV-GP | 4 | 100% |
| rAd5-EBOV-GP | 1 | 100%* |
| None | 1 | 0%** |

Figure 9A
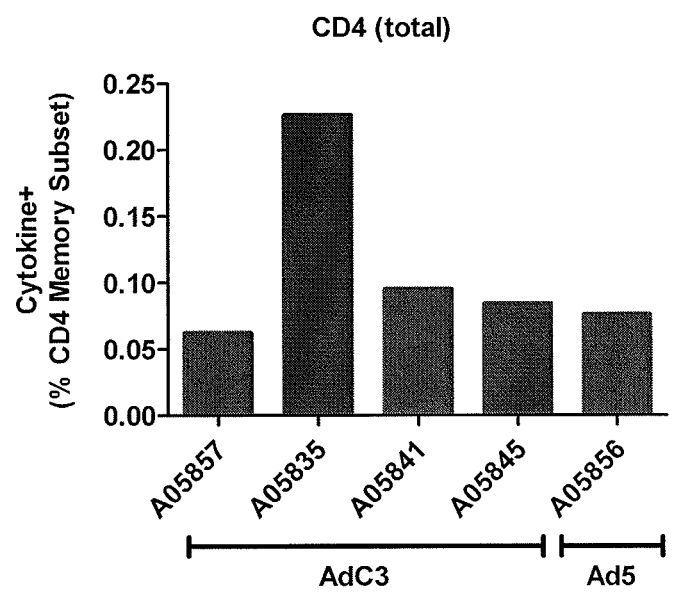
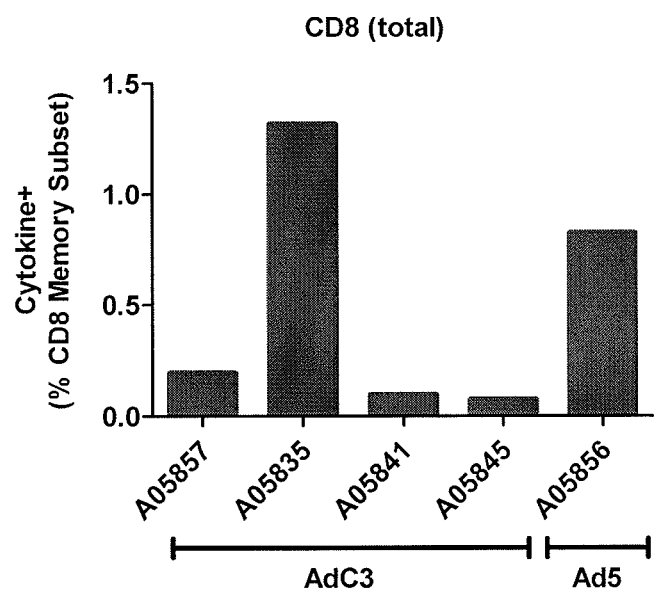
Figure 9B

Figure 10

| Vaccine | N | Survival |
|---|---|---|
| rChAd3-EBOV-GP | 4 | % |
| rAd5-EBOV-GP | 1 | 100%* |
| None | 1 | 0%** |

\* p<0.05
\*\* p<0.01
\*\*\* p<0.001

SEQUENCE LISTING

```
<160> NUMBER OF SEQ ID NOS: 14

<210> SEQ ID NO 1
<211> LENGTH: 33104
<212> TYPE: DNA
<213> ORGANISM: Artificial Sequence
<220> FEATURE:
<223> OTHER INFORMATION: synthetic chimpanzee adenovirus serotype ChAd3
      with Ebola virus Zaire wild type transmembrane
      envelope glycoprotein (GP) insert (ChAd3 Ebola
      Zaire (PB/6001))
<220> FEATURE:
<221> NAME/KEY: CDS
<222> LOCATION: (2143)...(4444)
<223> OTHER INFORMATION: Ebola virus Zaire wild type transmembrane
      envelope glycoprotein (GP) insert in ChAd3 Ebola Zaire (PB/6001)
<220> FEATURE:
<221> NAME/KEY: CDS
<222> LOCATION: (15413)...(17194)
<223> OTHER INFORMATION: chimpanzee adenovirus serotype ChAd3 penton
<220> FEATURE:
<221> NAME/KEY: CDS
<222> LOCATION: (19086)...(21968)
<223> OTHER INFORMATION: chimpanzee adenovirus serotype ChAd3 hexon
<220> FEATURE:
<221> NAME/KEY: CDS
<222> LOCATION: (29962)...(31647)
<223> OTHER INFORMATION: chimpanzee adenovirus serotype ChAd3 fiber

<400> SEQUENCE: 1
catcatcaat aatataccct attttggatt gaagccaata tgataatgag atgggcggcg      60
cggggcgggg cgcggggcgg gaggcgggtt tgggggcggg ccggcgggcg gggcggtgtg     120
gcggaagtgg actttgtaag tgtggcggat gtgacttgct agtgccgggc gcggtaaaag     180
tgacgttttc cgtgcgcgac aacgccccg ggaagtgaca ttttccccgc ggttttttacc     240 ggatgttgta gtgaatttgg gcgtaaccaa gtaagatttg gccatttttcg cgggaaaact     300 gaaacgggga agtgaaatct gattaatttt gcgttagtca taccgcgtaa tatttgtcta     360
gggccgaggg actttggccg attacgtgga ggactcgccc aggtgttttt tgaggtgaat     420
ttccgcgttc cgggtcaaag tctccgttttt attattatag gatatcccat tgcatacgtt     480
gtatccatat cataatatgt acatttatat tggctcatgt ccaacattac cgccatgttg     540
acattgatta ttgactagtt attaatagta atcaattacg gggtcattag ttcatagccc     600
atatatggag ttccgcgtta cataacttac ggtaaatggc ccgcctggct gaccgcccaa     660 cgaccccgc ccattgacgt caataatgac gtatgttccc atagtaacgc caatagggac     720
tttccattga cgtcaatggg tggagtattt acggtaaact gcccacttgg cagtacatca     780
agtgtatcat atgccaagta cgccccctat tgacgtcaat gacggtaaat ggcccgcctg     840
gcattatgcc cagtacatga ccttatggga ctttcctact ggcagtacat tctacgtatt     900
agtcatcgct attaccatgg tgatgcggtt ttggcagtac atcaatgggc gtggatagcg     960
```

```
gtttgactca cggggatttc caagtctcca ccccattgac gtcaatggga gtttgttttg    1020
gaaccaaaat caacgggact ttccaaaatg tcgtaacaac tccgccccat tgacgcaaat    1080
gggcggtagg cgtgtacggt gggaggtcta tataagcaga gctctcccta tcagtgatag    1140
agatctccct atcagtgata gagatcgtcg acgagctcgt ttagtgaacc gtcagatcgc    1200
ctggagacgc catccacgct gttttgacct ccatagaaga caccgggacc gatccagcct    1260
ccgcggccgg gaacggtgca ttggaacgcg gattccccgt gccaagagtg acgtaagtac    1320
cgcctataga ctctataggc acccccttt ggctcttatg catgctatac tgttttggc     1380 ttggggccta tacccccccg cttccttatg ctataggtga tggtatagct tagcctatag    1440
gtgtgggtta ttgaccatta ttgaccactc ccctattggt gacgatactt tccattacta    1500
atccataaca tggctctttg ccacaactat ctctattggc tatatgccaa tactctgtcc    1560
ttcagagact gacacggact ctgtattttt acaggatggg gtcccattta ttatttacaa    1620
attcacatat acaacaacgc cgtccccgt gcccgcagtt tttattaaac atagcgtggg     1680
atctccacgc gaatctcggg tacgtgttcc ggacatgggc tcttctccgg tagcggcgga    1740
gcttccacat ccgagccctg gtcccatgcc tccagcggct catggtcgct cggcagctcc    1800
ttgctcctaa cagtggaggc cagacttagg cacagcacaa tgcccaccac caccagtgtg    1860
ccgcacaagg ccgtggcggt agggtatgtg tctgaaaatg agcgtggaga ttgggctcgc    1920
acggctgacg cagatggaag acttaaggca gcggcagaag aagatgcagg cagctgagtt    1980
gttgtattct gataagagtc agaggtaact cccgttgcgg tgctgttaac ggtggagggc    2040
agtgtagtct gagcagtact cgttgctgcc gcgcgcgcca ccagacataa tagctgacag    2100
actaacagac tgttcctttc catgggtctt ttctgcagtc accgtcgtcg acacgtgtga    2160
tcagatatcg cggccgctct agaccaggcc ctggatcgat ccaacaacac aatgggcgtt    2220
acaggaatat tgcagttacc tcgtgatcga ttcaagagga catcattctt tctttgggta    2280
attatccttt tccaaagaac attttccatc ccacttggag tcatccacaa tagcacatta    2340
caggttagtg atgtcgacaa actagtttgt cgtgacaaac tgtcatccac aaatcaattg    2400
agatcagttg gactgaatct cgaagggaat ggagtggcaa ctgacgtgcc atctgcaact    2460
aaaagatggg gcttcaggtc cggtgtccca ccaaaggtgg tcaattatga agctggtgaa    2520
tgggctgaaa actgctacaa tcttgaaatc aaaaaacctg acgggagtga gtgtctacca    2580
gcagcgccag acgggattcg gggcttcccc cggtgccggt atgtgcacaa agtatcagga    2640 acggaccgt gtgccggaga cttttgcctc cataaagagg gtgctttctt cctgtatgat     2700
cgacttgctt ccacagttat ctaccgagga acgactttcg ctgaaggtgt cgttgcattt    2760
ctgatactgc cccaagctaa gaaggacttc ttcagctcac ccccttgag agagccggtc     2820 aatgcaacgg aggacccgtc tagtggctac tattctacca caattagata tcaggctacc    2880
ggttttggaa ccaatgagac agagtacttg ttcgaggttg acaatttgac ctacgtccaa    2940
cttgaatcaa gattcacacc acagtttctg ctccagctga atgagacaat atatacaagt    3000
gggaaaagga gcaataccac gggaaaacta atttggaagg tcaaccccga aattgataca    3060
acaatcgggg agtgggcctt ctgggaaact aaaaaaaacc tcactagaaa aattcgcagt    3120
gaagagttgt cttcacagt tgtatcaaac ggagccaaaa acatcagtgg tcagagtccg     3180
gcgcgaactt cttccgaccc agggaccaac acaacaactg aagaccacaa aatcatggct    3240
tcagaaaatt cctctgcaat ggttcaagtg cacagtcaag gaagggaagc tgcagtgtcg    3300
catctaacaa cccttgccac aatctccacg agtccccaat ccctcacaac caaaccaggt    3360
```

```
ccggacaaca gcacccataa tacacccgtg tataaacttg acatctctga ggcaactcaa    3420
gttgaacaac atcaccgcag aacagacaac gacagcacag cctccgacac tccctctgcc    3480
acgaccgcag ccggaccccc aaaagcagag aacaccaaca cgagcaagag cactgacttc    3540
ctggaccccg ccaccacaac aagtccccaa accacagcg agaccgctgg caacaacaac    3600
actcatcacc aagataccgg agaagagagt gccagcagcg ggaagctagg cttaattacc    3660
aatactattg ctggagtcgc aggactgatc acaggcggga gaagaactcg aagagaagca    3720
attgtcaatg ctcaacccaa atgcaaccct aatttacatt actggactac tcaggatgaa    3780
ggtgctgcaa tcggactggc ctggatacca tatttcgggc cagcagccga gggaatttac    3840 atagagggc taatgcacaa tcaagatggt ttaatctgtg ggttgagaca gctggccaac    3900
gagacgactc aagctcttca actgttcctg agagccacaa ctgagctacg cacctttca    3960 atcctcaacc gtaaggcaat tgatttcttg ctgcagcgat ggggcggcac atgccacatt    4020
ctgggaccgg actgctgtat cgaaccacat gattggacca agaacataac agacaaaatt    4080
gatcagatta ttcatgattt tgttgataaa acccttccgg accaggggga caatgacaat    4140
tggtggacag gatggagaca atggataccg gcaggtattg gagttacagg cgttgtaatt    4200
gcagttatcg ctttattctg tatatgcaaa tttgtctttt agttttctt cagattgctt    4260 catgaaaaag ctcagcctca aatcaatgaa accaggattt aattatatgg attacttgaa    4320
tctaagatta cttgacaaat gataatataa tacactggag ctttaaacat agccaatgtg    4380
attctaactc ctttaaactc acagttaatc ataaacaagg tttgaggtac cgagctcgaa    4440
ttgatctgct gtgccttcta gttgccagcc atctgttgtt tgcccctccc ccgtgccttc    4500
cttgaccctg gaaggtgcca ctcccactgt cctttcctaa taaaatgagg aaattgcatc    4560
gcattgtctg agtaggtgtc attctattct ggggggtggg gtggggcagg acagcaaggg    4620
ggaggattgg gaagacaata gcaggcatgc tggggatgcg gtgggcgata tcagcgatcg    4680
ctgaggtggg tgagtgggcg tggcctgggg tggtcatgaa aatatataag ttgggggtct    4740
tagggtctct ttatttgtgt tgcagagacc gccggagcca tgagcgggag cagcagcagc    4800
agcagtagca gcagcgcctt ggatggcagc atcgtgagcc cttatttgac gacgcggatg    4860
ccccactggg ccggggtgcg tcagaatgtg atgggctcca gcatcgacgg ccgacccgtc    4920
ctgcccgcaa attccgccac gctgacctat gcgaccgtcg cggggacgcc gttggacgcc    4980
accgccgccg ccgccgccac cgcagccgcc tcggccgtgc gcagcctggc cacggacttt    5040
gcattcctgg accactggc gacaggggct acttctcggg ccgctgctgc cgccgttcgc    5100
gatgacaagc tgaccgcccct gctggcgcag ttggatgcgc ttactcggga actgggtgac    5160 cttctcagc aggtcatggc cctgcgccag caggtctcct ccctgcaagc tggcgggaat    5220
gcttctccca caaatgccgt ttaagataaa taaaaccaga ctctgtttgg attaaagaaa    5280
agtagcaagt gcattgctct ctttatttca aatttttccg cgcgcgatag gcccctagacc    5340 agcgttctcg gtcgttgagg gtgcggtgta tcttctccag gacgtggtag aggtggctct    5400
ggacgttgag atacatgggc atgagcccgt cccgggggtg gaggtagcac cactgcagag    5460
cttcatgctc cggggtggtg ttgtagatga tccagtcgta gcaggagcgc tgggcatggt    5520
gcctaaaaat gtccttcagc agcaggccga tggccagggg gaggcccttg tgtaagtgt    5580 ttacaaaacg gttaagttgg gaagggtgca ttcggggaga gatgatgtgc atcttggact    5640
gtatttttag attggcgatg tttccgccca gatcccttct gggattcatg ttgtgcagga    5700
```

```
ccaccagtac agtgtatccg gtgcacttgg ggaatttgtc atgcagctta gagggaaaag    5760
cgtggaagaa cttggagacg cccttgtggc ctcccagatt ttccatgcat tcgtccatga    5820
tgatggcaat gggcccgcgg gaggcagctt gggcaaagat atttctgggg tcgctgacgt    5880
cgtagttgtg ttccagggtg aggtcgtcat aggccatttt tacaaagcgc gggcggaggg    5940
tgcccgactg ggggatgatg gtcccctctg gccctggggc gtagttgccc tcgcagatct    6000
gcatttccca ggccttaatc tcggaggggg gaatcatatc cacctgcggg gcgatgaaga    6060
aaacggtttc cggagccggg gagattaact gggatgagag caggtttcta agcagctgtg    6120
attttccaca accggtgggc ccataaataa cacctataac cggttgcagc tggtagttta    6180
gagagctgca gctgccgtcg tcccggagga ggggggccac ctcgttgagc atgtccctga    6240
cgcgcatgtt ctccccgacc agatccgcca aaggcgctc ccgcccagg acagcagct    6300 cttgcaagga agcaaagttt ttcagcggct tgaggccgtc cgccgtgggc atgttttca    6360 gggtctggct cagcagctcc aggcggtccc agagctcggt gacgtgctct acggcatctc    6420
tatccagcat atctcctcgt ttcgcgggtt ggggcgactt tcgctgtagg gcaccaagcg    6480
gtggtcgtcc agcggggcca aagtcatgtc cttccatggg cgcagggtcc tcgtcagggt    6540
ggtctgggtc acggtgaagg ggtgcgctcc gggctgagcg cttgccaagg tgcgcttgag    6600
gctggttctg ctggtgctga agcgctgccg gtcttcgccc tgcgcgtcgg ccaggtagca    6660
tttgaccatg gtgtcatagt ccagcccctc cgcggcgtgt cccttggcgc gcagcttgcc    6720
cttggaggtg gcgccgcacg aggggcagag caggctcttg agcgcgtaga gcttggggc    6780 gaggaagacc gattcggggg agtaggcgtc gcgccgcag accccgcaca cggtctcgca    6840
ctccaccagc caggtgagct cggggcgcgc cgggtcaaaa accaggtttc ccccatgctt    6900
tttgatgcgt ttcttacctc gggtctccat gaggtggtgt cccgctcgg tgacgaagag    6960 gctgtccgtg tctccgtaga ccgacttgag gggtcttttc tccagggggg tccctcggtc    7020
ttcctcgtag aggaactcgg accactctga gacgaaggcc cgcgtccagg ccaggacgaa    7080
ggaggctatg tgggagggt agcggtcgtt gtccactagg gggtccacct tctccaaggt    7140
gtgaagacac atgtcgcctt cctcggcgtc caggaaggtg attggcttgt aggtgtaggc    7200
cacgtgaccg ggggttcctg acgggggggt ataaaagggg gtggggcgc gctcgtcgtc    7260 actctcttcc gcatcgctgt ctgcgagggc cagctgctgg ggtgagtatt ccctctcgaa    7320
ggcgggcatg acctccgcgc tgaggttgtc agtttccaaa aacgaggagg atttgatgtt    7380
cacctgtccc gaggtgatac ctttgagggt acccgcgtcc atctggtcag aaaacacgat    7440 cttttttattg tccagcttgg tggcgaacga cccgtagagg gcgttggaga gcagcttggc    7500
gatggagcgc agggtctggt tcttgtccct gtcggcgcgc tccttggccg cgatgttgag    7560
ctgcacgtac tcgcgcgcga cgcagcgcca ctcggggaag acggtggtgc gctcgtcggg    7620
caccaggcgc acgcgccagc cgcggttgtg caggtgacc aggtccacgc tggtggcgac    7680
ctcgccgcgc aggcgctcgt tggtccagca gagacggccg cccttgcgcg agcagaaggg    7740
gggcaggggg tcgagctggg tctcgtccgg ggggtccgcg tccacggtga aaaccccggg    7800
gcgcaggcgc gcgtcgaagt agtctatctt gcaaccttgc atgtccagcg cctgctgcca    7860
gtcgcgggcg gcgagcgcgc gctcgtaggg gttgagcggc gggcccagg gcatggggtg    7920 ggtgagtgcg gaggcgtaca tgccgcagat gtcatagacg tagagggct cccgcaggac    7980 cccgatgtag gtggggtagc agcggccgcc gcggatgctg gcgcgcacgt agtcatacag    8040
ctcgtgcgag ggggcgagga ggtcggggcc caggttggtg cgggcggggc gctccgcgcg    8100
```

```
gaagacgatc tgcctgaaga tggcatgcga gttggaagag atggtggggc gctggaagac    8160
gttgaagctg gcgtcctgca ggccgacggc gtcgcgcacg aaggaggcgt aggagtcgcg    8220
cagcttgtgt accagctcgg cggtgacctg cacgtcgagc gcgcagtagt cgagggtctc    8280
gcggatgatg tcatatttag cctgccccct cttttccac agctcgcggt tgaggacaaa     8340
ctcttcgcgg tctttccagt actcttggat cgggaaaccg tccggttccg aacggtaaga    8400
gcctagcatg tagaactggt tgacggcctg gtaggcgcag cagcccttct ccacggggag    8460
ggcgtaggcc tgcgcggcct tgcggagcga ggtgtgggtc agggcgaagg tgtccctgac    8520
catgactttg aggtactggt gcttgaagtc ggagtcgtcg cagccgcccc gctcccagag    8580
cgagaagtcg gtgcgcttct tggagcgggg gttgggcaga gcgaaggtga catcgttgaa    8640
gaggattttg cccgcgcggg gcatgaagtt gcggtgatg cggaagggcc ccggcacttc     8700
agagcggttg ttgatgacct gggcggcgag cacgatctcg tcgaagccgt tgatgttgtg    8760
gcccacgatg tagagttcca ggaagcgggg ccggccctt acgtgggca gcttctttag      8820
ctcttcgtag gtgagctcct cgggcgaggc gaggccgtgc tcggccaggg cccagtccgc    8880
gaggtgcggg ttgtctctga ggaaggactc ccagaggtcg cgggccagga gggtctgcag    8940
gcggtccctg aaggtcctga actggcggcc cacggccatt ttttcggggg tgatgcagta    9000
gaaggtgagg gggtcttgct gccagcggtc ccagtcgagc tgcagggcga ggtcgcgcgc    9060
ggcggtgacc aggcgctcgt cgcccccgaa tttcatgacc agcatgaagg gcacgagctg    9120
cttccgaag gccccatcc aagtgtaggt ctctacatcg taggtgacaa agaggcgctc      9180
cgtgcgagga tgcgagccga tcgggaagaa ctggatctcc cgccaccagt tggaggagtg    9240
gctgttgatg tggtggaagt agaagtcccg tcgccgggcc gaacactcgt gctggctttt    9300
gtaaaagcga gcgcagtact ggcagcgctg cacgggctgt acctcctgca cgagatgcac    9360
ctttcgcccg cgcacgagga agccgagggg aaatctgagc cccccgcctg gctcgcggca    9420
tggctggtgc tcttctactt tggatgcgtg tccgtctccg tctggctcct cgagggggtgt   9480
tacggtggag cggaccacca cgccgcgcga gccgcaggtc cagatatcgg cgcgcggcgg    9540
tcggagtttg atgacgacat cgcgcagctg ggagctgtcc atggtctgga gctcccgcgg    9600
cggcggcagg tcagccggga gttcttgcag gttcacctcg cagagtcggg ccagggcgcg    9660
gggcaggtct agtggtacc tgatctctag gggcgtgttg gtggcggcgt cgatggcttg     9720
caggagcccg catccccggg gggcgacgac ggtgccccgc ggggtggtgg tggtggtggt    9780
ggtggtggtg gtggcggtgc agctcagaag cggtgccgcg ggcgggcccc cggaggtagg    9840
ggggctccg gtcccgccgg caggggcggc agcggcacgt cggcgtggag cgcgggcagg     9900
agttggtgct gtgcccggag gttgctgcg aaggcgacga cgcggcggtt gatctcctgg     9960
atctggcgcc tctgcgtgaa gacgacgggc ccggtgagct tgaacctgaa agagagttcg    10020
acagaatcaa tctcggtgtc attgaccgcg gcctggcgca ggatctcctg cacgtctccc    10080
gagttgtctt ggtaggcgat ctcggccatg aactgctcga tctcttcctc ctggaggtct    10140
ccgcgtccgg cgcgttccac ggtggccgcc aggtcgttgg agatgcgccc catgagctgc    10200
gagaaggcgt tgagtccgcc ctcgttccag actcggctgt agaccacgcc ccctggtca    10260
tcgcgggcgc gcatgaccac ctgcgcgagg ttgagctcca cgtgccgcgc gaagacggcg    10320
tagttgcgca cacgctggaa gaggtagttg agggtggtgg cggtgtgctc ggccacgaag    10380
aagttcatga cccagcggcg caacgtggat tcgttgatgt cccccaaggc ctccagccgt    10440
```

```
tccatggcct cgtagaagtc cacggcgaag ttgaaaaact gggagttgcg cgccgacacg    10500
gtcaactcct cctccagaag acggatgagc tcggcgacgg tgtcgcgcac ctcgcgctcg    10560
aaggctatgg ggatctcttc ctccgctagc atcaccacct cctcctcttc ctcctcttct    10620
ggcacttcca tgatggcttc ctcctcttcg ggggcggcg gcggcggcgg tgggggaggg      10680
ggcgctctgc gccggcggcg gcgcaccggg aggcggtcca cgaagcgcgc gatcatctcc    10740
ccgcggcggc ggcgcatggt ctcggtgacg gcgcggccgt tctcccgggg gcgcagttgg    10800
aagacgccgc cggacatctg gtgctggggc gggtggccgt gaggcagcga acggcgctg      10860 acgatgcatc tcaacaattg ctgcgtaggt acgccgccga gggacctgag ggagtccata    10920
tccaccggat ccgaaaacct ttcgaggaag gcgtctaacc agtcgcagtc gcaaggtagg    10980
ctgagcaccg tggcgggcgg cgggggggtgg ggggagtgtc tggcggaggt gctgctgatg   11040
atgtaattga agtaggcgga cttgacacgg cggatggtcg acaggagcac catgtccttg    11100
ggtccggcct gctggatgcg gaggcggtcg gctatgcccc aggcttcgtt ctggcatcgg    11160
cgcaggtcct tgtagtagtc ttgcatgagc ctttccaccg gcacctcttc tccttcctct    11220
tctgcttctt ccatgtctgc ttcggccctg gggcggcgcc gcgcccccct gcccccatg     11280 cgcgtgaccc cgaaccccct gagcggttgg agcagggcca ggtcggcgac gacgcgctcg    11340
gccaggatgg cctgctgcac ctgcgtgagg gtggtttgga agtcatccaa gtccacgaag    11400
cggtggtagg cgcccgtgtt gatggtgtag gtgcagttgg ccatgacgga ccagttgacg    11460
gtctggtggc ccggttgcga catctcggtg tacctgagtc gcgagtaggc gcggagtcg     11520 aagacgtagt cgttgcaagt ccgcaccagg tactggtagc ccaccaggaa gtgcggcggc    11580
ggctggcggt agaggggcca gcgcaggggtg gcgggggctc cgggggccag gtcttccagc   11640
atgaggcggt ggtaggcgta gatgtacctg gacatccagg tgatacccgc ggcggtggtg    11700
gaggcgcgcg ggaagtcgcg caccccggttc cagatgttgc gcaggggcag aaagtgctcc   11760
atggtaggcg tgctctgtcc agtcagacgc gcgcagtcgt tgatactcta gaccagggaa    11820
aacgaaagcc ggtcagcggg cactcttccg tggtctggtg aatagatcgc aagggtatca    11880
tggcggaggg cctcggttcg agccccgggt ccgggccgga cggtccgcca tgatccacgc    11940
ggttaccgcc cgcgtgtcga acccaggtgt gcgacgtcag acaacggtgg agtgttcctt    12000
ttggcgtttt tctggccggg cgccggcgtc gcgtaagaga ctaagccgcg aaagcgaaag    12060
cagtaagtgg ctcgctcccc gtagccggag ggatccttgc taagggttgc gttgcggcga    12120
accccggttc gaatcccgta ctcgggccgg ccggacccgc ggctaaggtg ttggattggc    12180 ctcccctcg tataaagacc ccgcttgcgg attgactccg gacacgggga cgagcccctt     12240
ttatttttgc tttccccaga tgcatccggt gctgcggcag atgcgccccc cgccccagca    12300
gcagcaacaa caccagcaag agcggcagca acagcagcgg gagtcatgca gggcccctc     12360 acccacccctc ggcgggccgg ccacctcggc gtccgcggcc gtgtctggcg cctgcggcgg   12420
cggcgggggg ccggctgacg accccgagga gccccgcgg cgcagggcca gacactacct     12480
ggacctggag gagggcgagg gcctggcgcg gctgggggcg ccgtctcccg agcgccaccc    12540
gcgggtgcag ctgaagcgcg actcgcgcga ggcgtacgtg cctcggcaga acctgttcag    12600
ggaccgcgcg ggcgaggagc ccgaggagat gcgggacagg aggttcagcg cagggcggga    12660
gctgcggcag gggctgaacc gcgagcggct gctgcgcgag gaggactttg agcccgacgc    12720
gcggacgggg atcagccccg cgcgcgcgca cgtggcggcc gccgacctgg tgacggcgta    12780
cgagcagacg gtgaaccagg agatcaactt ccaaaagagt ttcaacaacc acgtgcgcac    12840
```

```
gctggtggcg cgcgaggagg tgaccatcgg gctgatgcac ctgtgggact ttgtaagcgc    12900
gctggtgcag aaccccaaca gcaagcctct gacggcgcag ctgttcctga tagtgcagca    12960
cagcagggac aacgaggcgt ttagggacgc gctgctgaac atcaccgagc ccgagggtcg    13020
gtggctgctg gacctgatta acatcctgca gagcatagtg gtgcaggagc gcagcctgag    13080
cctggccgac aaggtggcgg ccatcaacta ctcgatgctg agcctgggca agttttacgc    13140
gcgcaagatc taccagacgc cgtacgtgcc catagacaag gaggtgaaga tcgacgtttt    13200
ttacatgcgc atggcgctga aggtgctcac cctgagcgac gacctgggcg tgtaccgcaa    13260
cgagcgcatc cacaaggccg tgagcgtgag ccggcggcgc gagctgagcg accgcgagct    13320
gatgcacagc ctgcagcggg cgctggcggg cgccggcagc ggcgacaggg aggcggagtc    13380
ctacttcgat gcggggcgg acctgcgctg ggcgcccagc cggcgggccc tggaggccgc    13440
gggggtccgc gaggactatg acgaggacgg cgaggaggat gaggagtacg agctagagga    13500
gggcgagtac ctggactaaa ccgcgggtgg tgtttccggt agatgcaaga cccgaacgtg    13560
gtggacccgg cgctgcgggc ggctctgcag agccagccgt ccggccttaa ctcctcagac    13620
gactggcgac aggtcatgga ccgcatcatg tcgctgacgg cgcgtaaccc ggacgcgttc    13680
cggcagcagc cgcaggccaa caggctctcc gccatcctgg aggcggtggt gcctgcgcgc    13740
tcgaacccca cgcacgagaa ggtgctggcc atagtgaacg cgctggccga gaacagggcc    13800
atccgcccgg acgaggccgg gctggtgtac gacgcgctgc tgcagcgcgt ggcccgctac    13860
aacagcggca acgtgcagac caacctggac cggctggtgg gggacgtgcg cgaggcggtg    13920
gcgcagcgcg agcgcgcgga tcggcagggc aacctgggct ccatggtggc gctgaatgcc    13980
ttcctgagca cgcagccggc caacgtgccg cgggggcagg aagactacac caactttgtg    14040
agcgcgctgc ggctgatggt gaccgagacc ccccagagcg aggtgtacca gtcgggcccg    14100
gactacttct tccagaccag cagacagggc ctgcagacgg tgaacctgag ccaggctttc    14160
aagaacctgc gggggctgtg gggcgtgaag gcgcccaccg gcgaccgggc gacggtgtcc    14220
agcctgctga cgcccaactc gcgcctgctg ctgctgctga tcgcgccgtt cacggacagc    14280
ggcagcgtgt cccgggacac ctacctgggg cacctgctga ccctgtaccg cgaggccatc    14340
gggcaggcgc aggtggacga gcacaccttc caggagatca ccagcgtgag ccgcgcgctg    14400
gggcaggagg acacgagcag cctggaggcg actctgaact acctgctgac caaccggcgg    14460
cagaagattc cctcgctgca cagcctgacc tccgaggagg agcgcatctt gcgctacgtg    14520
cagcagagcg tgagcctgaa cctgatgcgc gacggggtga cgcccagcgt ggcgctggac    14580
atgaccgcgc gcaacatgga accgggcatg tacgccgcgc accggcctta catcaaccgc    14640
ctgatggact acctgcatcg cgcggcggcc gtgaaccccg agtactttac caacgccatc    14700
ctgaacccgc actggctccc gccgcccggg ttctacagcg ggggcttcga ggtcccggag    14760
gccaacgatg gcttcctgtg ggacgacatg acgacagcg tgttctcccc gcggccgcag    14820
gcgctggcgg aagcgtccct gctgcgtccc aagaaggagg aggaggaggc gagtcgccgc    14880
cgcggcagca gcggcgtggc ttctctgtcc gagctggggg cggcagccgc gcgcgcgccc    14940
gggtccctgg gcgcagcccc ctttccgagc ctggtggggt ctctgcacag cgagcgcacc    15000 acccgcccctc ggctgctggg cgaggacgag tacctgaata actccctgct gcagccggtg    15060
cgggagaaaa acctgcccc cgccttcccc aacaacggga tagagagcct ggtggacaag    15120
atgagcagat ggaagaccta tgcgcaggag cacagggacg cgcccgcgct ccggccgccc    15180
```

```
acgcggcgcc agcgccacga ccggcagcgg gggctggtgt gggatgacga ggactccgcg    15240
gacgatagca gcgtgctgga cctgggaggg agcggcaacc cgttcgcgca cctgcgcccc    15300
cgcctgggga ggatgtttta aaaaaaaaaa aagcaagaag catgatgcaa aattaaataa    15360
aactcaccaa ggccatggcg accgagcgtt ggtttcttgt gttcccttca gtatgcggcg    15420
cgcggcgatg taccaggagg gacctcctcc ctcttacgag agcgtggtgg gcgcggcggc    15480
ggcggcgccc tcttctccct ttgcgtcgca gctgctggag ccgccgtacg tgcctccgcg    15540
ctacctgcgg cctacggggg ggagaaacag catccgttac tcggagctgg cgcccctgtt    15600
cgacaccacc cggggtgtacc tggtggacaa caagtcggcg gacgtggcct ccctgaacta    15660
ccagaacgac cacagcaatt ttttgaccac ggtcatccag aacaatgact acagcccgag    15720
cgaggccagc acccagacca tcaatctgga tgaccggtcg cactggggcg gcgacctgaa    15780
aaccatcctg cacaccaaca tgcccaacgt gaacgagttc atgttcacca ataagttcaa    15840
ggcgcgggtg atggtgtcgc gctcgcacac caaggaagac cgggtggagc tgaagtacga    15900
gtgggtggag ttcgagctgc cagagggcaa ctactccgag accatgacca ttgacctgat    15960
gaacaacgcg atcgtggagc actatctgaa agtgggcagg caaaacgggg tcctggagag    16020
cgacatcggg gtcaagttcg acaccaggaa cttccgcctg gggctggacc ccgtgaccgg    16080
gctggttatg cccggggtgt acaccaacga ggccttccat cccgacatca tcctgctgcc    16140
cggctgcggg gtgacttca cttacagccg cctgagcaac ctcctgggca tccgcaagcg    16200
gcagcccttc caggagggct tcaggatcac ctacgaggac ctggaggggg gcaacatccc    16260
cgcgctcctc gatgtggagg cctaccagga tagcttgaag gaaaatgagg cgggacagga    16320
ggataccacc cccgccgcct ccgccgccgc cgagcagggc gaggatgctg ctgacaccgc    16380
ggccgcggac ggggcagagg ccgaccccgc tatggtggtg gaggctcccg agcaggagga    16440
ggatatgaat gacagtgcgg tgcgcggaga caccttcgtc acccggggggg aggaaaagca    16500 agcggaggcc gaggccgcgg ccgaggaaaa gcaactggcg gcagcagcgg cggcggcggc    16560
gttggccgcg gcggaggctg agtctgaggg gaccaagccc gccaaggagc ccgtgattaa    16620 gccccctgacc gaagatagca agaagcgcag ttacaacctg ctcaaggaca gcaccaacac    16680
cgcgtaccgc agctggtacc tggcctacaa ctacggcgac ccgtcgacgg gggtgcgctc    16740
ctggaccctg ctgtgcacgc cggacgtgac ctgcggctcg gagcaggtgt actggtcgct    16800
gcccgacatg atgcaagacc ccgtgacctt ccgctccacg cggcaggtca gcaacttccc    16860
ggtggtgggc gccgagctgc tgcccgtgca ctccaagagc ttctacaacg accaggccgt    16920
ctactcccag ctcatccgcc agttcacctc tctgacccac gtgttcaatc gctttcctga    16980
gaaccagatt ctggcgcgcc cgcccgcccc caccatcacc accgtcagtg aaaacgttcc    17040
tgctctcaca gatcacggga cgctaccgct gcgcaacagc atcggaggag tccagcgagt    17100
gaccgttact gacgccagac gccgcacctg ccccctacgtt tacaaggcct tgggcatagt    17160
ctcgccgcgc gtccttttcca gccgcacttt ttgagcaaca ccaccatcat gtccatcctg    17220
atctcaccca gcaataactc cggctgggga ctgctgcgcg cgcccagcaa gatgttcgga    17280
ggggcgagga agcgttccga gcagcacccc gtgcgcgtgc gcgggcactt ccgcgccccc    17340
tggggagcgc acaaacgcgg ccgcgcgggg cgcaccaccg tggacgacgc catcgactcg    17400
gtggtggagc aggcgcgcaa ctacaggccc gcggtctcta ccgtggacgc ggccatccag    17460
accgtggtgc ggggcgcgcg gcggtacgcc aagctgaaga ccgccggaa gcgcgtggcc    17520 cgccgccacc gccgccgacc cggggccgcc gccaaacgcg ccgccgcggc cctgcttcgc    17580
```

```
cgggccaagc gcacgggccg ccgcgccgcc atgagggccg cgcgccgctt ggccgccggc   17640
atcaccgccg ccaccatggc cccccgtacc cgaagacgcg cggccgccgc cgccgccgcc   17700
gccatcagtg acatggccag caggcgccgg ggcaacgtgt actgggtgcg cgactcggtg   17760
accggcacgc gcgtgcccgt gcgcttccgc cccccgcgga cttgagatga tgtgaaaaaa   17820
caacactgag tctcctgctg ttgtgtgtat cccagcggcg gcggcgcgcg cagcgtcatg   17880
tccaagcgca aaatcaaaga agagatgctc caggtcgtcg cgccggagat ctatgggccc   17940
ccgaagaagg aagagcagga ttcgaagccc cgcaagataa agcgggtcaa aaagaaaaag   18000
aaagatgatg acgatgccga tggggaggtg gagttcctgc gcgccacggc gcccaggcgc   18060
ccggtgcagt ggaagggccg gcgcgtaaag cgcgtcctgc gccccggcac cgcggtggtc   18120
ttcacgcccg cgagcgctc cacccggact ttcaagcgcg tctatgacga ggtgtacggc   18180
gacgaagacc tgctggagca ggccaacgag cgcttcggag agtttgctta cgggaagcgt   18240
cagcgggcgc tggggaagga ggacctgctg gcgctgccgc tggaccaggg caaccccacc   18300
cccagtctga agcccgtgac cctgcagcag gtgctgccga gcagcgcacc ctccgaggcg   18360
aagcggggtc tgaagcgcga gggcggcgac ctggcgccca ccgtgcagct catggtgccc   18420
aagcggcaga ggctggagga tgtgctggag aaaatgaaag tagaccccgg tctgcagccg   18480
gacatcaggg tccgtcccat caagcaggtg gcgccgggcc tcggcgtgca gaccgtggac   18540
gtggtcatcc ccaccggcaa ctcccccgcc gccaccacca ctaccgctgc ctccacggac   18600
atggagacac agaccgatcc cgccgcagcc gcagccgccg ccgcagccgc gacctcctcg   18660
gcggaggtgc agacggaccc ctggctgccg ccggcgatgt cagctccccg cgcgcgccgc   18720
ggacgcagaa agtacggcgc cgccaacgcg ctcctgcccg agtacgcctt gcatccttcc   18780
atcgcgccca ccccggcta ccgaggctat acctaccgcc cgcgaagagc caagggttcc   18840
acccgccgtc cccgccgacg cgccgccgcc accacccgcc gccgccgcg cagacgccag   18900 cccgcactgg ctccagtctc cgtgaggaga gtggcgcgcg acggacacac cctggtgctg   18960
cccagggcgc gctaccaccc cagcatcgtt taaaagcctg ttgtggttct tgcagatatg   19020
gccctcactt gccgcctccg tttccggtg ccgggatacc gaggaggaag atcgcgccgc   19080
aggaggggtc tggccggccg cggcctgagc ggaggcagcc gccgcgcgca ccggcggcga   19140
cgcgccacca ccgacgcat gcgcggcggg gtgctgcccc tgttaatccc cctgatcgcc   19200
gcggcgatcg cgccgtgcc cgggatcgcc tccgtggcct tgcaagcgtc ccagaggcat   19260
tgacagactt gcaaacttgc aaatatggaa aaaaaaaaa aaccccaata aaagtctag   19320 actctcacgc tcgcttggtc ctgtgactat tttgtagaat ggaagacatc aactttgcgt   19380
cgctggcccc cgtcacggc tcgcgcccgt tcctgggaca ctgaacgat atcggcacca   19440 gcaacatgag cggtggcgcc ttcagttggg gctctctgtg gagcggcatt aaaagtatcg   19500
ggtctgccgt taaaaattac ggctcccggg cctggaacag cagcacgggc cagatgttga   19560
gagacaagtt gaaagagcag aacttccagc agaaggtggt ggagggcctg gcctccggca   19620 tcaacgggt ggtggacctg gccaaccagg ccgtgcagaa taaaatcaac agcagactgg   19680
acccccggcc gccggtggag gaggtgccgc cggcgctgga cggtgtcc cccgatgggc   19740 gtggcgagaa gcgccgcgg cccgataggg aagagaccac tctggtcacg cagaccgatg   19800
agccgccccc gtatgaggag gccctaaagc aaggtctgcc caccacgcgg cccatcgcgc   19860
ccatggccac cggggtggtg ggccgccaca cccccgccac gctggacttg cctccgcccg   19920
```

```
ccgatgtgcc gcagcagcag aaggcggcac agccgggccc gcccgcgacc gcctcccgtt   19980
cctccgccgg tcctctgcgc cgcgcggcca gcggcccccg cggggggtc gcgaggcacg     20040 gcaactggca gagcacgctg aacagcatcg tgggtctggg ggtgcggtcc gtgaagcgcc   20100
gccgatgcta ctgaatagct tagctaacgt gttgtatgtg tgtatgcgcc ctatgtcgcc   20160
gccagaggag ctgctgagtc gccgccgttc gcgcgcccac caccaccgcc actccgcccc   20220
tcaagatggc gacccatcg atgatgccgc agtggtcgta catgcacatc tcgggccagg    20280
acgcctcgga gtacctgagc cccgggctgg tgcagttcgc ccgcgccacc gagagctact   20340
tcagcctgag taacaagttt aggaacccca cggtggcgcc cacgcacgat gtgaccaccg   20400
accggtctca gcgcctgacg ctgcggttca ttcccgtgga ccgcgaggac accgcgtact   20460
cgtacaaggc gcggttcacc ctggccgtgg gcgacaaccg cgtgctggac atggcctcca   20520
cctactttga catccgcggg gtgctggacc ggggtcccac tttcaagccc tactctggca   20580
ccgcctacaa ctccctggcc cccaagggcg ctcccaactc ctgcgagtgg gagcaagagg   20640
aaactcaggc agttgaagaa gcagcagaag aggaagaaga agatgctgac ggtcaagctg   20700
aggaagagca agcagctacc aaaaagactc atgtatatgc tcaggctccc ctttctggcg   20760
aaaaaattag taaagatggt ctgcaaatag aacggacgc tacagctaca gaacaaaaac    20820
ctatttatgc agaccctaca ttccagcccg aaccccaaat cggggagtcc cagtggaatg   20880
aggcagatgc tacagtcgcc ggcggtagag tgctaaagaa atctactccc atgaaaccat   20940
gctatggttc ctatgcaaga cccacaaatg ctaatggagg tcagggtgta ctaacggcaa   21000
atgcccaggg acagctagaa tctcaggttg aaatgcaatt cttttcaact tctgaaaacg   21060
cccgtaacga ggctaacaac attcagccca aattggtgct gtatagtgag gatgtgcaca   21120
tggagacccc ggatacgcac cttcttaca agcccgcaaa aagcgatgac aattcaaaaa     21180
tcatgctggg tcagcagtcc atgcccaaca gacctaatta catcggcttc agagacaact   21240
ttatcggcct catgtattac aatagcactg gcaacatggg agtgcttgca ggtcaggcct   21300
ctcagttgaa tgcagtggtg gacttgcaag acagaaacac agaactgtcc taccagctct   21360
tgcttgattc catgggtgac agaaccagat acttttccat gtggaatcag gcagtggaca   21420
gttatgaccc agatgttaga attattgaaa atcatggaac tgaagacgag ctccccaact   21480
attgtttccc tctgggtggc ataggggtaa ctgacactta ccaggctgtt aaaaccaaca   21540
atggcaataa cggggggccag gtgacttgga caaaagatga aacttttgca gatcgcaatg   21600
aaataggggt gggaaacaat ttcgctatgg agatcaacct cagtgccaac ctgtggagaa   21660
acttcctgta ctccaacgtg gcgctgtacc taccagacaa gcttaagtac aacccctcca   21720
atgtggacat ctctgacaac cccaacacct acgattacat gaacaagcga gtggtggccc   21780
cggggctggt ggactgctac atcaacctgg gcgcgcgctg gtcgctggac tacatggaca   21840
acgtcaaccc cttcaaccac caccgcaatg cgggcctgcg ctaccgctcc atgctcctgg   21900
gcaacgggcg ctacgtgccc ttccacatcc aggtgccccg gaagttcttt gccatcaaga   21960
acctcctcct cctgccgggc tcctacacct acgagtggaa cttcaggaag gatgtcaaca   22020
tggtcctcca gagctctctg ggtaacgatc tcagggtgga cggggccagc atcaagttcg   22080
agagcatctg cctctacgcc accttcttcc ccatggccca caacacggcc tccacgctcg   22140
aggccatgct caggaacgac accaacgacc agtccttcaa tgactacctt tccgccgcca   22200
acatgctcta ccccataccc gccaacgcca ccaacgtccc catctccatc cctcgcgca    22260 actgggcggc cttccgcggc tgggccttca cccgcctcaa gaccaaggag accccctccc   22320
```

```
tgggctcggg attcgacccc tactacacct actcgggctc tattccctac ctggacggca    22380
ccttctacct caaccacact ttcaagaagg tctcggtcac cttcgactcc tcggtcagct    22440
ggccgggcaa cgaccgtctg ctcaccccca acgagttcga gatcaagcgc tcggtcgacg    22500
gggaaggcta caacgtggcc cagtgcaaca tgaccaagga ctggttcctg gtccagatgc    22560
tggccaacta caacatcggc taccagggct tctacatccc agagagctac aaggacagga    22620
tgtactcctt cttcaggaac ttccagccca tgagccggca ggtggtggac cagaccaagt    22680
acaaggacta ccaggaggtg ggcatcatcc accagcacaa caactcgggc ttcgtgggct    22740
acctcgcccc caccatgcgc gagggacagg cctaccccgc caacttcccc tacccgctca    22800
taggcaagac cgcggtcgac agcatcaccc agaaaaagtt cctctgcgac cgcaccctct    22860
ggcgcatccc cttctccagc aacttcatgt ccatgggtgc gctctcggac ctgggccaga    22920
acttgctcta cgccaactcc gcccacgccc tcgacatgac cttcgaggtc gaccccatgg    22980
acgagcccac ccttctctat gttctgttcg aagtctttga cgtggtccgg gtccaccagc    23040
cgcaccgcgg cgtcatcgag accgtgtacc tgcgtacgcc cttctcggcc ggcaacgcca    23100
ccacctaaag aagcaagccg cagtcatcgc cgcctgcatg ccgtcgggtt ccaccgagca    23160
agagctcagg gccatcgtca gagacctggg atgcgggccc tattttttgg gccacttcga    23220
caagcgcttc cctggctttg tctccccaca caagctggcc tgcgccatcg tcaacacggc    23280
cggccgcgag accgggggcg tgcactggct ggcctttgcc tggaacccgc gctccaaaac    23340
atgcttcctc tttgacccct tcggcttttc ggaccagcgg ctcaagcaaa tctacgagtt    23400
cgagtacgag ggcttgctgc gtcgcagcgc catcgcctcc tcgcccgacc gctgcgtcac    23460
cctcgaaaag tccacccaga ccgtgcaggg gcccgactcg gccgcctgcg gtctcttctg    23520
ctgcatgttt ctgcacgcct tgtgcactg gcctcagagt cccatggacc gcaacccac     23580 catgaacttg ctgacggggg tgcccaactc catgctccaa gcccccagg tcgagcccac      23640 cctgcgccgc aaccaggagc agctctacag cttcctggag cgccactcgc cctacttccg    23700
ccgccacagc gcacagatca ggagggccac ctccttctgc cacttgcaag agatgcaaga    23760
agggtaataa cgatgtacac actttttttct caataaatgg cattttttt tttatttatac    23820 aagctctctg gggtattcat ttcccaccac caccacccgc cgttgtcgcc atctggctct    23880
atttagaaat cgaagggtt ctgccggag tcgccgtgcg ccacgggcag ggacacgttg       23940
cgatactggt agcgggtgcc ccacttgaac tcgggcacca ccaggcgagg cagctcgggg    24000
aagttttcgc tccacaggct gcgggtcagc accagcgcgt tcatcaggtc gggcgccgag    24060
atcttgaagt cgcagttggg gccgccgccc tgcgcgcgcg agttgcggta caccgggttg    24120
cagcactgga acaccaacag cgccgggtgc ttcacgctgg ccagcacgct gcggtcgag     24180 atcagctcgg cgtccaggtc ctccgcgttg ctcagcgcga acggggtcat cttgggcact    24240
tgccgcccca ggaagggcgc gtgccccggt ttcgagttgc agtcgcagcg cagcgggatc    24300
agcaggtgcc cgtgcccgga ctcggcgttg gggtacagcg cgcgcatgaa ggcctgcatc    24360
tggcggaagg ccatctgggc cttggcgccc tccgagaaga acatgccgca ggacttgccc    24420
gagaactggt ttgcggggca gctggcgtcg tgcaggcagc agcgcgcgtc ggtgttggcg    24480
atctgcacca cgttgcgccc ccaccggttc ttcacgatct tggccttgga cgattgctcc    24540
ttcagcgcgc gctgccgtt ctcgctggtc acatccatct cgatcacatg ttccttgttc     24600
accatgctgc tgccgtgcag acacttcagc tcgccctccg tctcggtgca gcggtgctgc    24660
```

-continued

```
cacagcgcgc agcccgtggg ctcgaaagac ttgtaggtca cctccgcgaa ggactgcagg   24720 taccccctgca aaaagcggcc catcatggtc acgaaggtct tgttgctgct gaaggtcagc   24780
tgcagcccgc ggtgctcctc gttcagccag gtcttgcaca cggccgccag cgcctccacc   24840
tggtcgggca gcatcttgaa gttcaccttc agctcattct ccacgtggta cttgtccatc   24900
agcgtgcgcg ccgcctccat gcccttctcc caggccgaca ccagcggcag gctcacgggg   24960
ttcttcacca tcaccgtggc cgccgcctcc gccgcgcttt cgctttccgc cccgctgttc   25020
tcttcctctt cctcctcttc ctcgccgccg cccactcgca gccccgcac cacggggtcg    25080 tcttcctgca ggcgctgcac cttgcgcttg ccgttgcgcc cctgcttgat gcgcacgggc   25140
gggttgctga agcccaccat caccagcgcg gcctcttctt gtcgtcctc gctgtccaga    25200 atgacctccg gggagggggg gttggtcatc ctcagtaccg aggcacgctt cttttctttc   25260
ctgggggcgt tcgccagctc cgcggctgcg gccgctgccg aggtcgaagg ccgagggctg   25320
ggcgtgcgcg gcaccagcgc gtcttgcgag ccgtcctcgt cctcctcgga ctcgagacgg   25380
aggcgggccc gcttcttcgg gggcgcgcgg ggcggcggag gcggcggcgg cgacggagac   25440
ggggacgaga catcgtccag ggtgggtgga cggcgggccg cgccgcgtcc gcgctcgggg   25500
gtggtttcgc gctggtcctc ttcccgactg gccatctccc actgctcctt ctcctatagg   25560
cagaaagaga tcatggagtc tctcatgcga gtcgagaagg aggaggacag cctaaccgcc   25620
ccctctgagc cctccaccac cgccgccacc accgccaatg ccgccgcgga cgacgcgccc   25680
accgagacca ccgccagtac caccctcccc agcgacgcac cccgctcga gaatgaagtg    25740 ctgatcgagc aggacccggg ttttgtgagc ggagaggagg atgaggtgga tgagaaggag   25800
aaggaggagg tcgccgcctc agtgccaaaa gaggataaaa agcaagacca ggacgacgca   25860
gataaggatg agacagcagt cgggcggggg aacggaagcc atgatgctga tgacggctac   25920
ctagacgtgg gagacgacgt gctgcttaag cacctgcacc gccagtgcgt catcgtctgc   25980
gacgcgctgc aggagcgctg cgaagtgccc ctggacgtgg cggaggtcag ccgcgcctac   26040
gagcggcacc tcttcgcgcc gcacgtgccc cccaagcgcc gggagaacgg cacctgcgag   26100
cccaacccgc gtctcaactt ctaccggtc ttcgcggtac ccgaggtgct ggccacctac   26160
cacatcttct tccaaaactg caagatcccc ctctcctgcc gcgctaaccg cacccgcgcc   26220
gacaaaaccc tgaccctgcg gcagggcgcc cacatacctg atattgcctc tctgaggaa    26280 gtgcccaaga tcttcgaggg tctcggtcgc gacgagaaac gggcggcgaa cgctctgcac   26340
ggagacagcg aaaacgagag tcactcgggg gtgctggtgg agctcgaggg cgacaacgcg   26400
cgcctggccg tactcaagcg cagcatagag gtcacccact ttgcctaccc ggcgctcaac   26460
ctgcccccca aggtcatgag tgtggtcatg ggcgagctca tcatgcgccg cgctcagccc   26520
ctggccgcgg atgcaaactt gcaagagtcc tccgaggaag gcctgccgc ggtcagcgac    26580 gagcagctag cgcgctggct ggagacccgc gaccccgcgc agctggagga gcggcgcaag   26640
ctcatgatgg ccgcggtgct ggtcaccgtg gagctcgagt gtctgcagcg cttcttcgcg   26700
gaccccgaga tgcagcgcaa gctcgaggag accctgcact acaccttccg ccagggctac   26760
gtgcgccagg cctgcaagat ctccaacgtg gagctctgca acctggtctc ctacctgggc   26820
atcctgcacg agaaccgcct cgggcagaac gtcctgcact ccaccctcaa aggggaggcg   26880
cgccgcgact acatccgcga ctgcgcctac ctcttcctct gctacacctg gcagacggcc   26940
atgggggtct ggcagcagtg cctggaggag cgcaacctca aggagctgga aaagctactc   27000
aagcgcaccc tcagggacct ctggacgggc ttcaacgagc gctcggtggc cgccgcgctg   27060
```

```
gcggacatca tcttccccga gcgcctgctc aagaccctgc agcagggcct gcccgacttc   27120
accagccaga gcatgctgca gaactttagg actttcatcc tggagcgctc gggcatcctg   27180
cctgccactt gctgcgcgct gcccagcgac ttcgtgccca tcaagtacag ggagtgcccg   27240
ccgccgctct ggggccactg ctacctcttc cagctggcca actacctcgc ctaccactcg   27300
gacctcatgg aagacgtgag cggcgagggc ctgctcgagt gccactgccg ctgcaacctc   27360
tgcacgcccc accgctctct agtctgcaac ccgcagctgc tcagcgagag tcagattatc   27420
ggtaccttcg agctgcaggg tccctcgcct gacgagaagt ccgcggctcc ggggctgaaa   27480
ctcactccgg ggctgtggac ttccgcctac ctacgcaaat ttgtacctga ggactaccac   27540
gcccacgaga tcaggttcta cgaagaccaa tcccgcccgc caaggcgga gctcaccgcc   27600 tgcgtcatca cccaggggca catcctgggc caattgcaag ccatcaacaa gcccgccga   27660 gagttcttgc tgaaaaaggg tcggggggtg tacctggacc cccagtccgg cgaggagcta   27720
aacccgctac ccccgccgcc gccccagcag cgggaccttg cttcccagga tgcacccag   27780 aaagaagcag cagccgccgc cgccgcagcc atacatgctt ctggaggaag aggaggagga   27840
ctgggacagt caggcagagg aggtttcgga cgaggagcag gaggagatga tggaagactg   27900
ggaggaggac agcagcctag acgaggaagc ttcagaggcc gaagaggtgg cagacgcaac   27960
accatcaccc tcggtcgcag cccctcgcc ggggcccctg aaatcctccg aacccagcac   28020
cagcgctata acctccgctc ctccggcgcc ggcgccaccc gcccgcagac ccaaccgtag   28080
atgggacacc acaggaaccg gggtcggtaa gtccaagtgc ccgccgccgc caccgcagca   28140
gcagcagcag cgccagggct accgctcgtg gcgcgggcac aagaacgcca tagtcgcctg   28200
cttgcaagac tgcgggggca acatctcttt cgcccggcgc ttcctgctat tccaccacgg   28260
ggtcgccttt ccccgcaatg tcctgcatta ctaccgtcat ctctacagcc cctactgcag   28320
cggcgaccca gaggcggcag cggcagccac agcggcgacc accacctagg aagatatcct   28380
ccgcgggcaa gacagcggca gcagcggcca ggagacccgc ggcagcagcg gcgggagcgg   28440
tgggcgcact gcgcctctcg cccaacgaac ccctctcgac ccgggagctc agacacagga   28500
tcttccccac tttgtatgcc atcttccaac agagcagagg ccaggagcag gagctgaaaa   28560
taaaaaacag atctctgcgc tccctcaccc gcagctgtct gtatcacaaa agcgaagatc   28620
agcttcggcg cacgctggag gacgcggagg cactcttcag caaatactgc gcgctcactc   28680
ttaaagacta gctccgcgcc cttctcgaat ttaggcggga gaaaactacg tcatcgccgg   28740
ccgccgccca gcccgcccag ccgagatgag caaagagatt cccacgccat acatgtggag   28800
ctaccagccg cagatgggac tcgcggcggg agcggcccag gactactcca cccgcatgaa   28860
ctacatgagc gcgggacccc acatgatctc acaggtcaac gggatccgcg cccagcgaaa   28920
ccaaatactg ctggaacagg cggccatcac cgccacgccc cgccataatc tcaaccccg   28980 aaattggccc gccgccctcg tgtaccagga aaccccctcc gccaccaccg tactacttcc   29040
gcgtgacgcc caggccgaag tccagatgac taactcaggg gcgcagctcg cggcggctt   29100 tcgtcacggg gcgcggccgc tccgaccagg tataagacac ctgatgatca gaggccgagg   29160
tatccagctc aacgacagtg cggtgagctc ttcgctcggt ctccgtccgg acggaacttt   29220
ccagctcgcc ggatccggcc gctcttcgtt cacgccccgc caggcgtacc tgactctgca   29280
gacctcgtcc tcggagcccc gctccggagg catcggaacc ctccagttcg tggaggagtt   29340
cgtgccctcg gtctacttca accccttctc gggacctccc ggacgctacc ccgaccagtt   29400
```

```
cattccgaac tttgacgcgg tgaaggactc ggcggacggc tacgactgaa tgtcaggtgc    29460
cgaggcagag cagcttcgcc tgagacacct cgagcactgc cgccgccaca agtgcttcgc    29520
ccgcggttcc ggtgagttct gctactttca gctacccgag gagcataccg aggggccggc    29580
gcacggcgtc cgcctgacca cccagggcga ggttacctgt tccctcatcc gggagttcac    29640
cctccgtccc ctgctagtgg agcgggagcg gggtccctgt gtcctaacta tcgcctgcaa    29700
ctgccctaac cctggattac atcaagatct ttgctgtcat ctctgtgctg agtttaataa    29760
acgctgagat cagaatctac tgggaattcg atttagtccc ctttaactaa tcaaacactg    29820
gaatcaataa aaagaatcac ttacttaaaa tcagacagca ggtctctgtc cagtttattc    29880
agcagcacct ccttcccctc ctcccaactc tggtactcca aacgccttct ggcggcaaac    29940
ttcctccaca ccctgaaggg aatgtcagat tcttgctcct gtccctccgc acccactatc    30000
ttcatgttgt tgcagatgaa gcgcaccaaa acgtctgacg agagcttcaa ccccgtgtac    30060
ccctatgaca cggaaagcgg ccctcccctc gtcccttttcc tcacccctcc cttcgtgtct    30120
cccgatggat tccaagaaag cccccccggg gtcctgtctc tgaacctggc cgagcccctg    30180
gtcacttccc acggcatgct cgccctgaaa atgggaagtg gcctctccct ggacgacgct    30240
ggcaacctca cctctcaaga tatcaccacc gctagccctc cctcaaaaa aaccaagacc    30300 aacctcagcc tagaaacctc atcccccccta actgtaagca cctcaggcgc cctcaccgta    30360
gcagccgccg ctcccctggc agtggccggc acctccctca ccatgcaatc agaggccccc    30420
ctgacagtac aggatgcaaa actcacccctg gccaccaaag gccccctgac cgtgtctgaa    30480
ggcaaactgg ccttgcaaac atcggcccccg ctgacggccg ctgacagcag caccctcacc    30540
gttagcgcca caccaccaat taatgtaagc agtggaagtt taggcttaga catggaagac    30600
cctatgtata ctcacgatgg aaaactggga ataagaattg ggggtccact aagagtagta    30660
gacagcttgc acacactcac tgtagttacc ggaaatggac taactgtaga taacaatgcc    30720
ctccaaacta gagttacggg cgccctaggt tatgacacat caggaaatct acaattgaga    30780
gctgcaggag gtatgcgaat tgatgcaaat ggccaactta tccttaatgt ggcataccca    30840
tttgatgctc agaacaatct cagccttaga cttggtcagg gaccccctgta tataaacaca    30900 gaccacaacc tggatttgaa ttgcaacaga ggtctaacca caactaccac caacaacaca    30960
aaaaaacttg agactaaaat tagctcaggc ttagactatg acaccaatgg tgctgtcatt    31020
attaaacttg gcactggtct aagcttcgac aacacaggcg ccctaactgt gggaaacact    31080
ggtgatgata aactgactct gtggacgacc ccagacccat ctccaaattg cagaattcac    31140
tcagacaaag actgcaagtt tactctagtc ctaactaagt gtggaagcca atcctggcc    31200 tctgtcgccg ccctagcggt atcaggaaat ctggcttcga taacaggcac cgttgccagc    31260
gttaccatct ttctcagatt tgatcagaat ggagtgctta tggaaaactc ctcgctagac    31320
aggcagtact ggaacttcag aaatggcaac tcaactaacg ctgcccccta caccaatgca    31380
gttgggttca tgccaaacct cgcagcatac cccaaaacgc aaagccagac tgctaaaaac    31440
aacattgtaa gtcaggttta cttgaatgga gacaaatcca aacccatgac ccttaccatc    31500
accctcaatg gaactaatga atccagtgaa actagccagg tgagtcacta ctccatgtca    31560
tttacatggg cttgggaaag tgggcaatat gccactgaaa cctttgccac caactccttc    31620 acctttttctt acattgctga acaataaaaa gcatgacact gatgttcatt tctgattctt    31680
attttattat tttcaaacac aacaaaatca ttcaagtcat tcttccatct tagcttaata    31740
gacacagtag cttaatagac ccagtagtgc aaagcccat tctagcttat aactagtgga    31800
```

```
gaagtactcg cctacatggg ggtagagtca taatcgtgca tcaggatagg gcggtggtgc    31860
tgcagcagcg cgcgaataaa ctgctgccgc cgccgctccg tcctgcagga atacaacatg    31920
gcagtggtct cctcagcgat gattcgcacc gcccgcagca taaggcgcct tgtcctccgg    31980
gcacagcagc gcaccctgat ctcacttaaa tcagcacagt aactgcagca cagcaccaca    32040
atattgttca aaatcccaca gtgcaaggcg ctgtatccaa agctcatggc ggggaccaca    32100
gaacccacgt ggccatcata ccacaagcgc aggtagatta agtggcgacc ctcataaac     32160 acgctggaca taaacattac ctcttttggc atgttgtaat tcaccacctc ccggtaccat    32220
ataaacctct gattaaacat ggcgccatcc accaccatcc taaaccagct ggccaaaacc    32280
tgcccgccgg ctatacactg cagggaaccg ggactggaac aatgacagtg gagagcccag    32340
gactcgtaac catggatcat catgctcgtc atgatatcaa tgttggcaca acacaggcac    32400
acgtgcatac acttcctcag gattacaagc tcctcccgcg ttagaaccat atcccaggga    32460
acaacccatt cctgaatcag cgtaaatccc acactgcagg gaagacctcg cacgtaactc    32520
acgttgtgca ttgtcaaagt gttacattcg ggcagcagcg gatgatcctc cagtatggta    32580
gcgcgggttt ctgtctcaaa aggaggtaga cgatccctac tgtacggagt gcgccgagac    32640
aaccgagatc gtgttggtcg tagtgtcatg ccaaatggaa cgccggacgt agtcatattt    32700
cctgaagtct tagatctctc aacgcagcac cagcaccaac acttcgcagt gtaaaaggcc    32760
aagtgccgag agagtatata taggaataaa aagtgacgta aacgggcaaa gtccaaaaaa    32820
cgcccagaaa aaccgcacgc gaacctacgc cccgaaacga aagccaaaaa acactagaca    32880
ctcccttccg gcgtcaactt ccgctttccc acgctacgtc acttgcccca gtcaaacaaa    32940
ctacatatcc cgaacttcca agtcgccacg cccaaaacac cgcctacacc tccccgcccg    33000
ccggcccgcc cccaaacccg cctcccgccc cgcgccccgc ccgcgccgc  ccatctcatt    33060 atcatattgg cttcaatcca aaataaggta tattattgat gatg                    33104
```

<210> SEQ ID NO 2
<211> LENGTH: 32337
<212> TYPE: DNA
<213> ORGANISM: Artificial Sequence
<220> FEATURE:
<223> OTHER INFORMATION: synthetic chimpanzee adenovirus serotype ChAd3
      with Ebola virus Sudan/Gulu codon optimized
      transmembrane envelope glycoprotein (GP) insert
      (ChAd3 GP Ebola S/G (PB/6611))
<220> FEATURE:
<221> NAME/KEY: CDS
<222> LOCATION: (1634)...(3664)
<223> OTHER INFORMATION: Ebola virus Sudan/Gulu codon optimized
      transmembrane envelope glycoprotein (GP) insert in ChAd3 GP Ebola
      S/G (PB/6611)
<220> FEATURE:
<221> NAME/KEY: CDS
<222> LOCATION: (14646)...(16427)
<223> OTHER INFORMATION: chimpanzee adenovirus serotype ChAd3 penton
<220> FEATURE:
<221> NAME/KEY: CDS
<222> LOCATION: (19459)...(22338)
<223> OTHER INFORMATION: chimpanzee adenovirus serotype ChAd3 hexon
<220> FEATURE:
<221> NAME/KEY: CDS
<222> LOCATION: (29195)...(30881)
<223> OTHER INFORMATION: chimpanzee adenovirus serotype ChAd3 fiber

<400> SEQUENCE: 2

```
catcatcaat aatataccct atttttggatt gaagccaata tgataatgag atgggcggcg    60
cggggcgggg cgcggggcgg gaggcgggtt tgggggcggg ccggcgggcg gggcggtgtg   120
```

```
gcggaagtgg actttgtaag tgtggcggat gtgacttgct agtgccgggc gcggtaaaag    180
tgacgttttc cgtgcgcgac aacgcccccg ggaagtgaca ttttcccgc ggttttacc    240 ggatgttgta gtgaatttgg gcgtaaccaa gtaagatttg gccattttcg cgggaaaact    300
gaaacgggga agtgaaatct gattaatttt gcgttagtca taccgcgtaa tatttgtcta    360
gggccgaggg actttggccg attacgtgga ggactcgccc aggtgttttt tgaggtgaat    420
ttccgcgttc cgggtcaaag tctccgtttt attattatag gatatcccat tgcatacgtt    480
gtatccatat cataatatgt acatttatat tggctcatgt ccaacattac cgccatgttg    540
acattgatta ttgactagtt attaatagta atcaattacg gggtcattag ttcatagccc    600
atatatggag ttccgcgtta cataacttac ggtaaatggc ccgcctggct gaccgcccaa    660 cgaccccgc ccattgacgt caataatgac gtatgttccc atagtaacgc caatagggac    720
tttccattga cgtcaatggg tggagtattt acggtaaact gcccacttgg cagtacatca    780
agtgtatcat atgccaagta cgccccctat tgacgtcaat gacggtaaat ggcccgcctg    840
gcattatgcc cagtacatga ccttatggga ctttcctact tggcagtaca tctacgtatt    900
agtcatcgct attaccatgg tgatgcggtt ttggcagtac atcaatgggc gtggatagcg    960
gtttgactca cggggatttc caagtctcca ccccattgac gtcaatggga gtttgttttg    1020
gaaccaaaat caacgggact ttccaaaatg tcgtaacaac tccgccccat tgacgcaaat    1080
gggcggtagg cgtgtacggt gggaggtcta tataagcaga gctctcccta tcagtgatag    1140
agatctccct atcagtgata gagatcgtcg acgagctcgt ttagtgaacc gtcagatcgc    1200
ctggagacgc catccacgct gttttgacct ccatagaaga caccgggacc gatccagcct    1260
ccatcggctc gcatctctcc ttcacgcgcc cgccgcccta cctgaggccg ccatccacgc    1320
cggttgagtc gcgttctgcc gcctcccgcc tgtggtgcct cctgaactgc gtccgccgtc    1380
taggtaagtt taaagctcag gtcgagaccg ggcctttgtc cggcgctccc ttggagccta    1440
cctagactca gccggctctc cacgctttgc ctgaccctgc ttgctcaact ctagttaacg    1500
gtggagggca gtgtagtctg agcagtactc gttgctgccg cgcgcgccac cagacataat    1560
agctgacaga ctaacagact gttcctttcc atgggtcttt tctgcagtca ccgtcgtcga    1620
cgatatcgcc gccatggagg gcctgagcct gctgcagctg cccagggaca agttcaggaa    1680
gagcagcttc ttcgtgtggg tgatcatcct gttccagaag gccttcagca tgcccctggg    1740
cgtggtgacc aacagcaccc tggaggtgac cgagatcgac cagctggtgt gcaaggacca    1800 cctgccagc accgaccagc tgaagagcgt gggcctgaac ctggagggca cgcggcgtgag    1860 caccgacatc cccagcgcca ccaagaggtg gggcttcagg agcggcgtgc ctcccaaggt    1920
ggtgagctac gaggccggcg agtgggccga gaactgctac aacctggaga tcaagaagcc    1980
cgacggcagc gagtgcctgc ctcctcctcc tgacggcgtg aggggcttcc ccaggtgcag    2040
gtacgtgcac aaggcccagg caccggccc ctgccccgc gactacgcct tccacaagga    2100
cggcgccttc ttcctgtacg acaggctggc cagcaccgtg atctacaggg gcgtgaactt    2160
cgccgagggc gtgatcgcct tcctgatcct ggccaagccc aaggagacct tcctgcagag    2220
ccctcccatc agggaggccg tgaactacac cgagaacacc agcagctact acgccaccag    2280
ctatctagag tacgagatcg agaacttcgg cgcccagcac agcaccaccc tgttcaagat    2340
cgacaacaac accttcgtga ggctggacag gccccacacc cctcagttcc tgttccagct    2400
gaacgacacc atccacctgc accagcagct gagcaacacc accggcaggc tgatctggac    2460
```

```
cctggacgcc aacatcaacg ccgacatcgg cgagtgggcc ttctgggaga acaagaagaa    2520
cctgagcgag cagctgaggg gcgaggagct gagcttcgag gccctgagcc tgaacgagac    2580
cgaggacgac gacgccgcca gcagcaggat caccaagggc aggatcagcg acagggccac    2640
caggaagtac agcgacctgg tgcccaagaa cagcccggc atggtgcccc tgcacatccc    2700
cgagggcgag accaccctgc ccagccagaa cagcaccgag ggcaggaggg tgggcgtgaa    2760
cacccaggag accatcaccg agaccgccgc caccatcatc ggcaccaacg gcaaccacat    2820
gcagatcagc accatcggca tcaggcccag cagcagccag atccccagca gcagccccac    2880
caccgcccct agccccgagg cccagacccc caccacccac accagcggac ccagcgtgat    2940
ggccaccgag gagcccacca cccctcccgg cagcagcccc ggacccacca ccgaggcccc    3000
taccctgacc cccctgaga acatcaccac cgccgtgaag accgtgctgc ccaggagag    3060 caccagcaac ggcctgatca ccagcaccgt gaccggcatc ctgggcagcc tgggcctgag    3120
gaagaggagc aggaggcaga ccaacaccaa ggccaccggc aagtgcaacc ccaacctgca    3180
ctactggacc gcccaggagc agcacaacgc cgccggcatc gcctggattc cctacttcgg    3240
ccccggcgcc gagggcatct acaccgaggg cctgatgcac aaccagaacg ccctggtgtg    3300
cggcctgagg cagctggcca acgagaccac ccaggccctg cagctgttcc tgagggccac    3360
caccgagctg aggacctaca ccatcctgaa caggaaggcc atcgacttcc tgctgaggag    3420
gtggggcggc acctgcagga ttctgggccc cgactgctgc atcgagcccc acgactggac    3480
caagaacatc accgacaaga tcaaccagat catccacgac ttcatcgaca accctctgcc    3540
caaccaggac aacgacgaca actggtggac cggctggcgg cagtggatac ctgccggcat    3600
cggcatcacc ggcatcatca tcgccatcat cgctctgctg tgcgtgtgca agctgctgtg    3660
ctgagaattc agatcgctgt gccttctag ttgccagcca tctgttgttt gcccctcccc    3720
cgtgccttcc ttgaccctgg aaggtgccac tcccactgtc cttttcctaat aaaatgagga    3780 aattgcatcg cattgtctga gtaggtgtca ttctattctg ggggggtgggg tggggcagga    3840 cagcaagggg gaggattggg aagacaatag caggcatgct ggggatgcgg tgggctctag    3900
atatcagcga tcgctgaggt gggtgagtgg gcgtggcctg gggtggtcat gaaaatatat    3960
aagttggggg tcttagggtc tctttatttg tgttgcagag accgccggag ccatgagcgg    4020
gagcagcagc agcagcagta gcagcagcgc cttggatggc agcatcgtga gcccttattt    4080
gacgacgcgg atgccccact gggccggggt gcgtcagaat gtgatgggct ccagcatcga    4140
cggccgaccc gtcctgcccg caaattccgc cacgctgacc tatgcgaccg tcgcggggac    4200
gccgttggac gccaccgccg ccgccgccgc caccgcagcc gcctcggccg tgcgcagcct    4260
ggccacggac tttgcattcc tgggaccact ggcgacaggg gctacttctc gggccgctgc    4320
tgccgccgtt cgcgatgaca agctgaccgc cctgctggcg cagttggatg cgcttactcg    4380
ggaactgggt gacctttctc agcaggtcat ggccctgcgc cagcaggtct cctcctgca    4440 agctggcggg aatgcttctc ccacaaatgc cgtttaagat aaataaaacc agactctgtt    4500
tggattaaag aaaagtagca agtgcattgc tctctttatt tcataatttt ccgcgcgcga    4560
taggccctag accagcgttc tcggtcgttg agggtgcggt gtatcttctc caggacgtgg    4620
tagaggtggc tctggacgtt gagatacatg ggcatgagcc cgtcccgggg gtggaggtag    4680
caccactgca gagcttcatg ctccggggtg gtgttgtaga tgatccagtc gtagcaggag    4740
cgctgggcat ggtgcctaaa aatgtccttc agcagcaggc cgatgccag ggggaggccc    4800 ttggtgtaag tgtttacaaa acggttaagt tgggaagggt gcattcgggg agagatgatg    4860
```

```
tgcatcttgg actgtatttt tagattggcg atgtttccgc ccagatccct tctgggattc    4920
atgttgtgca ggaccaccag tacagtgtat ccggtgcact tggggaattt gtcatgcagc    4980
ttagagggaa aagcgtggaa gaacttggag acgcccttgt ggcctccag attttccatg     5040 cattcgtcca tgatgatggc aatgggcccg cgggaggcag cttgggcaaa gatatttctg    5100
gggtcgctga cgtcgtagtt gtgttccagg gtgaggtcgt cataggccat ttttacaaag    5160
cgcgggcgga gggtgcccga ctgggggatg atggtcccct ctggccctgg ggcgtagttg    5220
ccctcgcaga tctgcatttc ccaggcctta atctcggagg gggaatcat atccacctgc     5280 ggggcgatga agaaaacggt ttccggagcc ggggagatta actgggatga gagcaggttt    5340
ctaagcagct gtgattttcc acaaccggtg ggcccataaa taacacctat aaccggttgc    5400
agctggtagt ttagagagct gcagctgccg tcgtcccgga ggagggggc cacctcgttg     5460 agcatgtccc tgacgcgcat gttctccccg accagatccg ccagaaggcg ctcgccgccc    5520
agggacagca gctcttgcaa ggaagcaaag ttttcagcg gcttgaggcc gtccgccgtg     5580
ggcatgtttt tcagggtctg gctcagcagc tccaggcggt cccagagctc ggtgacgtgc    5640
tctacggcat ctctatccag catatctcct cgtttcgcgg gttggggcga ctttcgctgt    5700
agggcaccaa gcggtggtcg tccagcgggg ccaaagtcat gtccttccat gggcgcaggg    5760
tcctcgtcag ggtggtctgg gtcacggtga agggtgcgc tccgggctga gcgcttgcca    5820
aggtgcgctt gaggctggtt ctgctggtgc tgaagcgctg ccggtcttcg ccctgcgcgt    5880
cggccaggta gcatttgacc atggtgtcat agtccagccc ctccgcggcg tgtcccttgg    5940
cgcgcagctt gcccttggag gtggcgccgc acgaggggca gagcaggctc ttgagcgcgt    6000
agagcttggg ggcgaggaag accgattcgg gggagtaggc gtccgcgccg cagaccccgc    6060
acacggtctc gcactccacc agccaggtga gctcggggcg cgccgggtca aaaccaggt     6120 ttcccccatg cttttttgatg cgtttcttac ctcgggtctc catgaggtgg tgtccccgct    6180
cggtgacgaa gaggctgtcc gtgtctccgt agaccgactt gagggtctt ttctccaggg     6240 gggtccctcg gtcttcctcg tagaggaact cggaccactc tgagacgaag gcccgcgtcc    6300
aggccaggac gaaggaggct atgtgggagg ggtagcggtc gttgtccact aggggtccaa    6360
ccttctccaa ggtgtgaaga cacatgtcgc cttcctcggc gtccaggaag gtgattggct    6420
tgtaggtgta ggcacgtgag ccgggggttc ctgacggggg ggtataaaag ggggtggggg    6480
cgcgctcgtc gtcactctct tccgcatcgc tgtctgcgag ggccagctgc tggggtgagt    6540
attccctctc gaaggcgggc atgacctccg cgctgaggtt gtcagtttcc aaaaacgagg    6600
aggatttgat gttcacctgt cccgaggtga tacctttgag ggtacccgcg tccatctggt    6660
cagaaaacac gatctttta ttgtccagct tggtggcgaa cgaccgtag agggcgttgg      6720 agagcagctt ggcgatggag cgcagggtct ggttcttgtc cctgtcggcg cgctccttgg    6780
ccgcgatgtt gagctgcacg tactcgcgcg cgacgcagcg ccactcgggg aagacggtgg    6840
tgcgctcgtc gggcaccagg cgcacgcgcc agccgcggtt gtgcagggtg accaggtcca    6900
cgctggtggc gacctcgccg cgcaggcgct cgttggtcca gcagacacgg ccgcccttgc    6960
gcgagcagaa ggggggcagg gggtcgagct gggtctcgtc cgggggtcc gcgtccacgg     7020 tgaaaacccc ggggcgcagg cgcgcgtcga agtagtctat cttgcaacct tgcatgtcca    7080
gcgcctgctg ccagtcgcgg gcggcgagcg cgcgctcgta ggggttgagc ggcgggcccc    7140
agggcatggg gtgggtgagt gcggaggcgt acatgccgca gatgtcatag acgtagaggg    7200
```

```
gctcccgcag accccgatg taggtggggt agcagcggcc gccgcggatg ctggcgcgca    7260
cgtagtcata cagctcgtgc gaggggggcga ggaggtcggg gcccaggttg gtgcgggcgg    7320
ggcgctccgc gcggaagacg atctgcctga agatggcatg cgagttggaa gagatggtgg    7380
ggcgctggaa gacgttgaag ctggcgtcct gcaggccgac ggcgtcgcgc acgaaggagg    7440
cgtaggagtc gcgcagcttg tgtaccagct cggcggtgac ctgcacgtcg agcgcgcagt    7500
agtcgagggt ctcgcggatg atgtcatatt tagcctgccc cttcttttc cacagctcgc    7560 ggttgaggac aaactcttcg cggtctttcc agtactcttg gatcgggaaa ccgtccggtt    7620
ccgaacggta agagcctagc atgtagaact ggttgacggc ctggtaggcg cagcagccct    7680
tctccacggg gagggcgtag gcctgcgcgg ccttgcggag cgaggtgtgg gtcagggcga    7740
aggtgtccct gaccatgact ttgaggtact ggtgcttgaa gtcggagtcg tcgcagccgc    7800
cccgctccca gagcgagaag tcggtgcgct tcttggagcg ggggttgggc agagcgaagg    7860
tgacatcgtt gaagaggatt ttgcccgcgc ggggcatgaa gttgcgggtg atgcggaagg    7920
gccccggcac ttcagagcgg ttgttgatga cctgggcggc gagcacgatc tcgtcgaagc    7980
cgttgatgtt gtggcccacg atgtagagtt ccaggaagcg gggccggccc tttacggtgg    8040
gcagcttctt tagctcttcg taggtgagct cctcggggcga ggcgaggccg tgctcggcca    8100
gggcccagtc cgcgaggtgc gggttgtctc tgaggaagga ctcccagagg tcgcgggcca    8160
ggagggtctg caggcggtcc ctgaaggtcc tgaactggcg gcccacgcc atttttcgg     8220 gggtgatgca gtagaaggtg aggggggtctt gctgccagcg gtcccagtcg agctgcaggg    8280
cgaggtcgcg cgcggcggtg accagcgct cgtcgccccc gaatttcatg accagcatga    8340
agggcacgag ctgctttccg aaggccccca tccaagtgta ggtctctaca tcgtaggtga    8400
caaagaggcg ctccgtgcga ggatgcgagc cgatcgggaa gaactggatc tcccgccacc    8460
agttggagga gtggctgttg atgtggtgga agtagaagtc ccgtcgccgg gccgaacact    8520
cgtgctggct tttgtaaaag cgagcgcagt actggcagcg ctgcacgggc tgtacctcct    8580
gcacgagatg cacctttcgc ccgcgcacga ggaagccgag gggaaatctg agccccccgc    8640
ctggctcgcg gcatggctgg tgctcttcta ctttggatgc gtgtccgtct ccgtctggct    8700
cctcgagggg tgttacggtg gagcggacca ccacgccgcg cgagccgcag gtccagatat    8760
cggcgcgcgc cggtcggagt ttgatgacga catcgcgcag ctgggagctg tccatggtct    8820
ggagctcccg cggcggcggc aggtcagccg ggagttcttg caggttcacc tcgcagagtc    8880 gggcagggc gcgggggcagg tctaggtggt acctgatctc tagggcgtg ttggtggcgg    8940 cgtcgatggc ttgcaggagc ccgcatcccc ggggggcgac gacggtgccc cgcggggtgg    9000
tggtggtggt ggtggtggtg gtggtggcgg tgcagctcag aagcggtgcc gcgggcgggc    9060
ccccggaggt aggggggggct ccggtcccgc cggcaggggc ggcagcggca cgtcggcgtg    9120
gagcgcgggg aggagttggt gctgtgcccg gaggttgctg gcgaaggcga cgacgcggcg    9180
gttgatctcc tggatctggc gcctctgcgt gaagacgacg ggcccggtga gcttgaacct    9240
gaaagagagt tcgacagaat caatctcggt gtcattgacc gcggcctggc gcaggatctc    9300
ctgcacgtct cccgagttgt cttggtaggc gatctcggcc atgaactgct cgatctcttc    9360
ctcctggagg tctccgcgtc cggcgcgttc cacggtggcc gccaggtcgt tggagatgcg    9420
ccccatgagc tgcgagaagg cgttgagtcc gccctcgttc cagactcggc tgtagaccac    9480
gcccccctgg tcatcgcggg cgcgcatgac cacctgcgcg aggttgagct ccacgtgccg    9540
cgcgaagacg gcgtagttgc gcagacgctg gaagaggtag ttgagggtgg tggcggtgtg    9600
```

```
ctcggccacg aagaagttca tgacccagcg gcgcaacgtg gattcgttga tgtcccccaa    9660
ggcctccagc cgttccatgg cctcgtagaa gtccacggcg aagttgaaaa actgggagtt    9720
gcgcgccgac acggtcaact cctcctccag aagacggatg agctcggcga cggtgtcgcg    9780
cacctcgcgc tcgaaggcta tggggatctc ttcctccgct agcatcacca cctcctcctc    9840
ttcctcctct tctggcactt ccatgatggc ttcctcctct cgggggggcg cggcggcgg    9900
cggtggggga gggggcgctc tgcgccggcg cggcgcacc gggaggcggt ccacgaagcg    9960
cgcgatcatc tccccgcggc ggcggcgcat ggtctcggtg acggcgcggc cgttctcccg   10020
ggggcgcagt tggaagacgc cgccggacat ctggtgctgg gcgggtggc cgtgaggcag   10080
cgaaacggcg ctgacgatgc atctcaacaa ttgctgcgta ggtacgccgc cgagggacct   10140
gagggagtcc atatccaccg gatccgaaaa cctttcgagg aaggcgtcta accagtcgca   10200
gtcgcaaggt aggctgagca ccgtggcggg cggcgggggg tgggggagt gtctggcgga   10260
ggtgctgctg atgatgtaat tgaagtaggc ggacttgaca cggcggatgg tcgacaggag   10320
caccatgtcc ttgggtccgg cctgctggat gcggaggcgg tcggctatgc cccaggcttc   10380
gttctggcat cggcgcaggt ccttgtagta gtcttgcatg agcctttcca ccggcacctc   10440
ttctccttcc tcttctgctt cttccatgtc tgcttcggcc ctggggcggc ccgcgcccc   10500
cctgcccccc atgcgcgtga ccccgaaccc cctgagcggt tggagcaggg ccaggtcggc   10560
gacgacgcgc tcggccagga tggcctgctg cacctgcgtg agggtggttt ggaagtcatc   10620
caagtccacg aagcggtggt aggcgcccgt gttgatggtg taggtgcagt tggccatgac   10680
ggaccagttg acggtctggt ggcccggttg cgacatctcg gtgtacctga gtcgcgagta   10740
ggcgcgggag tcgaagacgt agtcgttgca agtccgcacc aggtactggt agcccaccag   10800
gaagtgcggc ggcggctggc ggtagagggg ccagcgcagg gtggcggggg ctccggggc   10860
caggtcttcc agcatgaggc ggtggtaggc gtagatgtac ctggacatcc aggtgatacc   10920
cgcggcggtg gtggaggcgc gcgggaagtc gcgcacccgg ttccagatgt tgcgcagggg   10980
cagaaagtgc tccatggtag gcgtgctctg tccagtcaga cgcgcgcagt cgttgatact   11040
ctagaccagg gaaaacgaaa gccggtcagc gggcactctt ccgtggtctg gtgaatagat   11100
cgcaagggta tcatggcgga gggcctcggt tcgagccccg ggtccgggcc ggacggtccg   11160
ccatgatcca cgcggttacc gcccgcgtgt cgaacccagg tgtgcgacgt cagacaacg   11220
tggagtgttc cttttggcgt ttttctggcc gggcgccggc gtcgcgtaag agactaagcc   11280
gcgaaagcga aagcagtaag tggctcgctc cccgtagccg gagggatcct tgctaagggt   11340
tgcgttgcgg cgaaccccgg ttcgaatccc gtactcgggc cggccggacc cgcggctaag   11400
gtgttggatt ggcctccccc tcgtataaag accccgcttg cggattgact ccggacacgg   11460
ggacgagccc cttttatttt tgctttcccc agatgcatcc ggtgctgcgg cagatgcgcc   11520
ccccgcccca gcagcagcaa caacaccagc aagagcggca gcaacagcag cgggagtcat   11580
gcagggcccc ctcacccacc ctcggcgggc cggccacctc ggcgtccgcg ccgtgtctg   11640
gcgcctgcgg cggcggcggg gggccggctg acgaccccga ggagccccg cggcgcaggg   11700
ccagacacta cctggacctg gaggaggcg agggcctggc gcggctgggg gcgccgtctc   11760
ccgagcgcca cccgcgggtg cagctgaagc gcgactcgcg cgaggcgtac gtgcctcggc   11820
agaacctgtt cagggaccgc gcgggcgagg agcccgagga gatgcgggac aggaggttca   11880
gcgcagggcg ggagctgcgg caggggctga accgcgagcg gctgctgcgc gaggaggact   11940
```

```
ttgagcccga cgcgcggacg gggatcagcc ccgcgcgcgc gcacgtggcg gccgccgacc   12000
tggtgacggc gtacgagcag acggtgaacc aggagatcaa cttccaaaag agtttcaaca   12060
accacgtgcg cacgctggtg gcgcgcgagg aggtgaccat cgggctgatg cacctgtggg   12120
actttgtaag cgcgctggtg cagaacccca acagcaagcc tctgacggcg cagctgttcc   12180
tgatagtgca gcacagcagg gacaacgagg cgtttaggga cgcgctgctg aacatcaccg   12240
agcccgaggg tcggtggctg ctggacctga ttaacatcct gcagagcata gtggtgcagg   12300
agcgcagcct gagcctggcc gacaaggtgg cggccatcaa ctactcgatg ctgagcctgg   12360
gcaagtttta cgcgcgcaag atctaccaga cgccgtacgt gcccatagac aaggaggtga   12420
agatcgacgg ttttttacatg cgcatggcgc tgaaggtgct caccctgagc gacgacctgg   12480
gcgtgtaccg caacgagcgc atccacaagg ccgtgagcgt gagccggcgg cgcgagctga   12540
gcgaccgcga gctgatgcac agcctgcagc gggcgctggc gggcgccggc agcggcgaca   12600
gggaggcgga gtcctacttc gatgcggggg cggacctgcg ctgggcgccc agccggcggg   12660
ccctggaggc cgcggggggtc cgcgaggact atgacgagga cggcgaggag gatgaggagt   12720
acgagctaga ggagggcgag tacctggact aaaccgcggg tggtgtttcc ggtagatgca   12780
agacccgaac gtggtggacc cggcgctgcg ggcggctctg cagagccagc cgtccggcct   12840
taactcctca gacgactggc gacaggtcat ggaccgcatc atgtcgctga cggcgcgtaa   12900
cccggacgcg ttccggcagc agccgcaggc caacaggctc tccgccatcc tggaggcggt   12960
ggtgcctgcg cgctcgaacc ccacgcacga aaggtgctg gccatagtga acgcgctggc   13020
cgagaacagg gccatccgcc cggacagggc cgggctggtg tacgacgcgc tgctgcagcg   13080
cgtggcccgc tacaacagcg gcaacgtgca gaccaacctg gaccggctgg tggggacgt   13140 gcgcgaggcg gtgcgcagc gcgagcgcgc ggatcggcag ggcaacctgg gctccatggt   13200
ggcgctgaat gccttcctga gcacgcagcc ggccaacgtg ccgcgggggc aggaagacta   13260
caccaacttt gtgagcgcgc tgcggctgat ggtgaccgag accccccaga gcgaggtgta   13320
ccagtcgggc ccggactact tcttccagac cagcagacag ggcctgcaga cggtgaacct   13380
gagccaggct ttcaagaacc tgcggggggct gtggggcgtg aaggcgccca ccggcgaccg   13440
ggcgacggtg tccagcctgc tgacgcccaa ctcgcgcctg ctgctgctgc tgatcgcgcc   13500
gttcacggac agcggcagcg tgtcccggga cacctacctg gggcacctgc tgaccctgta   13560
ccgcgaggcc atcgggcagg cgcaggtgga cgagcacacc ttccaggaga tcaccagcgt   13620
gagccgcgcg ctggggcagg aggacacgag cagcctggag gcgactctga actacctgct   13680
gaccaaccgg cggcagaaga ttccctcgct gcacagcctg acctccgagg aggagcgcat   13740
cttgcgctac gtgcagcaga gcgtgagcct gaacctgatg cgcgacgggg tgacgcccag   13800
cgtggcgctg gacatgaccg cgcgcaacat ggaaccgggc atgtacgccg cgcaccggcc   13860
ttacatcaac cgcctgatgg actacctgca tcgcgcggcg gccgtgaacc ccgagtactt   13920
taccaacgcc atcctgaacc cgcactggct cccgccgccc gggttctaca gcgggggctt   13980
cgaggtcccg gaggccaacg atggcttcct gtgggacgac atggacgaca gcgtgttctc   14040
cccgcggccg cagcgctggg cggaagcgtc cctgctgcgt cccaagaagg aggaggaga   14100 ggcgagtcgc cgccgcggca gcagcggcgt ggcttctctg tccgagctgg ggcggcagc   14160 cgccgcgcgc cccgggtccc tgggcggcag ccccttccg agcctggtgg ggtctctgca   14220
cagcgagcgc accaccccgcc ctcggctgct gggcgaggac gagtacctga ataactccct   14280
gctgcagccg gtgcgggaga aaaacctgcc ccccgccttc cccaacaacg ggatagagag   14340
```

```
cctggtggac aagatgagca gatggaagac ctatgcgcag gagcacaggg acgcgcccgc   14400
gctccggccg cccacgcggc gccagcgcca cgaccgcag cggggctgg tgtgggatga    14460 cgaggactcc gcggacgata gcagcgtgct ggacctggga gggagcggca acccgttcgc   14520
gcacctgcgc ccccgcctgg ggaggatgtt ttaaaaaaaa aaaaagcaag aagcatgatg   14580
caaaattaaa taaaactcac caaggccatg gcgaccgagc gttggtttct tgtgttccct   14640
tcagtatgcg gcgcgcggcg atgtaccagg agggacctcc tccctcttac gagagcgtgg   14700
tgggcgcggc ggcggcggcg ccctcttctc cctttgcgtc gcagctgctg gagccgccgt   14760
acgtgcctcc gcgctacctg cggcctacgg ggggagaaa cagcatccgt tactcggagc    14820
tggcgcccct gttcgacacc acccgggtgt acctggtgga caacaagtcg gcggacgtgg   14880
cctccctgaa ctaccagaac gaccacagca atttttgac cacggtcatc cagaacaatg    14940
actacagccc gagcgaggcc agcacccaga ccatcaatct ggatgaccgg tcgcactggg   15000
gcggcgacct gaaaaccatc ctgcacacca acatgcccaa cgtgaacgag ttcatgttca   15060
ccaataagtt caaggcgcgg gtgatggtgt cgcgctcgca caccaaggaa gaccgggtgg   15120
agctgaagta cgagtgggtg gagttcgagc tgccagaggg caactactcc gagaccatga   15180
ccattgacct gatgaacaac gcgatcgtgg agcactatct gaaagtgggc aggcaaaacg   15240
gggtcctgga gagcgacatc ggggtcaagt tcgacaccag gaacttccgc ctggggctgg   15300
accccgtgac cgggctggtt atgcccgggg tgtacaccaa cgaggccttc catcccgaca   15360
tcatcctgct gcccggctgc ggggtggact tcacttacag ccgcctgagc aacctcctgg   15420
gcatccgcaa gcggcagccc ttccaggagg gcttcaggat cacctacgag gacctggagg   15480
ggggcaacat ccccgcgctc ctcgatgtgg aggcctacca ggatagcttg aaggaaaatg   15540
aggcgggaca ggaggatacc accccgccg cctccgccgc cgccgagcag ggcgaggatg   15600
ctgctgacac cgcggccgcg gacggggcag aggccgaccc cgctatggtg gtggaggctc   15660
ccgagcagga ggaggatatg aatgacagtg cggtgcgcgg agacaccttc gtcacccggg   15720
gggaggaaaa gcaagcggag gccgaggccg cggccgagga aaagcaactg gcggcagcag   15780
cggcggcggc ggcgttggcc gcggcggagg ctgagtctga ggggaccaag cccgccaagg   15840
agcccgtgat taagcccctg accgaagata gcaagaagcg cagttacaac ctgctcaagg   15900
acagcaccaa caccgcgtac cgcagctggt acctggccta caactacggc gacccgtcga   15960
cgggggtgcg ctcctggacc ctgctgtgca cgccggacgt gacctgcggc tcggagcagg   16020
tgtactggtc gctgcccgac atgatgcaag accccgtgac cttccgctcc acgcggcagg   16080
tcagcaactt cccggtggtg ggcgccgagc tgctgcccgt gcactccaag agcttctaca   16140
acgaccaggc cgtctactcc cagctcatcc gccagttcac ctctctgacc cacgtgttca   16200
atcgctttcc tgagaaccag attctggcgc gcccgcccgc cccaccatc accaccgtca    16260 gtgaaaacgt tcctgctctc acagatcacg ggacgctacc gctgcgcaac agcatcggag   16320
gagtccagcg agtgaccgtt actgacgcca gacgccgcac ctgcccctac gtttacaagg   16380
ccttgggcat agtctcgccg cgcgtccttt ccagccgcac tttttgagca acaccaccat   16440
catgtccatc ctgatctcac ccagcaataa ctccggctgg ggactgctgc gcgcgcccag   16500
caagatgttc ggaggggcga ggaagcgttc cgagcagcac cccgtgcgcg tgcgcgggca   16560
cttccgcgcc ccctggggag cgcacaaacg cggccgcgcg gggcgcacca ccgtggacga   16620
cgccatcgac tcggtggtgg agcaggcgcg caactacagg cccgcggtct ctaccgtgga   16680
```

-continued

```
cgcggccatc cagaccgtgg tgcgggcgc gcggcggtac gccaagctga agagccgccg    16740
gaagcgcgtg gcccgccgcc accgccgccg acccggggcc gccgccaaac gcgccgccgc    16800
ggccctgctt cgccgggcca agcgcacggg ccgccgcgcc gccatgaggg ccgcgcgccg    16860
cttggccgcc ggcatcaccg ccgccaccat ggcccccgt acccgaagac gcgcggccgc    16920
cgccgccgcc gccgccatca gtgacatggc cagcaggcgc cggggcaacg tgtactgggt    16980
gcgcgactcg gtgaccggca cgcgcgtgcc cgtgcgcttc cgccccccgc ggacttgaga    17040
tgatgtgaaa aacaacact gagtctcctg ctgttgtgtg tatcccagcg gcggcggcgc    17100
gcgcagcgtc atgtccaagc gcaaaatcaa agaagagatg ctccaggtcg tcgcgccgga    17160
gatctatggg ccccccgaaga aggaagagca ggattcgaag ccccgcaaga taaagcgggt    17220
caaaaagaaa aagaaagatg atgacgatgc cgatggggag gtggagttcc tgcgcgccac    17280
ggcgcccagg cgcccggtgc agtggaaggg ccggcgcgta aagcgcgtcc tgcgcccccgg    17340
caccgcggtg gtcttcacgc ccggcgagcg ctccacccgg actttcaagc gcgtctatga    17400
cgaggtgtac ggcgacgaag acctgctgga gcaggccaac gagcgcttcg gagagtttgc    17460
ttacgggaag cgtcagcggg cgctggggaa ggaggacctg ctggcgctgc cgctggacca    17520
gggcaacccc acccccagtc tgaagcccgt gaccctgcag caggtgctgc cgagcagcgc    17580
accctccgag gcgaagcggg gtctgaagcg cgagggcggc gacctggcgc ccaccgtgca    17640
gctcatggtg cccaagcggc agaggctgga ggatgtgctg gagaaaatga agtagaccc    17700
cggtctgcag ccggacatca gggtccgtcc catcaagcag gtggcgccgg gcctcggcgt    17760
gcagaccgtg gacgtggtca tcccccaccgg caactccccc gccgccacca ccactaccgc    17820
tgcctccacg gacatggaga cacagaccga tcccgccgca gccgcagccg ccgccgcagc    17880
cgcgacctcc tcggcggagg tgcagacgga ccccctggctg ccgccggcga tgtcagctcc    17940
ccgcgcgcgc gcggacgca gaaagtacgg cgccgccaac gcgctcctgc ccgagtacgc    18000
cttgcatcct tccatcgcgc ccaccccgg ctaccgaggc tatacctacc gcccgcgaag    18060
agccaagggt tccacccgcc gtccccgccg acgcgccgcc gccaccaccc gccgccgccg    18120
ccgcagacgc cagcccgcac tggctccagt tccgtgagg agagtggcgc gcgacgggaca    18180
caccctggtg ctgcccaggg cgcgctacca ccccagcatc gtttaaaagc ctgttgtggt    18240
tcttgcagat atgccctca cttgccgcct ccgttccccg gtgccgggat accgaggagg    18300
aagatcgcgc cgcaggaggg gtctggccgg ccgcggcctg agcggaggca gccgccgcgc    18360
gcaccggcgg cgacgcgcca ccagccgacg catgcgcgg ggggtgctgc ccctgttaat    18420
cccctgatc gccgcggcga tcggcgccgt gcccgggatc gcctccgtgg ccttgcaagc    18480
gtccagagg cattgacaga cttgcaaact tgcaaatatg gaaaaaaaaa aaaaccccca    18540
ataaaaagtc tagactctca cgctcgcttg gtcctgtgac tatttgtag aatggaagac    18600
atcaactttg cgtcgctggc cccgcgtcac ggctcgcgcc cgttcctggg acactggaac    18660
gatatcggca ccagcaacat gagcggtggc gccttcagtt ggggctctct gtggagcggc    18720
attaaaagta tcgggtctgc cgttaaaaat tacggctccc gggcctggaa cagcagcacg    18780
ggccagatgt tgagacaa gttgaaagag cagaacttcc agcagaaggt ggtggagggc    18840
ctggcctccg gcatcaacgg ggtggtggac ctggccaacc aggccgtgca gaataaaatc    18900
aacagcagac tggaccccg gccgccggtg gaggaggtgc cgccggcgct ggagacggtg    18960
tccccgatg ggcgtggcga gaagcgcccg cggcccgata gggaagagac cactctggtc    19020
acgcagaccg atgagccgcc cccgtatgag gaggccctaa agcaaggtct gcccaccacg    19080
```

```
cggcccatcg cgcccatggc caccggggtg gtgggccgcc acaccccgc cacgctggac    19140 ttgcctccgc ccgccgatgt gccgcagcag cagaaggcgg cacagccggg cccgcccgcg    19200
accgcctccc gttcctccgc cggtcctctg cgccgcgcgg ccagcggccc cgcgggggg     19260 gtcgcgaggc acggcaactg gcagagcacg ctgaacagca tcgtgggtct gggggtgcgg    19320
tccgtgaagc gccgccgatg ctactgaata gcttagctaa cgtgttgtat gtgtgtatgc    19380
gccctatgtc gccgccagag gagctgctga gtcgccgccg ttcgcgcgcc caccaccacc    19440
gccactccgc ccctcaagat ggcgacccca tcgatgatgc cgcagtggtc gtacatgcac    19500
atctcgggcc aggacgcctc ggagtacctg agccccgggc tggtgcagtt cgcccgcgcc    19560
accgagagct acttcagcct gagtaacaag tttaggaacc ccacggtggc gcccacgcac    19620
gatgtgacca ccgaccggtc tcagcgcctg acgctgcggt tcattcccgt ggaccgcgag    19680
gacaccgcgt actcgtacaa ggcgcggttc accctggccg tgggcgacaa ccgcgtgctg    19740
gacatggcct ccacctactt tgacatccgc ggggtgctgg accgggggtcc cactttcaag    19800 ccctactctg gcaccgccta caactccctg gcccccaagg gcgctcccaa ctcctgcgag    19860
tgggagcaag aggaaactca ggcagttgaa gaagcagcag aagaggaaga agaagatgct    19920
gacggtcaag ctgaggaaga gcaagcagct accaaaaaga ctcatgtata tgctcaggct    19980
cccctttctg gcgaaaaaat tagtaaagat ggtctgcaaa taggaacgga cgctacagct    20040
acagaacaaa aacctattta tgcagaccct acattccagc ccgaacccca aatcggggag    20100
tcccagtgga tgaggcaga tgctacagtc gccggcggta gagtgctaaa gaaatctact    20160
cccatgaaac catgctatgg ttcctatgca agacccacaa atgctaatgg aggtcagggt    20220
gtactaacgg caaatgccca gggacagcta gaatctcagg ttgaaatgca attcttttca    20280
acttctgaaa acgcccgtaa cgaggctaac aacattcagc ccaaattggt gctgtatagt    20340
gaggatgtgc acatggagac cccggatacg caccttttctt acaagcccgc aaaaagcgat    20400
gacaattcaa aaatcatgct gggtcagcag tccatgccca acagacctaa ttacatcggc    20460
ttcagagaca actttatcgg cctcatgtat tacaatagca ctggcaacat gggagtgctt    20520
gcaggtcagg cctctcagtt gaatgcagtg gtggacttgc aagacagaaa cacagaactg    20580
tcctaccagc tcttgcttga ttccatgggt gacagaacca gatacttttc catgtggaat    20640
caggcagtgg acagttatga cccagatgtt agaattattg aaaatcatgg aactgaagac    20700
gagctcccca actattgttt ccctctgggt ggcataggg taactgacac ttaccaggct    20760
gttaaaacca acaatggcaa taacggggc caggtgactt ggacaaaaga tgaaactttt    20820
gcagatcgca atgaaatagg ggtgggaaac aatttcgcta tggagatcaa cctcagtgcc    20880
aacctgtgga gaaacttcct gtactccaac gtggcgctgt acctaccaga caagcttaag    20940
tacaacccct ccaatgtgga catctctgac aaccccaaca cctacgatta catgaacaag    21000
cgagtggtgg ccccggggct ggtggactgc tacatcaacc tgggcgcgcg ctggtcgctg    21060
gactacatgg acaacgtcaa ccccttcaac caccaccgca atgcgggcct gcgctaccgc    21120
tccatgctcc tggcaacgg gcgctacgtg cccttccaca tccaggtgcc ccagaagttc    21180
tttgccatca agaacctcct cctcctgccg ggctcctaca cctacgagtg gaacttcagg    21240
aaggatgtca acatggtcct ccagagctct ctgggtaacg atctcagggt ggacggggcc    21300
agcatcaagt tcgagagcat ctgcctctac gccaccttct tccccatggc ccacaacacg    21360
gcctccacgc tcgaggccat gctcaggaac gacaccaacg accagtcctt caatgactac    21420
```

```
ctttccgccg ccaacatgct ctaccccata cccgccaacg ccaccaacgt ccccatctcc   21480 atccctcgc gcaactgggc ggccttccgc ggctgggcct tcacccgcct caagaccaag    21540
gagaccccct ccctgggctc gggattcgac ccctactaca cctactcggg ctctattccc   21600
tacctggacg gcaccttcta cctcaaccac actttcaaga aggtctcggt caccttcgac   21660
tcctcggtca gctggccggg caacgaccgt ctgctcaccc caacgagtt cgagatcaag    21720 cgctcggtcg acggggaagg ctacaacgtg gcccagtgca acatgaccaa ggactggttc   21780
ctggtccaga tgctggccaa ctacaacatc ggctaccagg gcttctacat cccagagagc   21840
tacaaggaca ggatgtactc cttcttcagg aacttccagc ccatgagccg gcaggtggtg   21900
gaccagacca agtacaagga ctaccaggag gtgggcatca tccaccagca caacaactcg   21960
ggcttcgtgg gctacctcgc ccccaccatg cgcgagggac aggcctaccc cgccaacttc   22020
ccctacccgc tcataggcaa gaccgcggtc gacagcatca cccagaaaaa gttcctctgc   22080
gaccgcaccc tctggcgcat ccccttctcc agcaacttca gtccatggg tgcgctctcg     22140 gacctgggcc agaacttgct ctacgccaac tccgcccacg ccctcgacat gaccttcgag   22200
gtcgacccca tggacgagcc cacccttctc tatgttctgt tcgaagtctt tgacgtggtc   22260
cgggtccacc agccgcaccg cggcgtcatc gagaccgtgt acctgcgtac gcccttctcg   22320
gccggcaacg ccaccaccta agaagcaag ccgcagtcat cgccgcctgc atgccgtcgg     22380
gttccaccga gcaagagctc agggccatcg tcagagacct gggatgcggg ccctattttt   22440
tgggcacctt cgacaagcgc ttccctggct ttgtctcccc acacaagctg gcctgcgcca   22500
tcgtcaacac ggccggccgc gagaccgggg gcgtgcactg gctggccttt gcctggaacc   22560
cgcgctccaa acatgcttc ctctttgacc ccttcggctt ttcggaccag cggctcaagc     22620
aaatctacga gttcgagtac gagggcttgc tgcgtcgcag cgccatcgcc tcctcgcccg   22680
accgctgcgt caccctcgaa aagtccaccc agaccgtgca ggggcccgac tcggccgcct   22740
gcggtctctt ctgctgcatg tttctgcacg ccttttgtgca ctggcctcag agtcccatgg   22800
accgcaaccc caccatgaac ttgctgacgg gggtgcccaa ctccatgctc caaagccccc   22860
aggtcgagcc caccctgcgc cgcaaccagg agcagctcta cagcttcctg gagcgccact   22920
cgccctactt ccgccgccac agcgcacaga tcaggagggc cacctccttc tgccacttgc   22980
aagagatgca agaagggtaa taacgatgta cactttttt tctcaataaa tggcatttt     23040 ttttattta tacaagctct ctggggtatt catttcccac caccaccacc cgccgttgtc   23100
gccatctggc tctatttaga aatcgaaagg gttctgccgg gagtcgccgt gcgccacggg   23160
cagggacacg ttgcgatact ggtagcgggt gccccacttg aactcgggca ccaccaggcg   23220
aggcagctcg gggaagtttt cgctccacag gctgcgggtc agcaccagcg cgttcatcag   23280
gtcgggcgcc gagatcttga agtcgcagtt ggggccgccg ccctgcgcgc gcgagttgcg   23340
gtacaccggg ttgcagcact ggaacaccaa cagcgccggg tgcttcacgc tggccagcac   23400
gctgcggtcg gagatcagct cggcgtccag gtcctccgcg ttgctcagcg cgaacggggt   23460
catcttgggc acttgccgcc ccaggaaggg cgcgtgcccc ggtttcgagt tgcagtcgca   23520
gcgcagcggg atcagcaggt gcccgtgccc ggactcggcg ttggggtaca gcgcgcgcat   23580
gaaggcctgc atctggcgga aggccatctg ggccttggcg ccctccgaga gaacatgcc     23640 gcaggacttg cccgagaact ggtttgcggg gcagctggcg tcgtgcaggc agcagcgcgc   23700
gtcggtgttg gcgatctgca ccacgttgcg ccccaccgg ttcttcacga tcttggcctt    23760
ggacgattgc tccttcagcg cgcgctgccc gttctcgctg gtcacatcca tctcgatcac   23820
```

```
atgttccttg ttcaccatgc tgctgccgtg cagacacttc agctcgccct ccgtctcggt   23880
gcagcggtgc tgccacagcg cgcagcccgt gggctcgaaa gacttgtagg tcacctccgc   23940
gaaggactgc aggtacccct gcaaaaagcg gcccatcatg gtcacgaagg tcttgttgct   24000
gctgaaggtc agctgcagcc cgcggtgctc ctcgttcagc caggtcttgc acacggccgc   24060
cagcgcctcc acctggtcgg gcagcatctt gaagttcacc ttcagctcat tctccacgtg   24120
gtacttgtcc atcagcgtgc gcgccgcctc catgcccttc tcccaggccg acaccagcgg   24180
caggctcacg gggttcttca ccatcaccgt ggccgccgcc tccgccgcgc tttcgctttc   24240 cgcccccgctg ttctcttcct cttcctcctc ttcctcgccg ccgcccactc gcagcccccg   24300
caccacgggg tcgtcttcct gcaggcgctg caccttgcgc ttgccgttgc gccctgctt    24360 gatgcgcacg gcggggttgc tgaagcccac catcaccagc gcggcctctt cttgctcgtc   24420
ctcgctgtcc agaatgacct ccggggaggg ggggttggtc atcctcagta ccgaggcacg   24480
cttctttttc ttcctggggg cgttcgccag ctccgcggct gcggccgctg ccgaggtcga   24540
aggccgaggg ctgggcgtgc gcggcaccag cgcgtcttgc gagccgtcct cgtcctcctc   24600
ggactcgaga cggaggcggg cccgcttctt cggggcgcg cggggcggcg gaggcggcgg   24660
cggcgacgga gacggggacg agacatcgtc cagggtgggt ggacggcggg ccgcgccgcg   24720
tccgcgctcg ggggtggttt cgcgctggtc tcttcccga ctggccatct cccactgctc    24780
cttctcctat aggcagaaag agatcatgga gtctctcatg cgagtcgaga aggaggagga   24840
cagcctaacc gccccctctg agccctccac caccgccgcc accacgccca atgccgccgc   24900
ggacgacgcg cccaccgaga ccaccgccag taccaccctc cccagcgacg cacccccgct   24960
cgagaatgaa gtgctgatcg agcaggaccc gggttttgtg agcggagagg aggatgaggt   25020
ggatgagaag gagaaggagg aggtcgccgc ctcagtgcca aaagaggata aaaagcaaga   25080
ccaggacgac gcagataagg atgagacagc agtcggcgg gggaacggaa gccatgatgc    25140
tgatgacggc tacctagacg tgggagacga cgtgctgctt aagcacctgc accgccagtg   25200
cgtcatcgtc tgcgacgcgc tgcaggagcc ctgcgaagtg cccctggacg tggcggaggt   25260
cagccgcgcc tacgagcggc acctcttcgc gccgcacgtg cccccaagc gccgggagaa    25320 cggcacctgc gagcccaacc cgcgtctcaa cttctacccg gtcttcgcgg tacccgaggt   25380
gctggccacc taccacatct tcttccaaaa ctgcaagatc cccctctcct gccgcgctaa   25440
ccgcacccgc gccgacaaaa ccctgaccct gcggcagggc gcccacatac ctgatattgc   25500
ctctctggag gaagtgccca agatcttcga gggtctcggt cgcgacgaga acgggcggc    25560 gaacgctctg cacggagaca gcgaaaacga gagtcactcg gggtgctgg tggagctcga   25620 gggcgacaac gcgcgcctgg ccgtactcaa gcgcagcata gaggtcaccc actttgccta   25680
cccggcgctc aacctgcccc ccaaggtcat gagtgtggtc atgggcgagc tcatcatgcg   25740
ccgcgctcag cccctggccg cggatgcaaa cttgcaagag tcctccgagg aaggcctgcc   25800
cgcggtcagc gacgagcagc tagcgcgctg gctggagacc cgcgaccccg cgcagctgga   25860
ggagcggcgc aagctcatga tggccgcggt gctggtcacc gtggagctcg agtgtctgca   25920
gcgcttcttc gcggaccccg agatgcagcg caagctcgag gagaccctgc actacacctt   25980
ccgccagggc tacgtgcgcc aggcctgcaa gatctccaac gtggagctct gcaacctggt   26040
ctcctacctg ggcatcctgc acgagaaccg cctcgggcag aacgtcctgc actccaccct   26100 caaagggggag gcgcgccgcg actacatccg cgactgcgcc tacctcttcc tctgctacac   26160
```

```
ctggcagacg gccatggggg tctggcagca gtgcctggag gagcgcaacc tcaaggagct   26220
ggaaaagcta ctcaagcgca ccctcaggga cctctggacg ggcttcaacg agcgctcggt   26280
ggccgccgcg ctggcggaca tcatcttccc cgagcgcctg ctcaagaccc tgcagcaggg   26340
cctgcccgac ttcaccagcc agagcatgct gcagaacttt aggactttca tcctggagcg   26400
ctcgggcatc ctgcctgcca cttgctgcgc gctgcccagc gacttcgtgc ccatcaagta   26460
cagggagtgc ccgccgccgc tctggggcca ctgctacctc ttccagctgg ccaactacct   26520
cgcctaccac tcggacctca tggaagacgt gagcggcgag ggcctgctcg agtgccactg   26580
ccgctgcaac ctctgcacgc cccaccgctc tctagtctgc aacccgcagc tgctcagcga   26640
gagtcagatt atcggtacct tcgagctgca gggtccctcg cctgacgaga agtccgcggc   26700
tccggggctg aaactcactc cggggctgtg gacttccgcc tacctacgca aatttgtacc   26760
tgaggactac cacgcccacg agatcaggtt ctacgaagac caatcccgcc cgcccaaggc   26820
ggagctcacc gcctgcgtca tcacccaggg gcacatcctg ggccaattgc aagccatcaa   26880
caaagcccgc cgagagttct tgctgaaaaa gggtcggggg gtgtacctgg accccagtc    26940 cggcgaggag ctaaacccgc tacccccgcc gccgccccag cagcgggacc ttgcttccca   27000
ggatggcacc cagaaagaag cagcagccgc cgccgccgca gccatacatg cttctggagg   27060
aagaggagga ggactgggac agtcaggcag aggaggtttc ggacgaggag caggaggaga   27120
tgatggaaga ctgggaggag gacagcagcc tagacgagga agcttcagag gccgaagagg   27180
tggcagacgc aacaccatca ccctcggtcg cagcccctc gccggggccc ctgaaatcct    27240
ccgaacccag caccagcgct ataacctccg ctcctccggc gccggcgcca cccgcccgca   27300
gacccaaccg tagatgggac accacaggaa ccggggtcgg taagtccaag tgcccgccgc   27360
cgccaccgca gcagcagcag cagcgccagg gctaccgctc gtggcgcggg cacaagaacg   27420
ccatagtcgc ctgcttgcaa gactgcgggg gcaacatctc tttcgcccgg cgcttcctgc   27480
tattccacca cggggtcgcc tttccccgca atgtcctgca ttactaccgt catctctaca   27540
gcccctactg cagcggcgac ccagaggcgg cagcggcagc cacagcggcg accaccacct   27600
aggaagatat cctccgcggg caagacacgc gcagcagcgg ccaggagacc cgcggcagca   27660
gcggcgggag cggtgggcgc actgcgcctc tcgcccaacg aacccctctc gacccgggag   27720
ctcagacaca ggatcttccc cactttgtat gccatcttcc aacagagcag aggccaggag   27780
caggagctga aaataaaaaa cagatctctg cgctccctca cccgcagctg tctgtatcac   27840
aaaagcgaag atcagcttcg gcgcacgctg gaggacgcgg aggcactctt cagcaaatac   27900
tgcgcgctca ctcttaaaga ctagctccgc gcccttctcg aatttaggcg ggagaaaact   27960
acgtcatcgc cggccgccgc ccagcccgcc cagccgagat gagcaaagag attcccacgc   28020
catacatgtg gagctaccag ccgcagatgg gactcgcggc gggagcggcc caggactact   28080
ccacccgcat gaactacatg agcgcgggac cccacatgat ctcacaggtc aacgggatcc   28140
gcgcccagcg aaaccaaata ctgctggaac aggcggccat caccgccacg ccccgccata   28200
atctcaaccc ccgaaattgg cccgccgccc tcgtgtacca ggaaaccccc tccgccacca   28260
ccgtactact tccgcgtgac gcccaggccg aagtccagat gactaactca ggggcgcagc   28320
tcgcgggcgg cttttcgtcac ggggcgcggc cgctccgacc aggtataaga cacctgatga   28380
tcagaggcca aggtatccag ctcaacgacg agtcggtgag ctcttcgctc ggtctccgtc   28440
cggacggaac tttccagctc gccggatccg gcgctcttc gttcacgccc cgccaggcgt   28500
acctgactct gcagacctcg tcctcggagc cccgctccgg aggcatcgga accctccagt   28560
```

```
tcgtggagga gttcgtgccc tcggtctact tcaaccccett ctcgggacct cccggacgct  28620
accccgacca gttcattccg aactttgacg cggtgaagga ctcggcggac ggctacgact  28680
gaatgtcagg tgccgaggca gagcagcttc gcctgagaca cctcgagcac tgccgccgcc  28740
acaagtgctt cgcccgcggt tccggtgagt tctgctactt tcagctaccc gaggagcata  28800
ccgagggggcc ggcgcacggc gtccgcctga ccacccaggg cgaggttacc tgttccctca  28860
tccgggagtt caccctccgt cccctgctag tggagcggga gcggggtccc tgtgtcctaa  28920
ctatcgcctg caactgccct aaccctggat tacatcaaga tctttgctgt catctctgtg  28980
ctgagtttaa taaacgctga gatcagaatc tactgggaat tcgatttagt ccccttttaac  29040
taatcaaaca ctggaatcaa taaaaagaat cacttactta aaatcagaca gcaggtctct  29100
gtccagttta ttcagcagca cctccttccc ctcctcccaa ctctggtact ccaaacgcct  29160
tctggcggca aacttcctcc acaccctgaa gggaatgtca gattcttgct cctgtccctc  29220
cgcacccact atcttcatgt tgttgcagat gaagcgcacc aaaacgtctg acgagagctt  29280
caaccccgtg taccectatg acacggaaag cggccctccc tccgtccctt tcctcacccc  29340
tcccttcgtg tctcccgatg gattccaaga aagccccccc ggggtcctgt ctctgaacct  29400
ggccgagccc ctggtcactt cccacggcat gctcgccctg aaaatgggaa gtggcctctc  29460
cctggacgac gctggcaacc tcacctctca agatatcacc accgctagcc ctcccctcaa  29520
aaaaaccaag accaacctca gcctagaaac ctcatcccce ctaactgtaa gcacctcagg  29580
cgccctcacc gtagcagccg ccgctcccct ggcagtggcc ggcacctccc tcaccatgca  29640
atcagaggcc cccctgacag tacaggatgc aaaactcacc ctggccacca aaggcccect  29700
gaccgtgtct gaaggcaaac tggccttgca aacatcggcc ccgctgacgg ccgctgacag  29760
cagcacccte accgttagcg ccacaccacc aattaatgta agcagtggaa gtttaggctt  29820
agacatggaa gaccctatgt atactcacga tggaaaactg ggaataagaa ttggggggtcc  29880
actaagagta gtagacagct tgcacacact cactgtagtt accggaaatg gactaactgt  29940
agataacaat gccctccaaa ctagagttac gggcgcccta ggttatgaca catcaggaaa  30000
tctacaattg agagctgcag gaggtatgcg aattgatgca aatggccaac ttatccttaa  30060
tgtggcatac ccatttgatg ctcagaacaa tctcagcctt agacttggtc agggacccct  30120
gtatataaac acagaccaca acctggattt gaattgcaac agaggtctaa ccacaactac  30180
caccaacaac acaaaaaaac ttgagactaa aattagctca ggcttagact atgacaccaa  30240
tggtgctgtc attattaaac ttggcactgg tctaagcttc gacaacacag gcgccctaac  30300
tgtgggaaac actggtgatg ataaactgac tctgtggacg accccagacc catctccaaa  30360
ttgcagaatt cactcagaca aagactgcaa gtttactcta gtcctaacta agtgtggaag  30420
ccaaatcctg gcctctgtcg ccgccctagc ggtatcagga aatctggctt cgataacagg  30480
caccgttgcc agcgttacca tctttctcag atttgatcag aatggagtgc ttatggaaaa  30540
ctcctcgcta gacaggcagt actggaactt cagaaatggc aactcaacta cgctgccccc  30600
ctacaccaat gcagttgggt tcatgccaaa cctcgcagca taccccaaaa cgcaaagcca  30660
gactgctaaa aacaacattg taagtcaggt ttacttgaat ggagacaaat ccaaacccat  30720
gacccttacc atcaccctca atggaactaa tgaatccagt gaaactagcc aggtgagtca  30780
ctactccatg tcatttacat gggcttggga aagtgggcaa tatgccactg aaacctttgc  30840
caccaactcc ttcaccttttt cttacattgc tgaacaataa aaagcatgac actgatgttc  30900
```

-continued

```
atttctgatt cttattttat tattttcaaa cacaacaaaa tcattcaagt cattcttcca    30960
tcttagctta atagacacag tagcttaata gacccagtag tgcaaagccc cattctagct    31020
tataactagt ggagaagtac tcgcctacat gggggtagag tcataatcgt gcatcaggat    31080
agggcggtgg tgctgcagca gcgcgcgaat aaactgctgc cgccgccgct ccgtcctgca    31140
ggaatacaac atggcagtgg tctcctcagc gatgattcgc accgcccgca gcataaggcg    31200
ccttgtcctc cgggcacagc agcgcaccct gatctcactt aaatcagcac agtaactgca    31260
gcacagcacc acaatattgt tcaaaatccc acagtgcaag gcgctgtatc caaagctcat    31320
ggcggggacc acagaaccca cgtggccatc ataccacaag cgcaggtaga ttaagtggcg    31380
acccctcata aacacgctgg acataaacat tacctctttt ggcatgttgt aattcaccac    31440
ctcccggtac catataaacc tctgattaaa catggcgcca tccaccacca tcctaaacca    31500
gctggccaaa acctgcccgc cggctataca ctgcagggaa ccgggactgg aacaatgaca    31560
gtggagagcc caggactcgt aaccatggat catcatgctc gtcatgatat caatgttggc    31620
acaacacagg cacacgtgca tacacttcct caggattaca agctcctccc gcgttagaac    31680
catatcccag ggaacaaccc attcctgaat cagcgtaaat cccacactgc agggaagacc    31740
tcgcacgtaa ctcacgttgt gcattgtcaa agtgttacat tcgggcagca gcggatgatc    31800
ctccagtatg gtagcgcggg tttctgtctc aaaggaggt agacgatccc tactgtacgg    31860
agtgcgccga gacaaccgag atcgtgttgg tcgtagtgtc atgccaaatg gaacgccgga    31920
cgtagtcata tttcctgaag tcttagatct ctcaacgcag caccagcacc aacacttcgc    31980
agtgtaaaag gccaagtgcc gagagagtat atataggaat aaaaagtgac gtaaacgggc    32040
aaagtccaaa aaacgcccag aaaaaccgca cgcgaaccta cgccccgaaa cgaaagccaa    32100
aaaacactag acactccctt ccggcgtcaa cttccgcttt cccacgctac gtcacttgcc    32160
ccagtcaaac aaactacata tcccgaactt ccaagtcgcc acgcccaaaa caccgcctac    32220
acctccccgc ccgccggccc gccccaaac ccgcctcccg ccccgcgccc cgccccgcgc    32280
cgcccatctc attatcatat tggcttcaat ccaaaataag gtatattatt gatgatg       32337
```

<210> SEQ ID NO 3
<211> LENGTH: 32381
<212> TYPE: DNA
<213> ORGANISM: Artificial Sequence
<220> FEATURE:
<223> OTHER INFORMATION: synthetic chimpanzee adenovirus serotype ChAd3
      with Marburg virus Angola codon optimized
      transmembrane envelope glycoprotein (GP) insert
      (ChAd3 Marburg (PB/6712))
<220> FEATURE:
<221> NAME/KEY: CDS
<222> LOCATION: (1666)...(3708)
<223> OTHER INFORMATION: Marburg virus Angola codon optimized transmembrane envelope glycoprotein (GP) insert in ChAd3 Marburg (PB/6712)
<220> FEATURE:
<221> NAME/KEY: CDS
<222> LOCATION: (14690)...(16470)
<223> OTHER INFORMATION: chimpanzee adenovirus serotype ChAd3 penton
<220> FEATURE:
<221> NAME/KEY: CDS
<222> LOCATION: (19503)...(22382)
<223> OTHER INFORMATION: chimpanzee adenovirus serotype ChAd3 hexon
<220> FEATURE:
<221> NAME/KEY: CDS
<222> LOCATION: (29239)...(30924)
<223> OTHER INFORMATION: chimpanzee adenovirus serotype ChAd3 fiber

<400> SEQUENCE: 3

```
catcatcaat aatatacctt attttggatt gaagccaata tgataatgag atgggcggcg    60
cggggcgggg cgcggggcgg gaggcgggtt tggggggcggg ccggcgggcg gggcggtgtg   120
gcggaagtgg actttgtaag tgtggcggat gtgacttgct agtgccgggc gcggtaaaag   180
tgacgttttc cgtgcgcgac aacgcccccg ggaagtgaca ttttccgc ggttttacc      240
ggatgttgta gtgaatttgg gcgtaaccaa gtaagatttg gccattttcg cgggaaaact   300
gaaacgggga agtgaaatct gattaatttt gcgttagtca taccgcgtaa tatttgtcta   360
gggccgaggg actttggccg attacgtgga ggactcgccc aggtgttttt tgaggtgaat   420
ttccgcgttc cgggtcaaag tctccgtttt attattatag gatatcccat tgcatacgtt   480
gtatccatat cataatatgt acatttatat tggctcatgt ccaacattac cgccatgttg   540
acattgatta ttgactagtt attaatagta atcaattacg gggtcattag ttcatagccc   600
atatatggag ttccgcgtta cataacttac ggtaaatggc ccgcctggct gaccgcccaa   660
cgacccccgc ccattgacgt caataatgac gtatgttccc atagtaacgc caatagggac   720
tttccattga cgtcaatggg tggagtattt acggtaaact gcccacttgg cagtacatca   780
agtgtatcat atgccaagta cgccccctat tgacgtcaat gacggtaaat ggcccgcctg   840
gcattatgcc cagtacatga ccttatggga ctttcctact tggcagtaca tctacgtatt   900
agtcatcgct attaccatgg tgatgcggtt ttggcagtac atcaatgggc gtggatagcg   960
gtttgactca cggggatttc caagtctcca ccccattgac gtcaatggga gtttgttttg  1020
gaaccaaaat caacgggact ttccaaaatg tcgtaacaac tccgcccat tgacgcaaat  1080
gggcggtagg cgtgtacggt gggaggtcta tataagcaga gctctcccta tcagtgatag  1140
agatctccct atcagtgata gagatcgtcg acgagctcgt ttagtgaacc gtcagatcgc  1200
ctggagacgc catccacgct gttttgacct ccatagaaga caccgggacc gatccagcct  1260
ccatcggctc gcatctctcc ttcacgcgcc cgccgcccta cctgaggccg ccatccacgc  1320
cggttgagtc gcgttctgcc gcctcccgcc tgtggtgcct cctgaactgc gtccgccgtc  1380
taggtaagtt taaagctcag gtcgagaccg ggcctttgtc cggcgctccc ttggagccta  1440
cctagactca gccggctctc cacgctttgc ctgaccctgc ttgctcaact ctagttaacg  1500
gtggagggca gtgtagtctg agcagtactc gttgctgccg cgcgcgccac cagacataat  1560
agctgacaga ctaacagact gttcctttcc atgggtcttt tctgcagtca ccgtcgtcga  1620
cacgtgtgat cagatatcgc ggccgctcta gagatatcgg ccgccatgaa gaccacctgc  1680
ctgctgatca gcctgatcct gatccagggc gtgaagaccc tgcccatcct ggagatcgcc  1740
agcaacatcc agcccagaa cgtggacagc gtgtgcagcg gcaccctgca gaagaccgag  1800
gacgtgcacc tgatgggctt caccctgagc ggccagaagg tggccgacag ccctctggag  1860
gccagcaaga ggtgggcctt cagggccggc gtgcccccca agaacgtgga gtacaccgag  1920
ggcgaggagg ccaagacctg ctacaacatc agcgtgaccg accccagcgg caagagcctg  1980
ctgctggacc ctcccaccaa catcagggac taccctaagt gcaagaccat ccaccacatc  2040
cagggccaga accctcacgc ccagggcatc gccctgcacc tgtgggcgc cttcttcctg  2100
tacgacagga tcgccagcac caccatgtac agaggaaaag tgttcacaga gggaaacatc  2160
gctgctatga tcgtgaacaa gaccgtgcat aagatgatct tcagcagaca gggacaggga  2220
tatagacata tgaacctgac atccacaaac aagtactgga caagcagcaa cggaacacag  2280
acaaacgata caggatgttt tggaacactg caggaataca actccaccaa gaaccagaca  2340
tgtgccccta gcaagaagcc tctgcctctg cctacagctc atcctgaagt gaagctgaca  2400
```

```
tccacaagca cagatgccac aaagctgaac acaacagatc ctaatagcga cgacgaggat    2460
ctgacaacaa gcggatccgg atccggagaa caggaacctt atacaacaag cgacgctgct    2520
acaaaacagg gactgtcctc cacaatgcct cctacaccta gccctcagcc tagcacacct    2580
cagcagggag gcaacaacac aaaccattcc cagggagtgg tgacagaacc tggaaagaca    2640
aacacaacag cccagcctag catgcctcct cataacacaa caacaatcag cacaaacaac    2700
acctccaagc acaatctgag cacacctagc gtgcctattc agaatgccac caactacaac    2760
acacagtcca cagcccctga aaacgaacag acctccgccc cttccaaaac aaccctgctg    2820
cctacagaaa accctacaac agccaagagc acaaacagca caaagagccc tacaacaaca    2880
gtgcctaaca caacaaacaa gtatagcaca agccctagcc ctacacctaa ttccacagct    2940
cagcatctgg tgtattttag aagaaagaga acatcctgt ggagagaagg agatatgttc     3000 cctttctgg atggactgat caacgctcct atcgattttg atcctgtgcc taacacaaag     3060
acaatctttg atgaaagcag cagcagcgga gcctccgccg aagaagatca gcatgcctcc    3120
cctaacatca gcctgacact gagctatttt cctaaggtga acgaaaacac agcccattcc    3180
ggagaaaacg aaaacgattg tgatgccgaa ctgagaatct ggagcgtgca ggaagatgat    3240
ctggccgccg gactgagctg gatcccttt tttgggcccg gaattgaagg actgtacacc      3300
gccggcctga tcaagaacca gaacaacctg gtgtgcaggc tgaggaggct ggccaaccag    3360
accgccaaga gcctggagct gctgctgagg gtgaccaccg aggagaggac cttcagcctg    3420
atcaacaggc acgccatcga cttcctgctg gctaggtggg gcggcacctg caaggtgctg    3480
ggccccgact gctgcatcgg catcgaggac ctgagcagga catcagcga gcagatcgac     3540 cagatcaaga aggacgagca aaggagggc accggctggg gcctgggcgg caagtggtgg    3600
accagcgact ggggagtgct gacaaacctg ggaatcctgc tgctgctgag cattgccgtg    3660
ctcattgctc tgtcctgtat ctgtagaatc tttaccaagt acatcggatg atagatccag    3720
atctgctgtg ccttctagtt gccagccatc tgttgtttgc ccctcccccg tgccttcctt    3780
gaccctggaa ggtgccactc ccactgtcct ttcctaataa aatgaggaaa ttgcatcgca    3840
ttgtctgagt aggtgtcatt ctattctggg ggtgggtg gggcaggaca gcaaggggga     3900
ggattgggaa gacaatagca ggcatgctgg ggatgcggtg ggcgatatca gcgatcgctg    3960
aggtgggtga gtgggcgtgg cctggggtgg tcatgaaaat atataagttg ggggtcttag    4020
ggtctcttta tttgtgttgc agagaccgcc ggagccatga gcgggagcag cagcagcagc    4080
agtagcagca gcgccttgga tggcagcatc gtgagccctt atttgacgac gcggatgccc    4140
cactgggccg gggtgcgtca gaatgtgatg ggctccagca tcgacggccg acccgtcctg    4200
cccgcaaatt ccgccacgct gacctatgcg accgtgcgg gacgccgtt ggacgccacc      4260 gccgccgccg ccgccaccgc agccgcctcg gccgtgcgca gcctggccac ggactttgca    4320
ttcctgggac cactgcgac aggggctact tctcggccg ctgctgccgc cgttcgcgat      4380
gacaagctga ccgccctgct ggcgcagttg gatgcgctta ctcgggaact gggtgacctt    4440
tctcagcagg tcatggccct gcgccagcag gtctcctccc tgcaagctgg cgggaatgct    4500
tctcccacaa atgccgttta agataaataa accagactc tgtttggatt aaagaaaagt    4560
agcaagtgca ttgctctctt tatttcataa ttttccgcgc gcgataggcc ctagaccagc    4620
gttctcggtc gttgagggtg cggtgtatct tctccaggac gtggtagagg tggctctgga    4680
cgttgagata catgggcatg agcccgtccc gggggtggag gtagcaccac tgcagagctt    4740
```

```
catgctccgg ggtggtgttg tagatgatcc agtcgtagca ggagcgctgg gcatggtgcc    4800
taaaaatgtc cttcagcagc aggccgatgg ccagggggag gcccttggtg taagtgttta    4860
caaaacggtt aagttgggaa gggtgcattc ggggagagat gatgtgcatc ttggactgta    4920
tttttagatt ggcgatgttt ccgcccagat cccttctggg attcatgttg tgcaggacca    4980
ccagtacagt gtatccggtg cacttgggga atttgtcatg cagcttagag ggaaaagcgt    5040
ggaagaactt ggagacgccc ttgtggcctc ccagattttc catgcattcg tccatgatga    5100
tggcaatggg cccgcgggag gcagcttggg caaagatatt tctggggtcg ctgacgtcgt    5160
agttgtgttc cagggtgagg tcgtcatagg ccatttttac aaagcgcggg cggagggtgc    5220
ccgactgggg gatgatggtc ccctctggcc ctggggcgta gttgccctcg cagatctgca    5280
tttcccaggc cttaatctcg gaggggggaa tcatatccac ctgcggggcg atgaagaaaa    5340
cggtttccgg agccggggag attaactggg atgagagcag gtttctaagc agctgtgatt    5400
ttccacaacc ggtgggccca taaataaacac ctataaccgg ttgcagctgg tagtttagag    5460
agctgcagct gccgtcgtcc cggaggaggg gggccacctc gttgagcatg tccctgacgc    5520
gcatgttctc cccgaccaga tccgccagaa ggcgctcgcc gcccagggac agcagctctt    5580
gcaaggaagc aaagtttttc agcggcttga ggccgtccgc cgtgggcatg tttttcaggg    5640
tctggctcag cagctccagg cggtcccaga gctcggtgac gtgctctacg gcatctctat    5700
ccagcatatc tcctcgtttc gcgggttggg gcgactttcg ctgtagggca ccaagcggtg    5760
gtcgtccagc ggggccaaag tcatgtcctt ccatgggcgc agggtcctcg tcagggtggt    5820
ctgggtcacg gtgaaggggt gcgctccggg ctgagcgctt gccaaggtgc gcttgaggct    5880
ggttctgctg gtgctgaagc gctgccggtc ttcgccctgc gcgtcggcca ggtagcattt    5940
gaccatggtg tcatagtcca gccctccgc ggcgtgtccc ttggcgcgca gcttgccctt    6000
ggaggtggcg ccgcacgagg ggcagagcag gctcttgagc gcgtagagct gggggcgag    6060 gaagaccgat tcggggagt aggcgtccgc gccgcagacc ccgcacacgg tctcgcactc    6120
caccagccag gtgagctcgg ggcgcgccgg gtcaaaaacc aggtttcccc catgcttttt    6180
gatgcgtttc ttacctcggg tctccatgag gtggtgtccc cgctcggtga cgaagaggct    6240
gtccgtgtct ccgtagaccg acttgagggg tcttttctcc aggggggtcc ctcggtcttc    6300
ctcgtagagg aactcggacc actctgagac gaaggcccgc gtccaggcca ggacgaagga    6360
ggctatgtgg gaggggtagc ggtcgttgtc cactaggggg tccaccttct ccaaggtgtg    6420
aagacacatg tcgccttcct cggcgtccag gaaggtgatt ggcttgtagg tgtaggccac    6480
gtgaccgggg gttcctgacg gggggtata aaaggggtg ggggcgcgct cgtcgtcact    6540
ctcttccgca tcgctgtctg cgagggccag ctgctgggt gagtattccc tctcgaaggc    6600
gggcatgacc tccgcgctga ggttgtcagt ttccaaaaac gaggaggatt tgatgttcac    6660
ctgtcccgag gtgataccct tgagggtacc cgcgtccatc tggtcagaaa acacgatctt    6720
tttattgtcc agcttggtgg cgaacgaccc gtagagggcg ttggagagca gcttggcgat    6780
ggagcgcagg gtctggttct tgtccctgtc ggcgcgctcc ttggccgcga tgttgagctg    6840
cacgtactcg cgcgcgacgc agcgccactc ggggaagacg gtggtgcgct cgtcgggcac    6900
caggcgcacg cgccagccgc ggttgtgcag ggtgaccagg tccacgctgg tggcgacctc    6960
gccgcgcagg cgctcgttgg tccagcagag acggccgccc ttgcgcgagc agaagggggg    7020 caggggtcc agctgggtct cgtccggggg gtccgcgtcc acggtgaaaa ccccggggcg    7080
caggcgcgcg tcgaagtagt ctatcttgca accttgcatg tccagcgcct gctgccagtc    7140
```

```
gcgggcggcg agcgcgcgct cgtaggggtt gagcggcggg ccccagggca tggggtgggt    7200
gagtgcggag gcgtacatgc cgcagatgtc atagacgtag aggggctccc gcaggacccc    7260
gatgtaggtg gggtagcagc ggccgccgcg gatgctggcg cgcacgtagt catacagctc    7320
gtgcgagggg cgcggaggagt cggggcccag gttggtgcgg gcggggcgct ccgcgcggaa    7380
```
```
gcgggcggcg agcgcgcgct cgtaggggtt gagcggcggg ccccagggca tggggtgggt    7200
gagtgcggag gcgtacatgc cgcagatgtc atagacgtag aggggctccc gcaggacccc    7260
gatgtaggtg gggtagcagc ggccgccgcg gatgctggcg cgcacgtagt catacagctc    7320
gtgcgagggg cgcggaggagt cggggcccag gttggtgcgg gcggggcgct ccgcgcggaa    7380
gacgatctgc ctgaagatgg catgcgagtt ggaagagatg gtgggcgct  ggaagacgtt    7440 gaagctggcg tcctgcaggc cgacggcgtc gcgcacgaag gaggcgtagg agtcgcgcag    7500
cttgtgtacc agctcggcgg tgacctgcac gtcgagcgcg cagtagtcga gggtctcgcg    7560
gatgatgtca tatttagcct gcccctttctt tttccacagc tcgcggttga ggacaaactc    7620
ttcgcggtct ttccagtact cttggatcgg gaaaccgtcc ggttccgaac ggtaagagcc    7680
tagcatgtag aactggttga cggcctggta ggcgcagcag cccttctcca cggggagggc    7740
gtaggcctgc gcggccttgc ggagcgaggt gtgggtcagg gcgaaggtgt ccctgaccat    7800
gactttgagg tactggtgct tgaagtcgga gtcgtcgcag ccgccccgct cccagagcga    7860
gaagtcggtg cgcttcttgg agcgggggtt gggcagagcg aaggtgacat cgttgaagag    7920
gattttgccc gcgcggggca tgaagttgcg ggtgatgcgg aagggccccg gcacttcaga    7980
gcggttgttg atgacctggg cggcgagcac gatctcgtcg aagccgttga tgttgtggcc    8040
cacgatgtag agttccagga agcggggccg gcccctttacg gtgggcagct tctttagctc    8100
ttcgtaggtg agctcctcgg gcgaggcgag gccgtgctcg gccagggccc agtccgcgag    8160
gtgcgggttg tctctgagga aggactccca gaggtcgcgg gccaggaggg tctgcaggcg    8220
gtccctgaag gtcctgaact ggcggcccac ggccattttt tcggggtga tgcagtagaa    8280 ggtgaggggg tcttgctgcc agcggtccca gtcgagctgc agggcgaggt cgcgcgcggc    8340
ggtgaccagg cgctcgtcgc ccccgaattt catgaccagc atgaagggca cgagctgctt    8400
tccgaaggcc cccatccaag tgtaggtctc tacatcgtag gtgacaaaga ggcgctccgt    8460
gcgaggatgc gagccgatcg ggaagaactg gatctcccgc caccagttgg aggagtggct    8520
gttgatgtgg tggaagtaga agtcccgtcg ccgggccgaa cactcgtgct ggcttttgta    8580
aaagcgagcg cagtactggc agcgctgcac gggctgtacc tcctgcacga gatgcacctt    8640
tcgcccgcgc acgaggaagc cgaggggaaa tctgagcccc ccgcctggct cgcggcatgg    8700
ctggtgctct tctactttgg atgcgtgtcc gtctccgtct ggctcctcga ggggtgttac    8760
ggtggagcgg accaccacgc cgcgcgagcc gcaggtccag atatcggcgc gcggcggtcg    8820
gagtttgatg acgacatcgc gcagctggga gctgtccatg gtctggagct cccgcggcgg    8880
cggcaggtca gccgggagtt cttgcaggtt cacctcgcag agtcgggcca gggcgcgggg    8940
caggtctagg tggtacctga tctctagggg cgtgttggtg gcggcgtcga tggcttgcag    9000
gagcccgcat ccccgggggg cgacgacggt gccccgcggg gtggtggtgg tggtggtggt    9060
ggtggtggtg gcggtgcagc tcagaagcgg tgccgcgggc gggcccccgg aggtagggg    9120 ggctccggtc ccgccggcag gggcggcagc ggcacgtcgg cgtggagcgc gggcaggagt    9180
tggtgctgtg cccggaggtt gctggcgaag gcgacgacgc ggcggttgat ctcctggatc    9240
tggcgcctct gcgtgaagac gacgggcccg gtgagcttga acctgaaaga gagttcgaca    9300
gaatcaatct cggtgtcatt gaccgcggcc tggcgcagga tctcctgcac gtctcccgag    9360
ttgtcttggt aggcgatctc ggccatgaac tgctcgatct cttcctcctg gaggtctccg    9420
cgtccggcgc gttccacggt ggccgccagg tcgttggaga tgcgcccat gagctgcgag    9480
```

```
aaggcgttga gtccgccctc gttccagact cggctgtaga ccacgccccc ctggtcatcg   9540
cgggcgcgca tgaccacctg cgcgaggttg agctccacgt gccgcgcgaa gacggcgtag   9600
ttgcgcagac gctggaagag gtagttgagg gtggtggcgg tgtgctcggc cacgaagaag   9660
ttcatgaccc agcggcgcaa cgtggattcg ttgatgtccc ccaaggcctc cagccgttcc   9720
atggcctcgt agaagtccac ggcgaagttg aaaaactggg agttgcgcgc cgacacggtc   9780
aactcctcct ccagaagacg gatgagctcg gcgacggtgt cgcgcacctc cgctcgaag   9840 gctatgggga tctcttcctc cgctagcatc accacctcct cctcttcctc ctcttctggc   9900
acttccatga tggcttcctc ctcttcgggg ggcggcggcg gcggcggtgg gggaggggc    9960 gctctgcgcc ggcggcggcg caccgggagg cggtccacga agcgcgcgat catctccccg  10020
cggcggcggc gcatggtctc ggtgacggcg cggccgttct cccgggggcg cagttggaag  10080
acgccgccgg acatctggtg ctggggcggg tggccgtgag gcagcgaaac ggcgctgacg  10140
atgcatctca acaattgctg cgtaggtacg ccgccgaggg acctgaggga gtccatatcc  10200
accggatccg aaaacctttc gaggaaggcg tctaaccagt cgcagtcgca aggtaggctg  10260
agcaccgtgg cgggcggcgg ggggtggggg gagtgtctgg cggaggtgct gctgatgatg  10320
taattgaagt aggcggactt gacacggcgg atggtcgaca ggagcaccat gtccttgggt  10380
ccggcctgct ggatgcggag gcggtcggct atgcccagg cttcgttctg catcggcgc    10440 aggtccttgt agtagtcttg catgagcctt tccaccggca cctcttctcc ttcctcttct  10500
gcttcttcca tgtctgcttc ggccctgggg cggcgccgcg ccccctgcc ccccatgcgc   10560 gtgaccccga accccctgag cggttggagc agggccaggt cggcgacgac gcgctcggcc  10620
aggatggcct gctgcacctg cgtgagggtg gtttggaagt catccaagtc cacgaagcgg  10680
tggtaggcgc ccgtgttgat ggtgtaggtg cagttggcca tgacggacca gttgacggtc  10740
tggtggcccg gttgcgacat ctcggtgtac ctgagtcgcg agtaggcgcg ggagtcgaag  10800
acgtagtcgt tgcaagtccg caccaggtac tggtagccca ccaggaagtg cggcggcggc  10860
tggcggtaga ggggccagcg cagggtggcg ggggctccgg gggccaggtc ttccagcatg  10920
aggcggtggt aggcgtagat gtacctggac atccaggtga tacccgcggc ggtggtggag  10980
gcgcgcggga agtcgcgcac ccggttccag atgttgcgca ggggcagaaa gtgctccatg  11040
gtaggcgtgc tctgtccagt cagacgcgcg cagtcgttga tactctagac cagggaaaac  11100
gaaagccggt cagcgggcac tcttccgtgg tctggtgaat agatcgcaag ggtatcatgg  11160
cggagggcct cggttcgagc cccgggtccg ggccggacgg tccgccatga tccacgcggt  11220
taccgcccgc gtgtcgaacc caggtgtgcg acgtcagaca acgtggagt gttccttttg   11280 gcgtttttct ggccgggcgc cggcgtcgcg taagagacta agccgcgaaa gcgaaagcag  11340
taagtggctc gctccccgta gccggaggga tccttgctaa gggttgcgtt gcggcgaacc  11400
ccggttcgaa tccgtactc gggcggccg accccgcgcc taaggtgttg gattggcctc    11460
cccctcgtat aaagaccccg cttgcggatt gactccggac acgggacgga gccccttta   11520 tttttgcttt cccagatgc atccggtgct gcggcagatg cgcccccgc cccagcagca    11580 gcaacaacac cagcaagagc ggcagcaaca gcagcgggag tcatgcaggg cccctcacc   11640 caccctcggc gggccggcca cctcggcgtc cgcggccgtg tctggcgcct gcggcggcgg  11700
cgggggccgc gctgacgacc ccgaggagcc cccgcggcgc agggccagac actacctgga  11760
cctggaggag ggcgagggcc tggcgcggct gggggcgccg tctcccgagc gccacccgcg  11820
ggtgcagctg aagcgcgact cgcgcgaggc gtacgtgcct cggcagaacc tgttcaggga  11880
```

```
ccgcgcgggc gaggagcccg aggagatgcg ggacaggagg ttcagcgcag ggcgggagct    11940
gcggcagggg ctgaaccgcg agcggctgct gcgcgaggac gactttgagc ccgacgcgcg    12000 gacgggatc agccccgcgc gcgcgcacgt ggcggccgcc gacctggtga cggcgtacga    12060
gcagacggtg aaccaggaga tcaacttcca aaagagtttc aacaaccacg tgcgcacgct    12120
ggtggcgcgc gaggaggtga ccatcgggct gatgcacctg tgggactttg taagcgcgct    12180
ggtgcagaac cccaacagca agcctctgac ggcgcagctg ttcctgatag tgcagcacag    12240
cagggacaac gaggcgttta gggacgcgct gctgaacatc accgagcccg agggtcggtg    12300
gctgctggac ctgattaaca tcctgcagag catagtggtg caggagcgca gcctgagcct    12360
ggccgacaag gtggcggcca tcaactactc gatgctgagc ctgggcaagt tttacgcgcg    12420
caagatctac cagacgccgt acgtgcccat agacaaggag gtgaagatcg acggttttta    12480
catgcgcatg gcgctgaagg tgctcaccct gagcgacgac ctgggcgtgt accgcaacga    12540
gcgcatccac aaggccgtga gcgtgagccg gggcgcgag ctgagcgacc gcagctgat    12600 gcacagcctg cagcgggcgc tggcgggcgc cggcagcggc gacagggagg cggagtccta    12660
cttcgatgcg gggcggacc tgcgctgggc gcccagccgg cgggccctgg aggccgcggg    12720
ggtccgcgag gactatgacg aggacggcga ggaggatgag gagtacgagc tagaggaggg    12780
cgagtacctg gactaaaccg cgggtggtgt ttccggtaga tgcaagaccc gaacgtggtg    12840
gacccggcgc tgcgggcggc tctgcagagc cagccgtccg gccttaactc ctcagacgac    12900
tggcgacagg tcatggaccg catcatgtcg ctgacggcgc gtaacccgga cgcgttccgg    12960
cagcagccgc aggccaacag gctctccgcc atcctggagg cggtggtgcc tgcgcgctcg    13020
aaccccacgc acgagaaggt gctggccata gtgaacgcgc tggccgagaa cagggccatc    13080
cgcccggacg aggccgggct ggtgtacgac gcgctgctgc agcgcgtggc ccgctacaac    13140
agcggcaacg tgcagaccaa cctgaccgg ctggtgggg acgtgcgcga ggcggtggcg    13200
cagcgcgagc gcgcggatcg gcagggcaac ctgggctcca tggtggcgct gaatgccttc    13260
ctgagcacgc agccggccaa cgtgccgcgg gggcaggaag actacaccaa ctttgtgagc    13320
gcgctgcggc tgatggtgac cgagaccccc cagagcgagg tgtaccagtc gggcccggac    13380
tacttcttcc agaccagcag acagggcctg cagacggtga acctgagcca ggctttcaag    13440
aacctgcggg ggctgtgggg cgtgaaggcg cccaccggcg accgggcgac ggtgtccagc    13500
ctgctgacgc ccaactcgcg cctgctgctg ctgctgatcg cgccgttcac ggacagcggc    13560
agcgtgtccc gggacaccta cctggggcac ctgctgaccc tgtaccgcga ggccatcggg    13620
caggcgcagg tggacgagca caccttccag gagatcacca gcgtgagccg cgcgctgggg    13680
caggaggaca cgagcagcct ggaggcgact ctgaactacc tgctgaccaa ccggcggcag    13740
aagattccct cgctgcacag cctgacctcc gaggaggagc gcatcttgcg ctacgtgcag    13800
cagagcgtga gcctgaacct gatgcgcgac ggggtgacgc ccagcgtggc gctggacatg    13860
accgcgcgca acatggaacc gggcatgtac gccgcgcacc ggccttacat caaccgcctg    13920
atggactacc tgcatcgcgc ggcggccgtg aaccccgagt actttaccaa cgccatcctg    13980
aacccgcact ggcctccgcc gcccgggttc tacagcgggg gcttcgaggt cccggaggcc    14040
aacgatggct tcctgtggga cgacatggac gacagcgtgt tctccccgcg gccgcaggcg    14100
ctggcggaag cgtccctgct gcgtcccaag aaggaggagg aggaggcgag tcgccgccgc    14160
ggcagcagcg gcgtggcttc tctgtccgag ctgggggcgg cagccgccgc gcgcccgggg    14220
```

```
tccctgggcg gcagccccctt tccgagcctg gtggggtctc tgcacagcga gcgcaccacc   14280
cgccctcggc tgctgggcga ggacgagtac ctgaataact ccctgctgca gccggtgcgg   14340
gagaaaaacc tgccccccgc cttccccaac aacgggatag agagcctggt ggacaagatg   14400
agcagatgga agacctatgc gcaggagcac agggacgcgc ccgcgctccg gccgcccacg   14460
cggcgccagc gccacgaccg gcagcggggg ctggtgtggg atgacgagga ctccgcggac   14520
gatagcagcg tgctggacct gggagggagc ggcaacccgt tcgcgcacct cgcccccgc    14580 ctggggagga tgttttaaaa aaaaaaaag caagaagcat gatgcaaaat taaataaaac   14640
tcaccaaggc catggcgacc gagcgttggt ttcttgtgtt ccccttcagta tgcggcgcgc   14700 ggcgatgtac caggagggac ctcctccctc ttacgagagc gtggtgggcg cggcggcggc   14760
ggcgccctct tctcccttg cgtcgcagct gctggagccg ccgtacgtgc ctccgcgcta   14820
cctgcggcct acgggggga gaaacagcat ccgttactcg gagctggcgc ccctgttcga   14880
caccacccgg gtgtacctgg tggacaacaa gtcggcggac gtggcctccc tgaactacca   14940
gaacgaccac agcaattttt tgaccacggt catccagaaac aatgactaca gcccgagcga   15000
ggccagcacc cagaccatca atctggatga ccggtcgcac tggggcggcg acctgaaaac   15060
catcctgcac accaacatgc ccaacgtgaa cgagttcatg ttcaccaata gttcaaggc   15120 gcgggtgatg gtgtcgcgct cgcacaccaa ggaagaccgg gtggagctga agtacgagtg   15180
ggtggagttc gagctgccag agggcaacta ctccagacc atgaccattg acctgatgaa   15240
caacgcgatc gtggagcact atctgaaagt gggcaggcaa aacgggtgcc tggagagcga   15300
catcggggtc aagttcgaca ccaggaactt ccgcctgggg ctggaccccg tgaccgggct   15360
ggttatgccc ggggtgtaca ccaacgaggc cttccatccc gacatcatcc tgctgcccgg   15420
ctgcggggtg gacttcactt acagccgcct gagcaacctc ctgggcatcc gcaagcggca   15480
gcccttccag gagggcttca ggatcaccta cgaggacctg gagggggca acatccccgc   15540 gctcctcgat gtgaggcct accaggatag cttgaaggaa aatgaggcgg acaggagga   15600 taccacccccc gccgcctccg ccgccgccga gcagggcgag gatgctgctg acaccgcggc   15660
cgcggacggg gcagaggccg acccccgctat ggtggtggag gctccccgagc aggaggagga   15720 tatgaatgac agtgcggtgc gcggagacac cttcgtcacc cggggggagg aaaagcaagc   15780
ggaggccgag gccgcggccg aggaaaaagca actggcggca gcagcggcgg cggcggcgtt   15840
ggccgcggcg gaggctgagt ctgaggggac caagcccgcc aaggagcccg tgattaagcc   15900
cctgaccgaa gatagcaaga agcgcagtta caacctgctc aaggacagca ccaacaccgc   15960
gtaccgcagc tggtacctgg cctacaacta cggcgacccg tcgacggggg tgcgctcctg   16020
gaccctgctg tgcacgccgg acgtgacctg cggctcggag caggtgtact ggtcgctgcc   16080
cgacatgatg caagaccccg tgaccttccg ctccacgcgg caggtcagca acttcccggt   16140
ggtgggcgcc gagctgctgc ccgtgcactc caagagcttc tacaacgacc aggccgtcta   16200
ctcccagctc atccgccagt tcacctctct gacccacgtg ttcaatcgct ttcctgagaa   16260
ccagattctg gcgcgcccgc ccgcccccac catcaccacc gtcagtgaaa acgttcctgc   16320
tctcacagat cacgggacgc taccgctgcg caacagcatc ggaggagtcc agcgagtgac   16380
cgttactgac gccagacgcc gcacctgccc ctacgtttac aaggccttgg gcatagtctc   16440
gccgcgcgtc ctttccagcc gcactttttg agcaacacca ccatcatgtc catcctgatc   16500
tcacccagca ataactccgg ctggggactg ctgcgcgcgc ccagcaagat gttcggaggg   16560
gcgaggaagc gttccgagca gcaccccgtg cgcgtgcgcg ggcacttccg cgcccctgg    16620
```

```
ggagcgcaca aacgcggccg cgcggggcgc accaccgtgg acgacgccat cgactcggtg    16680
gtggagcagg cgcgcaacta caggcccgcg gtctctaccg tggacgcggc catccagacc    16740
gtggtgcggg gcgcgcggcg gtacgccaag ctgaagagcc gccggaagcg cgtggcccgc    16800
cgccaccgcc gccgacccgg ggccgccgcc aaacgcgccg ccgcggccct gcttcgccgg    16860
gccaagcgca cgggccgccg cgccgccatg agggccgcgc gccgcttggc cgccggcatc    16920
accgccgcca ccatggcccc ccgtacccga agacgcgcgg ccgccgccgc cgccgccgcc    16980
atcagtgaca tggccagcag gcgccggggc aacgtgtact gggtgcgcga ctcggtgacc    17040
ggcacgcgcg tgcccgtgcg cttccgcccc ccgcggactt gagatgatgt gaaaaaacaa    17100
cactgagtct cctgctgttg tgtgtatccc agcggcggcg gcgcgcgcag cgtcatgtcc    17160
aagcgcaaaa tcaaagaaga gatgctccag gtcgtcgcgc cggagatcta tgggcccccg    17220
aagaaggaag agcaggattc gaagcccccg aagataaagc gggtcaaaaa gaaaaagaaa    17280
gatgatgacg atgccgatgg ggaggtggag ttcctgcgcg ccacggcgcc caggcgcccg    17340
gtgcagtgga agggccggcg cgtaaagcgc gtcctgcgcc ccggcaccgc ggtggtcttc    17400
acgcccggcg agcgctccac ccggactttc aagcgcgtct atgacgaggt gtacggcgac    17460
gaagacctgc tggagcaggc caacgagcgc ttcggagagt ttgcttacgg gaagcgtcag    17520
cgggcgctgg ggaaggagga cctgctggcg ctgccgctgg accagggcaa ccccaccccc    17580
agtctgaagc ccgtgaccct gcagcaggtg ctgccgagca gcgcaccctc cgaggcgaag    17640
cggggtctga agcgcgaggg cggcgacctg gcgcccaccg tgcagctcat ggtgcccaag    17700
cggcagaggc tggaggatgt gctggagaaa atgaaagtag accccggtct gcagccggac    17760
atcagggtcc gtcccatcaa gcaggtggcg ccgggcctcg gcgtgcagac cgtggacgtg    17820
gtcatcccca ccggcaactc ccccgccgcc accaccacta ccgctgcctc cacggacatg    17880
gagacacaga ccgatcccgc cgcagccgca gccgccgccg cagccgcgac ctcctcggcg    17940
gaggtgcaga cggacccctg gctgccgccg gcgatgtcag ctccccgcgc gcgccgcgga    18000
cgcagaaagt acggcgccgc caacgcgctc ctgcccgagt acgccttgca tccttccatc    18060
gcgcccaccc ccggctaccg aggctatacc taccgcccgc gaagagccaa gggttccacc    18120
cgccgtcccc gccgacgcgc cgccgccacc acccgccgcc gccgccgcag acgccagccc    18180
gcactggctc cagtctccgt gaggagagtg gcgcgcgacg gacacaccct ggtgctgccc    18240
agggcgcgct accaccccag catcgtttaa aagcctgttg tggttcttgc agatatggcc    18300
ctcacttgcc gcctccgttt cccggtgccg ggataccgag gaggaagatc gcgccgcagg    18360
aggggtctgg ccggccgcgg cctgagcgga ggcagccgcc gcgcgcaccg gcggcgacgc    18420
gccaccagcc gacgcatgcg cggcggggtg ctgcccctgt taatccccct gatcgccgcg    18480
gcgatcggcg ccgtgcccgg gatcgcctcc gtggccttgc aagcgtccca gaggcattga    18540
cagacttgca aacttgcaaa tatgaaaaaa aaaaaaaaac cccaataaaa agtctagact    18600
ctcacgctcg cttggtcctg tgactatttt gtagaatgga agacatcaac tttgcgtcgc    18660
tggccccgcg tcacggctcg cgcccgttcc tgggacactg gaacgatatc ggcaccagca    18720
acatgagcgg tggcgccttc agttgggcct ctctgtggag cggcattaaa agtatcgggt    18780
ctgccgttaa aaattacggc tcccgggcct ggaacagcag cacgggccag atgttgagag    18840
acaagttgaa agagcagaac ttccagcaga aggtggtgga gggcctggcc tccggcatca    18900
acgggggtggt ggacctggcc aaccaggccg tgcagaataa aatcaacagc agactggacc    18960
```

```
cccggccgcc ggtggaggag gtgccgccgg cgctggagac ggtgtccccc gatgggcgtg    19020
gcgagaagcg cccgcggccc gatagggaag agaccactct ggtcacgcag accgatgagc    19080
cgcccccgta tgaggaggcc ctaaagcaag gtctgcccac cacgcggccc atcgcgccca    19140
tggccaccgg ggtggtgggc cgccacaccc ccgccacgct ggacttgcct ccgcccgccg    19200
atgtgccgca gcagcagaag gcggcacagc cgggcccgcc cgcgaccgcc tcccgttcct    19260
ccgccggtcc tctgcgccgc gcggccagcg gcccccgcgg ggggtcgcg aggcacggca    19320 actggcagag cacgctgaac agcatcgtgg gtctgggggt gcggtccgtg aagcgccgcc    19380
gatgctactg aatagcttag ctaacgtgtt gtatgtgtgt atgcgcccta tgtcgccgcc    19440
agaggagctg ctgagtcgcc gccgttcgcg cgcccaccac caccgccact ccgcccctca    19500
agatggcgac cccatcgatg atgccgcagt ggtcgtacat gcacatctcg ggccaggacg    19560
cctcggagta cctgagcccc gggctggtgc agttcgcccg cgccaccgag agctacttca    19620
gcctgagtaa caagtttagg aaccccacgg tggcgcccac gcacgatgtg accaccgacc    19680
ggtctcagcg cctgacgctg cggttcattc ccgtggaccg cgaggacacc gcgtactcgt    19740
acaaggcgcg gttcaccctg gccgtgggcg acaaccgcgt gctggacatg gcctccacct    19800
actttgacat ccgcggggtg ctggaccggg gtcccacttt caagccctac tctggcaccg    19860
cctacaactc cctggccccc aagggcgctc ccaactcctg cgagtgggag caagaggaaa    19920
ctcaggcagt tgaagaagca gcagaagagg aagaagaaga tgctgacggt caagctgagg    19980
aagagcaagc agctaccaaa aagactcatg tatatgctca ggctccccTt tctggcgaaa    20040
aaattagtaa agatggtctg caaataggaa cggacgctac agctacagaa caaaaaccta    20100
tttatgcaga ccctacattc cagcccgaac cccaaatcgg ggagtcccag tggaatgagg    20160
cagatgctac agtcgccggc ggtagagtgc taaagaaatc tactcccatg aaaccatgct    20220
atggttccta tgcaagaccc acaaatgcta atggaggtca gggtgtacta acggcaaatg    20280
cccagggaca gctagaatct caggttgaaa tgcaattctt ttcaacttct gaaaacgccc    20340
gtaacgaggc taacaacatt cagcccaaat tggtgctgta tagtgaggat gtgcacatgg    20400
agaccccgga tacgcacctt tcttacaagc ccgcaaaaag cgatgacaat tcaaaaatca    20460
tgctgggtca gcagtccatg cccaacagac ctaattacat cggcttcaga gacaacttta    20520
tcggcctcat gtattacaat agcactggca acatgggagt gcttgcaggt caggcctctc    20580
agttgaatgc agtggtggac ttgcaagaca gaaacacaga actgtcctac cagctcttgc    20640
ttgattccat gggtgacaga accagatact tttccatgtg gaatcaggca gtggacagtt    20700
atgacccaga tgttagaatt attgaaaatc atggaactga agacgagctc cccaactatt    20760
gtttccctct gggtggcata ggggtaactg acacttacca ggctgttaaa accaacaatg    20820
gcaataacgg gggccaggtg acttggacaa agatgaaac ttttgcagat cgcaatgaaa    20880
tagggggtgg aaacaatttc gctatggaga tcaacctcag tgccaacctg tggagaaact    20940
tcctgtactc caacgtggcg ctgtacctac cagacaagct taagtacaac ccctccaatg    21000
tggacatctc tgacaacccc aacacctacg attacatgaa caagcgagtg gtggccccgg    21060
ggctggtgga ctgctacatc aacctggccg cgcgctggtc gctggactac atggacaacg    21120
tcaacccctt caaccaccac cgcaatgcgg gcctgcgcta ccgctccatg ctcctgggca    21180
acgggcgcta cgtgcccttc cacatccagg tgccccagaa gttctttgcc atcaagaacc    21240
tcctcctcct gccgggctcc tacacctacg agtggaactt caggaaggat gtcaacatgg    21300
tcctccagag ctctctgggt aacgatctca gggtggacgg ggccagcatc aagttcgaga    21360
```

```
gcatctgcct ctacgccacc ttcttcccca tggcccacaa cacggcctcc acgctcgagg    21420
ccatgctcag gaacgacacc aacgaccagt ccttcaatga ctacctttcc gccgccaaca    21480
tgctctaccc catacccgcc aacgccacca acgtccccat ctccatcccc tcgcgcaact    21540
gggcggcctt ccgcggctgg gccttcaccc gcctcaagac caaggagacc ccctccctgg    21600
gctcgggatt cgacccctac tacacctact cgggctctat tccctacctg acggcacct    21660 tctacctcaa ccacactttc aagaaggtct cggtcacctt cgactcctcg gtcagctggc    21720
cgggcaacga ccgtctgctc accccaacg agttcgagat caagcgctcg gtcgacgggg    21780
aaggctacaa cgtggcccag tgcaacatga ccaaggactg gttcctggtc cagatgctgg    21840
ccaactacaa catcggctac cagggcttct acatcccaga gagctacaag gacaggatgt    21900
actccttctt caggaacttc cagcccatga gccggcaggt ggtggaccag accaagtaca    21960
aggactacca ggaggtgggc atcatccacc agcacaacaa ctcgggcttc gtgggctacc    22020
tcgcccccac catgcgcgag ggacaggcct accccgccaa cttcccctac ccgctcatag    22080
gcaagaccgc ggtcgacagc atcacccaga aaaagttcct ctgcgaccgc accctctggc    22140 gcatccccttt ctccagcaac ttcatgtcca tgggtgcgct ctcggacctg gccagaact    22200 tgctctacgc caactccgcc cacgccctcg acatgacctt cgaggtcgac cccatggacg    22260
agcccaccct tctctatgtt ctgttcgaag tctttgacgt ggtccgggtc caccagccgc    22320
accgcggcgt catcgagacc gtgtacctgc gtacgcccct ctcggccggc aacgccacca    22380
cctaaagaag caagccgcag tcatcgccgc ctgcatgccg tcgggttcca ccgagcaaga    22440
gctcagggcc atcgtcagag acctgggatg cgggccctat tttttgggca ccttcgacaa    22500
gcgcttccct ggctttgtct ccccacacaa gctggcctgc gccatcgtca acacggccgg    22560
ccgcgagacc ggggcgtgc actggctggc ctttgcctgg aacccgcgct ccaaaacatg    22620 cttcctctttt gacccctccg gcttttcgga ccagcggctc aagcaaatct acgagttcga    22680
gtacgagggc ttgctgcgtc gcagcgccat cgcctcctcg cccgaccgct gcgtcaccct    22740
cgaaaagtcc acccagaccg tgcagggggcc cgactcggcc gcctgcggtc tcttctgctg    22800
catgtttctg cacgcctttg tgcactggcc tcagagtccc atggaccgca cccccaccat    22860
gaacttgctg acggggggtgc ccaactccat gctccaaagc ccccaggtcg agcccaccct    22920
gcgccgcaac caggagcagc tctacagctt cctggagcgc cactcgccct acttccgccg    22980
ccacagcgca cagatcagga gggccaccctc cttctgccac ttgcaagaga tgcaagaagg    23040
gtaataacga tgtacacact tttttctcaa taaatggcat tttttttta tttatacaag    23100 ctctctgggg tattcatttc ccaccaccac cacccgccgt tgtcgccatc tggctctatt    23160
tagaaatcga aagggttctg ccgggagtcg ccgtgcgcca cgggcaggga cacgttcgca    23220
tactggtagc gggtgccca cttgaactcg ggcaccacca ggcgaggcag ctcggggaag    23280
ttttcgctcc acaggctgcg ggtcagcacc agcgcgttca tcaggtcggg cgccgagatc    23340
ttgaagtcgc agttggggcc gccgccctgc gcgcgcgagt tgcggtacac cgggttgcag    23400
cactggaaca ccaacagcgc cgggtgcttc acgctggcca gcacgctgcg gtcggagatc    23460
agctcggcgt ccaggtcctc cgcgttgctc agcgcgaacg gggtcatctt gggcacttgc    23520
cgccccagga agggcgcgtg ccccggtttc gagttgcagt cgcagcgcag cgggatcagc    23580
aggtgcccgt gcccggactc ggcgttgggg tacagcgcgc gcatgaaggc ctgcatctgg    23640
cggaaggcca tctgggcctt ggcgcccctcc gagaagaaca tgccgcagga cttgcccgag    23700
```

```
aactggtttg cggggcagct ggcgtcgtgc aggcagcagc gcgcgtcggt gttggcgatc    23760
tgcaccacgt tgcgccccca ccggttcttc acgatcttgg ccttggacga ttgctccttc    23820
agcgcgcgct gcccgttctc gctggtcaca tccatctcga tcacatgttc cttgttcacc    23880
atgctgctgc cgtgcagaca cttcagctcg ccctccgtct cggtgcagcg gtgctgccac    23940
agcgcgcagc ccgtgggctc gaaagacttg taggtcacct ccgcgaagga ctgcaggtac    24000
ccctgcaaaa agcggcccat catggtcacg aaggtcttgt tgctgctgaa ggtcagctgc    24060
agcccgcggt gctcctcgtt cagccaggtc ttgcacacgg ccgccagcgc ctccacctgg    24120
tcgggcagca tcttgaagtt caccttcagc tcattctcca cgtggtactt gtccatcagc    24180
gtgcgcgccg cctccatgcc cttctcccag gccgacacca gcggcaggct cacggggttc    24240
ttcaccatca ccgtggccgc cgcctccgcc gcgctttcgc tttccgcccc gctgttctct    24300
tcctcttcct cctcttcctc gccgccgccc actcgcagcc cccgcaccac ggggtcgtct    24360
tcctgcaggc gctgcacctt gcgcttgccg ttgcgcccct gcttgatgcg cacgggcggg    24420
ttgctgaagc ccaccatcac cagcgcggcc tcttcttgct cgtcctcgct gtccagaatg    24480
acctccgggg aggggggtt ggtcatcctc agtaccgagg cacgcttctt tttcttcctg    24540
ggggcgttcg ccagctccgc ggctgcggcc gctgccgagg tcgaaggccg agggctgggc    24600
gtgcgcggca ccagcgcgtc ttgcgagccg tcctcgtcct cctcggactc gagacggagg    24660
cgggcccgct tcttcggggg cgcgcggggc ggcgaggcg gcgcggcga cggagacggg    24720 gacgagacat cgtccagggt gggtggacgg cgggccgcgc cgcgtccgcg ctcggggtg    24780 gtttcgcgct ggtcctcttc ccgactggcc atctcccact gctccttctc ctataggcag    24840
aaagagatca tggagtctct catgcgagtc gagaaggagg aggacagcct aaccgccccc    24900
tctgagccct ccaccaccgc cgccaccacc gccaatgccg ccgcggacga cgcgcccacc    24960
gagaccaccg ccagtaccac cctcccccagc gacgcacccc cgctcgagaa tgaagtgctg    25020
atcgagcagg acccgggttt tgtgagcgga gaggaggatg aggtggatga aggagaag    25080 gaggaggtcg ccgcctcagt gccaaaagag gataaaaagc aagaccagga cgacgcagat    25140
aaggatgaga cagcagtcgg gcgggggaac ggaagccatg atgctgatga cggctaccta    25200
gacgtgggag acgacgtgct gcttaagcac ctgcaccgcc agtgcgtcat cgtctgcgac    25260
gcgctgcagg agcgctgcga agtgcccctg gacgtggcgg aggtcagccg cgcctacgag    25320
cggcacctct tcgcgccgca cgtgccccc aagcgccggg agaacggcac ctgcgagccc    25380
aacccgcgtc tcaacttcta cccggtcttc gcggtacccg aggtgctggc cacctaccac    25440
atcttcttcc aaaactgcaa gatccccctc tcctgccgcg ctaaccgcac ccgcgccgac    25500 aaaacccctga ccctgcggca gggcgcccac atacctgata ttgcctctct ggaggaagtg    25560
cccaagatct tcgagggtct cggtcgcgac gagaaacggg cggcgaacgc tctgcacgga    25620
gacagcgaaa acgagagtca ctcgggggtg ctggtggagc tcgagggcga caacgcgcgc    25680
ctggccgtac tcaagcgcag catagaggtc acccactttg cctacccggc gctcaacctg    25740
ccccccaagg tcatgagtgt ggtcatgggc gagctcatca tgcgccgcgc tcagcccctg    25800
gccgcggatg caaacttgca agagtcctcc gaggaaggcc tgcccgcggt cagcgacgag    25860
cagctagcgc gctggctgga gacccgcgac cccgcgcagc tggaggagcg gcgcaagctc    25920
atgatggccg cggtgctggt caccgtggag ctcgagtgtc tgcagcgctt cttcgcggac    25980
cccgagatgc agcgcaagct cgaggagacc ctgcactaca ccttccgcca gggctacgtg    26040
cgccaggcct gcaagatctc caacgtggag ctctgcaacc tggtctccta cctgggcatc    26100
```

```
ctgcacgaga accgcctcgg gcagaacgtc ctgcactcca ccctcaaagg ggaggcgcgc   26160
cgcgactaca tccgcgactg cgcctacctc ttcctctgct acacctggca gacggccatg   26220
ggggtctggc agcagtgcct ggaggagcgc aacctcaagg agctggaaaa gctactcaag   26280
cgcaccctca gggacctctg gacgggcttc aacgagcgct cggtggccgc cgcgctggcg   26340
gacatcatct tccccgagcg cctgctcaag accctgcagc agggcctgcc cgacttcacc   26400
agccagagca tgctgcagaa ctttaggact ttcatcctgg agcgctcggg catcctgcct   26460
gccacttgct gcgcgctgcc cagcgacttc gtgcccatca agtacaggga gtgcccgccg   26520
ccgctctggg gccactgcta cctcttccag ctggccaact acctcgccta ccactcggac   26580
ctcatggaag acgtgagcgg cgagggcctg ctcgagtgcc actgccgctg caacctctgc   26640
acgccccacc gctctctagt ctgcaacccg cagctgctca gcgagagtca gattatcggt   26700
accttcgagc tgcagggtcc ctcgcctgac gagaagtccg cggctccggg gctgaaactc   26760
actccggggc tgtggacttc cgcctaccta cgcaaatttg tacctgagga ctaccacgcc   26820
cacgagatca ggttctacga agaccaatcc cgcccgccca aggcggagct caccgcctgc   26880
gtcatcaccc aggggcacat cctgggccaa ttgcaagcca tcaacaaagc ccgccgagag   26940
ttcttgctga aaaagggtcg gggggtgtac ctggaccccc agtccggcga ggagctaaac   27000
ccgctacccc cgccgccgcc ccagcagcgg gaccttgctt cccaggatgg cacccagaaa   27060
gaagcagcag ccgccgccgc cgcagccata catgcttctg gaggaagagg aggaggactg   27120
ggacagtcag gcagaggagg tttcggacga ggagcaggag gagatgatgg aagactggga   27180
ggaggacagc agcctagacg aggaagcttc agaggccgaa gaggtggcag acgcaacacc   27240
atcaccctcg gtcgcagccc cctcgccggg gcccctgaaa tcctccgaac ccagcaccag   27300
cgctataacc tccgctcctc cggcgccggc gccacccgcc cgcagaccca accgtagatg   27360
ggacaccaca ggaaccgggg tcggtaagtc caagtgcccg ccgccgccac cgcagcagca   27420
gcagcagcgc cagggctacc gctcgtggcg cgggcacaag aacgccatag tcgcctgctt   27480
gcaagactgc gggggcaaca tctctttcgc ccggcgcttc ctgctattcc accacggggt   27540 cgccttttccc cgcaatgtcc tgcattacta ccgtcatctc tacagcccct actgcagcgg   27600
cgacccagag gcggcagcgg cagccacagc ggcgaccacc acctaggaag atatcctccg   27660
cgggcaagac agcggcagca gcggccagga gacccgcggc agcagcggcg ggagcggtgg   27720
gcgcactgcg cctctcgccc aacgaacccc tctcgacccg ggagctcaga cacaggatct   27780
tccccacttt gtatgccatc ttccaacaga gcagaggcca ggagcaggag ctgaaaataa   27840
aaaacagatc tctgcgctcc ctcacccgca gctgtctgta tcacaaaagc gaagatcagc   27900
ttcggcgcac gctggaggac gcggaggcac tcttcagcaa atactgcgcg ctcactctta   27960
aagactagct ccgcgccctt ctcgaattta ggcgggagaa aactacgtca tcgccggccg   28020
ccgcccagcc cgcccagccg agatgagcaa agagattccc acgccataca tgtggagcta   28080
ccagccgcag atgggactcg cggcgggagc ggcccaggac tactccaccc gcatgaacta   28140
catgagcgcg ggaccccaca tgatctcaca ggtcaacggg atccgcgccc agcgaaacca   28200
aatactgctg gaacaggcgg ccatcaccgc cacgccccgc cataatctca cccccgaaa   28260 ttggcccgcc gccctcgtgt accaggaaac cccctccgcc accaccgtac tacttccgcg   28320
tgacgcccag gccgaagtcc agatgactaa ctcaggggcg cagctcgcgg gcggctttcg   28380
tcacggggcg cggccgctcc gaccaggtat aagacacctg atgatcagag gccgaggtat   28440
```

```
ccagctcaac gacgagtcgg tgagctcttc gctcggtctc cgtccggacg gaacttccca    28500
gctcgccgga tccggccgct cttcgttcac gccccgccag gcgtacctga ctctgcagac    28560
ctcgtcctcg gagccccgct ccggaggcat cggaaccctc cagttcgtgg aggagttcgt    28620
gccctcggtc tacttcaacc ccttctcggg acctcccgga cgctaccccg accagttcat    28680
tccgaacttt gacgcggtga aggactcggc ggacggctac gactgaatgt caggtgccga    28740
ggcagagcag cttcgcctga gacacctcga gcactgccgc cgccacaagt gcttcgcccg    28800
cggttccggt gagttctgct actttcagct acccgaggag cataccgagg ggccggcgca    28860
cggcgtccgc ctgaccaccc agggcgaggt tacctgttcc ctcatccggg agttcaccct    28920
ccgtcccctg ctagtggagc gggagcgggg tccctgtgtc ctaactatcg cctgcaactg    28980
ccctaaccct ggattacatc aagatctttg ctgtcatctc tgtgctgagt ttaataaacg    29040
ctgagatcag aatctactgg gaattcgatt tagtccccctt taactaatca aacactggaa    29100
tcaataaaaa gaatcactta cttaaaatca gacagcaggt ctctgtccag tttattcagc    29160
agcacctcct tcccctcctc ccaactctgg tactccaaac gccttctggc ggcaaacttc    29220
ctccacaccc tgaagggaat gtcagattct tgctcctgtc cctccgcacc cactatcttc    29280
atgttgttgc agatgaagcg caccaaaacg tctgacgaga gcttcaaccc cgtgtacccc    29340
tatgacacgg aaagcggccc tccctccgtc ccttttcctca cccctcccctt cgtgtctccc    29400 gatggattcc aagaaagccc ccccggggtc ctgtctctga acctggccga gccccctggtc    29460 acttcccacg gcatgctcgc cctgaaaatg ggaagtggcc tctccctgga cgacgctggc    29520
aacctcacct ctcaagatat caccaccgct agccctcccc tcaaaaaaac caagaccaac    29580
ctcagcctag aaacctcatc cccctaact gtaagcacct caggcgccct caccgtagca    29640
gccgccgctc ccctggcagt ggccggcacc tccctcacca tgcaatcaga ggcccccctg    29700
acagtacagg atgcaaaact caccctggcc accaaaggcc cctgaccgt gtctgaaggc    29760 aaactggcct tgcaaacatc ggcccccgctg acggccgctg acagcagcac cctcaccgtt    29820
agcgccacac caccaattaa tgtaagcagt ggaagtttag gcttagacat ggaagaccct    29880
atgtatactc acgatggaaa actgggaata agaattgggg gtccactaag agtagtagac    29940
agcttgcaca cactcactgt agttaccgga aatggactaa ctgtagataa caatgccctc    30000
caaactagag ttacgggcgc cctaggttat gacacatcag gaaatctaca attgagagct    30060
gcaggaggta tgcgaattga tgcaaatggc caacttatcc ttaatgtggc atacccattt    30120
gatgctcaga caatctcagc cttagactt ggtcagggac ccctgtatat aaacacagac    30180
cacaacctgg atttgaattg caacagaggt ctaaccacaa ctaccaccaa caacacaaaa    30240
aaacttgaga ctaaaattag ctcaggctta gactatgaca ccaatggtgc tgtcattatt    30300
aaacttggca ctggtctaag cttcgacaac acaggcgccc taactgtggg aaacactggt    30360
gatgataaac tgactctgtg gacgaccccca gacccatctc caaattgcag aattcactca    30420
gacaaagact gcaagtttac tctagtccta actaagtgtg gaagccaaat cctggcctct    30480
gtcgccgccc tagcggtatc aggaaatctg gcttcgataa caggcaccgt tgccagcgtt    30540
accatctttc tcagatttga tcagaatgga gtgcttatgg aaaactcctc gctagacagg    30600
cagtactgga acttcagaaa tggcaactca actaacgctg cccctacac caatgcagtt    30660 gggttcatgc caaacctcgc agcataccc aaaacgcaaa gccagactgc taaaacaac    30720 attgtaagtc aggtttactt gaatggagac aaatccaaac ccatgaccct taccatcacc    30780
ctcaatggaa ctaatgaatc cagtgaaact agccaggtga gtcactactc catgtcattt    30840
```

```
acatgggctt gggaaagtgg gcaatatgcc actgaaacct ttgccaccaa ctccttcacc    30900 tttcttaca ttgctgaaca ataaaaagca tgacactgat gttcatttct gattcttatt    30960
ttattatttt caaacacaac aaaatcattc aagtcattct tccatcttag cttaatagac    31020
acagtagctt aatagaccca gtagtgcaaa gccccattct agcttataac tagtggagaa    31080
gtactcgcct acatgggggt agagtcataa tcgtgcatca ggatagggcg gtggtgctgc    31140
agcagcgcgc gaataaactg ctgccgccgc cgctccgtcc tgcaggaata caacatggca    31200
gtggtctcct cagcgatgat tcgcaccgcc cgcagcataa ggcgccttgt cctccgggca    31260
cagcagcgca ccctgatctc acttaaatca gcacagtaac tgcagcacag caccacaata    31320
ttgttcaaaa tcccacagtg caaggcgctg tatccaaagc tcatggcggg gaccacagaa    31380
cccacgtggc catcatacca caagcgcagg tagattaagt ggcgacccct cataaacacg    31440
ctggacataa acattacctc ttttggcatg ttgtaattca ccacctcccg gtaccatata    31500
aacctctgat taaacatggc gccatccacc accatcctaa accagctggc caaaacctgc    31560
ccgccggcta tacactgcag ggaaccggga ctggaacaat gacagtggag agcccaggac    31620
tcgtaaccat ggatcatcat gctcgtcatg atatcaatgt tggcacaaca caggcacacg    31680
tgcatacact tcctcaggat tacaagctcc tcccgcgtta gaaccatatc ccagggaaca    31740
acccattcct gaatcagcgt aaatcccaca ctgcagggaa gacctcgcac gtaactcacg    31800
ttgtgcattg tcaaagtgtt acattcgggc agcagcggat gatcctccag tatggtagcg    31860
cgggtttctg tctcaaaagg aggtagacga tccctactgt acggagtgcg ccagacaaac    31920
cgagatcgtg ttggtcgtag tgtcatgcca aatggaacgc cggacgtagt catatttcct    31980
gaagtcttag atctctcaac gcagcaccag caccaacact tcgcagtgta aaaggccaag    32040
tgccgagaga gtatatatag gaataaaaag tgacgtaaac gggcaaagtc caaaaaacgc    32100
ccagaaaaac cgcacgcgaa cctacgcccc gaaacgaaag ccaaaaaaca ctagacactc    32160
ccttccggcg tcaacttccg cttttccacg ctacgtcact tgccccagtc aaacaaacta    32220
catatcccga acttccaagt cgccacgccc aaaacaccgc ctacacctcc ccgcccgccg    32280
gcccgccccc aaacccgcct cccgcccgc gccccgcccc gcgccgccca tctcattatc    32340
atattggctt caatccaaaa taaggtatat tattgatgat g                       32381
```

<210> SEQ ID NO 4
<211> LENGTH: 31881
<212> TYPE: DNA
<213> ORGANISM: Artificial Sequence
<220> FEATURE:
<223> OTHER INFORMATION: synthetic chimpanzee adenovirus serotype ChAd63
      with Ebola virus Zaire wild type transmembrane
      envelope glycoprotein (GP) insert (ChAd63 Ebola
      Zaire (PB/6001))
<220> FEATURE:
<221> NAME/KEY: CDS
<222> LOCATION: (2139)...(4440)
<223> OTHER INFORMATION: Ebola virus Zaire wild type transmembrane
      envelope glycoprotein (GP) insert in ChAd63 Ebola Zaire (PB/6001)
<220> FEATURE:
<221> NAME/KEY: CDS
<222> LOCATION: (15152)...(16771)
<223> OTHER INFORMATION: chimpanzee adenovirus serotype ChAd63 penton
<220> FEATURE:
<221> NAME/KEY: CDS
<222> LOCATION: (19538)...(22414)
<223> OTHER INFORMATION: chimpanzee adenovirus serotype ChAd63 hexon
<220> FEATURE:
<221> NAME/KEY: CDS
<222> LOCATION: (28942)...(30219)

<223> OTHER INFORMATION: chimpanzee adenovirus serotype ChAd63 fiber

<400> SEQUENCE: 4

```
catcatcaat aatatacctc aaacttttgg tgcgcgttaa tatgcaaatg aggtgtttga    60
atttggggat gcggggcgct gattggctga gagacgggcg accgttaggg gcggggcggg   120
tgacgttttg atgacgtggc cgtgaggcgg agccggtttg caagttctcg tgggaaaagt   180
gacgtcaaac gaggtgtggt ttgaacacgg aaatactcaa ttttcccgcg ctctctgaca   240
ggaaatgagg tgtttctggg cggatgcaag tgaaaacggg ccattttcgc gcgaaaactg   300
aatgaggaag tgaaaatctg agtaattccg cgtttatggc agggaggagt atttgccgag   360
ggccgagtag actttgaccg attacgtggg ggtttcgatt accgtatttt tcacctaaat   420
ttccgcgtac ggtgtcaaag tccggtgttt ttacggatat ctccattgca tacgttgtat   480
ccatatcata atatgtacat ttatattggc tcatgtccaa cattaccgcc atgttgacat   540
tgattattga ctagttatta atagtaatca attacgggt cattagttca tagcccatat   600
atggagttcc gcgttacata acttacgta atggcccgc ctggctgacc gcccaacgac   660
ccccgcccat tgacgtcaat aatgacgtat gttcccatag taacgccaat agggactttc   720
cattgacgtc aatgggtgga gtatttacgg taaactgccc acttggcagt acatcaagtg   780
tatcatatgc caagtacgcc ccctattgac gtcaatgacg gtaaatggcc cgcctggcat   840
tatgcccagt acatgacctt atgggacttt cctacttggc agtacatcta cgtattagtc   900
atcgctatta ccatggtgat gcggttttgg cagtacatca atgggcgtgg atagcggttt   960
gactcacggg gatttccaag tctccacccc attgacgtca atgggagttt gttttggaac  1020
caaaatcaac gggactttcc aaaatgtcgt aacaactccg ccccattgac gcaaatgggc  1080
ggtaggcgtg tacggtggga ggtctatata agcagagctc tccctatcag tgatagagat  1140
ctccctatca gtgatagaga tcgtcgacga gctcgtttag tgaaccgtca gatcgcctgg  1200
agacgccatc cacgctgttt tgacctccat agaagacacc gggaccgatc cagcctccgc  1260
ggccgggaac ggtgcattgg aacgcggatt ccccgtgcca agagtgacgt aagtaccgcc  1320
tatagactct ataggcacac ccctttggct cttatgcatg ctatactgtt tttggcttgg  1380
ggcctataca ccccgcttc cttatgctat aggtgatggt atagcttagc ctataggtgt  1440
gggttattga ccattattga ccactcccct attggtgacg atactttcca ttactaatcc  1500
ataacatggc tctttgccac aactatctct attggctata tgccaatact ctgtccttca  1560
gagactgaca cggactctgt attttttacag gatggggtcc catttattat ttacaaattc  1620
acatatacaa caacgccgtc ccccgtgccc gcagttttta ttaaacatag cgtgggatct  1680
ccacgcgaat ctcgggtacg tgttccggac atggctcttt ctccggtagc ggcggagctt  1740
ccacatccga gccctggtcc catgcctcca gcggctcatg gtcgctcggc agctccttgc  1800
tcctaacagt ggaggccaga cttaggcaca gcacaatgcc caccaccacc agtgtgccgc  1860
acaaggccgt ggcggtaggg tatgtgtctg aaaatgagcg tggagattgg gctcgcacgg  1920
ctgacgcaga tggaagactt aaggcagcgg cagaagaaga tgcaggcagc tgagttgttg  1980
tattctgata agagtcagag gtaactcccg ttgcggtgct gttaacggtg gagggcagtg  2040
tagtctgagc agtactcgtt gctgccgcgc gcgccaccag acataatagc tgacagacta  2100
acagactgtt cctttccatg ggtctttttct gcagtcaccg tcgtcgacac gtgtgatcag  2160
atatcgcggc cgctctagac caggccctgg atcgatccaa caacacaatg ggcgttacag  2220
gaatattgca gttacctcgt gatcgattca agaggacatc attctttctt tgggtaatta  2280
```

```
tccttttcca aagaacattt tccatcccac ttggagtcat ccacaatagc acattacagg   2340
ttagtgatgt cgacaaacta gtttgtcgtg acaaactgtc atccacaaat caattgagat   2400
cagttggact gaatctcgaa gggaatggag tggcaactga cgtgccatct gcaactaaaa   2460
gatgggcttt caggtccggt gtcccaccaa aggtggtcaa ttatgaagct ggtgaatggg   2520
ctgaaaactg ctacaatctt gaaatcaaaa aacctgacgg gagtgagtgt ctaccagcag   2580
cgccagacgg gattcggggc ttccccggt gccggtatgt gcacaaagta tcaggaacgg    2640
gaccgtgtgc cggagacttt gccttccata agagggtgc tttcttcctg tatgatcgac    2700
ttgcttccac agttatctac cgaggaacga ctttcgctga aggtgtcgtt gcatttctga   2760
tactgcccca agctaagaag gacttcttca gctcacaccc cttgagagag ccggtcaatg   2820
caacggagga cccgtctagt ggctactatt ctaccacaat tagatatcag ctaccggtt    2880 ttggaaccaa tgagacagag tacttgttcg aggttgacaa tttgacctac gtccaacttg   2940
aatcaagatt cacaccacag tttctgctcc agctgaatga caatatat acaagtggga     3000 aaaggagcaa taccacggga aaactaattt ggaaggtcaa ccccgaaatt gatacaacaa   3060
tcggggagtg ggccttctgg gaaactaaaa aaaacctcac tagaaaaatt cgcagtgaag   3120
agttgtcttt cacagttgta tcaaacggag ccaaaaacat cagtggtcag agtccggcgc   3180
gaacttcttc cgacccaggg accaacacaa caactgaaga ccacaaaatc atggcttcag   3240
aaaattcctc tgcaatggtt caagtgcaca gtcaaggaag ggaagctgca gtgtcgcatc   3300
taacaaccct tgccacaatc tccacgagtc cccaatccct cacaaccaaa ccaggtccgg   3360
acaacagcac ccataataca cccgtgtata aacttgacat ctctgaggca actcaagttg   3420
aacaacatca ccgcagaaca gacaacgaca gcacagcctc cgacactccc tctgccacga   3480
ccgcagccgg accccaaaa gcagagaaca ccaacacgag caagagcact gacttcctgg    3540 acccgccac cacaacaagt ccccaaaacc acagcgagac cgctggcaac aacaacactc    3600
atcaccaaga taccggagaa gagagtgcca gcagcgggaa gctaggctta attaccaata   3660
ctattgctgg agtcgcagga ctgatcacag gcgggagaag aactcgaaga gaagcaattg   3720
tcaatgctca acccaaatgc aaccctaatt tacattactg gactactcag gatgaaggtg   3780
ctgcaatcgg actggcctgg ataccatatt tcgggccagc agccgaggga atttacatag   3840
aggggctaat gcacaatcaa gatggtttaa tctgtgggtt gagacagctg ccaacgagga   3900
cgactcaagc tcttcaactg ttcctgagag ccacaactga gctacgcacc ttttcaatcc   3960
tcaaccgtaa ggcaattgat ttcttgctgc agcgatgggg cggcacatgc cacattctgg   4020
gaccggactg ctgtatcgaa ccacatgatt ggaccaagaa cataacagac aaaattgatc   4080
agattattca tgattttgtt gataaaaccc ttccggacca gggggacaat gacaattggt   4140
ggacaggatg gagacaatgg ataccggcag gtattggagt tacaggcgtt gtaattgcag   4200
ttatcgcttt attctgtata tgcaaatttg tcttttagtt tttcttcaga ttgcttcatg   4260
gaaaagctca gcctcaaatc aatgaaacca ggatttaatt atatggatta cttgaatcta   4320
agattacttg acaaatgata atataataca ctggagcttt aaacatagcc aatgtgattc   4380
taactccttt aaactcacag ttaatcataa acaaggtttg aggtaccgag ctcgaattga   4440
tctgctgtgc cttctagttg ccagccatct gttgtttgcc cctccccgt gccttccttg    4500 accctggaag gtgccactcc cactgtcctt tcctaataaa atgaggaaat tgcatcgcat   4560
tgtctgagta ggtgtcattc tattctgggg ggtgggtgg ggcaggacag caaggggag    4620
```

```
gattgggaag acaatagcag gcatgctggg gatgcggtgg gctctagata tcagcgatcg   4680
cgtgagtagt gtttgggggt gggtgggagc ctgcatgatg ggcagaatga ctaaaatctg   4740
tgtttttctg tgtgttgcag cagcatgagc ggaagcgcct cctttgaggg aggggtattc   4800
agcccttatc tgacggggcg tctcccctcc tgggcgggag tgcgtcagaa tgtgatggga   4860
tccacggtgg acggccggcc cgtgcagccc gcgaactctt caaccctgac ctacgcgacc   4920
ctgagctcct cgtccgtgga cgcagctgcc gccgcagctg ctgcttccgc cgccagcgcc   4980
gtgcgcggaa tggccctggg cgccggctac tacagctctc tggtggccaa ctcgagttcc   5040
accaataatc ccgccagcct gaacgaggag aagctgttgc tgctgatggc ccagctcgag   5100
gccctgaccc agcgcctggg cgagctgacc cagcaggtgg ctcagctgca ggcggagacg   5160
cgggccgcgg ttgccacggt gaaaaccaaa taaaaaatga atcaataaat aaacggagac   5220
ggttgttgat tttaacacag agtcttgaat ctttatttga ttttttcgcgc gcggtaggcc   5280 ctggaccacc ggtctcgatc attgagcacc cggtggatct tttccaggac ccggtagagg   5340
tgggcttgga tgttgaggta catgggcatg agcccgtccc gggggtggag gtagctccat   5400
tgcagggcct cgtgctcggg ggtggtgttg taaatcaccc agtcatagca ggggcgcagg   5460
gcgtggtgct gcacgatgtc tttgaggagg agactgatgg ccacgggcag cccctttggtg   5520 taggtgttga cgaacctatt gagctgggag ggatgcatgc gggggagat gagatgcatc   5580 ttggcctgga tcttgagatt ggcgatgttc ccgcccagat cccgccgggg gttcatgttg   5640
tgcaggacca ccagcacggt gtatccggtg cacttgggga atttgtcatg caacttggaa   5700
gggaaggcgt gaaagaattt ggagacgccc ttgtgaccgc ccaggttttc catgcactca   5760
tccatgatga tggcgatggg cccgtgggcg gcggcctggg caaagacgtt tcgggggtcg   5820
gacacatcgt agttgtggtc ctgggtgagc tcgtcatagg ccattttaat gaatttgggg   5880
cggagggtac ccgactgggg gacaaaggtg ccctcgatcc cggggggcgta gttccccctcg   5940 cagatctgca tctcccaggc cttgagctcg gagggggga tcatgtccac ctgcggggcg   6000
atgaaaaaaa cggtttccgg ggcggggag atgagctgcg ccgaaagcag gttccggagc   6060
agctgggact gccgcagcc ggtggggccg tagatgaccc cgatgaccgg ctgcaggtgg   6120
tagttgaggg agagacagct gccgtcctcg cggaggaggg gggccacctc gttcatcatc   6180
tcgcgcacat gcatgttctc gcgcacgagt tccgccagga ggcgctcgcc ccccagcgag   6240
aggagctctt gcagcgaggc gaagttttc agcggcttga gcccgtcggc catgggcatt   6300
ttggagaggg tctgttgcaa gagttccaga cggtcccaga gctcggtgat gtgctctagg   6360
gcatctcgat ccagcagacc tcctcgtttc gcgggttggg gcgactgcgg gagtagggca   6420
ccaggcgatg ggcgtccagc gaggccaggg tccggtcctt ccagggtcgc agggtccgcg   6480
tcagcgtggt ctccgtcacg gtgaaggggt gcgcgccggg ctgggcgctt gcgagggtgc   6540
gcttcaggct catccggctg gtcgagaacc gctcccggtc ggcgccctgc gcgtcggcca   6600
ggtagcaatt gagcatgagt tcgtagttga gcgcctcggc cgcgtgggcc ttggcgcgga   6660
gcttaccttt ggaagtgtgt ccgcagacgg gacagaggag ggacttgagg gcgtagagct   6720
tgggggcgag gaagacggac tcgggggcgt aggcgtccgc gccgcagctg gcgcagacgg   6780
tctcgcactc cacgagccag gtgaggtcgg ggcggtcggg gtcaaaaacg aggtttcctc   6840
cgtgcttttt gatgcgtttc ttacctctgg tctccatgag ctcgtgtccc gctgggtga   6900 caaagaggct gtccgtgtcc ccgtagaccg actttatggg ccggtcctcg agcggggtgc   6960
cgcggtcctc gtcgtagagg aaccccgccc actccgagac gaaggcccgg gtccaggcca   7020
```

```
gcacgaagga ggccacgtgg gaggggtagc ggtcgttgtc caccagcggg tccaccttct   7080
ccagggtatg caagcacatg tccccctcgt ccacatccag gaaggtgatt ggcttgtaag   7140
tgtaggccac gtgaccgggg gtcccggccg gggggtata  aaaggggggcg ggcccctgct   7200 cgtcctcact gtcttccgga tcgctgtcca ggagcgccag ctgttggggt aggtattccc   7260
tctcgaaggc gggcatgacc tcggcactca ggttgtcagt ttctagaaac gaggaggatt   7320
tgatattgac ggtgccgttg gagacgcctt tcatgagccc ctcgtccatc tggtcagaaa   7380
agacgatctt tttgttgtcg agcttggtgg cgaaggagcc gtagagggcg ttggagagca   7440
gcttggcgat ggagcgcatg gtctggttct tttccttgtc ggcgcgctcc ttggcggcga   7500
tgttgagctg cacgtactcg cgcgccacgc acttccattc ggggaagacg gtggtgagct   7560
cgtcgggcac gattctgacc cgccagccgc ggttgtgcag ggtgatgagg tccacgctgg   7620
tggccacctc gccgcgcagg ggctcgttgg tccagcagag gcgcccgccc ttgcgcgagc   7680
agaagggggg cagcgggtcc agcatgagct cgtcgggggg gtcggcgtcc acggtgaaga   7740
tgccgggcag gagctcgggg tcgaagtagc tgatgcaggt gcccagatcg tccagacttg   7800
cttgccagtc gcgcacggcc agcgcgcgct cgtaggggct gaggggcgtg ccccagggca   7860
tggggtgcgt gagcgcggag gcgtacatgc cgcagatgtc gtagacgtag aggggctcct   7920
ggaggacgcc gatgtaggtg gggtagcagc gcccccgcg  gatgctggcg cgcacgtagt   7980
cgtacagctc gtgcgagggc gcgaggagcc ccgtgccgag attggagcgc tgcggctttt   8040
cggcgcggta gacgatctgg cggaagatgg cgtgggagtt ggaggagatg gtgggcctct   8100
ggaagatgtt gaagtgggca tggggcagtc cgaccgagtc cctgatgaag tgggcgtagg   8160
agtcctgcag cttggcgacg agctcggcgg tgacgaggac gtccagggcg cagtagtcga   8220
gggtctcttg gatgatgtcg tacttgagct ggccccttctg cttccacagc tcgcggttga   8280
gaaggaactc ttcgcggtcc ttccagtact cttcgagggg gaacccgtcc tgatcggcac   8340
ggtaagagcc caccatgtag aactggttga cggccttgta ggcgcagcag cccttctcca   8400
cggggagggc gtaagcttgc gcggccttgc gcagggaggt gtgggtgagg gcgaaggtgt   8460
cgcgcaccat gactttgagg aactggtgct tgaagtcgag gtcgtcgcag ccgccctgct   8520
cccagagctg gaagtccgtg cgcttcttgt aggcggggtt gggcaaagcg aaagtaacat   8580
cgttgaagag gatcttgccc gcgcggggca tgaagttgcg agtgatgcgg aaaggctggg   8640
gcacctcggc ccggttgttg atgacctggg cggcgaggac gatctcgtcg aagccgttga   8700
tgttgtgccc gacgatgtag agttccacga atcgcgggcg gcccttgacg tggggcagct   8760
tcttgagctc gtcgtaggtg agctcggcgg ggtcgctgag cccgtgctgc tcgagggccc   8820
agtcggcgac gtgggggttg gcgctgagga aggaagtcca gagatccacg ccagggcgg   8880 tctgcaagcg gtcccggtac tgacggaact gctggcccac ggccattttt tcggggggtga   8940 cgcagtagaa ggtgcggggg tcgccgtgcc agcggtccca cttgagctgg agggcgaggt   9000
cgtgggcgag ctcgacgagc ggcgggtccc cggagagttt catgaccagc atgaagggga   9060
cgagctgctt gccgaaggac cccatccagg tgtaggtttc cacatcgtag gtgaggaaga   9120
gcctttcggt gcgaggatgc gagccgatgg ggaagaactg gatctcctgc caccagttgg   9180
aggaatggct gttgatgtga tggaagtaga aatgccgacg gcgcgccgag cactcgtgct   9240
tgtgtttata caagcgtccg cagtgctcgc aacgctgcac gggatgcacg tgctgcacga   9300
gctgtacctg ggttcctttg acgaggaatt tcagtgggca gtggagcgct ggcggctgca   9360
```

```
tctggtgctg tactacgtcc tggccatcgg cgtggccatc gtctgcctcg atggtggtca      9420
tgctgacgag cccgcgcggg aggcaggtcc agacctcggc tcggacgggt cggagagcga      9480
ggacgagggc gcgcaggccg gagctgtcca gggtcctgag acgctgcgga gtcaggtcag      9540
tgggcagcgg cggcgcgcgg ttgacttgca ggagcttttc cagggcgcgc gggaggtcca      9600
gatggtactt gatctccacg gcgccgttgg tggcgacgtc cacggcttgc agggtcccgt      9660 gccccctgggg cgccaccacc gtgccccgtt tcttcttggg cggcggcggc tccatgctta     9720
gaagcggcgg cgaggacgcg cgccgggcgg caggggcggc tcggggcccg gaggcagggg      9780
cggcaggggc acgtcggcgc cgcgcgcggg caggttctgg tactgcgccc ggagaagact      9840
ggcgtgagcg acgacgcgac ggttgacgtc ctggatctga cgcctctggg tgaaggccac      9900
gggacccgtg agtttgaacc tgaaagagag ttcgacagaa tcaatctcgg tatcgttgac      9960
ggcggcctgc cgcaggatct cttgcacgtc gcccgagttg tcctggtagg cgatctcggt     10020
catgaactgc tcgatctcct cctcctgaag gtctccgcgg ccggcgcgct cgacggtggc     10080
cgcgaggtcg ttggagatgc ggcccatgag ctgcagaag gcgttcatgc cggcctcgtt      10140
ccagacgcgg ctgtagacca cggctccgtc ggggtcgcgc gcgcgcatga ccacctgggc     10200
gaggttgagc tcgacgtggc gcgtgaagac cgcgtagttg cagaggcgct ggtagaggta     10260
gttgagcgtg gtggcgatgt gctcggtgac gaagaagtac atgatccagc ggcggagcgg     10320
catctcgctg acgtcgccca gggcttccaa gcgctccatg gcctcgtaga agtccacggc     10380
gaagttgaaa aactgggagt tgcgcgccga gacggtcaac tcctcctcca gaagacggat     10440
gagctcggcg atggtggcgc gcacctcgcg ctcgaaggcc ccgggggggct cctcttccat    10500 ttcctcctct tcctcctcca ctaacatctc ttctacttcc tcctcaggag gcggcggcgg     10560
gggaggggcc ctgcgtcgcc ggcggcgcac gggcagacgg tcgatgaagc gctcgatggt     10620
ctccccgcgc cggcgacgca tggtctcggt gacggcgcgc ccgtcctcgc ggggccgcag     10680
cgtgaagacg ccgccgcgca tctccaggtg gccgccgggg gggtctccgt tgggcaggga     10740
gagggcgctg acgatgcatc ttatcaattg acccgtaggg actccgcgca aggacctgag     10800
cgtctcgaga tccacgggat ccgaaaaccg ctgaacgaag gcttcgagcc agtcgcagtc     10860
gcaaggtagg ctgagcccgg tttcttgttc ttcgggtatt tggtcgggag gcgggcgggc     10920
gatgctgctg gtgatgaagt tgaagtaggc ggtcctgaga cggcggatgg tggcgaggag     10980
caccaggtcc ttgggcccgg cttgctggat gcgcagacgg tcggccatgc cccaggcgtg     11040
gtcctgacac ctggcgaggt ccttgtagta gtcctgcatg agccgctcca cgggcacctc     11100
ctcctcgccc gcgcggccgt gcatgcgcgt gagcccgaac ccgcgctgcg gctggacgag     11160
cgccaggtcg gcgacgacgc gctcggcgag gatggcctgc tggatctggg tgagggtggt     11220
ctggaagtcg tcgaagtcga cgaagcggtg gtaggctccg gtgttgatgg tgtaggagca     11280
gttggccatg acggaccagt tgacggtctg gtggccgggg gcgcacgagct cgtggtactt    11340 gaggcgcgag taggcgcgcg tgtcgaagat gtagtcgttg caggtgcgca cgaggtactg     11400
gtatccgacg aggaagtgcg gcggcggctg gcggtagagc ggccatcgct cggtggcggg     11460
ggcgccgggc gcgaggtcct cgagcatgag gcggtggtag ccgtagatgt acctggacat     11520
ccaggtgatg ccggcggcgg tggtggaggc gcgcgggaac tcgcggacgc ggttccagat     11580
gttgcgcagc ggcaggaagt agttcatggt ggccgcggtc tggcccgtga ggcgcgcgca     11640
gtcgtggatg ctctagacat acgggcaaaa acgaaagcgg tcagcggctc gactccgtgg     11700
cctggaggct aagcgaacgg gttgggctgc gcgtgtaccc cggttcgaat ctcgaatcag     11760
```

```
gctggagccg cagctaacgt ggtactggca ctcccgtctc gacccaagcc tgctaacgaa   11820
acctccagga tacggaggcg ggtcgttttt tggccttggt cgctggtcat gaaaaactag   11880
taagcgcgga aagcggccgc ccgcgatggc tcgctgccgt agtctggaga aagaatcgcc   11940
agggttgcgt tgcggtgtgc cccggttcga gcctcagcgc tcggcgccgg ccggattccg   12000
cggctaacgt gggcgtggct gccccgtcgt ttccaagacc ccttagccag ccgacttctc   12060
cagttacgga gcgagcccct cttttttct tgtgttttg ccagatgcat cccgtactgc   12120
ggcagatgcg cccccaccct ccaccacaac cgccctacc gcagcagcag caacagccgg   12180
cgcttctgcc cccgccccag cagcagcagc cagccactac cgcggcgcc gccgtgagcg   12240 gagccggcgt tcagtatgac ctggccttgg aagagggcga ggggctggcg cggctggggg   12300
cgtcgtcgcc ggagcggcac ccgcgcgtgc agatgaaaag ggacgctcgc gaggcctacg   12360
tgcccaagca gaacctgttc agagacagga gcggcgagga gcccgaggag atgcgcgcct   12420
cccgcttcca cgcggggcgg gagctgcggc gcggcctgga ccgaaagcgg gtgctgaggg   12480
acgaggattt cgaggcggac gagctgacgg ggatcagccc cgcgcgcgcg cacgtggccg   12540
cggccaacct ggtcacggcg tacgagcaga ccgtgaagga ggagagcaac ttccaaaaat   12600
ccttcaacaa ccacgtgcgc acgctgatcg cgcgcgagga ggtgaccctg ggcctgatgc   12660
acctgtggga cctgctggag gccatcgtgc agaaccccac gagcaagccg ctgacgcgc   12720 agctgtttct ggtggtgcag cacagtcggg acaacgagac gttcagggag gcgctgctga   12780
atatcaccga gcccgagggc cgctggctcc tggacctggt gaacattctg cagagcatcg   12840
tggtgcagga gcgcgggctg ccgctgtccg agaagctggc ggccatcaac ttctcggtgc   12900
tgagcctggg caagtactac gctaggaaga tctacaagac cccgtacgtg cccatagaca   12960
aggaggtgaa gatcgatggg ttttacatgc gcatgaccct gaaagtgctg accctgagcg   13020
acgatctggg ggtgtaccgc aacgacagga tgcaccgcgc ggtgagcgcc agccgccggc   13080
gcgagctgag cgaccaggag ctgatgcaca gcctgcagcg ggccctgacc ggggccggga   13140
ccgaggggga gagctacttt gacatgggcg cggacctgcg ctggcagccc agccgccggg   13200
ccttggaagc tgccggcggc gtgccctacg tggaggaggt ggacgatgag gaggaggagg   13260
gcgagtacct ggaagactga tggcgcgacc gtattttgc tagatgcagc aacagccacc   13320
gccgccgcct cctgatcccg cgatgcgggc ggcgctgcag agccagccgt ccggcattaa   13380
ctcctcggac gattggaccc aggccatgca acgcatcatg gcgctgacga cccgcaatcc   13440
cgaagccttt agacagcagc ctcaggccaa ccggctctcg gccatcctgg aggccgtggt   13500
gccctcgcgc tcgaaccccca cgcacgagaa ggtgctggcc atcgtgaacg cgctggtgga   13560
gaacaaggcc atccgcggcg acgaggcgg gctggtgtac aacgcgctgc tggagcgcgt   13620
ggcccgctac aacagcacca acgtgcagac gaacctggac cgcatggtga ccgacgtgcg   13680
cgaggcggtg tcgcagcgcg agcggttcca ccgcagtcg aacctgggct ccatggtggc   13740
gctgaacgcc ttcctgagca cgcagcccgc caacgtgccc cggggccagg aggactacac   13800
caacttcatc agcgcgctgc ggctgatggt ggccgaggtg cccagagcg aggtgtacca   13860 gtcgggccg gactacttct tccagaccag tcgccagggc ttgcagaccg tgaacctgag   13920
ccaggctttc aagaacttgc agggactgtg gggcgtgcag gccccggtcg gggaccgcgc   13980
gacggtgtcg agcctgctga cgccgaactc gcgcctgctg ctgctgctgg tggcgccctt   14040
cacggacagc ggcagcgtga ccgcgactc gtacctgggc tacctgctta acctgtaccg   14100
```

```
cgaggccatc gggcaggcgc acgtggacga gcagacctac caggagatca cccacgtgag    14160
ccgcgcgctg ggccaggagg acccgggcaa cctggaggcc accctgaact tcctgctgac    14220
caaccggtcg cagaagatcc cgccccagta cgcgctgagc accgaggagg agcgcatcct    14280
gcgctacgtg cagcagagcg tggggctgtt cttgatgcag gaggggggcca cgcccagcgc    14340 cgcgctcgac atgaccgcgc gcaacatgga gcccagcatg tacgcccgca accgcccgtt    14400
catcaataag ctgatggact acttgcatcg ggcggccgcc atgaactcgg actactttac    14460
caacgccatc ttgaacccgc actggctccc gccgcccggg ttctacacgg gcgagtacga    14520
catgcccgac cccaacgacg ggttcctgtg ggacgacgtg gacagcagcg tgttctcgcc    14580
gcggcccacc accaccaccg tgtggaagaa agagggcggg gaccggcggc cgtcctcggc    14640
gctgtccggt cgcgcgggtg ctgccgcggc ggtgcccgag gctgccagcc ccttcccgag    14700
cctgcccttt tcgctgaaca gcgtgcgcag cagcgagctg ggtcggctga cgcggccgcg    14760
cctgctgggc gaggaggagt acctgaacga ctccttgttg aagcccgagc gcgagaagaa    14820
cttccccaat aacgggatag agagcctggt ggacaagatg agccgctgga agacgtacgc    14880
gcacgagcac agggacgagc ccgagctagc agcgcaggc acccgtagac gccagcggca    14940
cgacaggcag cggggactgg tgtgggacga tgaggattcc gccgacgaca gcagcgtgtt    15000
ggacttgggt gggagtggtg gtggtaaccc gttcgctcac ctgcgccccc gtatcgggcg    15060
cctgatgtaa gaatctgaaa aaataaaaga cggtactcac caaggccatg gcgaccagcg    15120
tgcgttcttc tctgttgttt gtagtagtat gatgaggcgc gtgtacccgg agggtcctcc    15180
tccctcgtac gagagcgtga tgcagcaggc ggtggcggcg gcgatgcagc cccgctgga    15240 ggcgccttac gtgccccgc ggtacctggc gcctacggag gggcggaaca gcattcgtta    15300
ctcggagctg gcacccttgt acgataccac ccggttgtac ctggtggaca caagtcggc    15360 ggacatcgcc tcgctgaact accagaacga ccacagcaac ttcctgacca ccgtggtgca    15420
gaacaacgat ttcacccccca cggaggccag cacccagacc atcaactttg acgagcgctc    15480
gcggtggggc ggccagctga aaccatcat gcacaccaac atgcccaacg tgaacgagtt    15540
catgtacagc aacaagttca aggcgcgggt gatggtctcg cgcaagaccc ccaacggggt    15600
cacggtaggg gatgattatg atggtagtca ggacgagctg acctacgagt gggtggagtt    15660
tgagctgccc gagggcaact tctcggtgac catgaccatc gatctgatga caacgccat    15720 catcgacaac tacttggcgg tggggcggca gaacgggtg ctggagagcg catcggcgt    15780 gaagttcgac acgcgcaact tccggctggg ctgggacccc gtgaccgagc tggtgatgcc    15840
gggcgtgtac accaacgagg ccttccaccc cgacatcgtc ctgctgcccg gctgcggcgt    15900
ggacttcacc gagagccgcc tcagcaacct gctgggcatc cgcaagcggc agccctccca    15960
ggagggcttc cagatcctgt acgaggacct ggagggggc aacatccccg cgctcttgga    16020
tgtcgaagcc tatgaagaaa gtaaggaaaa agcagaggct gaggcaacta cagccgtggc    16080
taccgccgcg actgtggcag atgccactgt caccaggggc gatacattcg ccacccaggc    16140
ggaggaagca gccgccctag cggcgaccga tgatagtgaa agtaagatag tcatcaagcc    16200
ggtggagaag acagcaagaa acaggagcta caacgttcta ccggatggaa agaacaccgc    16260
ctaccgcagc tggtacctgg cctacaacta cggcgacccc gagaagggcg tgcgctcctg    16320
gacgctgctc accacctcgg acgtcacctg cggcgtggag caagtctact ggtcgctgcc    16380
cgacatgatg caagacccgg tcaccttccg ctccacgcga caagttagca actacccggt    16440
ggtgggcgcc gagctcctgc ccgtctactc caagagcttc ttcaacgagc aggccgtcta    16500
```

```
ctcgcagcag ctgcgtgcct tcacctcgct cacgcacgtc ttcaaccgct tccccgagaa   16560
ccagatcctc gtccgcccgc ccgcgcccac cattaccacc gtcagtgaaa acgttcctgc   16620
tctcacagat cacgggaccc tgccgctgcg cagcagtatc cggggagtcc agcgcgtgac   16680
cgtcactgac gccagacgcc gcacctgccc ctacgtctac aaggccctgg gcgtagtcgc   16740
gccgcgcgtc ctctcgagcc gcaccttcta aaaaatgtcc attctcatct cgcccagtaa   16800
taacaccggt tggggcctgc gcgcgcccag caagatgtac ggaggcgctc gccaacgctc   16860
cacgcaacac cccgtgcgcg tgcgcgggca cttccgcgct ccctggggcg ccctcaaggg   16920
ccgcgtgcgc tcgcgcacca ccgtcgacga cgtgatcgac caggtggtgg ccgacgcgcg   16980
caactacacg cccgccgccg cgcccgcctc caccgtggac gccgtcatcg acagcgtggt   17040
ggccgacgcg cgccggtacg cccgcgccaa gagccggcgg cggcgcatcg cccggcggca   17100
ccggagcacc cccgccatgc gcgcggcgcg agccttgctg cgcagggcca ggcgcacggg   17160
acgcagggcc atgctcaggg cggccagacg cgcggcctcc ggcagcagca gcgccggcag   17220
gacccgcaga cgcgcggcca cggcggcggc ggcggccatc gccagcatgt cccgcccgcg   17280
gcgcggcaac gtgtactggg tgcgcgacgc cgccaccggt gtgcgcgtgc ccgtgcgcac   17340
ccgcccccct cgcacttgaa gatgctgact tcgcgatgtt gatgtgtccc agcggcgagg   17400
aggatgtcca agcgcaaata caaggaagag atgctccagg tcatcgcgcc tgagatctac   17460
ggccccgcgg cggcggtgaa ggaggaaaga aagccccgca aactgaagcg ggtcaaaaag   17520
gacaaaaagg aggaggaaga tgacggactg gtggagtttg tgcgcgagtt cgccccccgg   17580
cggcgcgtgc agtggcgcgg gcggaaagtg aaaccggtgc tgcggcccgg caccacggtg   17640
gtcttcacgc ccggcgagcg ttccggctcc gcctccaagc gctcctacga cgaggtgtac   17700
ggggacgagg acatcctcga gcaggcggtc gagcgtctgg gcgagtttgc ttacggcaag   17760
cgcagccgcc ccgcgccctt gaaagaggag gcggtgtcca tcccgctgga ccacggcaac   17820
cccacgccga gcctgaagcc ggtgaccctg cagcaggtgc tgccgagcgc ggcgccgcgc   17880
cggggcttca gcgcgagggg cggcgaggat ctgtacccga ccatgcagct gatggtgccc   17940
aagcgccaga agctggagga cgtgctggag cacatgaagg tggaccccga ggtgcagccc   18000
gaggtcaagg tgcggcccat caagcaggtg gccccgggcc tgggcgtgca gaccgtggac   18060
atcaagatcc ccacggagcc catggaaacg cagaccgagc ccgtgaagcc cagcaccagc   18120
accatggagg tgcagacgga tccctggatg ccagcggctt ccaccaccac cactcgccga   18180
agacgcaagt acgcgcgggc cagcctgctg atgcccaact acgcgctgca tccttccatc   18240
atccccacgc cgggctaccg cggcacgcgc ttctaccgcg gctacaccag cagccgccgc   18300
cgcaagacca ccaccgccg ccgtcgtcgc agccgccgca gcagcaccgc gacttccgcc   18360
ttggtgcgga gagtgtatcg cagcgggcgc gagcctctga ccctgccgcg cgcgcgctac   18420
cacccgagca tcgccattta actaccgcct cctacttgca gatatggccc tcacatgccg   18480
cctccgcgtc cccattacgg gctaccgagg aagaaagccg cgccgtagaa ggctgacggg   18540
gaacgggctg cgtcgccatc accaccggcg gcggcgcgcc atcagcaagc ggttgggggg   18600
aggcttcctg ccccgcgctga tccccatcat cgccgcggcg atcggggcga tccccggcat   18660
agcttccgtg gcggtgcagg cctctcagcg ccactgagac acaaaaaagc atggatttgt   18720
aataaaaaaa tggactgacg ctcctggtcc tgtgatgtgt gttttagat ggaagacatc   18780 aattttcgt ccctggcacc gcgacacggc acgcggccgt ttatgggcac ctggagcgac   18840
```

```
atcggcaaca gccaactgaa cggggcgcc ttcaattgga gcagtctctg gagcgggctt    18900
aagaatttcg ggtccacgct caaaacctat ggcaacaagg cgtggaacag cagcacaggg    18960
caggcgctga gggaaaagct gaaagagcag aacttccagc agaaggtggt cgatggcctg    19020
gcctcgggca tcaacggggt ggtggacctg gccaaccagg ccgtgcagaa acagatcaac    19080
agccgcctgg acgcggtccc gcccgcgggg tccgtggaga tgccccaggt ggaggaggag    19140
ctgcctcccc tggacaagcg cggcgacaag cgaccgcgtc ccgacgcgga ggagacgctg    19200
ctgacgcaca cggacgagcc gcccccgtac gaggaggcgg tgaaactggg tctgcccacc    19260
acgcggcccg tggcgcctct ggccaccggg gtgctgaaac ccagcagcag cagccagccc    19320
gcgaccctgg acttgcctcc gcctgcttcc cgcccctcca cagtggctaa gcccctgccg    19380
ccggtggccg tcgcgtcgcg cgcccccga ggccgccccc aggcgaactg gcagagcact    19440
ctgaacagca tcgtgggtct gggagtgcag agtgtgaagc gccgccgctg ctattaaaag    19500
acactgtagc gcttaacttg cttgtctgtg tgtgtatatg tatgtccgcc gaccagaagg    19560
aggaagaggc gcgtcgccga gttgcaagat ggccaccca tcgatgctgc cccagtgggc    19620
gtacatgcac atcgccggac aggacgcttc ggagtacctg agtccgggtc tggtgcagtt    19680
cgcccgcgcc acagacacct acttcagtct ggggaacaag tttaggaacc ccacggtggc    19740
gcccacgcac gatgtgacca ccgaccgcag ccagcggctg acgctgcgct tcgtgcccgt    19800
ggaccgcgag gacaacacct actcgtacaa agtgcgctac acgctggccg tgggcgacaa    19860
ccgcgtgctg gacatggcca gcacctactt tgacatccgc ggcgtgctgg atcggggccc    19920
cagcttcaaa ccctactccg gcaccgccta caacagccta gctcccaagg gagcgcccaa    19980
cacctcacag tggaaggatt ccgacagcaa aatgcatact tttggagttg ctgccatgcc    20040
cggtgttgtt ggtaaaaaaa tagaagccga tggtctgcct attggaatag attcatcctc    20100
tggaactgac accataattt atgctgataa aactttccaa ccagagccac aggttggaag    20160
tgacagttgg gtcgacacca atggtgcaga ggaaaaatat ggaggtagag ctcttaagga    20220
cactacaaac atgaagccct gctacggttc ttttgccagg cctaccaaca aagaaggtgg    20280
acaggctaac ataaaagatt ctgaaactgc cagcactact cctaactatg atatagattt    20340
ggcattcttt gacagcaaaa atattgcagc taactacgat ccagatattg taatgtacac    20400
agaaaatgtt gagttgcaaa ctccagatac tcatattgtg tttaagccag gaacttcaga    20460
tgaaagttca gaagccaatt tgggccagca ggccatgccc aacagaccca actacatcgg    20520
gttcagagac aactttatcg ggctcatgta ctacaacagc actggcaata tgggtgtact    20580
ggctggtcag gcctcccagc taaatgctgt ggtggacttg caggacagaa acaccgaact    20640
gtcctaccag ctcttgcttg actctctggg tgacagaacc aggtatttca gtatgtggaa    20700
tcaggcggtg gacagctatg accccgatgt gcgcattatt gaaaatcacg gtgtggagga    20760
tgaactcccc aattattgct tccctttgaa tggtgtaggc tttacagata cttaccaggg    20820
tgttaaagtt aagacagata cagccgctac tggtaccaat ggaacgcagt gggacaaaga    20880
tgataccaca gtcagcactg ccaatgagat ccactcaggc aatcctttcg ccatggagat    20940
caacatccag gccaacctgt ggcggaactt cctctacgcg aacgtggcgc tgtacctgcc    21000
cgactcctac aagtacacgc cggccaacat cacgctgccg accaacacca cacctacga    21060
ttacatgaac ggccgcgtgg tggcgccctc gctggtggac gcctacatca acatcgggc    21120
gcgctggtcg ctggacccca tggacaacgt caacccccttc aaccaccacc gcaacgcggg    21180
cctgcgctac cgctccatgc tcctgggcaa cgggcgctac gtgcccttcc acatccaggt    21240
```

```
gccccaaaag ttttttcgcca tcaagagcct cctgctcctg cccgggtcct acacctacga   21300
gtggaacttc cgcaaggacg tcaacatgat cctgcagagc tccctcggca acgacctgcg   21360
cacggacggg gcctccatcg ccttcaccag catcaacctc tacgccacct tcttccccat   21420
ggcgcacaac accgcctcca cgctcgaggc catgctgcgc aacgacacca acgaccagtc   21480
cttcaacgac tacctctcgg cggccaacat gctctacccc atcccggcca acgccaccaa   21540
cgtgcccatc tccatcccct cgcgcaactg ggccgccttc cgcggatggt ccttcacgcg   21600
cctcaagacc cgcgagacgc cctcgctcgg ctccgggttc gaccccatact tcgtctactc   21660
gggctccatc ccctacctcg acggcacctt ctacctcaac cacaccttca agaaggtctc   21720
catcaccttc gactcctccg tcagctggcc cggcaacgac cgcctcctga cgcccaacga   21780
gttcgaaatc aagcgcaccg tcgacggaga gggatacaac gtgggcccagt gcaacatgac   21840
caaggactgg ttcctggtcc agatgctggc ccactacaac atcggctacc agggcttcta   21900
cgtgcccgag ggctacaagg accgcatgta ctccttcttc cgcaacttcc agcccatgag   21960
ccgccaggtc gtggacgagg tcaactacaa ggactaccag gccgtcaccc tggcctacca   22020
gcacaacaac tcgggcttcg tcggctacct cgcgcccacc atgcgccagg gccagccta   22080
ccccgccaac taccoctacc cgctcatcgg caagagcgcc gtcgccagcg tcacccagaa   22140
aaagttcctc tgcgacccgg gtcatgtggcg catccccttc tccagcaact tcatgtccat   22200
gggcgcgctc accgacctcg gccagaacat gctctacgcc aactccgccc acgcgctaga   22260
catgaatttc gaagtcgacc ccatggatga gtccaccctt ctctatgttg tcttcgaagt   22320
cttcgacgtc gtccgagtgc accagcccca ccgcggcgtc atcgaggccg tctacctgcg   22380
cacgcccttc tcggccggca acgccaccac ctaaagcccc gctcttgctt cttgcaagat   22440
gacggcctgt ggctccggcg agcaggagct cagggccatc ctccgcgacc tgggctgcgg   22500
gccctgcttc ctgggcacct tcgacaagcg cttcccggga ttcatggccc cgcacaagct   22560
ggcctgcgcc atcgtcaaca cggccggccg cgagaccggg ggcgagcact ggctggcctt   22620
cgcctggaac ccgcgctccc acacctgcta cctcttcgac cccttcgggt tctcggacga   22680
gcgcctcaag cagatctacc agttcgagta cgagggcctg ctgcgccgca gcgccctggc   22740
caccgaggac cgctgcatca ccctggaaaa gtccacccag accgtgcagg tccgcgctc   22800
ggccgcctgc gggctcttct gctgcatgtt cctgcacgcc ttcgtgcact ggcccgaccg   22860
ccccatggac aagaaccccca ccatgaactt gctgacgggg gtgcccaacg gcatgctcca   22920
gtcgccccag gtgaacccca ccctgcgccg caaccaggag gcgctctacc gcttcctcaa   22980
cgcccactcc gcctactttc gctcccaccg cgcgcgcatc gagaaggcca ccgccttcga   23040
ccgcatgaat caagacatgt aaactgtgtg tatgtgaatg ctttattcat cataataaac   23100
agcacatgtt tatgccacct tctctgaggc tctgacttta tttagaaatc gaaggggttc   23160
tgccggctct cggcgtgccc cgcgggcagg gatacgttgc ggaactggta cttgggcagc   23220
cacttgaact cggggatcag cagcttcggc acggggaggt cggggaacga gtcgctccac   23280
agcttgcgcg tgagttgcag ggcgcccagc aggtcgggcg cggagatctt gaaatcgcag   23340
ttgggacccg cgttctgcgc gcgagagttg cggtacacgg ggttgcagca ctggaacacc   23400
atcagggccg ggtgcttcac gctcgccagc accgtcgcgt cggtgatgcc ctccacgtcc   23460
agatcctcgg cgttggccat cccgaaggggg tcatcttgc aggtctgccg ccccatgctg   23520
ggcacgcagc cgggcttgtg gttgcaatcg cagtgcaggg ggatcagcat catctgagcc   23580
```

```
tgctcggagc tcatgcccgg gtacatggcc ttcatgaaag cctccagctg gcggaaggcc   23640
tgctgcgcct tgccgccctc ggtgaagaag accccacagg acttgctaga gaactggttg   23700
gtggcgcagc ccgcgtcgtg cacgcagcag cgcgcgtcgt tgttggccag ctgcaccacg   23760
ctgcgccccc agcggttctg ggtgatcttg gcccggtcgg ggttctcctt cagcgcgcgc   23820
tgcccgttct cgctcgccac atccatctcg atcgtgtgct ccttctggat catcacggtc   23880
ccgtgcaggc accgcagctt gccctcggcc tcggtgcacc cgtgcagcca cagcgcgcag   23940
ccggtgcact cccagttctt gtgggcgatc tgggagtgcg agtgcacgaa gccctgcagg   24000
aagcggccca tcatcgtggt cagggtcttg ttgctggtga aggtcagcgg gatgccgcgg   24060
tgctcctcgt tcacatacag gtggcagatg cggcggtaca cctcgccctg ctcgggcatc   24120
agctggaagg cggacttcag gtcgctctcc acgcggtacc gctccatcag cagcgtcatc   24180
acttccatgc ccttctccca ggccgaaacg atcggcaggc tcaggggggtt cttcaccgtc   24240 atcttagtcg ccgccgccga agtcaggggg tcgttctcgt ccagggtctc aaacactcgc   24300
ttgccgtcct tctcggtgat gcgcacgggg ggaaagctga agcccacggc cgccagctcc   24360
tcctcggcct gcctttcgtc ctcgctgtcc tggctgatgt cttgcaaagg cacatgcttg   24420
gtcttgcggg gtttcttttt gggcggcaga ggcggcggcg gagacgtgct gggcgagcgc   24480
gagttctcgc tcaccacgac tatttcttct tcttggccgt cgtccgagac cacgcggcgg   24540
taggcatgcc tcttctgggg cagaggcgga ggcgacgggc tctcgcggtt cggcgggcgg   24600
ctggcagagc cccttccgcg ttcgggggtg cgctcctggc ggcgctgctc tgactgactt   24660
cctccgcggc cggccattgt gttctcctag ggagcaacaa gcatggagac tcagccatcg   24720
tcgccaacat cgccatctgc ccccgccgcc gacgagaacc agcagcagca gaatgaaagc   24780
ttaaccgccc cgccgcccag ccccaccctcc gacgccgccg cggccccaga catgcaagag   24840
atggaggaat ccatcgagat tgacctgggc tacgtgacgc ccgcggagca cgaggaggag   24900
ctggcagcgc gcttttcagc cccggaagag aaccaccaag agcagccaga gcaggaagca   24960
gagagcgagc agcagcaggc tgggctcgag catggcgact acctgagcgg ggcagaggac   25020
gtgctcatca agcatctggc ccgccaaagc atcatcgtca aggacgcgct gctcgaccgc   25080
gccgaggtgc ccctcagcgt ggcggagctc agccgcgcct acgagcgcaa cctcttctcg   25140
ccgcgcgtgc cccccaagcg ccagcccaac ggcacctgcg agcccaaccc cgcgcctcaac   25200 ttctacccgg tcttcgcggt gcccgaggcc ctggccacct accacctctt tttcaagaac   25260
caaaggatcc ccgtctcctg ccgcgccaac cgcaccgcg ccgacgccct gctcaacctg   25320
ggtcccggcg cccgcctacc tgatatcacc tccttggaag aggttcccaa gatcttcgag   25380
ggtctgggca cgacgagac tcgggccgcg aacgctctgc aaggaagcgg agaggagcat   25440
gagcaccaca gcgccctggt ggagttggaa ggcgacaacg cgcgcctggc ggtgctcaag   25500
cgcacggtcg agctgaccca cttcgcctac ccggcgctca acctgccccc caaggtcatg   25560
agcgccgtca tggaccaggt gctcatcaag cgcgcctcgc ccctctcaga ggaggagatg   25620
caggaccccg agagctcgga cgagggcaag cccgtggtca gcgacgagca gctggcgcgc   25680
tggctgggag cgagcagcac cccccagagc ctggaagagc ggcgcaagct catgatggcc   25740
gtggtcctgg tgaccgtgga gctggagtgt ctgcgccgct tcttcgccga cgcggagacc   25800
ctgcgcaagg tcgaggagaa cctgcactac ctcttcaggc acgggttcgt gcgccaggcc   25860
tgcaagatct ccaacgtgga gctgaccaac ctggtctcct acatgggcat cctgcacgag   25920
aaccgcctgg ggcagaacgt gctgcacacc accctgcgcg gggaggcccg ccgcgactac   25980
```

```
atccgcgact gcgtctacct gtacctctgc cacacctggc agacgggcat gggcgtgtgg   26040
cagcagtgcc tggaggagca gaacctgaaa gagctctgca agctcctgca gaagaacctc   26100
aaggccctgt ggaccgggtt cgacgagcgc accaccgcct cggacctggc cgacctcatc   26160
ttccccgagc gcctgcggct gacgctgcgc aacgggctgc ccgactttat gagccaaagc   26220
atgttgcaaa actttcgctc tttcatcctc gaacgctccg ggatcctgcc cgccacctgc   26280
tccgcactgc cctcggactt cgtgccgctg accttccgcg agtgccccc gccgctctgg   26340 agccactgct acttgctgcg cctggccaac tacctggcct accactcgga cgtgatcgag   26400
gacgtcagca gcgagggtct gctcgagtgc cactgccgct gcaacctctg cacgccgcac   26460
cgctccttgg cctgcaaccc ccagctgctg agcgagaccc agatcatcgg caccttcgag   26520
ttgcaaggcc ccggcgaggg caaggggggt ctcaaactca ccccggggct gtggacctcg   26580
gcctacttgc gcaagttcgt gcccgaggac taccatccct tcgagatcag gttctacgag   26640
gaccaatccc agccgcccaa ggcgagctg tcggcctgcg tcatcaccca ggggccatc   26700 ctggcccaat tgcaagccat ccagaaatcc cgccaagaat ttctgctgaa aaagggccac   26760
ggggtctact tggacccca gaccggagag gagctcaacc ccagcttccc ccaggatgcc   26820
ccgaggaagc agcaagaagc tgaaagtgga gctgccgctg ccgccggagg atttggagga   26880
agactgggag agcagtcagg cagaggagat ggaagactgg gacagcactc aggcagagga   26940
ggacagcctg caagacagtc tggaggagga agacgaggtg gaggaggagg cagaggaaga   27000
agcagccgcc gccagaccgt cgtcctcggc ggaggagaaa gcaagcagca cggataccat   27060
ctccgctccg ggtcggggtc gcggcggccg ggcccacagt agatgggacg agaccgggcg   27120
cttcccgaac cccaccaccc agaccggtaa gaggagcgg cagggataca agtcctggcg   27180
ggggcacaaa aacgccatcg tctcctgctt gcaagcctgc gggggcaaca tctccttcac   27240
ccggcgctac ctgctcttcc accgcggggt gaacttcccc cgcaacatct tgcattacta   27300
ccgtcacctc cacagcccct actactgttt ccaagaagag gcagaaaccc agcagcagca   27360
gcagaaaacc agcggcagca gcagcagcta gaaaatccac agcggcggca ggtggactga   27420
ggatcgcggc gaacgagccg gcgcagaccc gggagctgag gaaccggatc tttcccaccc   27480
tctatgccat cttccagcag agtcgggggc aggagcagga actgaaagtc aagaaccgtt   27540
ctctgcgctc gctcacccgc agttgtctgt atcacaagag cgaagaccaa cttcagcgca   27600
ctctcgagga cgccgaggct ctcttcaaca agtactgcgc gctcactctt aaagagtagc   27660
ccgcgccccc cacacacgg aaaaaggcgg gaattacgtc accacctgcg cccttcgccc   27720
gaccatcatc atgagcaaag agattccca gccttacatg tggagctacc agccccagat   27780
gggcctggcc gccggcgccg cccaggacta ctccacccgc atgaactggc tcagtgccgg   27840
gcccgcgatg atctcacggg tgaatgacat ccgcgcccac cgaaaccaga tactcctaga   27900
acagtcagcg atcaccgcca cgccccgcca tcaccttaat ccgcgtaatt ggcccgccgc   27960
cctggtgtac caggaaattc cccagcccac gaccgtacta cttccgcgag acgcccaggc   28020
cgaagtccag ctgactaact caggtgtcca gctggccggc ggcgccgccc tgtgtcgtca   28080
ccgccccgct cagggtataa agcggctggt gatccgagge agaggcacac agctcaacga   28140
cgaggtggtg agctcttcgc tgggtctgcg acctgacgga gtcttccaac tcgccggatc   28200
ggggagatct tccttcacgc ctcgtcaggc cgtcctgact ttggagagtt cgtcctcgca   28260
gccccgctcg ggcggcatcg gcactctcca gttcgtggag gagttcactc cctcggtcta   28320
```

```
cttcaacccc ttctccggct ccccggcca ctacccggac gagttcatcc cgaacttcga   28380
cgccatcagc gagtcggtgg acggctacga ttgaatgtcc catggtggcg cggctgacct   28440
agctcggctt cgacacctgg accactgtta attaatcgcc tctcctacga gctcctgcag   28500
cagcgccaga agttcacctg cctggtcgga gtcaaccca tcgtcatcac ccagcagtcg    28560
ggcgatacca aggggtgcat ccactgctcc tgcgactccc ccgactgcgt ccacactctg   28620
atcaagaccc tctgcggcct ccgcgacctc ctccccatga actaatcacc cccttatcca   28680
gtgaaataaa gatcatattg atgatgattt tacagaaata aagatacaat catattgatg   28740
atttgagttt aataaaaaat aaagaatcac ttacttgaaa tctgatacca ggtctctgtc   28800
catgttttct gccaacacca cttcactccc ctcttcccag ctctggtact gcaggccccg   28860
gcgggctgca aacttcctcc acacgctgaa ggggatgtca aattcctcct gtccctcaat   28920
cttcatttta tcttctatca gatgtccaaa aagcgcgtcc gggtggatga tgacttcgac   28980
cccgtctacc cctacgatgc agacaacgca ccgaccgtgc ccttcatcaa ccccccttc    29040
gtctcttcag atggattcca agagaagccc ctggggtgc tgtccctgcg actggccgac   29100
cccgtcacca ccaagaacgg ggaaatcacc ctcaagctgg agagggggt ggacctcgac   29160
tcctcgggaa aactcatctc caacacggcc accaaggccg ccgcccctct cagttttcc   29220
aacaacacca tttcccttaa catggatcac ccctttaca ctaaagatgg aaaattatcc   29280
ttacaagttt ctccaccatt aaatatactg agaacaagca ttctaaacac actagcttta   29340
ggttttggat caggtttagg actccgtggc tctgccttgg cagtacagtt agtctctcca   29400
cttacatttg atactgatgg aaacataaag cttaccttag acagaggttt gcatgttaca   29460
acaggagatg caattgaaag caacataagc tgggctaaag gtttaaaatt tgaagatgga   29520
gccatagcaa ccaacattgg aaatgggtta gagtttggaa gcagtagtac agaaacaggt   29580
gttgatgatg cttacccaat ccaagttaaa cttggatctg gccttagctt tgacagtaca   29640
ggagccataa tggctggtaa caaagaagac gataaactca ctttgtggac aacacctgat   29700
ccatcgccaa actgtcaaat actcgcagaa aatgatgcaa actaacact ttgcttgact    29760
aaatgtggta gtcaaatact ggccactgtg tcagtcttag ttgtaggaag tggaaaccta   29820
aaccccatta ctggcaccgt aagcagtgct caggtgtttc tacgttttga tgcaaacggt   29880
gttcttttaa cagaacattc tacactaaaa aaatactggg gtataggca gggagatagc    29940
atagatggca ctccatatac caatgctgta ggattcatgc ccaatttaaa agcttatcca   30000
aagtcacaaa gttctactac taaaaataat atagtagggc aagtatacat gaatggagat   30060
gtttcaaaac ctatgcttct cactataacc ctcaatggta ctgatgacag caacagtaca   30120
tattcaatgt cattttcata cacctggact aatggaagct atgttggagc aacatttggg   30180
gctaactctt ataccttctc atacatcgcc caagaatgaa cactgtatcc caccctgcat   30240
gccaacccctt cccaccccac tctgtggaaa aaactctgaa acacaaaata aaataaagtt   30300
caagtgtttt attgattcaa cagttttaca ggattcgagc agttattttt cctccaccct   30360
cccaggacat ggaatacacc accctctccc cccgcacagc cttgaacatc tgaatgccat   30420
tggtgatgga catgcttttg gtctccacgt tccacacagt ttcagagcga ccagtctcg    30480
ggtcggtcag ggagatgaaa ccctccgggc acaattggga gaagtactcg cctacatggg   30540
ggtagagtca taatcgtgca tcaggatagg gcggtggtgc tgcagcagcg cgcgaataaa   30600
ctgctgccgc cgccgctccg tcctgcagga atacaacatg gcagtggtct cctcagcgat   30660
gattcgcacc gcccgcagca taaggcgcct tgtcctccgg gcacagcagc gcaccctgat   30720
```

```
ctcacttaaa tcagcacagt aactgcagca cagcaccaca atattgttca aaatcccaca    30780
gtgcaaggcg ctgtatccaa agctcatggc ggggaccaca gaacccacgt ggccatcata    30840
ccacaagcgc aggtagatta agtggcgacc cctcataaac acgctggaca taaacattac    30900
ctcttttggc atgttgtaat tcaccacctc ccggtaccat ataaacctct gattaaacat    30960
ggcgccatcc accaccatcc taaccagct ggccaaaacc tgcccgccgg ctatacactg     31020
cagggaaccg ggactggaac aatgacagtg gagagcccag gactcgtaac catggatcat    31080
catgctcgtc atgatatcaa tgttggcaca acacaggcac acgtgcatac acttcctcag    31140
gattacaagc tcctcccgcg ttagaaccat atcccaggga acaacccatt cctgaatcag    31200
cgtaaatccc acactgcagg gaagacctcg cacgtaactc acgttgtgca ttgtcaaagt    31260
gttacattcg ggcagcagcg gatgatcctc cagtatggta gcgcgggttt ctgtctcaaa    31320
aggaggtaga cgatccctac tgtacggagt gcgccgagac aaccgagatc gtgttggtcg    31380
tagtgtcatg ccaaatggaa cgccggacgt agtcatattt cctgaagtct tggcgcgcca    31440
aagtctagaa gcggtccata gcttaccgag cggcagcagc agcggcacac aacaggcgca    31500
agagtcagag aaaagactga gctctaacct gtccgcccgc tctctgctca atatatagcc    31560
cagatctaca ctgacgtaaa ggccaaagtc taaaaatacc cgccaaatag tcacacacgc    31620
ccagcacacg cccagaaacc ggtgacacac tcaaaaaaat acgcgcactt cctcaaacgc    31680
ccaaactgcc gtcatttccg ggttcccacg ctacgtcatc aaaacacgac tttcaaattc    31740
cgtcgaccgt taaaaacgtc acccgccccg cccctaacgg tcgcccgtct ctcagccaat    31800
cagcgccccg catccccaaa ttcaaacacc tcatttgcat attaacgcgc accaaaagtt    31860
tgaggtatat tattgatgat g                                              31881

<210> SEQ ID NO 5
<211> LENGTH: 31110
<212> TYPE: DNA
<213> ORGANISM: Artificial Sequence
<220> FEATURE:
<223> OTHER INFORMATION: synthetic chimpanzee adenovirus serotype ChAd63
      with Ebola virus Sudan/Gulu codon optimized
      transmembrane envelope glycoprotein (GP) insert
      (ChAd63 GP Ebola S/G (PB/6611))
<220> FEATURE:
<221> NAME/KEY: CDS
<222> LOCATION: (1630)...(3660)
<223> OTHER INFORMATION: Ebola virus Sudan/Gulu codon optimized
      transmembrane envelope glycoprotein (GP) insert in ChAd63 GP Ebola
      S/G (PB/6611)
<220> FEATURE:
<221> NAME/KEY: CDS
<222> LOCATION: (14372)...(16000)
<223> OTHER INFORMATION: chimpanzee adenovirus serotype ChAd63 penton
<220> FEATURE:
<221> NAME/KEY: CDS
<222> LOCATION: (18767)...(21643)
<223> OTHER INFORMATION: chimpanzee adenovirus serotype ChAd63 hexon
<220> FEATURE:
<221> NAME/KEY: CDS
<222> LOCATION: (28171)...(29448)
<223> OTHER INFORMATION: chimpanzee adenovirus serotype ChAd63 fiber

<400> SEQUENCE: 5
catcatcaat aatatacctc aaacttttgg tgcgcgttaa tatgcaaatg aggtgtttga     60
atttggggat gcggggcgct gattggctga gagacgggcg accgttaggg gcggggcggg    120
tgacgttttg atgacgtggc cgtgaggcgg agccggtttg caagttctcg tgggaaaagt    180
gacgtcaaac gaggtgtggt ttgaacacgg aaatactcaa ttttcccgcg ctctctgaca    240
```

```
ggaaatgagg tgtttctggg cggatgcaag tgaaaacggg ccattttcgc gcgaaaactg      300
aatgaggaag tgaaaatctg agtaattccg cgtttatggc agggaggagt atttgccgag      360
ggccgagtag actttgaccg attacgtggg ggtttcgatt accgtatttt tcacctaaat      420
ttccgcgtac ggtgtcaaag tccgtgtttt ttacggatat ctccattgca tacgttgtat      480
ccatatcata atatgtacat ttatattggc tcatgtccaa cattaccgcc atgttgacat      540
tgattattga ctagttatta atagtaatca attacgggt cattagttca tagcccatat       600
atggagttcc gcgttacata acttacggta aatggcccgc ctggctgacc gcccaacgac      660
ccccgcccat tgacgtcaat aatgacgtat gttcccatag taacgccaat agggactttc      720
cattgacgtc aatgggtgga gtatttacgg taaactgccc acttggcagt acatcaagtg      780
tatcatatgc caagtacgcc ccctattgac gtcaatgacg gtaaatggcc cgcctggcat      840
tatgcccagt acatgacctt atgggacttt cctacttggc agtacatcta cgtattagtc      900
atcgctatta ccatggtgat gcggttttgg cagtacatca atgggcgtgg atagcggttt      960
gactcacggg gatttccaag tctccacccc attgacgtca atgggagttt gttttggaac      1020
caaaatcaac gggactttcc aaaatgtcgt aacaactccg ccccattgac gcaaatgggc      1080
ggtaggcgtg tacggtggga ggtctatata agcagagctc tccctatcag tgatagagat     1140
ctccctatca gtgatagaga tcgtcgacga gctcgtttag tgaaccgtca gatcgcctgg     1200
agacgccatc cacgctgttt tgacctccat agaagacacc gggaccgatc cagcctccat     1260
cggctcgcat ctctccttca cgcgcccgcc gccctacctg aggccgccat ccacgccggt     1320
tgagtcgcgt tctgccgcct cccgcctgtg gtgcctcctg aactgcgtcc gccgtctagg     1380
taagtttaaa gctcaggtcg agaccgggcc tttgtccggc gctcccttgg agcctaccta    1440
gactcagccg gctctccacg ctttgcctga ccctgcttgc tcaactctag ttaacggtgg     1500
agggcagtgt agtctgagca gtactcgttg ctgccgcgcg cgccaccaga cataatagct     1560
gacagactaa cagactgttc ctttccatgg gtcttttctg cagtcaccgt cgtcgacgat     1620
atcgccgcca tggagggcct gagcctgctg cagctgccca gggacaagtt caggaagagc     1680
agcttcttcg tgtgggtgat catcctgttc cagaaggcct tcagcatgcc cctgggcgtg     1740
gtgaccaaca gcaccctgga ggtgaccgag atcgaccagc tggtgtgcaa ggaccacctg     1800
gccagcaccg accagctgaa gagcgtgggc ctgaacctgg agggcagcgg cgtgagcacc     1860
gacatcccca cgccaccaa gaggtggggc ttcaggagcg gcgtgcctcc caaggtggtg      1920
agctacgagg ccggcgagtg ggccgagaac tgctacaacc tggagatcaa gaagcccgac     1980
ggcagcgagt gcctgcctcc tcctcctgac ggcgtgaggg cttccccag gtgcaggtac      2040 gtgcacaagg cccagggcac cggccctgc cccggcgact acgccttcca aggacggc       2100 gccttcttcc tgtacgacag gctggccagc accgtgatct acagggcgt gaacttcgcc      2160 gagggcgtga tcgccttcct gatcctggcc aagcccaagg agaccttcct gcagagccct     2220
cccatcaggg aggccgtgaa ctacaccgag aacaccagca gctactacgc caccagctat     2280
ctagagtacg agatcgagaa cttcggcgcc cagcacagca ccaccctgtt caagatcgac     2340
aacaacacct tcgtgaggct ggacaggccc cacacccctc agttcctgtt ccagctgaac     2400
gacaccatcc acctgcacca gcagctgagc aacaccaccg gcaggctgat ctggaccctg     2460
gacgccaaca tcaacgccga catcggcgag tgggccttct gggagaacaa gaagaacctg     2520
agcgagcagc tgaggggcga ggagctgagc ttcgaggccc tgagcctgaa cgagaccgag     2580
```

```
gacgacgacg ccgccagcag caggatcacc aagggcagga tcagcgacag ggccaccagg    2640
aagtacagcg acctggtgcc caagaacagc cccggcatgg tgcccctgca catccccgag    2700
ggcgagacca ccctgcccag ccagaacagc accgagggca ggagggtggg cgtgaacacc    2760
caggagacca tcaccgagac cgccgccacc atcatcggca ccaacggcaa ccacatgcag    2820
atcagcacca tcggcatcag gcccagcagc agccagatcc ccagcagcag ccccaccacc    2880
gcccctagcc ccgaggccca gaccccccacc acccacacca gcggacccag cgtgatggcc    2940
accgaggagc ccaccacccc tcccggcagc agccccggac ccaccaccga gcccctacc     3000 ctgaccaccc ctgagaacat caccaccgcc gtgaagaccg tgctgcccca ggagagcacc    3060
agcaacggcc tgatcaccag caccgtgacc ggcatcctgg gcagcctggg cctgaggaag    3120
aggagcagga ggcagaccaa caccaaggcc accggcaagt gcaaccccaa cctgcactac    3180
tggaccgccc aggagcagca caacgccgcc ggcatcgcct ggattcccta cttcggcccc    3240
ggcgccgagg gcatctacac cgagggcctg atgcacaacc agaacgccct ggtgtgcggc    3300
ctgaggcagc tggccaacga gaccacccag gccctgcagc tgttcctgag gccaccacc     3360 gagctgagga cctacaccat cctgaacagg aaggccatcg acttcctgct gaggaggtgg    3420
ggcggcacct gcaggattct gggccccgac tgctgcatcg agcccaccga ctggaccaag    3480
aacatcaccg acaagatcaa ccagatcatc cacgacttca tcgacaaccc tctgcccaac    3540
caggacaacg acgacaactg gtggaccggc tggcggcagt ggatacctgc cggcatcggc    3600
atcaccggca tcatcatcgc catcatcgct ctgctgtgcg tgtgcaagct gctgtgctga    3660
gaattcagat ctgctgtgcc ttctagttgc cagccatctg ttgtttgccc ctcccccgtg    3720
ccttccttga ccctggaagg tgccactccc actgtccttt cctaataaaa tgaggaaatt    3780
gcatcgcatt gtctgagtag gtgtcattct attctggggg gtggggtggg caggacagc     3840 aaggggagg attgggaaga caatagcagg catgctgggg atgcggtggg ctctagatat     3900
cagcgatcgc gtgagtagtg tttggggtg ggtgggagcc tgcatgatgg gcagaatgac     3960
taaaatctgt gttttctgt gtgttgcagc agcatgagcg gaagcgcctc ctttgaggga    4020
ggggtattca gcccttatct gacggggcgt ctcccctcct gggcgggagt gcgtcagaat    4080
gtgatgggat ccacggtgga cggccggccc gtgcagcccg cgaactcttc aaccctgacc    4140
tacgcgaccc tgagctcctc gtccgtggac gcagctgccg ccgcagctgc tgcttccgcc    4200
gccagcgccg tgcgcggaat ggccctgggc gccggctact acagctctct ggtggccaac    4260
tcgagttcca ccaataatcc cgccagcctg aacgaggaga gctgttgct gctgatggcc     4320 cagctcgagg ccctgaccca gcgcctgggc gagctgaccc agcaggtggc tcagctgcag    4380
gcggagacgc gggccgcggt tgccacggtg aaaaccaaat aaaaaatgaa tcaataaata    4440
aacggagacg gttgttgatt ttaacacaga gtcttgaatc tttatttgat tttcgcgcg     4500 cggtaggccc tggaccaccg gtctcgatca ttgagcaccc ggtggatctt ttccaggacc    4560
cggtagaggt gggcttggat gttgaggtac atgggcatga gccgtcccg ggggtggagg     4620 tagctccatt gcagggcctc gtgctcgggg gtggtgttgt aaatcaccca gtcatagcag    4680
gggcgcaggc cgtggtgctg cacgatgtct tgaggagga gactgatggc cacgggcagc     4740
cccttggtgt aggtgttgac gaacctattg agctgggagg gatgcatgcg ggggagatg     4800 agatgcatct tggcctggat cttgagattg gcgatgttcc cgcccagatc ccgccggggg    4860
ttcatgttgt gcaggaccac cagcacggtg tatccggtgc acttgggaa tttgtcatgc     4920 aacttggaag ggaaggcgtg aaagaatttg agacgccct tgtgaccgcc caggttttcc     4980
```

```
atgcactcat ccatgatgat ggcgatgggc ccgtgggcgg cggcctgggc aaagacgttt    5040
cgggggtcgg acacatcgta gttgtggtcc tgggtgagct cgtcataggc cattttaatg    5100
aatttggggc ggagggtacc cgactggggg acaaaggtgc cctcgatccc ggggcgtag     5160 ttcccctcgc agatctgcat ctcccaggcc ttgagctcgg aggggggat catgtccacc     5220 tgcggggcga tgaaaaaaac ggtttccggg gcggggaga tgagctgcgc cgaaagcagg     5280
ttccggagca gctgggactt gccgcagccg gtggggccgt agatgacccc gatgaccggc    5340
tgcaggtggt agttgaggga gagacagctg ccgtcctcgc ggaggagggg ggccacctcg    5400
ttcatcatct cgcgcacatg catgttctcg cgcacgagtt ccgccaggag cgctcgccc     5460 cccagcgaga ggagctcttg cagcgaggcg aagttttttca gcggcttgag cccgtcggcc    5520
atgggcattt tggagagggt ctgttgcaag agttccagac ggtcccagag ctcggtgatg    5580
tgctctaggg catctcgatc cagcagacct cctcgtttcg cgggttgggg cgactgcggg    5640
agtagggcac caggcgatgg gcgtccagcg aggccaggt ccggtccttc cagggtcgca     5700
gggtccgcgt cagcgtggtc tccgtcacgg tgaaggggtg cgcgccgggc tgggcgcttg    5760
cgagggtgcg cttcaggctc atccggctgg tcgagaaccg ctcccggtcg cgccctgcg     5820 cgtcggccag gtagcaattg agcatgagtt cgtagttgag cgcctcggcc gcgtggccct    5880
tggcgcggag cttacctttg gaagtgtgtc cgcagacggg acagaggagg acttgaggg     5940 cgtagagctt gggggcgagg aagacggact cgggggcgta ggcgtccgcg ccgcagctgg    6000
cgcagacggt ctcgcactcc acgagccagg tgaggtcggg gcggtcgggg tcaaaaacga    6060
ggtttcctcc gtgctttttg atgcgtttct tacctctggt ctccatgagc tcgtgtcccc    6120
gctgggtgac aaagaggctg tccgtgtccc cgtagaccga ctttatgggc cggtcctcga    6180
gcggggtgcc gcggtcctcg tcgtagagga accccgccca ctccgagacg aaggcccggg    6240
tccaggccag cacgaaggag gccacgtggg aggggtagcg gtcgttgtcc accagcgggt    6300
ccaccttctc cagggtatgc aagcacatgt cccccctcgtc cacatccagg aaggtgattg    6360
gcttgtaagt gtaggccacg tgaccggggg tccccggccgg gggggtataa aaggggggcgg  6420 gcccctgctc gtcctcactg tcttccggat cgctgtccag gagcgccagc tgttggggta    6480
ggtattccct ctcgaaggcg ggcatgacct cggcactcag gttgtcagtt tctagaaacg    6540
aggaggattt gatattgacg gtgccgttgg agacgccttt catgagcccc tcgtccatct    6600
ggtcagaaaa gacgatcttt ttgttgtcga gcttggtggc gaaggagccg tagagggcgt    6660
tggagagcag cttggcgatg gagcgcatgg tctggttctt ttccttgtcg gcgcgctcct    6720
tggcggcgat gttgagctgc acgtactcgc gcgccacgca cttccattcg gggaagacgg    6780
tggtgagctc gtcgggcacg attctgaccc gccagccgcg gttgtgcagg gtgatgaggt    6840
ccacgctggt ggccacctcg ccgcgcaggg gctcgttggt ccagcagagg cgcccgccct    6900
tgcgcgagca aaggggggc agcgggtcca gcatgagctc gtcgggggg tcggcgtcca     6960 cggtgaagat gccgggcagg agctcgggt cgaagtagct gatgcaggtg cccagatcgt    7020
ccagacttgc ttgccagtcg cgcacggcca gcgcgcgctc gtaggggctg aggggcgtgc    7080
cccagggcat ggggtgcgtg agcgcggagg cgtacatgcc gcagatgtcg tagacgtaga    7140
ggggctcctg gaggacgccg atgtaggtgg ggtagcagcg ccccccgcgg atgctggcgc    7200
gcacgtagtc gtacagctcg tgcgagggcg cgaggagccc cgtgccgaga ttggagcgct    7260
gcggcttttc ggcgcggtag acgatctggc ggaagatggc gtgggagttg gaggagatgg    7320
```

```
tgggcctctg gaagatgttg aagtgggcat ggggcagtcc gaccgagtcc ctgatgaagt    7380
gggcgtagga gtcctgcagc ttggcgacga gctcggcggt gacgaggacg tccagggcgc    7440
agtagtcgag ggtctcttgg atgatgtcgt acttgagctg gcccttctgc ttccacagct    7500
cgcggttgag aaggaactct cgcggtcct tccagtactc ttcgaggggg aacccgtcct    7560
gatcggcacg gtaagagccc accatgtaga actggttgac ggccttgtag gcgcagcagc    7620
ccttctccac ggggagggcg taagcttgcg cggccttgcg cagggaggtg tgggtgaggg    7680
cgaaggtgtc gcgcaccatg actttgagga actggtgctt gaagtcgagg tcgtcgcagc    7740
cgccctgctc ccagagctgg aagtccgtgc gcttcttgta ggcggggttg ggcaaagcga    7800
aagtaacatc gttgaagagg atcttgcccg cgcggggcat gaagttgcga gtgatgcgga    7860
aaggctgggg cacctcggcc cggttgttga tgacctgggc ggcgaggacg atctcgtcga    7920
agccgttgat gttgtgcccg acgatgtaga gttccacgaa tcgcgggcgg cccttgacgt    7980
ggggcagctt cttgagctcg tcgtaggtga gctcggcggg gtcgctgagc ccgtgctgct    8040
cgagggccca gtcggcgacg tgggggttgg cgctgaggaa ggaagtccag agatccacgg    8100
ccagggcggt ctgcaagcgg tcccggtact gacggaactg ctggcccacg gccattttt    8160
cggggtgac gcagtagaag gtgcgggggt cgccgtgcca gcggtccac ttgagctgga    8220
gggcgaggtc gtgggcgagc tcgacgagcg gcgggtcccc ggagagtttc atgaccagca    8280
tgaaggggac gagctgcttg ccgaaggacc ccatccaggt gtaggtttcc acatcgtagg    8340
tgaggaagag cctttcggtg cgaggatgcg agccgatggg gaagaactgg atctcctgcc    8400
accagttgga ggaatggctg ttgatgtgat ggaagtagaa atgccgacgg cgcgccgagc    8460
actcgtgctt gtgtttatac aagcgtccgc agtgctcgca acgctgcacg ggatgcacgt    8520
gctgcacgag ctgtacctgg gttcctttga cgaggaattt cagtgggcag tggagcgctg    8580
gcggctgcat ctggtgctgt actacgtcct ggccatcggc gtggccatcg tctgcctcga    8640
tggtggtcat gctgacgagc ccgcgcggga ggcaggtcca gacctcggct cggacgggtc    8700
ggagagcgag gacgagggcg cgcaggccgg agctgtccag ggtcctgaga cgctgcggag    8760
tcaggtcagt gggcagcggc ggcgcgcggt tgacttgcag gagcttttcc agggcgcgcg    8820
ggaggtccag atggtacttg atctccacgg cgccgttggt ggcgacgtcc acggcttgca    8880
gggtcccgtg ccctggggc gccaccaccg tgccccgttt cttcttgggc ggcggcggct    8940
ccatgcttag aagcggcggc gaggacgcgc gccgggcggc aggggcggct cggggcccgg    9000
aggcaggggc ggcaggggca cgtcggcgcc gcgcgcgggc aggttctggt actgcgcccg    9060
gagaagactg gcgtgagcga cgacgcgacg gttgacgtcc tggatctgac gcctctgggt    9120
gaaggccacg ggaccgtgac gtttgaacct gaaagagagt tcgacagaat caatctcggt    9180
atcgttgacg gcggcctgcc gcaggatctc ttgcacgtcg cccgagttgt cctggtaggc    9240
gatctcggtc atgaactgct cgatctcctc ctcctgaagg tctccgcggc cggcgcgctc    9300
gacggtggcc gcgaggtcgt tggagatgcg gcccatgagc tgcgagaagg cgttcatgcc    9360
ggcctcgttc cagacgcggc tgtagaccac ggctccgtcg gggtcgcgcg cgcgcatgac    9420
cacctgggcg aggttgagct cgacgtggcg cgtgaagacc gcgtagttgc agaggcgctg    9480
gtagaggtag ttgagcgtgg tggcgatgtg ctcggtgacg aagaagtaca tgatccagcg    9540
gcggagcggc atctcgctga cgtcgcccag ggcttccaag cgctccatgg cctcgtagaa    9600
gtccacggcg aagttgaaaa actgggagtt gcgcgccgag acggtcaact cctcctccag    9660
aagacggatg agctcggcga tggtggcgcg cacctcgcgc tcgaaggccc cggggggctc    9720
```

```
ctcttccatt tcctcctctt cctcctccac taacatctct tctacttcct cctcaggagg    9780
cggcggcggg ggaggggccc tgcgtcgccg gcggcgcacg ggcagacggt cgatgaagcg    9840
ctcgatggtc tccccgcgcc ggcgacgcat ggtctcggtg acggcgcgcc cgtcctcgcg    9900
gggccgcagc gtgaagacgc cgccgcgcat ctccaggtgg ccgccggggg ggtctccgtt    9960
gggcagggag agggcgctga cgatgcatct tatcaattga cccgtaggga ctccgcgcaa   10020
ggacctgagc gtctcgagat ccacgggatc cgaaaaccgc tgaacgaagg cttcgagcca   10080
gtcgcagtcg caaggtaggc tgagcccggt ttcttgttct tcgggtattt ggtcgggagg   10140
cgggcgggcg atgctgctgg tgatgaagtt gaagtaggcg gtcctgagac ggcggatggt   10200
ggcgaggagc accaggtcct tgggcccggc ttgctggatg cgcagacggt cggccatgcc   10260
ccaggcgtgg tcctgacacc tggcgaggtc cttgtagtag tcctgcatga gccgctccac   10320
gggcacctcc tcctcgcccg cgcggccgtg catgcgcgtg agcccgaacc cgcgctgcgg   10380
ctggacgagc gccaggtcgg cgacgacgcg ctcggcgagg atggcctgct ggatctgggt   10440
gagggtggtc tggaagtcgt cgaagtcgac gaagcggtgg taggctccgg tgttgatggt   10500
gtaggagcag ttggccatga cggaccagtt gacggtctgg tggccggggc gcacgagctc   10560
gtggtacttg aggcgcgagt aggcgcgcgt gtcgaagatg tagtcgttgc aggtgcgcac   10620
gaggtactgg tatccgacga ggaagtgcgg cggcggctgg cggtagagcg gccatcgctc   10680
ggtggcgggg gcgccgggcg cgaggtcctc gagcatgagg cggtggtagc cgtagatgta   10740
cctggacatc caggtgatgc cggcggcggt ggtggaggcg cgcgggaact cgcggacgcg   10800
gttccagatg ttgcgcagcg gcaggaagta gttcatggtg gccgcggtct ggcccgtgag   10860
gcgcgcgcag tcgtggatgc tctagacata cgggcaaaaa cgaaagcggt cagcggctcg   10920
actccgtggc ctggaggcta agcgaacggg ttgggctgcg cgtgtacccc ggttcgaatc   10980
tcgaatcagg ctggagccgc agctaacgtg gtactggcac tcccgtctcg acccaagcct   11040
gctaacgaaa cctccaggat acggaggcgg gtcgtttttt ggccttggtc gctggtcatg   11100
aaaaactagt aagcgcggaa agcggccgcc cgcgatggct cgctgccgta gtctggagaa   11160
agaatcgcca gggttgcgtt gcggtgtgcc ccggttcgag cctcagcgct cggcgccggc   11220
cggattccgc ggctaacgtg ggcgtggctg ccccgtcgtt tccaagaccc cttagccagc   11280
cgacttctcc agttacggag cgagcccctc tttttttctt gtgttttttgc cagatgcatc   11340
ccgtactgcg gcagatgcgc ccccaccctc caccacaacc gccccctaccg cagcagcagc   11400
aacagccggc gcttctgccc ccgccccagc agcagcagcc agccactacc gcggcggccg   11460
ccgtgagcgg agccggcgtt cagtatgacc tggccttgga agagggcgag gggctggcgc   11520
ggctgggggc gtcgtcgccg gagcggcacc cgcgcgtgca gatgaaaagg gacgctcgcg   11580
aggcctacgt gcccaagcag aacctgttca gagacaggag cggcgaggag cccgaggaga   11640
tgcgcgcctc ccgcttccac gcggggcggg agctgcggcg cggcctggac cgaaagcggg   11700
tgctgaggga cgaggatttc gaggcggacg agctgacggg gatcagcccc gcgcgcgcgc   11760
acgtggccgc ggccaacctg gtcacggcgt acgagcagac cgtgaaggag gagagcaact   11820
tccaaaaatc cttcaacaac cacgtgcgca cgctgatcgc gcgcgaggag gtgaccctgg   11880
gcctgatgca cctgtgggac ctgctggagg ccatcgtgca gaaccccacg agcaagccgc   11940
tgacggcgca gctgtttctg gtggtgcagc acagtcggga caacgagacg ttcagggagg   12000
cgctgctgaa tatcaccgag cccgagggcc gctggctcct ggacctggtg aacattctgc   12060
```

```
agagcatcgt ggtgcaggag cgcgggctgc cgctgtccga gaagctggcg gccatcaact    12120
tctcggtgct gagcctgggc aagtactacg ctaggaagat ctacaagacc ccgtacgtgc    12180
ccatagacaa ggaggtgaag atcgatgggt tttacatgcg catgaccctg aaagtgctga    12240
ccctgagcga cgatctgggg gtgtaccgca acgacaggat gcaccgcgcg gtgagcgcca    12300
gccgccggcg cgagctgagc gaccaggagc tgatgcacag cctgcagcgg gccctgaccg    12360
gggccgggac cgaggggggag agctactttg acatgggcgc ggacctgcgc tggcagccca    12420
gccgccgggc cttggaagct gccggcggcg tgccctacgt ggaggaggtg gacgatgagg    12480
aggaggaggg cgagtacctg gaagactgat ggcgcgaccg tattttttgct agatgcagca    12540
acagccaccg ccgccgcctc ctgatcccgc gatgcgggcg gcgctgcaga gccagccgtc    12600
cggcattaac tcctcggacg attggaccca ggccatgcaa cgcatcatgg cgctgacgac    12660
ccgcaatccc gaagccttta gacagcagcc tcaggccaac cggctctcgg ccatcctgga    12720
ggccgtggtg ccctcgcgct cgaaccccac gcacgagaag gtgctggcca tcgtgaacgc    12780
gctggtggag aacaaggcca tccgcggcga cgaggccggg ctggtgtaca acgcgctgct    12840
ggagcgcgtg gcccgctaca acagcaccaa cgtgcagacg aacctggacc gcatggtgac    12900
cgacgtgcgc gaggcggtgt cgcagcgcga gcggttccac cgcgagtcga acctgggctc    12960
catggtggcg ctgaacgcct tcctgagcac gcagcccgcc aacgtgcccc ggggccagga    13020
ggactacacc aacttcatca gcgcgctgcg gctgatggtg gccgaggtgc cccagagcga    13080
ggtgtaccag tcggggccgg actacttctt ccagaccagt cgccagggct gcagaccgt     13140
gaacctgagc caggctttca agaacttgca gggactgtgg ggcgtgcagg ccccggtcgg    13200
ggaccgcgcg acggtgtcga gcctgctgac gccgaactcg cgcctgctgc tgctgctggt    13260
ggcgcccttc acggacagcg gcagcgtgag ccgcgactcg tacctgggct acctgcttaa    13320
cctgtaccgc gaggccatcg ggcaggcgca cgtggacgag cagacctacc aggagatcac    13380
ccacgtgagc cgcgcgctgg gccaggagga cccgggcaac ctggaggcca ccctgaactt    13440
cctgctgacc aaccggtcgc agaagatccc gccccagtac gcgctgagca ccgaggagga    13500
gcgcatcctg cgctacgtgc agcagagcgt ggggctgttc ttgatgcagg aggggggccac    13560
gcccagcgcc gcgctcgaca tgaccgcgcg caacatggag cccagcatgt acgcccgcaa    13620
ccgcccgttc atcaataagc tgatggacta cttgcatcgg gcggccgcca tgaactcgga    13680
ctactttacc aacgccatct tgaacccgca ctggctcccg ccgcccgggt tctacacggg    13740
cgagtacgac atgcccgacc ccaacgacgg gttcctgtgg gacgacgtgg acagcagcgt    13800
gttctcgccg cggcccacca ccaccaccgt gtggaagaaa gagggcgggg accggcggcc    13860
gtcctcggcg ctgtccggtc gcgcgggtgc tgccgcggcg gtgcccgagg ctgccagccc    13920
cttcccgagc ctgcccttt cgctgaacag cgtgcgcagc agcgagctgg gtcggctgac    13980
gcggccgcgc ctgctgggcg aggaggagta cctgaacgac tccttgttga agcccgagcg    14040
cgagaagaac ttccccaata acgggataga gagcctggtg gacaagatga gccgctggaa    14100
gacgtacgcg cacgagcaca gggacgagcc ccgagctagc agcgcaggca cccgtagacg    14160
ccagcggcac gacaggcagc ggggactggt gtggacgat gaggattccg ccgacgcag    14220
cagcgtgttg gacttgggtg ggagtggtgg tggtaacccg ttcgctcacc tgccgccccg    14280
tatcgggcgc ctgatgtaag aatctgaaaa aataaaagac ggtactcacc aaggccatgg    14340
cgaccagcgt gcgttcttct ctgttgtttg tagtagtatg atgaggcgcg tgtacccgga    14400
gggtcctcct ccctcgtacg agagcgtgat gcagcaggcg gtggcggcgg cgatgcagcc    14460
```

```
cccgctggag gcgccttacg tgcccccgcg gtacctggcg cctacggagg ggcggaacag    14520
cattcgttac tcggagctgg caccttgta cgataccacc cggttgtacc tggtggacaa    14580
caagtcggcg gacatcgcct cgctgaacta ccagaacgac cacagcaact tcctgaccac    14640
cgtggtgcag aacaacgatt tcaccccac ggaggccagc acccagacca tcaactttga    14700
cgagcgctcg cggtggggcg gccagctgaa aaccatcatg cacaccaaca tgcccaacgt    14760
gaacgagttc atgtacagca acaagttcaa ggcgcgggtg atggtctcgc gcaagacccc    14820
caacggggtc acgtagggg atgattatga tggtagtcag gacgagctga cctacgagtg    14880
ggtggagttt gagctgcccg agggcaactt ctcggtgacc atgaccatcg atctgatgaa    14940
caacgccatc atcgacaact acttggcggt ggggcggcag aacggggtgc tggagagcga    15000
catcggcgtg aagttcgaca cgcgcaactt ccggctgggc tgggaccccg tgaccgagct    15060
ggtgatgccg ggcgtgtaca ccaacgaggc cttccacccc gacatcgtcc tgctgcccgg    15120
ctgcggcgtg gacttcaccg agagccgcct cagcaacctg ctgggcatcc gcaagcggca    15180
gcccttccag gagggcttcc agatcctgta cgaggacctg gagggggca acatccccgc    15240
gctcttggat gtcgaagcct atgaagaaag taaggaaaaa gcagaggctg aggcaactac    15300
agccgtggct accgccgcga ctgtggcaga tgccactgtc accaggggcg atacattcgc    15360
cacccaggcg gaggaagcag ccgccctagc ggcgaccgat gatagtgaaa gtaagatagt    15420
catcaagccg gtggagaagg acagcaagaa caggagctac aacgttctac cggatggaaa    15480
gaacaccgcc taccgcagct ggtacctggc ctacaactac ggcgaccccg agaagggcgt    15540
gcgctcctgg acgctgctca ccacctcgga cgtcacctgc ggcgtggagc aagtctactg    15600
gtcgctgccc gacatgatgc aagacccggt caccttccgc tccacgcgac aagttagcaa    15660
ctacccggtg gtgggcgccg agctcctgcc cgtctactcc aagagcttct tcaacgagca    15720
ggccgtctac tcgcagcagc tgcgtgcctt cacctcgctc acgcacgtct tcaaccgctt    15780
ccccgagaac cagatcctcg tccgcccgcc cgcgcccacc attaccaccg tcagtgaaaa    15840
cgttcctgct ctcacagatc acgggaccct gccgctgcgc agcagtatcc ggggagtcca    15900
gcgcgtgacc gtcactgacg ccagacgccg cacctgcccc tacgtctaca aggccctggg    15960
cgtagtcgcg ccgcgcgtcc tctcgagccg caccttctaa aaaatgtcca ttctcatctc    16020
gcccagtaat aacaccggtt ggggcctgcg cgcgcccagc aagatgtacg gaggcgctcg    16080
ccaacgctcc acgcaacacc ccgtgcgcgt gcgcgggcac ttccgcgctc cctggggcgc    16140
cctcaagggc gcgtgcgct cgcgcaccac cgtcgacgac gtgatcgacc aggtggtggc    16200
cgacgcgcgc aactacacgc ccgccgccgc gcccgcctcc accgtggacg ccgtcatcga    16260
cagcgtggtg gccgacgcgc gccggtacgc ccgcgccaag agccggcggc ggcgcatcgc    16320
ccggcggcac cggagcaccc ccgccatgcg cgcggcgcga gccttgctgc gcagggccag    16380
gcgcacggga cgcagggcca tgctcagggc ggccagacgc gcggcctccg gcagcagcag    16440
cgccggcagg acccgcagac gcgcggccac ggcggcggcg gcggccatcg ccagcatgtc    16500
ccgcccgcgg cgcggcaacg tgtactgggt gcgcgacgcc gccaccggtg tgcgcgtgcc    16560
cgtgcgcacc cgcccccctc gcacttgaag atgctgactt cgcgatgttg atgtgtccca    16620
gcggcgagga ggatgtccaa gcgcaaatac aaggaagaga tgctccaggt catcgcgcct    16680
gagatctacg gccccgcggc ggcggtgaag gaggaaagaa agccccgcaa actgaagcgg    16740
gtcaaaaagg acaaaaagga ggaggaagat gacggactgg tggagtttgt gcgcgagttc    16800
```

```
gcccccggc   ggcgcgtgca   gtggcgcggg   cggaaagtga   aaccggtgct   gcggcccggc    16860
accacggtgg   tcttcacgcc   cggcgagcgt   tccggctccg   cctccaagcg   ctcctacgac    16920
gaggtgtacg   gggacgagga   catcctcgag   caggcggtcg   agcgtctggg   cgagtttgct    16980
tacggcaagc   gcagccgccc   cgcgcccttg   aaagaggagg   cggtgtccat   cccgctggac    17040
cacggcaacc   ccacgccgag   cctgaagccg   gtgaccctgc   agcaggtgct   gccgagcgcg    17100
gcgccgcgcc   ggggcttcaa   gcgcgagggc   ggcgaggatc   tgtacccgac   catgcagctg    17160
atggtgccca   agcgccagaa   gctggaggac   gtgctggagc   acatgaaggt   ggaccccgag    17220
gtgcagcccg   aggtcaaggt   gcggcccatc   aagcaggtgg   ccccgggcct   gggcgtgcag    17280
accgtggaca   tcaagatccc   cacggagccc   atggaaacgc   agaccgagcc   cgtgaagccc    17340
agcaccagca   ccatggaggt   gcagacggat   ccctggatgc   cagcggcttc   caccaccacc    17400
actcgccgaa   gacgcaagta   cggcgcggcc   agcctgctga   tgcccaacta   cgcgctgcat    17460
ccttccatca   tccccacgcc   gggctaccgc   ggcacgcgct   tctaccgcgg   ctacaccagc    17520
agccgccgcc   gcaagaccac   cacccgccgc   cgtcgtcgca   gccgccgcag   cagcaccgcg    17580
acttccgcct   tggtgcggag   agtgtatcgc   agcgggcgcg   agcctctgac   cctgccgcgc    17640
gcgcgctacc   acccgagcat   cgccatttaa   ctaccgcctc   ctacttgcag   atatggccct    17700
cacatgccgc   ctccgcgtcc   ccattacggg   ctaccgagga   agaaagccgc   gccgtagaag    17760
gctgacgggg   aacgggctgc   gtcgccatca   ccaccggcgg   cggcgcgcca   tcagcaagcg    17820
gttgggggga   ggcttcctgc   ccgcgctgat   ccccatcatc   gccgcggcga   tcggggcgat    17880
ccccggcata   gcttccgtgg   cggtgcaggc   ctctcagcgc   cactgagaca   caaaaaagca    17940
tggatttgta   ataaaaaaat   ggactgacgc   tcctggtcct   gtgatgtgtg   ttttagatg     18000 gaagacatca   attttccgtc   cctggcaccg   cgacacggca   cgcggccgtt   tatgggcacc    18060
tggagcgaca   tcggcaacag   ccaactgaac   gggggcgcct   tcaattggag   cagtctctgg    18120
agcgggctta   agaatttcgg   gtccacgctc   aaaacctatg   caacaaggc   gtggaacagc     18180 agcacagggc   aggcgctgag   ggaaaagctg   aaagagcaga   acttccagca   gaaggtggtc    18240
gatggcctgg   cctcgggcat   caacggggtg   gtggacctgg   ccaaccaggc   cgtgcagaaa    18300
cagatcaaca   gccgcctgga   cgcggtcccg   cccgcggggt   ccgtggagat   gccccaggtg    18360
gaggaggagc   tgcctcccct   ggacaagcgc   ggcgacaagc   gaccgcgtcc   cgacgcggag    18420
gagacgctgc   tgacgcacac   ggacgagccg   cccccgtacg   aggaggcggt   gaaactgggt    18480
ctgcccacca   cgcggcccgt   ggcgcctctg   ccaccggggg   tgctgaaacc   cagcagcagc    18540
agccagcccg   cgaccctgga   cttgcctccg   cctgcttccc   gcccctccac   agtggctaag    18600
cccctgccgc   cggtggccgt   cgcgtcgcgc   gcccccgag   gccgccccca   ggcgaactgg     18660
cagagcactc   tgaacagcat   cgtgggtctg   ggagtgcaga   gtgtgaagcg   ccgccgctgc    18720
tattaaaaga   cactgtagcg   cttaacttgc   ttgtctgtgt   gtgtatatgt   atgtccgccg    18780
accagaagga   ggaagaggcg   cgtcgccgag   ttgcaagatg   gccacccat   cgatgctgcc     18840 ccagtgggcg   tacatgcaca   tcgccggaca   ggacgcttcg   gagtacctga   gtccgggtct    18900
ggtgcagttc   gcccgcgcca   cagacaccta   cttcagtctg   gggaacaagt   ttaggaaccc    18960
cacggtggcg   cccacgcacg   atgtgaccac   cgaccgcagc   cagcggctga   cgctgcgctt    19020
cgtgcccgtg   gaccgcgagg   acaacaccta   ctcgtacaaa   gtgcgctaca   cgctggccgt    19080
gggcgacaac   cgcgtgctgg   acatggccag   cacctacttt   gacatccgcg   gcgtgctgga    19140
tcggggcccc   agcttcaaac   cctactccgg   caccgcctac   aacagcctag   ctcccaaggg    19200
```

```
agcgcccaac acctcacagt ggaaggattc cgacagcaaa atgcatactt ttggagttgc   19260
tgccatgccc ggtgttgttg gtaaaaaaat agaagccgat ggtctgccta ttggaataga   19320
ttcatcctct ggaactgaca ccataattta tgctgataaa actttccaac cagagccaca   19380
ggttggaagt gacagttggg tcgacaccaa tggtgcagag gaaaaatatg gaggtagagc   19440
tcttaaggac actacaaaca tgaagccctg ctacggttct tttgccaggc ctaccaacaa   19500
agaaggtgga caggctaaca taaaagattc tgaaactgcc agcactactc ctaactatga   19560
tatagatttg gcattctttg acagcaaaaa tattgcagct aactacgatc cagatattgt   19620
aatgtacaca gaaaatgttg agttgcaaac tccagatact catattgtgt ttaagccagg   19680
aacttcagat gaaagttcag aagccaattt gggccagcag gccatgccca acagacccaa   19740
ctacatcggt tcagagaca actttatcgg gctcatgtac tacaacagca ctggcaatat   19800
gggtgtactg gctggtcagg cctcccagct aaatgctgtg gtggacttgc aggacagaaa   19860
caccgaactg tcctaccagc tcttgcttga ctctctgggt gacagaacca ggtatttcag   19920
tatgtggaat caggcggtgg acagctatga ccccgatgtg cgcattattg aaaatcacgg   19980
tgtggaggat gaactcccca attattgctt ccctttgaat ggtgtaggct ttacagatac   20040
ttaccagggt gttaaagtta agacagatac agccgctact ggtaccaatg gaacgcagtg   20100
ggacaaagat gataccacag tcagcactgc caatgagatc cactcaggca atcctttcgc   20160
catggagatc aacatccagg ccaacctgtg gcggaacttc ctctacgcga acgtggcgct   20220
gtacctgccc gactcctaca gtacacgcc ggccaacatc acgctgccga ccaacaccaa   20280
cacctacgat tacatgaacg ccgcgtggt ggcgccctcg ctggtggacg cctacatcaa   20340
catcggggcg cgctggtcgc tggacccat ggacaacgtc aacccttca accaccaccg   20400
caacgcgggc ctgcgctacc gctccatgct cctgggcaac gggcgctacg tgcccttcca   20460
catccaggtg ccccaaaagt ttttcgccat caagagcctc ctgctcctgc ccgggtccta   20520
cacctacgag tggaacttcc gcaaggacgt caacatgatc ctgcagagct ccctcggcaa   20580
cgacctgcgc acggacgggg cctccatcgc cttcaccagc atcaacctct acgccacctt   20640
cttccccatg gcgcacaaca ccgcctccac gctcgaggcc atgctgcgca acgacaccaa   20700
cgaccagtcc ttcaacgact acctctcggc ggccaacatg ctctacccca tcccggccaa   20760
cgccaccaac gtgcccatct ccatcccctc gcgcaactgg gccgccttcc gcggatggtc   20820
cttcacgcgc ctcaagaccc gcgagacgcc ctcgctcggc tccgggttcg accctactt   20880
cgtctactcg ggctccatcc cctacctcga cggcaccttc tacctcaacc acaccttcaa   20940
gaaggtctcc atcaccttcg actcctccgt cagctggccc ggcaacgacc gctcctgac   21000
gcccaacgag ttcgaaatca gcgcaccgt cgacggagag ggatacaacg tggccccagtg   21060
caacatgacc aaggactggt tcctggtcca gatgctggcc cactacaaca tcggctacca   21120
gggcttctac gtgcccgagg gctacaagga ccgcatgtac tccttcttcc gcaacttcca   21180
gcccatgagc cgccaggtcg tggacgaggt caactacaag gactaccagg ccgtcaccct   21240
ggcctaccag cacaacaact cgggcttcgt cggctacctc gcgccaccga tgcgccagggs  21300
ccagccctac ccgccaact accccttaccc gctcatcggc aagagcgccg tcgccagcgt   21360
cacccagaaa aagttcctct gcgaccgggt catgtggcgc atccccttct ccagcaactt   21420
catgtccatg ggcgcgctca ccgacctcgg ccagaacatg ctctacgcca actccgccca   21480
cgcgctagac atgaatttcg aagtcgaccc catggatgag tccacccttc tctatgttgt   21540
```

```
cttcgaagtc ttcgacgtcg tccgagtgca ccagccccac cgcggcgtca tcgaggccgt    21600
ctacctgcgc acgcccttct cggccggcaa cgccaccacc taaagccccg ctcttgcttc    21660
ttgcaagatg acggcctgtg gctccggcga gcaggagctc agggccatcc tccgcgacct    21720
gggctgcggg ccctgcttcc tgggcaccett cgacaagcgc ttcccgggat tcatggcccc    21780
gcacaagctg gcctgcgcca tcgtcaacac ggccggccgc gagaccgggg gcgagcactg    21840
gctggccttc gcctggaacc cgcgctccca cacctgctac ctcttcgacc ccttcgggtt    21900
ctcggacgag cgcctcaagc agatctacca gttcgagtac gagggcctgc tgcgccgcag    21960
cgccctggcc accgaggacc gctgcatcac cctggaaaag tccacccaga ccgtgcaggg    22020
tccgcgctcg gccgcctgcg ggctcttctg ctgcatgttc ctgcacgcct tcgtgcactg    22080
gcccgaccgc cccatggaca gaaccccac catgaacttg ctgacggggg tgcccaacgg    22140
catgctccag tcgccccagg tggaacccac cctgcgccgc aaccaggagg cgctctaccg    22200
cttcctcaac gcccactccg cctactttcg ctcccaccgc gcgcgcatcg agaaggccac    22260
cgccttcgac cgcatgaatc aagacatgta aactgtgtgt atgtgaatgc tttattcatc    22320
ataataaaca gcacatgttt atgccacctt ctctgaggct ctgactttat ttagaaatcg    22380
aaggggttct gccggctctc ggcgtgcccc gcgggcaggg atacgttgcg gaactggtac    22440
ttgggcagcc acttgaactc ggggatcagc agcttcggca cggggaggtc ggggaacgag    22500
tcgctccaca gcttgcgcgt gagttgcagg gcgcccagca ggtcgggcgc ggagatcttg    22560
aaatcgcagt tgggacccgc gttctgcgcg cgagagttgc ggtacacggg gttgcagcac    22620
tggaacacca tcagggccgg gtgcttcacg ctcgccagca ccgtcgcgtc ggtgatgccc    22680
tccacgtcca gatcctcggc gttggccatc ccgaaggggg tcatcttgca ggtctgccgc    22740
cccatgctgg gcacgcagcc gggcttgtgg ttgcaatcgc agtgcagggg gatcagcatc    22800
atctgagcct gctcggagct catgcccggg tacatggcct tcatgaaagc ctccagctgg    22860
cggaaggcct gctgcgcctt gccgcccteg gtgaagaaga ccccacagga cttgctagag    22920
aactggttgg tggcgcagcc cgcgtcgtgc acgcagcagc gcgcgtcgtt gttggccagc    22980
tgcaccacgc tgcgccccca gcggttctgg gtgatcttgg cccggtcggg gttctccttc    23040
agcgcgcgct gcccgttctc gctcgccaca tccatctcga tcgtgtgctc cttctggatc    23100
atcacggtcc cgtgcaggca ccgcagcttg ccctcggcct cggtgcaccc gtgcagccac    23160
agcgcgcagc cggtgcactc ccagttcttg tgggcgatct gggagtgcga gtgcacgaag    23220
ccctgcagga agcggcccat catcgtggtc agggtcttgt tgctggtgaa ggtcagcggg    23280
atgccgcggt gctcctcgtt cacatacagg tggcagatgc ggcggtacac ctcgccctgc    23340
tcgggcatca gctggaaggc ggacttcagg tcgctctcca cgcggtaccg ctccatcagc    23400
agcgtcatca cttccatgcc cttctcccag gccgaaacga tcggcaggct caggggttc    23460 ttcaccgtca tcttagtcgc cgccgccgaa gtcagggggt cgttctcgtc cagggtctca    23520
aacactcgct tgccgtcctt ctcggtgatg cgcacggggg aaagctgaa gcccacggcc    23580 gccagctcct cctcggcctg ccttcgtcc tcgctgtcct ggctgatgtc ttgcaaaggc    23640
acatgcttgg tcttgcgggg tttctttttg ggcggcagag gcggcggcgg agacgtgctg    23700
ggcgagcgcg agttctcgct caccacgact atttcttctt cttggccgtc gtccgagacc    23760
acgcggcggt aggcatgcct cttctggggc agaggcggag gcgacgggct ctcgcggttc    23820
ggcgggcggc tggcagagcc ccttccgcgt tcggggggtgc gctcctggcg gcgctgctct    23880
gactgacttc ctccgcggcc ggccattgtg ttctcctagg gagcaacaag catggagact    23940
```

-continued

```
cagccatcgt cgccaacatc gccatctgcc cccgccgccg acgagaacca gcagcagcag   24000
aatgaaagct taaccgcccc gccgcccagc cccacctccg acgccgccgc ggccccagac   24060
atgcaagaga tggaggaatc catcgagatt gacctgggct acgtgacgcc cgcggagcac   24120
gaggaggagc tggcagcgcg cttttcagcc ccggaagaga accaccaaga gcagccgag    24180 caggaagcag agagcgagca gcagcaggct gggctcgagc atggcgacta cctgagcggg   24240
gcagaggacg tgctcatcaa gcatctggcc cgccaaagca tcatcgtcaa ggacgcgctg   24300
ctcgaccgcg ccgaggtgcc cctcagcgtg gcggagctca gccgcgccta cgagcgcaac   24360
ctcttctcgc cgcgcgtgcc ccccaagcgc cagcccaacg gcacctgcga gcccaacccg   24420
cgcctcaact tctacccggt cttcgcggtg cccgaggccc tggccaccta ccacctcttt   24480
ttcaagaacc aaaggatccc cgtctcctgc gcgccaacc gcacccgcgc cgacgccctg    24540
ctcaacctgg gtcccggcgc ccgcctacct gatatcacct ccttggaaga ggttcccaag   24600
atcttcgagg gtctgggcag cgacgagact cgggccgcga acgctctgca aggaagcgga   24660
gaggagcatg agcaccacag cgccctggtg gagttggaag gcgacaacgc gcgcctggcg   24720
gtgctcaagc gcacggtcga gctgacccac ttcgcctacc cggcgctcaa cctgcccccc   24780
aaggtcatga gcgccgtcat ggaccaggtg ctcatcaagc gcgcctcgcc cctctcagag   24840
gaggagatgc aggaccccga gagctcggac gagggcaagc ccgtggtcag cgacgagcag   24900
ctggcgcgct ggctgggagc gagcagcacc ccccagagcc tggaagagcg gcgcaagctc   24960
atgatggccg tggtcctggt gaccgtggag ctggagtgtc tgcgccgctt cttcgccgac   25020
gcggagaccc tgcgcaaggt cgaggagaac ctgcactacc tcttcaggca cgggttcgtg   25080
cgccaggcct gcaagatctc caacgtggag ctgaccaacc tggtctccta catgggcatc   25140
ctgcacgaga accgcctggg gcagaacgtg ctgcacacca ccctgcgcgg ggaggccgc    25200 cgcgactaca tccgcgactg cgtctacctg tacctctgcc acacctggca gacgggcatg   25260
ggcgtgtggc agcagtgcct ggaggagcag aacctgaaag agctctgcaa gctcctgcag   25320
aagaacctca aggccctgtg gacccgggttc gacgagcgca ccaccgcctc ggacctggcc   25380
gacctcatct tccccgagcg cctgcggctg acgctgcgca acgggctgcc cgactttatg   25440
agccaaagca tgttgcaaaa cttctcgctct ttcatcctcg aacgctccgg gatcctgccc   25500
gccacctgct ccgcactgcc ctcggacttc gtgccgctga ccttccgcga gtgcccccg    25560 ccgctctgga gccactgcta cttgctgcgc ctggccaact acctggccta ccactcggac   25620
gtgatcgagg acgtcagcag cgagggtctg ctcgagtgcc actgccgctg caacctctgc   25680
acgccgcacc gctccttggc ctgcaacccc cagctgctga gcgagaccca gatcatcggc   25740
accttcgagt tgcaaggccc cggcgaggc aaggggggtc tcaaactcac cccgggggctg   25800 tggacctcgg cctacttgcg caagttcgtg cccgaggact accatcccct cgagatcagg   25860
ttctacgagg accaatccca gccgcccaag gccgagctgt cggcctgcgt catcacccag   25920 gggggccatcc tggcccaatt gcaagccatc cagaaatccc gccaagaatt tctgctgaaa   25980
aagggccacg gggctctactt ggacccccag accggagagg agctcaaccc cagcttcccc   26040
caggatgccc cgaggaagca gcaagaagct gaaagtggag ctgccgctgc cgccggagga   26100
tttggaggaa gactgggaga gcagtcaggc agaggagatg gaagactggg acagcactca   26160
ggcagaggag gacagcctgc aagacagtct ggaggaggaa gacgaggtgg aggaggaggc   26220
agaggaagaa gcagccgccg ccagaccgtc gtcctcggcg gaggagaaag caagcagcac   26280
```

```
ggataccatc tccgctccgg gtcggggtcg cggcggccgg gcccacagta gatgggacga   26340
gaccgggcgc ttcccgaacc ccaccaccca gaccggtaag aaggagcggc agggatacaa   26400
gtcctggcgg gggcacaaaa acgccatcgt ctcctgcttg caagcctgcg ggggcaacat   26460
ctccttcacc cggcgctacc tgctcttcca ccgcggggtg aacttccccc gcaacatctt   26520
gcattactac cgtcacctcc acagcccta ctactgtttc caagaagagg cagaaaccca    26580
gcagcagcag cagaaaacca gcggcagcag cagcagctag aaaatccaca gcggcggcag   26640
gtggactgag gatcgcggcg aacgagccgg cgcagacccg ggagctgagg aaccggatct   26700
ttcccaccct ctatgccatc ttccagcaga gtcgggggca ggagcaggaa ctgaaagtca   26760
agaaccgttc tctgcgctcg ctcacccgca gttgtctgta tcacaagagc gaagaccaac   26820
ttcagcgcac tctcgaggac gccgaggctc tcttcaacaa gtactgcgcg ctcactctta   26880
aagagtagcc cgcgcccgcc cacacacgga aaaaggcggg aattacgtca ccacctgcgc   26940
ccttcgcccg accatcatca tgagcaaaga gattcccacg ccttacatgt ggagctacca   27000
gccccagatg ggcctggccg ccggcgccgc ccaggactac tccacccgca tgaactggct   27060
cagtgccggg cccgcgatga tctcacgggt gaatgacatc cgcgcccacc gaaaccagat   27120
actcctagaa cagtcagcga tcaccgccac gccccgccat caccttaatc cgcgtaattg   27180
gcccgccgcc ctggtgtacc aggaaaattc ccagcccacg accgtactac ttccgcgaga   27240
cgcccaggcc gaagtccagc tgactaactc aggtgtccag ctggccggcg cgccgccct   27300 gtgtcgtcac cgccccgctc agggtataaa gcggctggtg atccgaggca gaggcacaca   27360
gctcaacgac gaggtggtga gctcttcgct gggtctgcga cctgacggag tcttccaact   27420
cgccggatcg gggagatctt ccttcacgcc tcgtcaggcc gtcctgactt tggagagttc   27480
gtcctcgcag ccccgctcgg gcggcatcgg cactctccag ttcgtggagg agttcactcc   27540
ctcggtctac ttcaaccccct tctccggctc ccccggccac tacccggacg agttcatccc   27600
gaacttcgac gccatcagcg agtcggtgga cggctacgat tgaatgtccc atggtggcgc   27660
ggctgaccta gctcggcttc gacacctgga ccactgttaa ttaatcgcct ctcctacgag   27720
ctcctgcagc agcgccagaa gttcacctgc ctggtcggag tcaaccccat cgtcatcacc   27780
cagcagtcgg gcgataccaa ggggtgcatc cactgctcct gcgactcccc cgactgcgtc   27840
cacactctga tcaagaccct ctgcggcctc cgcgacctcc tccccatgaa ctaatcaccc   27900
ccttatccag tgaaataaag atcatattga tgatgatttt acagaaataa agatacaatc   27960
atattgatga tttgagtttta ataaaaaata aagaatcact tacttgaaat ctgataccag   28020
gtctctgtcc atgttttctg ccaacaccac ttcactcccc tcttcccagc tctggtactg   28080 caggcccccgg cgggctgcaa acttcctcca cacgctgaag gggatgtcaa attcctcctg   28140
tccctcaatc ttcattttat cttctatcag atgtccaaaa agcgcgtccg ggtggatgat   28200
gacttcgacc ccgtctaccc ctacgatgca gacaacgcac cgaccgtgcc cttcatcaac   28260
ccccccttcg tctcttcaga tggattccaa gagaagcccc tggggggtgct gtccctgcga   28320 ctggccgacc ccgtcaccac caagaacggg gaaatcaccc tcaagctggg agaggggtg   28380 gacctcgact cctcgggaaa actcatctcc aacacggcca ccaaggccgc cgcccctctc   28440
agtttttcca acaacaccat ttcccttaac atggatcacc ccttttacac taaagatgga   28500
aaattatcct tacaagtttc tccaccatta aatatactga gaacaagcat tctaaacaca   28560
ctagctttag gttttggatc aggtttagga ctccgtggct ctgccttggc agtacagtta   28620
gtctctccac ttacatttga tactgatgga aacataaagc ttaccttaga cagaggtttg   28680
```

```
catgttacaa caggagatgc aattgaaagc aacataagct gggctaaagg tttaaaattt   28740
gaagatggag ccatagcaac caacattgga aatgggttag agtttggaag cagtagtaca   28800
gaaacaggtg ttgatgatgc ttacccaatc caagttaaac ttggatctgg ccttagcttt   28860
gacagtacag gagccataat ggctggtaac aaagaagacg ataaactcac tttgtggaca   28920
acacctgatc catcgccaaa ctgtcaaata ctcgcagaaa atgatgcaaa actaacactt   28980
tgcttgacta aatgtggtag tcaaatactg gccactgtgt cagtcttagt tgtaggaagt   29040
ggaaacctaa accccattac tggcaccgta agcagtgctc aggtgtttct acgttttgat   29100
gcaaacggtg ttcttttaac agaacattct acactaaaaa aatactgggg gtataggcag   29160
ggagatagca tagatggcac tccatatacc aatgctgtag gattcatgcc caatttaaaa   29220
gcttatccaa agtcacaaag ttctactact aaaaataata tagtagggca agtatacatg   29280
aatggagatg tttcaaaacc tatgcttctc actataaccc tcaatggtac tgatgacagc   29340
aacagtacat attcaatgtc attttcatac acctggacta atggaagcta tgttggagca   29400
acatttgggg ctaactctta taccttctca tacatcgccc aagaatgaac actgtatccc   29460
accctgcatg ccaacccttc ccaccccact ctgtggaaaa aactctgaaa cacaaaataa   29520
aataaagttc aagtgtttta ttgattcaac agttttacag gattcgagca gttatttttc   29580
ctccaccctc ccaggacatg gaatacacca ccctctcccc ccgcacagcc ttgaacatct   29640
gaatgccatt ggtgatggac atgcttttgg tctccacgtt ccacacagtt tcagagcgag   29700
ccagtctcgg gtcggtcagg gagatgaaac cctccgggca caattgggag aagtactcgc   29760
ctacatgggg gtagagtcat aatcgtgcat caggataggg cggtggtgct gcagcagcgc   29820
gcgaataaac tgctgccgcc gccgctccgt cctgcaggaa tacaacatgg cagtggtctc   29880
ctcagcgatg attcgcaccg cccgcagcat aaggcgcctt gtcctccggg cacagcagcg   29940
caccctgatc tcacttaaat cagcacagta actgcagcac agcaccacaa tattgttcaa   30000
aatcccacag tgcaaggcgc tgtatccaaa gctcatggcg gggaccacag aacccacgtg   30060
gccatcatac cacaagcgca ggtagattaa gtggcgaccc ctcataaaca cgctggacat   30120
aaacattacc tcttttggca tgttgtaatt caccacctcc cggtaccata taaacctctg   30180
attaaacatg gcgccatcca ccaccatcct aaaccagctg gccaaaacct gcccgccggc   30240
tatacactgc agggaaccgg gactggaaca atgacagtgg agagcccagg actcgtaacc   30300
atggatcatc atgctcgtca tgatatcaat gttggcacaa cacaggcaca cgtgcataca   30360
cttcctcagg attacaagct cctcccgcgt tagaaccata tcccagggaa caacccattc   30420
ctgaatcagc gtaaatccca cactgcaggg aagacctcgc acgtaactca cgttgtgcat   30480
tgtcaaagtg ttacattcgg gcagcagcgg atgatcctcc agtatggtag cgcgggtttc   30540
tgtctcaaaa ggaggtagac gatccctact gtacggagtg cgccgagaca accgagatcg   30600
tgttggtcgt agtgtcatgc caaatggaac gccggacgta gtcatatttc ctgaagtctt   30660
ggcgcgccaa agtctagaag cggtccatag cttaccgagc ggcagcagca gcggcacaca   30720
acaggcgcaa gagtcagaga aaagactgag ctctaacctg tccgcccgct ctctgctcaa   30780
tatatagccc agatctacac tgacgtaaag gccaaagtct aaaataccc gccaaatagt    30840
cacacacgcc cagcacacgc ccagaaaccg gtgacacact caaaaaaata cgcgcacttc   30900
ctcaaacgcc caaactgccg tcatttccgg gttcccacgc tacgtcatca aaacacgact   30960
ttcaaattcc gtcgaccgtt aaaaacgtca cccgccccgc ccctaacggt cgcccgtctc   31020
```

```
tcagccaatc agcgccccgc atccccaaat tcaaacacct catttgcata ttaacgcgca    31080
ccaaaagttt gaggtatatt attgatgatg                                    31110

<210> SEQ ID NO 6
<211> LENGTH: 31158
<212> TYPE: DNA
<213> ORGANISM: Artificial Sequence
<220> FEATURE:
<223> OTHER INFORMATION: synthetic chimpanzee adenovirus serotype ChAd63
      with Marburg virus Angola codon optimized
      transmembrane envelope glycoprotein (GP) insert
      (ChAd63 GP Marburg (PB/6712))
<220> FEATURE:
<221> NAME/KEY: CDS
<222> LOCATION: (1662)...(3704)
<223> OTHER INFORMATION: Marburg virus Angola codon optimized
      transmembrane envelope glycoprotein (GP) insert in ChAd63 GP
      Marburg (PB/6712)
<220> FEATURE:
<221> NAME/KEY: CDS
<222> LOCATION: (14420)...(16048)
<223> OTHER INFORMATION: chimpanzee adenovirus serotype ChAd63 penton
<220> FEATURE:
<221> NAME/KEY: CDS
<222> LOCATION: (18815)...(21691)
<223> OTHER INFORMATION: chimpanzee adenovirus serotype ChAd63 hexon
<220> FEATURE:
<221> NAME/KEY: CDS
<222> LOCATION: (28219)...(29496)
<223> OTHER INFORMATION: chimpanzee adenovirus serotype ChAd63 fiber

<400> SEQUENCE: 6
catcatcaat aatatacctc aaacttttgg tgcgcgttaa tatgcaaatg aggtgtttga      60
atttggggat gcggggcgct gattggctga gagacgggcg accgttaggg gcggggcggg     120
tgacgttttg atgacgtggc cgtgaggcgg agccggtttg caagttctcg tgggaaaagt     180
gacgtcaaac gaggtgtggt ttgaacacgg aaatactcaa ttttcccgcg ctctctgaca     240
ggaaatgagg tgtttctggg cggatgcaag tgaaaacggg ccattttcgc gcgaaaactg     300
aatgaggaag tgaaaatctg agtaattccg cgtttatggc agggaggagt atttgccgag     360
ggccgagtag actttgaccg attacgtggg ggtttcgatt accgtatttt tcacctaaat     420
ttccgcgtac ggtgtcaaag tccggtgttt ttacggatat ctccattgca tacgttgtat     480
ccatatcata atatgtacat ttatattggc tcatgtccaa cattaccgcc atgttgacat     540
tgattattga ctagttatta atagtaatca attacgggt cattagttca tagcccatat     600
atggagttcc gcgttacata acttacggta aatggcccgc ctggctgacc gcccaacgac     660
ccccgcccat tgacgtcaat aatgacgtat gttcccatag taacgccaat agggactttc     720
cattgacgtc aatgggtgga gtatttacgg taaactgccc acttggcagt acatcaagtg     780
tatcatatgc caagtacgcc ccctattgac gtcaatgacg taaatggcc cgcctggcat     840 tatgcccagt acatgacctt atgggacttt cctacttggc agtacatcta cgtattagtc     900
atcgctatta ccatggtgat gcggttttgg cagtacatca atgggcgtgg atagcggttt     960
gactcacggg gatttccaag tctccacccc attgacgtca atgggagttt gttttggaac    1020
caaaatcaac gggactttcc aaaatgtcgt aacaactccg ccccattgac gcaaatgggc    1080
ggtaggcgtg tacggtggga ggtctatata agcagagctc tccctatcag tgatagagat    1140
ctccctatca gtgatagaga tcgtcgacga gctcgtttag tgaaccgtca gatcgcctgg    1200
agacgccatc cacgctgttt tgacctccat agaagacacc gggaccgatc agcctccat     1260 cggctcgcat ctctccttca cgcgcccgcc gccctacctg aggccgccat ccacgccggt    1320
```

```
tgagtcgcgt tctgccgcct cccgcctgtg gtgcctcctg aactgcgtcc gccgtctagg    1380
taagtttaaa gctcaggtcg agaccgggcc tttgtccggc gctcccttgg agcctaccta    1440
gactcagccg gctctccacg cttttgcctga ccctgcttgc tcaactctag ttaacggtgg    1500
agggcagtgt agtctgagca gtactcgttg ctgccgcgcg cgccaccaga cataatagct    1560
gacagactaa cagactgttc cttttccatgg gtctttttctg cagtcaccgt cgtcgacacg    1620
tgtgatcaga tatcgcggcc gctctagaga tatcggccgc catgaagacc acctgcctgc    1680
tgatcagcct gatcctgatc cagggcgtga agaccctgcc catcctggag atcgccagca    1740
acatccagcc ccagaacgtg gacagcgtgt gcagcggcac cctgcagaag accgaggacg    1800
tgcacctgat gggcttcacc ctgagcggcc agaaggtggc cgacagccct ctggaggcca    1860
gcaagaggtg ggccttcagg gccggcgtgc cccccaagaa cgtggagtac accgagggcg    1920
aggaggccaa gacctgctac aacatcagcg tgaccgaccc cagcggcaag agcctgctgc    1980
tggaccctcc caccaacatc agggactacc ctaagtgcaa gaccatccac cacatccagg    2040
gccagaaccc tcacgcccag ggcatcgccc tgcacctgtg gggcgccttc ttcctgtacg    2100
acaggatcgc cagcaccacc atgtacagag gaaaagtgtt cacagaggga aacatcgctg    2160
ctatgatcgt gaacaagacc gtgcataaga tgatcttcag cagacaggga cagggatata    2220
gacatatgaa cctgacatcc acaaacaagt actggacaag cagcaacgga acacagacaa    2280
acgatacagg atgttttgga acactgcagg aatacaactc caccaagaac cagacatgtg    2340
cccctagcaa gaagcctctg cctctgccta cagctcatcc tgaagtgaag ctgacatcca    2400
caagcacaga tgccacaaag ctgaacacaa cagatcctaa tagcgacgac gaggatctga    2460
caacaagcgg atccggatcc ggagaacagg aaccttatac aacaagcgac gctgctacaa    2520
aacagggact gtcctccaca atgcctccta cacctagccc tcagcctagc acacctcagc    2580
agggaggcaa caacacaaac cattcccagg gagtggtgac agaacctgga agacaaaaca    2640
caacagccca gcctagcatg cctcctcata acacaacaac aatcagcaca aacaacacct    2700
ccaagcacaa tctgagcaca cctagcgtgc ctattcagaa tgccaccaac tacaacacac    2760
agtccacagc ccctgaaaac gaacagacct ccgcccttc caaaacaacc ctgctgccta    2820
cagaaaaccc tacaacagcc aagagcacaa acagcacaaa gagccctaca caacagtgc    2880 ctaacacaac aaacaagtat agcacaagcc ctagccctac acctaattcc acagctcagc    2940
atctggtgta ttttagaaga aagagaaaca tcctgtggag agaaggagat atgttccctt    3000
ttctggatgg actgatcaac gctccctatcg attttgatcc tgtgcctaac acaaagacaa    3060
tctttgatga aagcagcagc agcggagcct ccgccgaaga agatcagcat gcctccccta    3120
acatcagcct gacactgagc tattttccta aggtgaacga aaacacagcc cattccggag    3180
aaaacgaaaa cgattgtgat gccgaactga gaatctggag cgtgcaggaa gatgatctgg    3240
ccgccggact gagctggatc ccttttttg ggcccggaat tgaaggactg tacaccgccg    3300
gcctgatcaa gaaccagaac aacctggtgt gcaggctgag gaggctggcc aaccagaccg    3360
ccaagagcct ggagctgctg ctgagggtga ccaccgagga gaggaccttc agcctgatca    3420
acaggcacgc catcgacttc ctgctggcta ggtggggcgg cacctgcaag gtgctgggcc    3480
ccgactgctg catcggcatc gaggacctga gcaggaacat cagcgagcag atcgaccaga    3540
tcaagaagga cgagcagaag gagggcaccg gctgggcct gggcggcaag tggtggacca    3600
gcgactgggg agtgctgaca aacctgggaa tcctgctgct gctgagcatt gccgtgctca    3660
ttgctctgtc ctgtatctgt agaatctta ccaagtacat cggatgatag atccagatct    3720
```

```
gctgtgcctt ctagttgcca gccatctgtt gtttgcccct cccccgtgcc ttccttgacc   3780
ctggaaggtg ccactcccac tgtcctttcc taataaaatg aggaaattgc atcgcattgt   3840
ctgagtaggt gtcattctat tctggggggt ggggtggggc aggacagcaa gggggaggat   3900
tgggaagaca atagcaggca tgctggggat gcggtgggct ctagatatca gcgatcgcgt   3960
gagtagtgtt tgggggtggg tgggagcctg catgatgggc agaatgacta aaatctgtgt   4020
ttttctgtgt gttgcagcag catgagcgga agcgcctcct ttgagggagg ggtattcagc   4080
ccttatctga cggggcgtct cccctcctgg gcgggagtgc gtcagaatgt gatgggatcc   4140
acggtggacg gccggcccgt gcagcccgcg aactcttcaa ccctgaccta cgcgaccctg   4200
agctcctcgt ccgtggacgc agctgccgcc gcagctgctg cttccgccgc cagcgccgtg   4260
cgcggaatgg ccctgggcgc cggctactac agctctctgg tggccaactc gagttccacc   4320
aataatcccg ccagcctgaa cgaggagaag ctgttgctgc tgatggccca gctcgaggcc   4380
ctgacccagc gcctgggcga gctgacccag caggtggctc agctgcaggc ggagacgcgg   4440
gccgcggttg ccacggtgaa aaccaaataa aaatgaatc aataaataaa cggagacggt   4500
tgttgatttt aacacagagt cttgaatctt tatttgattt ttcgcgcgcg gtaggccctg   4560
gaccaccggt ctcgatcatt gagcacccgg tggatctttt ccaggacccg gtagaggtgg   4620
gcttggatgt tgaggtacat gggcatgagc ccgtcccggg ggtggaggta gctccattgc   4680
agggcctcgt gctcggggt ggtgttgtaa atcacccagt catagcaggg gcgcagggcg   4740
tggtgctgca cgatgtcttt gaggaggaga ctgatggcca cgggcagccc cttggtgtag   4800
gtgttgacga acctattgag ctgggaggga tgcatgcggg gggagatgag atgcatcttg   4860
gcctggatct tgagattggc gatgttcccg cccagatccc gccgggggtt catgttgtgc   4920
aggaccacca gcacggtgta tccggtgcac ttggggaatt tgtcatgcaa cttggaaggg   4980
aaggcgtgaa agaatttgga gacgcccttg tgaccgccca ggttttccat gcactcatcc   5040
atgatgatgg cgatgggccc gtgggcggcg gcctgggcaa agacgtttcg ggggtcggac   5100
acatcgtagt tgtggtcctg ggtgagctcg tcataggcca ttttaatgaa tttggggcgg   5160
agggtacccg actgggggac aaaggtgccc tcgatcccgg gggcgtagtt cccctcgcag   5220
atctgcatct cccaggcctt gagctcggag gggggggatca tgtccacctg cggggcgatg   5280
aaaaaaacgg tttccggggc gggggagatg agctgcgccg aaagcaggtt ccggagcagc   5340
tgggacttgc cgcagccggt ggggccgtag atgaccccga tgaccggctg caggtggtag   5400
ttgagggaga gacagctgcc gtcctcgcgg aggaggggg ccacctcgtt catcatctcg   5460
cgcacatgca tgttctcgcg cacgagttcc gccaggaggc gctcgccccc cagcgagagg   5520
agctcttgca gcgaggcgaa gttttttcagc ggcttgagcc cgtcggccat gggcatttg   5580
gagagggtct gttgcaagag ttccagacgg tcccagagct cggtgatgtg ctctagggca   5640
tctcgatcca gcagacctcc tcgtttcgcg ggttggggcg actgcgggag tagggcacca   5700
ggcgatgggc gtccagcgag gccagggtcc ggtccttcca gggtcgcagg gtccgcgtca   5760
gcgtggtctc cgtcacggtg aagggggtgcg cgccgggctg ggcgcttgcg agggtgcgct   5820
tcaggctcat ccggctggtc gagaaccgct cccggtcggc gccctgcgcg tcggccaggt   5880
agcaattgag catgagttcg tagttgagcg cctcggccgc gtggcccttg gcgcggagct   5940
tacctttgga agtgtgtccg cagacgggac agaggaggga cttgagggcg tagagcttgg   6000
gggcgaggaa gacggactcg ggggcgtagg cgtccgcgcc gcagctggcg cagacggtct   6060
```

```
cgcactccac gagccaggtg aggtcgggc  ggtcgggtc  aaaaacgagg tttcctccgt   6120
gctttttgat gcgtttctta cctctggtct ccatgagctc gtgtcccgc  tgggtgacaa   6180
agaggctgtc cgtgtccccg tagaccgact ttatgggccg gtcctcgagc ggggtgccgc   6240
ggtcctcgtc gtagaggaac cccgcccact ccgagacgaa ggcccgggtc caggccagca   6300
cgaaggaggc cacgtgggag gggtagcggt cgttgtccac cagcgggtcc accttctcca   6360
gggtatgcaa gcacatgtcc ccctcgtcca catccaggaa ggtgattggc ttgtaagtgt   6420
aggccacgtg accggggtc  ccggccgggg gggtataaaa gggggcgggc cctgctcgt   6480
cctcactgtc ttccggatcg ctgtccagga gcgccagctg ttggggtagg tattccctct   6540
cgaaggcggg catgacctcg gcactcaggt tgtcagtttc tagaaacgag gaggatttga   6600
tattgacggt gccgttggag acgcctttca tgagcccctc gtccatctgg tcagaaaaga   6660
cgatcttttt gttgtcgagc ttggtggcga aggagccgta gagggcgttg gagagcagct   6720
tggcgatgga gcgcatggtc tggttctttt ccttgtcggc gcgctccttg gcggcgatgt   6780
tgagctgcac gtactcgcgc gccacgcact tccattcggg gaagacggtg gtgagctcgt   6840
cgggcacgat tctgacccgc cagccgcggt tgtgcagggt gatgaggtcc acgctggtgg   6900
ccacctcgcc gcgcaggggc tcgttggtcc agcagaggcg cccgcccttg cgcgagcaga   6960
agggggggcag cgggtccagc atgagctcgt cggggggtc  ggcgtccacg gtgaagatgc   7020
cgggcaggag ctcggggtcg aagtagctga tgcaggtgcc cagatcgtcc agacttgctt   7080
gccagtcgcg cacggccagc gcgcgctcgt aggggctgag gggcgtgccc cagggcatgg   7140
ggtgcgtgag cgcggaggcg tacatgccgc agatgtcgta gacgtagagg ggctcctgga   7200
ggacgccgat gtaggtgggg tagcagcgcc ccccgcggat gctggcgcgc acgtagtcgt   7260
acagctcgtg cgagggcgcg aggagccccg tgccgagatt ggagcgctgc ggcttttcgg   7320
cgcggtagac gatctggcgg aagatggcgt gggagttgga ggagatggtg gcctctgga   7380
agatgttgaa gtgggcatgg ggcagtccga ccgagtccct gatgaagtgg gcgtaggagt   7440
cctgcagctt ggcgacgagc tcggcggtga cgaggacgtc cagggcgcag tagtcgaggg   7500
tctcttggat gatgtcgtac ttgagctggc ccttctgctt ccacagctcg cggttgagaa   7560
ggaactcttc gcggtccttc cagtactctt cgaggggaa  cccgtcctga tcggcacggt   7620
aagagcccac catgtagaac tggttgacgg ccttgtaggc gcagcagccc ttctccacgg   7680
ggagggcgta agcttgcgcg gccttgcgca gggaggtgtg ggtgagggcg aaggtgtcgc   7740
gcaccatgac tttgaggaac tggtgcttga agtcgaggtc gtcgcagccg ccctgctccc   7800
agagctggaa gtccgtgcgc ttcttgtagg cggggttggg caaagcgaaa gtaacatcgt   7860
tgaagaggat cttgccccgcg cggggcatga agttgcgagt gatgcggaaa ggctggggca   7920
cctcggcccg gttgttgatg acctgggcgg cgaggacgat ctcgtcgaag ccgttgatgt   7980
tgtgcccgac gatgtagagt tccacgaatc gcggcggcc  cttgacgtgg ggcagcttct   8040
tgagctcgtc gtaggtgagc tcggcggggt cgctgagccc gtgctgctcg agggcccagt   8100
cggcgacgtg ggggttggcg ctgaggaagg aagtccagag atccacggcc agggcggtct   8160
gcaagcggtc ccgtactga  cggaactgct ggccacggc  catttttcg  ggggtgacgc   8220
agtagaaggt gcggggtcg  ccgtgccagc ggtcccactt gagctggagg gcgaggtcgt   8280
gggcgagctc gacgagcggc gggtccccg  agagtttcat gaccagcatg aaggggacga   8340
gctgcttgcc gaaggacccc atccaggtgt aggtttccac atcgtaggtg aggaagagcc   8400
tttcggtgcg aggatgcgag ccgatgggga agaactggat ctcctgccac cagttggagg   8460
```

```
aatggctgtt gatgtgatgg aagtagaaat gccgacggcg cgccgagcac tcgtgcttgt   8520
gtttatacaa gcgtccgcag tgctcgcaac gctgcacggg atgcacgtgc tgcacgagct   8580
gtacctgggt tcctttgacg aggaatttca gtgggcagtg gagcgctggc ggctgcatct   8640
ggtgctgtac tacgtcctgg ccatcggcgt ggccatcgtc tgcctcgatg gtggtcatgc   8700
tgacgagccc gcgcgggagg caggtccaga cctcggctcg gacgggtcgg agagcgagga   8760
cgagggcgcg caggccggag ctgtccaggg tcctgagacg ctgcgagtc aggtcagtgg    8820
gcagcggcgg cgcgcggttg acttgcagga gcttttccag ggcgcgcggg aggtccagat   8880
ggtacttgat ctccacggcg ccgttggtgg cgacgtccac ggcttgcagg gtcccgtgcc   8940
cctggggcgc caccaccgtg ccccgtttct tcttgggcgg cggcggctcc atgcttagaa   9000
gcggcggcga ggacgcgcgc cgggcggcag gggcggctcg gggcccggag gcaggggcgg   9060
caggggcacg tcggcgccgc gcgcgggcag gttctggtac tgcgcccgga gaagactggc   9120
gtgagcgacg acgcgacggt tgacgtcctg gatctgacgc ctctgggtga aggccacggg   9180
acccgtgagt ttgaacctga agagagttc gacagaatca atctcggtat cgttgacggc    9240
ggcctgccgc aggatctctt gcacgtcgcc cgagttgtcc tggtaggcga tctcggtcat   9300
gaactgctcg atctcctcct cctgaaggtc tccgcggccg gcgcgctcga cggtggccgc   9360
gaggtcgttg gagatgcggc ccatgagctg cgagaaggcg ttcatgccgg cctcgttcca   9420
gacgcggctg tagaccacgg ctccgtcggg gtcgcgcgcg cgcatgacca cctgggcgag   9480
gttgagctcg acgtggcgcg tgaagaccgc gtagttgcag aggcgctggt agaggtagtt   9540
gagcgtggtg gcgatgtgct cggtgacgaa gaagtacatg atccagcggc ggagcggcat   9600
ctcgctgacg tcgcccaggg cttccaagcg ctccatggcc tcgtagaagt ccacggcgaa   9660
gttgaaaaac tgggagttgc gcgccgagac ggtcaactcc tcctccagaa gacggatgag   9720
ctcggcgatg tggcgcgca cctcgcgctc gaaggcccg gggggctcct cttccatttc      9780
ctcctcttcc tcctccacta acatctcttc tacttcctcc tcaggaggcg gcggcggggg   9840
aggggccctg cgtcgccggc ggcgcacggg cagacggtcg atgaagcgct cgatggtctc   9900
cccgcgccgg cgacgcatgg tctcggtgac ggcgcgcccc tcctcgcggg gccgcagcgt   9960
gaagacgccg ccgcgcatct ccaggtggcc gccggggggg tctccgttgg gcagggagag  10020
ggcgctgacg atgcatctta tcaattgacc cgtagggact ccgcgcaagg acctgagcgt  10080
ctcgagatcc acgggatccg aaaaccgctg aacgaaggct tcgagccagt cgcagtcgca  10140
aggtaggctg agcccggttt cttgttcttc gggtatttgg tcgggaggcg ggcggcgat   10200
gctgctggtg atgaagttga agtaggcggt cctgagacgg cggatggtgg cgaggagcac  10260
caggtccttg ggcccggctt gctggatgcg cagacggtcg gccatgcccc aggcgtggtc  10320
ctgacacctg gcgaggtcct tgtagtagtc ctgcatgagc cgctccacgg gcacctcctc  10380
ctcgcccgcg cggccgtgca tgcgcgtgag cccgaacccg cgctgcggct ggacgagcgc  10440
caggtcggcg acgacgcgct cggcgaggat ggcctgctgg atctgggtga gggtggtctg  10500
gaagtcgtcg aagtcgacga agcggtggta ggctccggtg ttgatggtgt aggagcagtt  10560
ggccatgacg gaccagttga cggtctggtg gccggggcgc acgagctcgt ggtacttgag  10620
gcgcgagtag gcgcgcgtgt cgaagatgta gtcgttgcag gtgcgcacga ggtactggta  10680
tccgacgagg aagtgcggcg gcggctggcg gtagagcggc catcgctcgg tggcggggc   10740
gccgggcgcg aggtcctcga gcatgaggcg gtggtagccg tagatgtacc tggacatcca  10800
```

```
ggtgatgccg gcggcggtgg tggaggcgcg cgggaactcg cggacgcggt tccagatgtt   10860
gcgcagcggc aggaagtagt tcatggtggc cgcggtctgg cccgtgaggc gcgcgcagtc   10920
gtggatgctc tagacatacg ggcaaaaacg aaagcggtca gcggctcgac tccgtggcct   10980
ggaggctaag cgaacggggt tgggctgcgcg tgtaccccgg ttcgaatctc gaatcaggct   11040
ggagccgcag ctaacgtggt actggcactc ccgtctcgac ccaagcctgc taacgaaacc   11100
tccaggatac ggaggcgggt cgttttttgg ccttggtcgc tggtcatgaa aaactagtaa   11160
gcgcggaaag cggccgcccg cgatggctcg ctgccgtagt ctggagaaag aatcgccagg   11220
gttgcgttgc ggtgtgcccc ggttcgagcc tcagcgctcg gcgccggccg gattccgcgg   11280
ctaacgtggg cgtggctgcc ccgtcgtttc caagacccct tagccagccg acttctccag   11340
ttacggagcg agccctctct tttttcttgt gtttttgcca gatgcatccc gtactgcggc   11400
agatgcgccc ccaccctcca ccacaaccgc ccctaccgca gcagcagcaa cagccggcgc   11460
ttctgccccc gccccagcag cagcagccag ccactaccgc ggcggccgcc gtgagcggag   11520
ccggcgttca gtatgacctg gccttggaag agggcgaggg gctggcgcgg ctgggggcgt   11580
cgtcgccgga gcggcacccg cgcgtgcaga tgaaaaggga cgctcgcgag gcctacgtgc   11640
ccaagcagaa cctgttcaga gacaggacgc gcgaggagcc cgaggagatg cgcgcctccc   11700
gcttccacgc ggggcgggag ctgcggcgcg gcctggaccg aaagcgggtg ctgagggacg   11760
aggatttcga ggcggacgag ctgacgggga tcagccccgc gcgcgcgcac gtggccgcgg   11820
ccaacctggt cacggcgtac gagcagaccg tgaaggagga gagcaacttc caaaaatcct   11880
tcaacaacca cgtgcgcacg ctgatcgcgc gcgaggaggt gaccctgggc ctgatgcacc   11940
tgtgggacct gctggaggcc atcgtgcaga accccacgag caagccgctg acggcgcagc   12000
tgtttctggt ggtgcagcac agtcgggaca acgagacgtt cagggaggcg ctgctgaata   12060
tcaccgagcc cgagggccgc tggctcctgg acctggtgaa cattctgcag agcatcgtgg   12120
tgcaggagcg cgggctgccg ctgtccgaga gctggcggc catcaacttc tcggtgctga   12180
gcctgggcaa gtactacgct aggaagatct acaagacccc gtacgtgccc atagacaagg   12240
aggtgaagat cgatgggttt tacatgcgca tgaccctgaa agtgctgacc ctgagcgacg   12300
atctgggggt gtaccgcaac gacaggatgc accgcgcggt gagcgccagc cgccggcgcg   12360
agctgagcga ccaggagctg atgcacagcc tgcagcgggc cctgaccggg gccgggaccg   12420
aggggggagag ctactttgac atgggcgcgg acctgcgctg gcagcccagc cgccgggcct   12480
tggaagctgc cggcggcgtg ccctacgtgg aggaggtgga cgatgaggag gaggagggcg   12540
agtacctgga agactgatgg cgcgaccgta ttttgctag atgcagcaac agccaccgcc   12600
gccgcctcct gatcccgcga tgcgggcggc gctgcagagc cagccgtccg gcattaactc   12660
ctcggacgat tggacccagg ccatgcaacg catcatggcg ctgacgaccc gcaatcccga   12720
agcctttaga cagcagcctc aggccaaccg gctctcggcc atcctggagg ccgtggtgcc   12780
ctcgcgctcg aaccccacgc acgagaaggt gctggccatc gtgaacgcgc tggtggagaa   12840
caaggccatc cgcggcgacg aggccgggct ggtgtacaac gcgctgctgg agcgcgtggc   12900
ccgctacaac agcaccaacg tgcagacgaa cctggaccgc atggtgaccg acgtgcgcga   12960
ggcggtgtcg cagcgcgagc ggttccaccg cgagtcgaac ctgggctcca tggtggcgct   13020
gaacgccttc ctgagcacgc agcccgccaa cgtgccccgg ggccaggagg actacaccaa   13080
cttcatcagc gcgctgcggc tgatggtggc cgaggtgccc cagagcgagg tgtaccagtc   13140
ggggccggac tacttcttcc agaccagtcg ccagggcttg cagaccgtga acctgagcca   13200
```

```
ggctttcaag aacttgcagg gactgtgggg cgtgcaggcc ccggtcgggg accgcgcgac   13260
ggtgtcgagc ctgctgacgc cgaactcgcg cctgctgctg ctgctggtgg cgcccttcac   13320
ggacagcggc agcgtgagcc gcgactcgta cctgggctac ctgcttaacc tgtaccgcga   13380
ggccatcggg caggcgcacg tggacagcga gacctaccag gagatcaccc acgtgagccg   13440
cgcgctgggc caggaggacc cgggcaacct ggaggccacc ctgaacttcc tgctgaccaa   13500
ccggtcgcag aagatcccgc cccagtacgc gctgagcacc gaggaggagc gcatcctgcg   13560
ctacgtgcag cagagcgtgg ggctgttctt gatgcaggag ggggccacgc ccagcgccgc   13620
gctcgacatg accgcgcgca acatggagcc cagcatgtac gcccgcaacc gcccgttcat   13680
caataagctg atggactact tgcatcgggc ggccgccatg aactcggact actttaccaa   13740
cgccatcttg aacccgcact ggctcccgcc gcccgggttc tacacgggcg agtacgacat   13800
gcccgacccc aacgacgggt tcctgtggga cgacgtggac agcagcgtgt tctcgccgcg   13860
gcccaccacc accaccgtgt ggaagaaaga gggcggggac cggcggccgt cctcggcgct   13920
gtccggtcgc gcgggtgctg ccgcggcggt gcccgaggct gccagcccct tcccgagcct   13980
gcccttttcg ctgaacagcg tgcgcagcag cgagctgggt cggctgacgc ggccgcgcct   14040
gctgggcgag gaggagtacc tgaacgactc cttgttgaag cccgagcgcg agaagaactt   14100
ccccaataac gggatagaga gcctggtgga caagatgagc cgctggaaga cgtacgcgca   14160
cgagcacagg gacgagcccc gagctagcag cgcaggcacc cgtagacgcc agcggcacga   14220
caggcagcgg ggactggtgt gggacgatga ggattccgcc gacgacagca gcgtgttgga   14280
cttgggtggg agtggtggtg gtaacccgtt cgctcacctg cgccccgta tcgggcgcct   14340
gatgtaagaa tctgaaaaaa taaaagacgg tactcaccaa ggccatggcg accagcgtgc   14400
gttcttctct gttgtttgta gtagtatgat gaggcgcgtg tacccggagg gtcctcctcc   14460
ctcgtacgag agcgtgatgc agcaggcggt ggcggcggcg atgcagcccc cgctggaggc   14520
gccttacgtg cccccgcggt acctggcgcc tacgaggggg cggaacagca ttcgttactc   14580
ggagctggca cccttgtacg ataccacccg gttgtacctg gtggacaaca agtcggcgga   14640
catcgcctcg ctgaactacc agaacgacca cagcaacttc ctgaccaccg tggtgcagaa   14700
caacgatttc accccacgg aggccagcac ccagaccatc aactttgacg agcgctcgcg   14760
gtggggcggc cagctgaaaa ccatcatgca caccaacatg cccaacgtga acgagttcat   14820
gtacagcaac aagttcaagg cgcgggtgat ggtctcgcgc aagaccccca acgggggtcac   14880
ggtagggagt gattatgatg gtagtcagga cgagctgacc tacgagtggg tggagtttga   14940
gctgcccgag ggcaacttct cggtgaccat gaccatcgat ctgatgaaca acgccatcat   15000
cgacaactac ttggcggtgg ggcggcagaa cggggtgctg gagagcgaca tcggcgtgaa   15060
gttcgacacg cgcaacttcc ggctgggctg ggaccccgtg accgagctgg tgatgccggg   15120
cgtgtacacc aacgaggcct tccaccccga catcgtcctg ctgcccggct gcggcgtgga   15180
cttcaccgag agccgcctca gcaacctgct gggcatccgc aagcggcagc ccttccagga   15240
gggcttccag atcctgtacg aggacctgga gggggcaac atccccgcgc tcttggatgt   15300
cgaagcctat gaagaaagta aggaaaaagc agaggctgag gcaactacag ccgtggctac   15360
cgccgcgact gtggcagatg ccactgtcac caggggcgat acattcgcca cccaggcgga   15420
ggaagcagcc gccctagcgg cgaccgatga tagtgaaagt aagatagtca tcaagccggt   15480
ggagaaggac agcaagaaca ggagctacaa cgttctaccg gatggaaaga acaccgccta   15540
```

-continued

```
ccgcagctgg tacctggcct acaactacgg cgaccccgag aagggcgtgc gctcctggac    15600
gctgctcacc acctcggacg tcacctgcgc cgtggagcaa gtctactggt cgctgcccga    15660
catgatgcaa gacccggtca ccttccgctc cacgcgacaa gttagcaact acccggtggt    15720
gggcgccgag ctcctgcccg tctactccaa gagcttcttc aacgagcagg ccgtctactc    15780
gcagcagctg cgtgccttca cctcgctcac gcacgtcttc aaccgcttcc ccgagaacca    15840
gatcctcgtc cgcccgcccg cgcccaccat taccaccgtc agtgaaaacg ttcctgctct    15900
cacagatcac gggaccctgc cgctgcgcag cagtatccgg ggagtccagc gcgtgaccgt    15960
cactgacgcc agacgccgca cctgccccta cgtctacaag gccctgggcg tagtcgcgcc    16020
gcgcgtcctc tcgagccgca ccttctaaaa aatgtccatt ctcatctcgc ccagtaataa    16080
caccggttgg ggcctgcgcg cgcccagcaa gatgtacgga ggcgctcgcc aacgctccac    16140
gcaacacccc gtgcgcgtgc gcgggcactt ccgcgctccc tggggcgccc tcaagggccg    16200
cgtgcgctcg cgcaccaccg tcgacgacgt gatcgaccag gtggtggccg acgcgcgcaa    16260
ctacacgccc gccgccgcgc ccgcctccac cgtggacgcc gtcatcgaca gcgtggtggc    16320
cgacgcgcgc cggtacgccc gcgccaagag ccggcggcgg cgcatcgccc ggcggcaccg    16380
gagcaccccc gccatgcgcg cggcgcgagc cttgctgcgc agggccaggc gcacgggacg    16440
cagggccatg ctcagggcgg ccagacgcgc ggcctccggc agcagcagcg ccggcaggac    16500
ccgcagacgc gcggccacgg cggcggcggc ggccatcgcc agcatgtccc gcccgcggcg    16560
cggcaacgtg tactgggtgc gcgacgccgc caccggtgtg cgcgtgcccg tgcgcacccg    16620
cccccctcgc acttgaagat gctgacttcg cgatgttgat gtgtcccagc ggcgaggagg    16680
atgtccaagc gcaaatacaa ggaagagatg ctccaggtca tcgcgcctga gatctacggc    16740
cccgcggcg cggtgaagga ggaaagaaag ccccgcaaac tgaagcgggt caaaaaggac    16800
aaaaaggagg aggaagatga cggactggtg gagtttgtgc gcgagttcgc ccccggcgg    16860
cgcgtgcagt ggcgcgggcg gaaagtgaaa ccggtgctgc ggcccggcac cacggtggtc    16920
ttcacgcccg gcgagcgttc cggctccgcc tccaagcgct cctacgacga ggtgtacggg    16980
gacgaggaca tcctcgagca ggcggtcgag cgtctgggcg agtttgctta cggcaagcgc    17040
agccgccccg cgcccttgaa agaggaggcg gtgtccatcc cgctggacca cggcaacccc    17100
acgccgagcc tgaagccggt gaccctgcag caggtgctgc cgagcgcggc gccgcgccgg    17160
ggcttcaagc gcgagggcgg cgaggatctg tacccgacca tgcagctgat ggtgcccaag    17220
cgccagaagc tggaggacgt gctggagcac atgaaggtgg accccgaggt gcagcccgag    17280
gtcaaggtgc ggcccatcaa gcaggtggcc ccgggcctgg gcgtgcagac cgtggacatc    17340
aagatcccca cggagcccat ggaaacgcag accgagcccg tgaagcccag caccagcacc    17400
atggaggtgc agacggatcc ctggatgcca gcggcttcca ccaccaccac tcgccgaaga    17460
cgcaagtacg gcgcggccag cctgctgatg cccaactacg cgctgcatcc ttccatcatc    17520
cccacgccgg gctaccgcgg cacgcgcttc taccgcggct acaccagcag ccgccgcgc    17580
aagaccacca cccgccgccg tcgtcgcagc gccgcagca gcaccgcgac ttccgccttg    17640
gtgcggagag tgtatcgcag cgggcgcgag cctctgaccc tgccgcgcgc gcgctaccac    17700
ccgagcatcg ccatttaact accgcctcct acttgcagat atggccctca catgccgcct    17760
ccgcgtcccc attacgggct accgaggaag aaagccgcgc cgtagaaggc tgacggggaa    17820
cgggctgcgt cgccatcacc accggcggcg gcgcgccatc agcaagcggt tgggggagg    17880
cttcctgccc gcgctgatcc ccatcatcgc cgcggcgatc ggggcgatcc ccggcatagc    17940
```

```
ttccgtggcg gtgcaggcct ctcagcgcca ctgagacaca aaaaagcatg gatttgtaat   18000
aaaaaaatgg actgacgctc ctggtcctgt gatgtgtgtt tttagatgga agacatcaat   18060
ttttcgtccc tggcaccgcg acacggcacg cggccgttta tgggcacctg gagcgacatc   18120
ggcaacagcc aactgaacgg gggcgccttc aattggagca gtctctggag cgggcttaag   18180
aatttcgggt ccacgctcaa aacctatggc aacaaggcgt ggaacagcag cacagggcag   18240
gcgctgaggg aaaagctgaa agagcagaac ttccagcaga aggtggtcga tggcctggcc   18300
tcgggcatca acggggtggt ggacctggcc aaccaggccg tgcagaaaca gatcaacagc   18360
cgcctggacg cggtcccgcc cgcggggtcc gtggagatgc cccaggtgga ggaggagctg   18420
cctcccctgg acaagcgcgg cgacaagcga ccgcgtcccg acgcggagga gacgctgctg   18480
acgcacacgg acgagccgcc cccgtacgag gaggcggtga aactgggtct gcccaccacg   18540
cggcccgtgg cgcctctggc caccggggtg ctgaaaccca gcagcagcag ccagcccgcg   18600
accctggact tgcctccgcc tgcttcccgc ccctccacag tggctaagcc cctgccgccg   18660
gtggccgtcg cgtcgcgcgc ccccgaggc cgcccccagg cgaactggca gagcactctg   18720
aacagcatcg tgggtctggg agtgcagagt gtgaagcgcc gccgctgcta ttaaaagaca   18780
ctgtagcgct taacttgctt gtctgtgtgt gtatatgtat gtccgccgac cagaaggagg   18840
aagaggcgcg tcgccgagtt gcaagatggc cacccccatcg atgctgcccc agtgggcgta   18900
catgcacatc gccggacagg acgcttcgga gtacctgagt ccgggtctgg tgcagttcgc   18960
ccgcgccaca gacacctact tcagtctggg gaacaagttt aggaaccccca cggtggcgcc   19020
cacgcacgat gtgaccaccg accgcagcca gcggctgacg ctgcgcttcg tgcccgtgga   19080
ccgcgaggac aacacctact cgtacaaagt gcgctacacg ctggccgtgg gcgacaaccg   19140
cgtgctggac atggccagca cctactttga catccgcggc gtgctggatc ggggcccccag   19200
cttcaaaccc tactccggca ccgcctacaa cagcctagct cccaagggag cgcccaacac   19260
ctcacagtgg aaggattccg acagcaaaat gcatactttt ggagttgctg ccatgcccgg   19320
tgttgttggt aaaaaaatag aagccgatgg tctgcctatt ggaatagatt catcctctgg   19380
aactgacacc ataatttatg ctgataaaac tttccaacca gagccacagg ttggaagtga   19440
cagttgggtc gacaccaatg gtgcagagga aaaatatgga ggtagagctc ttaaggacac   19500
tacaaacatg aagccctgct acggttcttt tgccaggcct accaacaaag aaggtggaca   19560
ggctaacata aaagattctg aaactgccag cactactcct aactatgata tagatttggc   19620
attctttgac agcaaaaata ttgcagctaa ctacgatcca gatattgtaa tgtacacaga   19680
aaatgttgag ttgcaaactc cagatactca tattgtgttt aagccaggaa cttcagatga   19740
aagttcagaa gccaatttgg gccagcaggc catgcccaac agacccaact acatcgggtt   19800
cagagacaac tttatcgggc tcatgtacta caacagcact ggcaatatgg gtgtactggc   19860
tggtcaggcc tccagctaa atgctgtggt ggacttgcag gacagaaaca ccgaactgtc   19920
ctaccagctc ttgcttgact ctctgggtga cagaaccagg tatttcagta tgtggaatca   19980
ggcggtggac agctatgacc ccgatgtgcg cattattgaa aatcacggtg tggaggatga   20040
actcccccaat tattgcttcc ctttgaatgg tgtaggcttt acagatactt accagggtgt   20100
taaagttaag acagatacag ccgctactgg taccaatgga acgcagtggg acaaagatga   20160
taccacagtc agcactgcca atgagatcca ctcaggcaat cctttcgcca tggagatcaa   20220
catccaggcc aacctgtggc ggaacttcct ctacgcgaac gtggcgctgt acctgccga   20280
```

```
ctcctacaag tacacgccgg ccaacatcac gctgccgacc aacaccaaca cctacgatta    20340
catgaacggc cgcgtggtgg cgccctcgct ggtggacgcc tacatcaaca tcggggcgcg    20400
ctggtcgctg gaccccatgg acaacgtcaa ccccttcaac caccaccgca acgcgggcct    20460
gcgctaccgc tccatgctcc tgggcaacgg gcgctacgtg cccttccaca tccaggtgcc    20520
ccaaaagttt ttcgccatca agagcctcct gctcctgccc gggtcctaca cctacgagtg    20580
gaacttccgc aaggacgtca acatgatcct gcagagctcc ctcggcaacg acctgcgcac    20640
ggacggggcc tccatcgcct tcaccagcat caacctctac gccaccttct tccccatggc    20700
gcacaacacc gcctccacgc tcgaggccat gctgcgcaac gacaccaacg accagtcctt    20760
caacgactac ctctcggcgg ccaacatgct ctaccccatc ccggccaacg ccaccaacgt    20820
gcccatctcc atccctcgc gcaactgggc cgccttccgc ggatggtcct tcacgcgcct    20880
caagacccgc gagacgccct cgctcggctc cgggttcgac ccctacttcg tctactcggg    20940
ctccatcccc tacctcgacg gcaccttcta cctcaaccac accttcaaga aggtctccat    21000
caccttcgac tcctccgtca gctggcccgg caacgaccgc ctcctgacgc ccaacgagtt    21060
cgaaatcaag cgcaccgtcg acggagaggg atacaacgtg gcccagtgca acatgaccaa    21120
ggactggttc ctggtccaga tgctggccca ctacaacatc ggctaccagg gcttctacgt    21180
gcccgagggc tacaaggacc gcatgtactc cttcttccgc aacttccagc ccatgagccg    21240
ccaggtcgtg gacgaggtca actacaagga ctaccaggcc gtcaccctgg cctaccagca    21300
caacaactcg ggcttcgtcg gctacctcgc gcccaccatg cgccagggcc agccctaccc    21360
cgccaactac ccctacccgc tcatcggcaa gagcgccgtc gccagcgtca cccagaaaaa    21420
gttcctctgc gaccgggtca tgtggcgcat ccccttctcc agcaacttca tgtccatggg    21480
cgcgctcacc gacctcggcc agaacatgct ctacgccaac tccgcccacg cgctagacat    21540
gaatttcgaa gtcgacccca tggatgagtc caccccttctc tatgttgtct tcgaagtctt    21600
cgacgtcgtc cgagtgcacc agccccaccg cggcgtcatc gaggccgtct acctgcgcac    21660
gcccttctcg gccggcaacg ccaccaccta agcccccgct cttgcttctt gcaagatgac    21720
ggcctgtggc tccggcgagc aggagctcag ggccatcctc cgcgacctgg gctgcgggcc    21780
ctgcttcctg ggcaccttcg acaagcgctt cccgggattc atggccccgc acaagctggc    21840
ctgcgccatc gtcaacacgg ccggccgcga gaccgggggc gagcactggc tggccttcgc    21900
ctggaacccg cgctcccaca cctgctacct cttcgacccc ttcgggttct cggacgagcg    21960
cctcaagcag atctaccagt tcgagtacga gggcctgctg cgccgcagcg ccctggccac    22020
cgaggaccgc tgcatcaccc tggaaaagtc cacccagacc gtgcagggtc cgcgctcggc    22080
cgcctgcggg ctcttctgct gcatgttcct gcacgccttc gtgcactggc ccgaccgccc    22140
catggacaag aaccccacca tgaacttgct gacgggggtg cccaacggca tgctccagtc    22200
gccccaggtg gaacccaccc tgcgccgcaa ccaggaggcg ctctaccgct tcctcaacgc    22260
ccactccgcc tactttcgct cccaccgcgc gcgcatcgag aaggccaccg ccttcgaccg    22320
catgaatcaa gacatgtaaa ctgtgtgtat gtgaatgctt tattcatcat aataaacagc    22380
acatgtttat gccaccttct ctgaggctct gactttatt agaaatcgaa ggggttctgc    22440
cggctctcgg cgtgccccgc gggcagggat acgttgcgga actggtactt gggcagccac    22500
ttgaactcgg ggatcagcag cttcggcacg gggaggtcgg ggaacgagtc gctccacagc    22560
ttgcgcgtga gttgcagggc gcccagcagg tcgggcgcgg agatcttgaa atcgcagttg    22620
ggacccgcgt tctgcgcgcg agagttgcgg tacacggggt tgcagcactg gaacaccatc    22680
```

```
agggccgggt gcttcacgct cgccagcacc gtcgcgtcgg tgatgccctc cacgtccaga  22740
tcctcggcgt tggccatccc gaaggggggtc atcttgcagg tctgccgccc catgctgggc  22800
acgcagccgg gcttgtggtt gcaatcgcag tgcaggggga tcagcatcat ctgagcctgc  22860
tcggagctca tgcccgggta catggccttc atgaaagcct ccagctggcg gaaggcctgc  22920
tgcgccttgc cgccctcggt gaagaagacc ccacaggact tgctagagaa ctggttggtg  22980
gcgcagcccg cgtcgtgcac gcagcagcgc gcgtcgttgt tggccagctg caccacgctg  23040
cgcccccagc ggttctgggt gatcttggcc cggtcggggt tctccttcag cgcgcgctgc  23100
ccgttctcgc tcgccacatc catctcgatc gtgtgctcct tctggatcat cacggtcccg  23160
tgcaggcacc gcagcttgcc ctcggcctcg gtgcacccgt gcagccacag cgcgcagccg  23220
gtgcactccc agttcttgtg ggcgatctgg gagtgcgagt gcacgaagcc ctgcaggaag  23280
cggcccatca tcgtggtcag ggtcttgttg ctggtgaagg tcagcgggat gccgcggtgc  23340
tcctcgttca catacaggtg gcagatgcgg cggtacacct cgccctgctc gggcatcagc  23400
tggaaggcgg acttcaggtc gctctccacg cggtaccgct ccatcagcag cgtcatcact  23460
tccatgccct tctcccaggc cgaaacgatc ggcaggctca gggggttctt caccgtcatc  23520
ttagtcgccg ccgccgaagt caggggggtcg ttctcgtcca gggtctcaaa cactcgcttg  23580
ccgtccttct cggtgatgcg cacgggggga aagctgaagc ccacggccgc cagctcctcc  23640
tcggcctgcc tttcgtcctc gctgtcctgg ctgatgtctt gcaaaggcac atgcttggtc  23700
ttgcggggtt tcttttttggg cggcagaggc ggcggcggag acgtgctggg cgagcgcgag  23760
ttctcgctca ccacgactat ttcttcttct tggccgtcgt ccgagaccac gcggcggtag  23820
gcatgcctct tctggggcag aggcggaggc gacgggctct cgcggttcgg cgggcggctg  23880
gcagagcccc ttccgcgttc gggggtgcgc tcctggcggc gctgctctga ctgacttcct  23940
ccgcggccgg ccattgtgtt ctcctaggga gcaacaagca tggagactca gccatcgtcg  24000
ccaacatcgc catctgcccc cgccgccgac gagaaccagc agcagcagaa tgaaagctta  24060
accgccccgc cgcccagccc cacctccgac gccgccgcgg ccccagacat gcaagagatg  24120
gaggaatcca tcgagattga cctgggctac gtgacgcccg cggagcacga ggaggagctg  24180
gcagcgcgct tttcagcccc ggaagagaac caccaagagc agccagagca ggaagcagag  24240
agcgagcagc agcaggctgg gctcgagcat ggcgactacc tgagcggggc agaggacgtg  24300
ctcatcaagc atctggcccg ccaaagcatc atcgtcaagg acgcgctgct cgaccgcgcc  24360
gaggtgcccc tcagcgtggc ggagctcagc cgcgcctacg agcgcaacct cttctcgccg  24420
cgcgtgcccc ccaagcgcca gcccaacggc acctgcgagc ccaacccgcg cctcaacttc  24480
tacccggtct tcgcggtgcc cgaggccctg gccacctacc acctcttttt caagaaccaa  24540
aggatccccg tctcctgccg cgccaaccgc accgcgccg acgccctgct caacctgggt  24600
cccggcgccc gcctacctga tatcacctcc ttggaagagg ttcccaagat cttcgagggt  24660
ctgggcagcg acgagactcg ggccgcgaac gctctgcaag gaagcggaga ggagcatgag  24720
caccacagcg ccctggtgga gttggaaggc gacaacgcgc gcctggcggt gctcaagcgc  24780
acggtcgagc tgacccactt cgcctacccg gcgctcaacc tgccccccaa ggtcatgagc  24840
gccgtcatgg accaggtgct catcaagcgc gcctcgcccc tctcagagga ggagatgcag  24900
gaccccgaga gctcggacga gggcaagccc gtggtcagcg acgagcagct ggcgcgctgg  24960
ctgggagcga gcagcacccc ccagagcctg gaagagcggc gcaagctcat gatggccgtg  25020
```

```
gtcctggtga ccgtggagct ggagtgtctg cgccgcttct tcgccgacgc ggagaccctg   25080
cgcaaggtcg aggagaacct gcactacctc ttcaggcacg ggttcgtgcg ccaggcctgc   25140
aagatctcca acgtggagct gaccaacctg gtctcctaca tgggcatcct gcacgagaac   25200
cgcctggggc agaacgtgct gcacaccacc ctgcgcgggg aggcccgccg cgactacatc   25260
cgcgactgcg tctacctgta cctctgccac acctggcaga cgggcatggg cgtgtggcag   25320
cagtgcctgg aggagcagaa cctgaaagag ctctgcaagc tcctgcagaa gaacctcaag   25380
gccctgtgga ccgggttcga cgagcgcacc accgcctcgg acctggccga cctcatcttc   25440
cccgagcgcc tgcggctgac gctgcgcaac gggctgcccg actttatgag ccaaagcatg   25500
ttgcaaaact ttcgctcttt catcctcgaa cgctccggga tcctgcccgc cacctgctcc   25560
gcactgccct cggacttcgt gccgctgacc ttccgcgagt gccccccgcc gctctggagc   25620
cactgctact tgctgcgcct ggccaactac ctggcctacc actcggacgt gatcgaggac   25680
gtcagcagcg agggtctgct cgagtgccac tgccgctgca acctctgcac gccgcaccgc   25740
tccttggcct gcaaccccca gctgctgagc gagacccaga tcatcggcac cttcgagttg   25800
caaggccccg gcgagggcaa gggggggtctc aaactcaccc cggggctgtg gacctcggcc   25860
tacttgcgca agttcgtgcc cgaggactac catcccttcg agatcaggtt ctacgaggac   25920
caatcccagc cgcccaaggc cgagctgtcg gcctgcgtca tcacccaggg ggccatcctg   25980
gcccaattgc aagccatcca gaaatcccgc caagaatttc tgctgaaaaa gggccacggg   26040
gtctacttgg accccagac cggagaggag ctcaaccccca gcttcccccca ggatgccccg   26100 aggaagcagc aagaagctga agtggagct ccgctgccg ccggaggatt tggaggaaga   26160
ctgggagagc agtcaggcag aggagatgga agactggac agcactcagg cagaggagga   26220
cagcctgcaa gacagtctgg aggaggaaga cgaggtggag gaggaggcag aggaagaagc   26280
agccgccgcc agaccgtcgt cctcggcgga ggagaaagca agcagcacgg ataccatctc   26340
cgctccgggt cggggtcgcg gcggccgggc ccacagtaga tgggacgaga ccgggcgctt   26400
cccgaacccc accacccaga ccggtaagaa ggagcggcag ggatacaagt cctggcgggg   26460
gcacaaaaac gccatcgtct cctgcttgca agcctgcggg ggcaacatct ccttcacccg   26520
gcgctacctg ctcttccacc gcggggtgaa cttcccccgc aacatcttgc attactaccg   26580
tcacctccac agccctact actgtttcca agaagaggca gaaacccagc agcagcagca   26640
gaaaaccagc ggcagcagca gcagctagaa atccacagc ggcggcaggt ggactgagga   26700
tcgcggcgaa cgagccggcg cagacccggg agctgaggaa ccggatcttt cccaccctct   26760
atgccatctt ccagcagagt cgggggcagg agcaggaact gaaagtcaag aaccgttctc   26820
tgcgctcgct caccgcagt tgtctgtatc acaagagcga agaccaactt cagcgcactc   26880
tcgaggacgc cgaggctctc ttcaacaagt actgcgcgct cactcttaaa gagtagcccg   26940
cgcccgccca cacacggaaa aaggcgggaa ttacgtcacc acctgcgccc ttcgcccgac   27000
catcatcatg agcaaagaga ttcccacgcc ttacatgtgg agctaccagc cccagatggg   27060
cctggccgcc ggcgccgccc aggactactc cacccgcatg aactggctca gtgccgggcc   27120
cgcgatgatc tcacgggtga atgacatccg cgccccaccga aaccagatac tcctagaaca   27180
gtcagcgatc accgccacgc cccgccatca ccttaatccg cgtaattggc ccgccgccct   27240
ggtgtaccag gaaattcccc agcccacgac cgtactactt ccgcgagacg cccaggccga   27300
agtccagctg actaactcag gtgtccagct ggccggcggc gccgccctgt gtcgtcaccg   27360
ccccgctcag ggtataaagc ggctggtgat ccgaggcaga ggcacacagc tcaacgacga   27420
```

```
ggtggtgagc tcttcgctgg gtctgcgacc tgacggagtc ttccaactcg ccggatcggg   27480
gagatcttcc ttcacgcctc gtcaggccgt cctgactttg gagagttcgt cctcgcagcc   27540
ccgctcgggc ggcatcggca ctctccagtt cgtggaggag ttcactccct cggtctactt   27600 caacccctc tccggctccc ccggccacta cccggacgag ttcatcccga acttcgacgc   27660
catcagcgag tcggtggacg gctacgattg aatgtcccat ggtggcgcgg ctgacctagc   27720
tcggcttcga cacctggacc actgttaatt aatcgcctct cctacgagct cctgcagcag   27780
cgccagaagt tcacctgcct ggtcggagtc aaccccatcg tcatcaccca gcagtcgggc   27840
gataccaagg ggtgcatcca ctgctcctgc gactcccccg actgcgtcca cactctgatc   27900
aagaccctct gcggcctccg cgacctcctc cccatgaact aatcaccccc ttatccagtg   27960
aaataaagat catattgatg atgattttac agaaataaag atacaatcat attgatgatt   28020
tgagtttaat aaaaaataaa gaatcactta cttgaaatct gataccaggt ctctgtccat   28080
gttttctgcc aacaccactt cactcccctc ttcccagctc tggtactgca ggccccggcg   28140
ggctgcaaac ttcctccaca cgctgaaggg gatgtcaaat tcctcctgtc cctcaatctt   28200 catttatct tctatcagat gtccaaaaag cgcgtccggg tggatgatga cttcgaccc    28260 gtctacccct acgatgcaga caacgcaccg accgtgccct tcatcaaccc cccttcgtc    28320 tcttcagatg gattccaaga gaagccctg ggggtgctgt ccctgcgact ggccgacccc    28380
gtcaccacca agaacgggga aatcaccctc aagctgggag aggggtgga cctcgactcc    28440 tcggaaaaac tcatctccaa cacggccacc aaggccgccg cccctctcag tttttccaac   28500
aacaccattt cccttaacat ggatcacccc ttttacacta aagatggaaa attatcctta   28560
caagtttctc caccattaaa tatactgaga acaagcattc taaacacact agctttaggt   28620
tttggatcag gtttaggact ccgtggctct gccttggcag tacagttagt ctctccactt   28680
acatttgata ctgatggaaa cataaagctt accttagaca gaggtttgca tgttacaaca   28740
ggagatgcaa ttgaaagcaa cataagctgg gctaaaggtt taaaatttga agatggagcc   28800
atagcaacca acattggaaa tgggttagag tttggaagca gtagtacaga aacaggtgtt   28860
gatgatgctt acccaatcca agttaaactt ggatctggcc ttagctttga cagtacagga   28920
gccataatgg ctggtaacaa agaagacgat aaactcactt tgtggacaac acctgatcca   28980
tcgccaaact gtcaaatact cgcagaaaat gatgcaaaac taacactttg cttgactaaa   29040
tgtggtagtc aaatactggc cactgtgtca gtcttagttg taggaagtgg aaacctaaac   29100
cccattactg gcaccgtaag cagtgctcag gtgtttctac gttttgatgc aaacggtgtt   29160
cttttaacag aacattctac actaaaaaaa tactgggggt ataggcaggg agatagcata   29220
gatggcactc catataccaa tgctgtagga ttcatgccca atttaaaagc ttatccaaag   29280
tcacaaagtt ctactactaa aaataatata gtagggcaag tatacatgaa tggagatgtt   29340
tcaaaaccta tgcttctcac tataaccctc aatggtactg atgacagcaa cagtacatat   29400
tcaatgtcat tttcatacac ctggactaat ggaagctatg ttggagcaac atttgggct    29460 aactcttata ccttctcata catcgcccaa gaatgaacac tgtatcccac cctgcatgcc   29520
aacccttccc accccactct gtggaaaaaa ctctgaaaca caaataaaaa taagttcaa    29580 gtgttttatt gattcaacag ttttacagga ttcgagcagt tatttttcct ccaccctccc   29640
aggacatgga atacaccacc ctctccccc gcacagcctt gaacatctga atgccattgg    29700
tgatggacat gcttttggtc tccacgttcc acacagtttc agagcgagcc agtctcgggt   29760
```

| | | | | |
|---|---|---|---|---|
| cggtcaggga | gatgaaaccc | tccgggcaca | attgggagaa | gtactcgcct acatgggggt | 29820 |
| agagtcataa | tcgtgcatca | ggatagggcg | gtggtgctgc | agcagcgcgc gaataaactg | 29880 |
| ctgccgccgc | cgctccgtcc | tgcaggaata | caacatggca | gtggtctcct cagcgatgat | 29940 |
| tcgcaccgcc | cgcagcataa | ggcgccttgt | cctccgggca | cagcagcgca ccctgatctc | 30000 |
| acttaaatca | gcacagtaac | tgcagcacag | caccacaata | ttgttcaaaa tcccacagtg | 30060 |
| caaggcgctg | tatccaaagc | tcatggcggg | gaccacagaa | cccacgtggc catcatacca | 30120 |
| caagcgcagg | tagattaagt | ggcgacccct | cataaacacg | ctggacataa acattacctc | 30180 |
| ttttggcatg | ttgtaattca | ccacctcccg | gtaccatata | aacctctgat taaacatggc | 30240 |
| gccatccacc | accatcctaa | accagctggc | caaaacctgc | ccgccggcta tacactgcag | 30300 |
| ggaaccggga | ctggaacaat | gacagtggag | agcccaggac | tcgtaaccat ggatcatcat | 30360 |
| gctcgtcatg | atatcaatgt | tggcacaaca | caggcacacg | tgcatacact tcctcaggat | 30420 |
| tacaagctcc | tcccgcgtta | gaaccatatc | ccagggaaca | acccattcct gaatcagcgt | 30480 |
| aaatcccaca | ctgcagggaa | gacctcgcac | gtaactcacg | ttgtgcattg tcaaagtgtt | 30540 |
| acattcgggc | agcagcggat | gatcctccag | tatggtagcg | cgggtttctg tctcaaaagg | 30600 |
| aggtagacga | tccctactgt | acggagtgcg | ccgagacaac | cgagatcgtg ttggtcgtag | 30660 |
| tgtcatgcca | aatggaacgc | cggacgtagt | catatttcct | gaagtcttgg cgcgccaaag | 30720 |
| tctagaagcg | gtccatagct | taccgagcgg | cagcagcagc | ggcacacaac aggcgcaaga | 30780 |
| gtcagagaaa | agactgagct | ctaacctgtc | cgcccgctct | ctgctcaata tatagcccag | 30840 |
| atctacactg | acgtaaaggc | caaagtctaa | aaatacccgc | caaatagtca cacacgccca | 30900 |
| gcacacgccc | agaaaccggt | gacacactca | aaaaaatacg | cgcacttcct caaacgccca | 30960 |
| aactgccgtc | atttccgggt | tcccacgcta | cgtcatcaaa | acacgacttt caaattccgt | 31020 |
| cgaccgttaa | aaacgtcacc | cgccccgccc | ctaacggtcg | cccgtctctc agccaatcag | 31080 |
| cgccccgcat | ccccaaattc | aaacacctca | tttgcatatt | aacgcgcacc aaaagtttga | 31140 |
| ggtatattat | tgatgatg | | | | 31158 |

<210> SEQ ID NO 7
<211> LENGTH: 37168
<212> TYPE: DNA
<213> ORGANISM: Artificial Sequence
<220> FEATURE:
<223> OTHER INFORMATION: synthetic chimpanzee adenovirus serotype PanAd3
      with Ebola virus Zaire wild type transmembrane
      envelope glycoprotein (GP) insert (PanAd3 Ebola
      Zaire (PB/6001))
<220> FEATURE:
<221> NAME/KEY: CDS
<222> LOCATION: (2133)...(4434)
<223> OTHER INFORMATION: Ebola virus Zaire wild type transmembrane
      envelope glycoprotein (GP) insert in PanAd3 Ebola Zaire (PB/6001)
<220> FEATURE:
<221> NAME/KEY: CDS
<222> LOCATION: (15442)...(17196)
<223> OTHER INFORMATION: chimpanzee adenovirus serotype ChAd63 penton
<220> FEATURE:
<221> NAME/KEY: CDS
<222> LOCATION: (20287)...(23181)
<223> OTHER INFORMATION: chimpanzee adenovirus serotype ChAd63 hexon
<220> FEATURE:
<221> NAME/KEY: CDS
<222> LOCATION: (34065)...(35693)
<223> OTHER INFORMATION: chimpanzee adenovirus serotype ChAd63 fiber

<400> SEQUENCE: 7
catcatcaat aatataccct attttggatt gaagccaata tgataatgag gtgggcggag    60

```
cggggcgggg cggggaggag cggcggcgcg gggcgggccg ggaggtgtgg cggaagttga    120
gtttgtaagt gtggcggatg tgacttgcta gcgccggatg tggtaaaagt gacgtttttt    180
ggagtgcgac aacgcccacg ggaagtgaca ttttccccgc ggttttacc ggatgtcgta    240 gtgaatttgg gcgttaccaa gtaagatttg gccattttcg cgggaaaact gaaatgggga    300
agtgaaatct gattaatttc gcgttagtca taccgcgtaa tatttgccga gggccgaggg    360
actttgaccg attacgtgga ggaatcgccc aggtgttttt tgaggtgaat ttccgcgttc    420
cgggtcaaag tctccgtttt attattatag gtatacccat tgcatacgtt gtatccatat    480
cataatatgt acatttatat tggctcatgt ccaacattac cgccatgttg acattgatta    540
ttgactagtt attaatagta atcaattacg gggtcattag ttcatagccc atatatggag    600
ttccgcgtta cataacttac ggtaaatggc ccgcctggct gaccgcccaa cgaccccgc     660 ccattgacgt caataatgac gtatgttccc atagtaacgc caatagggac tttccattga    720
cgtcaatggg tggagtattt acggtaaact gcccacttgg cagtacatca agtgtatcat    780
atgccaagta cgccccctat tgacgtcaat gacggtaaat ggcccgcctg gcattatgcc    840
cagtacatga ccttatggga cttcctact tggcagtaca tctacgtatt agtcatcgct    900
attaccatgg tgatgcggtt ttggcagtac atcaatgggc gtggatagcg gtttgactca    960
cggggatttc caagtctcca ccccattgac gtcaatggga gtttgttttg gaaccaaaat   1020
caacgggact ttccaaaatg tcgtaacaac tccgccccat tgacgcaaat gggcggtagg   1080
cgtgtacggt gggaggtcta tataagcaga gctctcccta tcagtgatag agatctccct   1140
atcagtgata gagatcgtcg acgagctcgt ttagtgaacc gtcagatcgc ctggagacgc   1200
catccacgct gttttgacct ccatagaaga caccgggacc gatccagcct ccgcggccgg   1260
gaacggtgca ttggaacgcg gattcccgt gccaagagtg acgtaagtac cgcctataga   1320
ctctataggc acacccctt ggctcttatg catgctatac tgttttggc ttggggccta    1380 tacaccccg cttccttatg ctataggtga tggtatagct tagcctatag gtgtgggtta   1440
ttgaccatta ttgaccactc ccctattggt gacgatactt tccattacta atccataaca   1500
tggctctttg ccacaactat ctctattggc tatatgccaa tactctgtcc ttcagagact   1560
gacacggact ctgtattttt acaggatggg gtcccattta ttatttacaa attcacatat   1620
acaacaacgc cgtccccgt gcccgcagtt tttattaaac atagcgtggg atctccacgc   1680
gaatctcggg tacgtgttcc ggacatgggc tcttctccgg tagcggcgga gcttccacat   1740
ccgagccctg tcccatgcc tccagcggct catggtcgct cggcagctcc ttgctcctaa    1800
cagtggaggc cagacttagg cacagcacaa tgcccaccac caccagtgtg ccgcacaagg    1860
ccgtggcggt agggtatgtg tctgaaaatg agcgtggaga ttgggctcgc acggctgacg   1920
cagatggaag acttaaggca gcggcagaag aagatgcagg cagctgagtt gttgtattct   1980
gataagagtc agaggtaact cccgttgcgg tgctgttaac ggtggagggc agtgtagtct   2040
gagcagtact cgttgctgcc gcgcgcgcca ccagacataa tagctgacag actaacagac   2100
tgttcctttc catgggtctt ttctgcagtc accgtcgtcg acacgtgtga tcagatatcg   2160
cggccgctct agaccaggcc ctggatcgat ccaacaacaa atgggcgtt acaggaatat    2220 tgcagttacc tcgtgatcga ttcaagagga catcattctt tctttgggta attatccttt   2280
tccaaagaac attttccatc ccacttggag tcatccacaa tagcacatta caggttagtg    2340
atgtcgacaa actagtttgt cgtgacaaac tgtcatccac aaatcaattg agatcagttg    2400
```

```
gactgaatct cgaagggaat ggagtggcaa ctgacgtgcc atctgcaact aaaagatggg    2460
gcttcaggtc cggtgtccca ccaaaggtgg tcaattatga agctggtgaa tgggctgaaa    2520
actgctacaa tcttgaaatc aaaaaacctg acgggagtga gtgtctacca gcagcgccag    2580
acgggattcg gggcttcccc cggtgccggt atgtgcacaa agtatcagga acgggaccgt    2640
gtgccggaga ctttgccttc ataaagagg gtgctttctt cctgtatgat cgacttgctt    2700
ccacagttat ctaccgagga acgactttcg ctgaaggtgt cgttgcattt ctgatactgc    2760
cccaagctaa gaaggacttc ttcagctcac accccttgag agagccggtc aatgcaacgg    2820
aggacccgtc tagtggctac tattctacca caattagata tcaggctacc ggttttggaa    2880
ccaatgagac agagtacttg ttcgaggttg acaatttgac ctacgtccaa cttgaatcaa    2940
gattcacacc acagtttctg ctccagctga atgagacaat atatacaagt gggaaaagga    3000
gcaataccac gggaaaacta atttggaagg tcaaccccga aattgataca acaatcgggg    3060
agtgggcctt ctgggaaact aaaaaaaacc tcactagaaa aattcgcagt gaagagttgt    3120 cttttcacagt tgtatcaaac ggagccaaaa acatcagtgg tcagagtccg gcgcgaactt    3180
cttccgaccc agggaccaac acaacaactg aagaccacaa aatcatggct tcagaaaatt    3240
cctctgcaat ggttcaagtg cacagtcaag gaagggaagc tgcagtgtcg catctaacaa    3300
cccttgccac aatctccacg agtccccaat ccctcacaac caaaccaggt ccggacaaca    3360
gcacccataa tacacccgtg tataaacttg acatctctga ggcaactcaa gttgaacaac    3420
atcaccgcag aacagacaac gacagcacag cctccgacac tccctctgcc acgaccgcag    3480
ccggaccccc aaaagcagag aacaccaaca cgagcaagag cactgacttc ctggaccccg    3540
ccaccacaac aagtccccaa aaccacagcg agaccgctgg caacaacaac actcatcacc    3600
aagataccgg agaagagagt gccagcagcg ggaagctagg cttaattacc aatactattg    3660
ctggagtcgc aggactgatc acaggcggga gaagaactcg aagagaagca attgtcaatg    3720
ctcaacccaa atgcaaccct aatttacatt actggactac tcaggatgaa ggtgctgcaa    3780
tcggactggc ctggatacca tatttcgggc cagcagccga gggaatttac atagaggggc    3840
taatgcacaa tcaagatggt ttaatctgtg ggttgagaca gctggccaac gagacgactc    3900
aagctcttca actgttcctg agagccacaa ctgagctacg cacctttttca atcctcaacc    3960 gtaaggcaat tgatttcttg ctgcagcgat ggggcggcac atgccacatt ctgggaccgg    4020
actgctgtat cgaaccacat gattggacca agaacataac agacaaaatt gatcagatta    4080
ttcatgattt tgttgataaa acccttccgg accaggggga caatgacaat tggtggacag    4140
gatggagaca atggatccg gcaggtattg gagttacagg cgttgtaatt gcagttatcg    4200
ctttattctg tatatgcaaa tttgtctttt agttttttctt cagattgctt catgaaaag    4260 ctcagcctca aatcaatgaa accaggattt aattatatgg attacttgaa tctaagatta    4320
cttgacaaat gataatataa tacactggag cttttaaacat agccaatgtg attctaactc    4380
ctttaaactc acagttaatc ataaacaagg tttgaggtac cgagctcgaa ttgatctgct    4440
gtgccttcta gttgccagcc atctgttgtt tgcccctccc ccgtgccttc cttgaccctg    4500
gaaggtgcca ctcccactgt cctttcctaa taaatgagg aaattgcatc gcattgtctg    4560
agtaggtgtc attctattct ggggggtggg gtggggcagg acagcaaggg ggaggattgg    4620
gaagacaata gcaggcatgc tggggatgcg gtgggctcta gatatcagcg atcgctgagg    4680
tgggtgagtg ggcgtggtct gggggtggga agcaatatat aagttggggg tcttagggtc    4740
tctgtgtctg ttttgcagag ggaccgccgg cgccatgagc gggagcagta gcagcaacgc    4800
```

```
cttggatggc agcatcgtga gcccttattt gacgacgcgc atgccccact gggccggggt    4860
gcgtcagaat gtgatgggct ccagcatcga cggacgaccc gtgctgcccg caaattccgc    4920
cacgctgacc tacgcgaccg tcgcggggac cccgttggac gccaccgccg ccgccgccgc    4980
caccgccgcc gcctcggccg tgcgcagcct ggccacggac tttgcattct tgggacccct    5040
ggccaccggg gcggccgccc gtgccgccgt tcgcgatgac aagctgaccg ccctgctggc    5100
gcagttggat gcgcttaccc gggaactggg tgaccttcg cagcaggtcg tggccctgcg    5160
ccagcaggtc tccgccctgc aggctagcgg gaatgcttct cctgcaaatg ccgtttaaga    5220
taaataaaac cagactctgt tgataaataa aaccagactc tgtttggatt aaagaaaagt    5280
agcaagtgca ttgctctctt tatttcataa ttttccgcgc gcgataggcc cgagtccagc    5340
gttctcggtc gttgagggtg cggtgtatct tctccaggac gtggtagagg tggctctgga    5400
cgttgagata catgggcatg agcccgtccc gggggtggag gtagcaccac tgcagagctt    5460
catgctccgg ggtggtgttg tagatgatcc agtcgtagca ggagcgctgg gcatggtgcc    5520
taaaaatgtc cttaagcagc aggccgatgg ccaggggag gcccttggtg taagtgttta    5580
caaaacggtt gagttgggaa gggtgcatgc ggggtgagat gatgtgcatc ttagattgta    5640
tttttagatt ggcgatgttt cctcccagat cccttctggg attcatgttg tggaggacca    5700
ccagcacagt atatccggtg cacttgggaa atttgtcatg cagcttagag ggaaatgcgt    5760
ggaagaactt ggagacgccc ttgtggcctc ccagattctc catgcattcg tccatgatga    5820
tggcaatggg cccgcgggag gcggcctggg caaagatgtt tctggggtca ctgcatcgt    5880 agttgtgttc cagggtgaga tcgtcatagg ccattttat aaagcgcggg cggagggtgc    5940
ccgactgggg gatgatggtt ccctcggccc ccggggcgta gttgccttcg cagatctgca    6000
tttcccaggc cttaatctct gagggggaa tcatatccac ttgcggggcg atgaagaaaa    6060
cggtttccgg agccggggag attaactggg atgagagcag gtttctcagc agctgtgact    6120
ttccacagcc ggtgggtcca taataacac ctataaccgg ctgcagctgg tagttgagcg    6180
agctgcagct gccgtcgtcc cggaggaggg gggccacctc attgagcatg tcccggacgc    6240
gcttgttctc ctcgaccagg tccgccagaa ggcgctcgcc gcccagggac agcagctctt    6300
gcaaggaagc aaagtttttc agcggtttga ggccgtccgc cgtgggcatg ttttcaggg    6360 tctggccgag cagctccagg cggtcccaga gctcggtgac gtgctctacg gcatctctat    6420
ccagcatatc tcctcgtttc gcgggttggg gcggctttcg ctgtagggca ccaggcgatg    6480
gtcgtccagc gcggccagag tcatgtcctt ccatgggcgc agggtcctcg tcagggtggt    6540
ctgggtcacg gtgaaggggt gcgccccggg ctgggcgctg ccagggtgc gcttgagact    6600 ggtcctgctg gtgctgaagc gctgccggtc ttcgccctgc gcgtcggcca ggtagcattt    6660
gaccatggtg tcgtagtcca gcccctccgc ggcgtgtccc ttggcgcgca gcttgccctt    6720
ggaggtggcg ccgcacgcgg ggcactgcag gctcttgagc gctagagct tgggggcgag    6780 gaagaccgat tcgggggagt aggcgtccgc gccgcaggcc ccgcacacgg tctcgcactc    6840
caccagccag gtgagctcgg ggcgctcggg gtcaaaaacc aggtttcccc catgcttttt    6900
gatgcgtttc ttacctcggg tctccatgag gcggtgtccc cgttcggtga cgaagaggct    6960
gtccgtgtct ccgtagaccg acttgagggg tctgtcctcc aggggggtcc ctcggtcctc    7020
ttcgtagaga aactcggacc actctgagac aaaggcccgc gtccaggcca ggacgaagga    7080
ggccaggtgg gaggggtacc ggtcgttgtc cactaggggg tccaccttct ccaaggtgtg    7140
```

```
aagacacatg tcgccctcct cggcgtccag gaaggtgatt ggcttgtagg tgtaggccac   7200
gtgacccggg gttccggacg ggggggtata aaagggggtg ggggcgcgct cgtcctcact   7260
ctcttccgca tcgctgtctg cgagggccag ctgctggggt gagtattccc tctcgaaggc   7320
gggcatgacc tcagcgctga ggctgtcagt ttctaaaaac gaggaggatt tgatgttcac   7380
ctgtcccgag ctgatgcctt tgagggtgcc cgcgtccatc tggtcagaaa acacgatctt   7440
tttattgtcc agcttggtgg cgaacgaccc gtagagggcg ttggagagca gcttggcgat   7500
ggagcgcagg gtctgattct tgtcccggtc ggcgcgctcc ttggccgcga tgttgagctg   7560
cacgtactcg cgcgcgacgc agcgccactc ggggaagacg gtggtgcgct cgtcgggcac   7620
caggcgcacg cgccagccgc ggttgtgcag ggtgacgagg tccacgctgg tggcgacctc   7680
gccgcgcagg cgctcgttgg tccagcagag gcgcccgccc ttgcgcgagc agaagggggg   7740 caggggggtcg agttgggttt cgtccggggg gtccgcgtcc accgtgaaga cccccggggcg   7800 caggcgcgcg tcgaagtagt cgatcttgca tccttgcaag tccagcgccc gctgccagtc   7860
gcgggcggcg agcgcgcgct cgtaggggtt gagcggcggg ccccagggca tggggtgggt   7920
gagcgcggag gcgtacatgc cgcagatgtc atagacgtag aggggctccc ggaggatgcc   7980
caggtaggtg gggtagcagc ggccgccgcg gatgctggcg cgcacgtagt cgtagagctc   8040
gtgcgagggg gcgaggaggt cggggcccag gttggtgcgg gcggggcgct ccgcgcggaa   8100
gacgatctgc ctgaagatgg catgcgagtt ggaagagatg gtggggcgct ggaagacgtt   8160
gaagctggcg tcctgcaggc cgacggcgtc gcgcacgaag gaggcgtagg actcgcgcag   8220
cttgtgcacc agctcggcgg tgacctgcac gtcgagcgcg cagtagtcga gggtctcgcg   8280
gatgatgtca tacttagcct gccccttctt tttccacagc tcgcggttga ggacgaactc   8340
ttcgcggtct ttccagtact cttggatcgg gaaaccgtcc ggctccgaac ggtaagagcc   8400
cagcatgtag aactggttga cggcctggta ggcgcagcag cccttctcca cgggcagggc   8460
gtaggcctgc gcggccttgc ggagcgaggt gtgggtcagg gcgaaggtgt ccctgaccat   8520
gaccttgagg tactggtgtt tgaagtcgga gtcgtcgcag ccgcccccgct cccagagcga   8580 gaagtcggtg cgcttttttgg agcggggggtt gggcagcgcg aaggtgacat cgttgtagag   8640
gatcttgccc gcgcgaggca tgaagttgcg ggtgatgcgg aagggccccg gcacttccga   8700
gcggttgttg atgacctggg cggcgagcac gatctcgtcg aagccgttga tgttgtggcc   8760
cacgatgtag agttccagga agcggggccg gcccttgacg ctgggcagct tctttagctc   8820
ttcgtaggtg agctcctcgg gcgaggcgag gccgtgctcg gccagggccc agtccgccag   8880 gtgcggggttg tccgcgagga aggaccgcca gaggtcgcgg gccaggaggg tctgcaggcg   8940
gtccctgaag gtcctgaact ggcggcctac ggccatcttt tcgggggtga cgcagtagaa   9000
ggtgaggggg tcttgctgcc aggggtccca gtcgagctcc agggcgaggt cgcgcgcggc   9060
ggcgaccagg cgctcgtcgc ccccgaattt catgaccagc atgaagggca cgagctgctt   9120
tccgaaggcg cccatccaag tgtaggtctc tacatcgtag gtgacaaaga gacgttccgt   9180
gcgaggatgc gagccgatcg ggaagaactg gatctcccgc caccagttgg aggagtggct   9240
gttgatgtgt tgaaagtaga agtcccgtcg gcgggccgag cactcgtgct ggcttttgta   9300
aaagcgagcg cagtactggc agcgctgcac gggctgtacc tcttgcacga gatgcacctg   9360
ccgaccgcgg acgaggaagc tgagtgggaa tctgagcccc ccgcatggct cgcggcctgg   9420
ctggtgctct tctactttgg atgcgtgcc gtcaccgtct ggctcctcga ggggtgttac   9480
ggtggagcgg atcaccacgc cgcgcgagcc gcaggtccag atatcggcgc gcggcggtcg   9540
```

```
gagtttgatg acgacatcgc gcagctggga gctgtccatg gtctggagct cccgcggcgg   9600
cggcaggtca gccgggagtt cttgcaggtt tacctcgcag agacgggcca gggcgcgggg   9660
caggtccagg tggtacttga attcgagagg cgtgttggtg gcggcgtcga tggcttgcag   9720
tatgccgcag ccccgggcg cgacgacggt gccccgcggg gcggtgaagc tcccgccgcc    9780
gctcctgctg tcgccgccgg tggcggggct tagaagcggt gccgcggtcg ggccccccgga  9840
ggtaggggg gctccggtcc cgcgggcagg ggcggcagcg gcacgtcggc gccgcgcgcg   9900
ggcaggagct ggtgctgcgc ccggaggttg ctggcgaagg cgacgacgcg gcggttgatc    9960
tcctggatct ggcgcctctg cgtgaagacg acgggtccgg tgagcttgaa cctgaaagag   10020
agttcgacag aatcaatctc ggtgtcattg accgcgacct ggcgcaggat ctcctgcacg   10080
tcgcccgagt tgtcttggta ggcgatctcg gccatgaact gttcaatctc ttcctcctgg   10140
aggtctccgc gtccggcgcg ctccacggtg gccgccaggt cgttggagat gcgcgccatg   10200
agctgcgaga aggcgttgag tccgccctcg ttccacactc ggctgtagac cacgccgccc   10260
tggtcgtcgc gggcgcgcat gaccacctgc gcgaggttga gttccacgtg gcgcgcaaag   10320
acggcgtagt tgcgcaggcg ctggaagagg tagttgaggg tggtggcggt gtgctcggcc   10380
acaaagaagt acatgaccca gcggcgcaac gtggattcgt tgatgtcccc caaggcctcc   10440
agtcgctcca tggcctcgta gaagtccacg gcgaagttga aaaactggga gttgcgcgcc   10500
gacacggtca actcctcctc cagaagacgg atgagctcgg cgacggtgtc gcgcacctcg   10560
cgctcgaagg ctatgggaat ctcttcctcc gccagcatca ccacctcttc ctcttcttcc   10620
tcctctggca cttccatgat ggcttcctcc tcttcggggg gtggcggcgg gggaggggc   10680
gctcggcgcc ggcggcggcg caccgggagg cggtccacga agcgctcgat catctccccg   10740
cggcggcgac gcatggtctc ggtgacggcg cggccgttct ctcggggacg cagctggaag   10800
acgccgccgg tcatctggtg ctggggcggg tggccgtggg gcagcgagac cgcgctgacg   10860
atgcatctta acaattgctg cgtaggtacg ccgccgaggg acctgaggga gtccagatcc   10920
accggatccg aaaaccttc gaggaaggca tctaaccagt cgcagtcgca aggtaggctg    10980
agcaccgtgg cgggcggcgg ggggtggggg gagtgtctgg cggaggtgct gctgatgatg   11040
taattgaagt aggcggtctt gacacggcgg atggtcgaca ggagcaccat gtctttgggc   11100
ccggcctgct ggatgcggag gcggtcggcc atgcccagg cttcgttctg gcatctgcgc    11160
aggtctttgt agtagtcttg catgagcctt tccaccggca cctcttctcc ttcttcttct   11220
gacatctctg ctgcatctgc ggccctgggg cgacggcgcg cgcccctgcc ccccatgcgc   11280
gtcaccccga accccctgag cggctggagc agggccaggt cggcgacgac gcgctcggcc   11340
aggatgccct gctggacctg cgtgagggtg gtttggaagt catccaagtc cacgaagcgg   11400
tggtaggcgc ccgtgttgat ggtgtaggtg cagttggcca tgacggacca gttgacggtc   11460
tggtggcccg gttgcgtcat ctcggtgtac ctgaggcgcg agtaggcgcg cgagtcgaag   11520
atgtagtcgt tgcaagtccg caccaggtac tggtagccca ccaggaagtg cggcggcggc   11580
tggcggtaga ggggccagcg gagggtggcg ggggctccgg gggccaggtc ttccagcatg   11640
aggcggtggt attcgtagat gtacctggac atccaggtga tgcccgcggc ggtggtggag   11700
gcgcgcggga agtcgcgcac ccggttccag atgttgcgca gcggcagaaa gtgctccatg   11760
gtaggcgtgc tctggccggt caggcgcgcg cagtcgttga tactctagac cagggaaaac   11820
gaaagccggt cagcgggcac tcttccgtgg tctggtggat aaattcgcaa gggtatcatg   11880
```

```
gcggagggcc tcggttcgag ccccgggccc gggccggacg gtccgccatg atccacgcgg   11940
ttaccgcccg cgtgtcgaac ccaggtggcg acgtcagaca acgtggagt gttccttttg    12000 ggttttttc caaattttc tggccgggcg ccgacgccgc cgcgtaagag actagagtgc     12060
aaaagcgaaa gcagtaagtg gctcgctccc tgtagcccgg aggatccttg ctaagggttg   12120
cgttgcggcg aaccccggtt cgagtctggc tctcgctggg ccgctcgggt cggccggaac   12180
cgcggctaag gcgggattgg cctccccctc attaaagacc ccgcttgcgg attcctccgg   12240
acacagggga cgagccccctt tttacttttg cttttctcag atgcatccgg tgctgcggca   12300
gatgcgcccc ccgccccagc agcagcagca gcaacatcag caagagcggc accagcagca   12360
gcgggagtca tgcagggccc cctcgcccac gctcggcggt ccggcgacct cggcgtccgc   12420
ggccgtgtct ggagccggcg gcggtgggct ggcggacgac ccggaggagc ccccgcggcg   12480
cagggccaga cagtacctgg acctggagga gggcgagggc ctggcgcgac tgggggcgcc   12540
gtcccccgag cgccaccccgc gggtgcagct gaagcgcgac tcgcgcgagg cgtacgtgcc   12600
tcggcagaac ctgttcagag accgcgcggg cgaggagccc gaggagatgc gggaccgcag   12660
gttcgccgcg gggcgggagc tgcggcaggg gctgaaccgg gagcggctgc tgcgcgagga   12720
ggactttgag cccgacgcgc ggacggggat cagccccgcg cgcgcgcacg tggcggccgc   12780
cgacctggtg acggcgtacg agcagacggt gaaccaggag atcaacttcc aaaaaagctt   12840
caacaaccac gtgcgcacgc tggtggcgcg cgaggaggtg accatcggcc tgatgcacct   12900
gtgggacttt gtgagcgcgc tggagcagaa ccccaacagc aagcctctga cggcgcagct   12960
gttcctgata gtgcagcaca gcagggacaa cgaggcgttc agggacgcgc tgctgaacat   13020
caccgagccc gagggtcggt ggctgctgga cctgattaac atcttgcaga gcatagtggt   13080
gcaggagcgc agcctgagcc tggccgacaa ggtggcggcc atcaattact cgatgctcag   13140
tctgggcaag ttttacgcgc gcaagatcta ccagacgccg tacgtgccca tagacaagga   13200
ggtgaagatc gacggcttct acatgcgcat ggcgctgaag gtgctgaccc tgagcgacga   13260
cctgggcgtg taccgcaacg agcgcatcca caaggccgtg agcgtgagcc ggcggcgcga   13320
gctgagcgac cgcgagctga tgcacagcct gcagcgggcg ctggcggggg ccggcagcgg   13380
cgacagggag gccgagtcct acttcgaggc ggggcggac ctgcgctggg tgcccagccg    13440
gagggccctg gaggccgcgg gggcccgccg cgaggactat gcagacgagg aggaggagga   13500
tgacgaggag tacgagctag aggagggcga gtacctggac taaaccgcag gtggtgtttt   13560
tggtagatgc aagacccgaa cgtggtggac ccggcgctgc gggcggctct gcagagccag   13620
ccgtccggcc ttaactctac agacgactgg cgacaggtca tggaccgcat catgtcgctg   13680
acggcgcgca atccggacgc gttccggcag cagccgcagg ccaacaggct ctccgccatc   13740
ttggaggcgg tggtgcctgc gcgcgcgaac cccacgcacg agaaggtgct ggccatagtg   13800
aacgcgctgg ccgagaacag ggccatccgc ccggacgagg ccgggctggt gtacgacgcg   13860
ctgctgcagc gcgtggcccg ctacaacagc ggcaacgtgc agaccaacct ggaccggctg   13920 gtggggacg tgcgcgaggc ggtggcgcag cgggagcgcg cggagcggca gggaaacctg   13980
ggctccatgg tggcgctgaa cgccttcctg agcacgcagc cggccaacgt gccgcggggg   14040
caggaggact acaccaactt tgtgagcgcg ctgcggctga tggtgaccga gaccccccag   14100
agcgaggtgt accagtcggg gccggactac ttttttccaga ccagcagaca gggcctgcag   14160
acggtgaact gagccaggc tttcaagaac ctgcgggggc tgtggggcgt gaaggcgccc   14220
accggggacc gggcgacggt gtccagcctg ctgacgccca actcgcgcct gctgctgctg   14280
```

```
ctgatcgcgc cgttcacgga cagcggcagc gtgtcccggg agacctacct cgggcacctg    14340
ctgacgctgt accgcgaggc catcgggcag acccaggtgg acgagcacac cttccaggag    14400
atcaccagcg tgagccgcgc gctggggcag gaggacacgg gcagcctgga ggcgaccctg    14460
aactacctgc tgaccaaccg gcggcagaag atccctcgc tgcatagttt gaccaccgag     14520
gaggagcgca tcctgcgcta cgtgcagcag agcgtgagcc tgaacctgat gcgcgacggg    14580
gtgacgccca gcgtggcgct ggacatgacc gcgcgcaaca tggaaccggg catgtacgcc    14640
gcgcatcggc cttacatcaa ccgcctgatg gactacttgc atcgcgcggc ggccgtgaac    14700
cccgagtact tcaccaacgc catcctgaac ccgcactggc tcccgccgcc cgggttctac    14760
agcgggggct tcgaggtccc cgaggccaac gacggcttcc tgtgggacga catggacgac    14820
agcgtgttct ccccgcggcc gcaggcgctg cggaggcgt cgctgctccg cctccccaag     14880
aaagaagaga gccgccggcc cagcagcgcg gcggcctctc tgtccgagct gggggcggcg    14940
gccgcgcggc ccgggtccct gggggcagc cccttccca gtctggtggg gtctctgcag      15000
agcgggcgca ccaccggcc ccggctgctg ggcgaggacg agtacctgaa caactccctg      15060
atgcagccgt tgcgggagaa aaacctgccc cccgccttcc ccaacaacgg gatagagagc    15120
ctggtagaca agatgagcag atggaagacc tatgcgcagg agcacaggga ctcgcccgtg    15180
ctccgtccgc ccacgcggcg ccagcgccac gaccggcagc gggggctggt atgggatgac    15240
gaggactccg cggacgatag cagcgtgctg gacctggggg ggagcggcgg taacccgttc    15300
gcgcacctgc gcccccgcct ggggaggatg tttcaataag aaaaatcaag catgatgcaa    15360
ggttttttaa gcggataaat aaaaaactca ccaaggccat ggcgaccgag cgttgttggt    15420
ttcttgttgt gttcccttag tatgcggcgc gcggcgatgt accacgaggg acctcctccc    15480
tcttatgaga gcgtggtggg cgcggcggcg gcctctccct ttgcgtcgca gctggagccg    15540
ccgtacgtgc ctccgcggta cctgcggcct acgggggaa gaaacagcat ccgttactcg     15600
gagctggcgc ccctgtacga caccacccgg gtgtacctgg tggacaacaa gtcggcggac    15660
gtggcctccc tgaactacca gaacgaccac agcaattttt tgaccacggt catccagaac    15720
aatgactaca ccccgagcga ggccagcacc cagaccatca atctggatga ccggtcgcac    15780
tggggcggcg acctgaaaac catcctgcac accaacatgc caacgtgaa cgagttcatg     15840 ttcaccaata agttcaaggc gcgggtgatg gtgtcgcgtt cgcacaccaa ggacgaccgg    15900
gtggagctga agtacgagtg ggtagagttc gagctgcccg agggcaacta ctcggagacc    15960
atgaccatag acctgatgaa caacgcgatc gtggagcact atctgaaagt gggcaggcag    16020 aacgggggtcc tggagagcga catcggggtc aagttcgaca ccaggaactt ccgcctgggg    16080
ctggaccccg tcaccgggct ggtcatgccc ggggtctaca ccaacgaggc cttccacccc    16140
gacatcatcc tgctgcccgg ctgcggggtg gacttcacct cagccgcct gagcaacctg    16200 ctgggcatcc gcaagcggca gcccttccag gagggcttta ggatcaccta cgaggacctg    16260 gagggggggca acatccccgc gctcctggat gtggaggcct accaggatag cttgaaggaa    16320
gaagaggcgg gagagggcag cggcggcggc ggcggcgccg gtcaggagga gggcggggcc    16380
tcctctgagg cctctgcgga cgccgccgct gccgccgagg cggaggcggc cgaccccgcg    16440
atggtggtag aggaagagaa ggatatgaat gacgaggcgg tgcgcggcga caccttttgcc   16500 acccggggggg aggagaagaa agcggaggcc gaggccgcgg cagaggaggc ggcagcggcc    16560
gcggcggcgg cagtagaggc ggcggccgag gcggagaagc cccccaagga gcccgtgatt    16620
```

```
aaggccctga ccgaagatag caagaagcgc agttacaacg tgctcaagga cagcaccaac   16680
accgcgtacc gcagctggta cctggcctac aactacggcg acccggcgac gggggtgcgc   16740
tcctggaccc tgctgtgtac gccggacgtg acctgcggct cggagcaggt gtactggtcg   16800
ctgcccgaca tgatgcaaga ccccgtgacc ttccgctcca cgcggcaggt cagcaacttc   16860
ccggtggtgg gcgccgagct gctgcccgtg cactccaaga gcttctacaa cgaccaggcc   16920
gtctactccc agctcatccg ccagttcacc tctctgaccc acgtgttcaa tcgctttcct   16980
gagaaccaga ttctggcgcg cccgcccgcc cccaccatca ccaccgtcag tgaaaacgtt   17040
cctgctctca cagatcacgg gacgctaccg ctgcgcaaca gcatcggagg agtccagcga   17100
gtgaccgtaa ctgacgccag acgccgcacc tgtccctacg tttacaaggc cctgggcata   17160
gtctcgccgc gcgtccttc cagccgcact ttttaagcat gtccatcctc atctcgccca   17220
gcaataacac cggctggggc ctgctgcgcg cgcccagcaa gatgtttgga ggggcgagga   17280
agcgctccga ccagcacccc gtgcgcgtgc gcgggcacta ccgcgccccc tgggcgcgc   17340
acaaacgcgg gcgcaccggc accgggggc gcaccaccgt ggacgaagcc atcgactcgg   17400
tggtggagca ggcgcgcaac tacacgcccg cggtctccac cgtggacgcg gctatcgaga   17460
gcgtggtgcg aggcgcgcgg cggtacgcca aggcgaagag ccgccggagg cgcgtggccc   17520
gccgccaccg ccgtcgaccc ggaagcgccg ccaagcgcgc cgccgccgcc ttgcttcgtc   17580
gggccagacg cacgggccgc cgccgccgcca tgagggccgc gcgccgcctg ccgccggca   17640
tcaccaccgt ggccccccgc ccagaagac gcgcggccgc tgccgccgcc gcggccatca   17700
gcgacctggc caccaggcgc cggggcaacg tgtactgggt gcgcgactcg gtgagcggca   17760
cgcgcgtgcc cgtgcgcttc cgccccccgc ggacttgaga ggagaggaca ggaaaaaagc   17820
atcaacaaca ccaccactga gtctcctgct gttgtgtgta cccagcggc gcgcgcgcac   17880
acggcgacat gtccaagcgc aaaatcaaag aagagatgct ccaggtcgtc gcgccggaaa   17940
tctatgggcc cccgaagaag gaagagcagg atttcaagcc ccgcaagata aagcgggtca   18000
aaaagaaaaa gaaagatgac gatgatggcg aggtggagtt tctgcgcgcc acggcgccca   18060
ggcgcccgct gcagtggaag ggtcggcgcg taaagcgcgt tctgcgcccc ggcaccgcgg   18120
tggtcttcac gcccggcgag cgctccaccc gcactttcaa gcgcgtctat gacgaggtgt   18180
acggcgacga agacctgctg gagcaggcca acgatcgctc cggagagtttt gcttacggga   18240
agcggcaccg ggcgatggag aaggacgagg tgctggcgct gccgctggac cggggcaacc   18300
ccaccccag cctgaagccc gtgaccctgc agcaggtgct gccggccagc gcgccctccg   18360
agatgaagcg gggcctgaag cgcgagggcg gcgacctggc gccaccgtg cagctgatgg   18420
tgcccaagcg gcagaggctg gaggacgtgc tggagaaaat gaaagtagac cccggcctgc   18480
agccggacat cagggtccgc cccatcaagc aggtggcgcc gggcctcggc gtgcagaccg   18540
tggacgtggt catccccacc ggcgcctcct cttccagcgc cgccgccgcc actagcaccg   18600
cggacatgga gacgcagact agctccgccc tcgccgcccc cgcggccgcc gccgccgcca   18660
cctcctcggc ggaggtacag acggacccct ggatgccgcc gccggcggcc gcccctcgc   18720
gcgcacgccg cggcgcagg aagtacgcg ccgcagcgc gctcatgccc gagtacgcct   18780
tgcatccttc catcgcgccc acccccggct accgaggcta cagctaccgc ccgcgaagag   18840
ccaagggctc caccgccgc agccgccgcg ccgccacctc tacccgccgc cgcagtcgcc   18900
gccgccgccg gcagccgcg ctggctccga tctccgtgag gagagtggcg cgcaacgggg   18960
acaccttggt gctgcccagg gcgcgctacc accccagcat cgtttaaaag cctgttgtgg   19020
```

```
ttcttgcaga tatggccctc acttgccgcc tccgtttccc ggtgccggga taccgaggaa   19080
gatcgcgccg tagaaggggt atggccggac gcggcctgag cggaggcagc cgccgtgcgc   19140
accggcggcg acgcgccacc agccgacgca tgcgcggcgg ggtgctgcct ctgctgatcc   19200
ccctgatcgc cgcggcgatc ggcgccgtgc ccgggatcgc ctccgtggcc ttgcaggcgt   19260
cccagaggcg ttgacacaga cttcttgcaa gcttgcaaaa atatggaaaa aatccccca   19320
ataaaaagt ctagactctc acgctcgctt ggtcctgtga ctattttgta gaaaaaaga   19380
tggaagacat caactttgcg tcgctggccc cgcgtcacgg ctcgcgcccg ttcctgggac   19440
actgaaacga tatcggcacc agcaacatga gcggtggcgc cttcagttgg ggctctctgt   19500
ggagcggcat taaaaatatc ggttctgccg ttaagaatta cggctccaag gcctggaaca   19560
gcagcacggg ccagatgttg agagacaagt tgaaagagca gaacttccag cagaaggtgg   19620
tggagggcct ggcctccggc atcaacgggg tggtggacct ggccaatcag gccgtgcaaa   19680
ataagatcaa cagcagactg gaccccggcc gccggtggga agagctgccg ccggcgctgg   19740
agacggtgtc ccccgatggg cggggcgaaa agcgcccgcg gcccgacagg gaagagacca   19800
ctctggtcac gcacaccgat gagccgcccc cctacgagga agctctgaag caaggcttgc   19860
ccaccactcg gcccatcgcg cccatggcca ccggggtggt gggccgccac accccgcca   19920
ggctggacct gcctcctcct cctgtttctt cttcggccgc cgatgcgcag cagcagaagg   19980
cggcgctgcc cggtccgccc gcggccgccc cccgtccac cgccagtcga gcgcccctgc   20040
gtcgcgcggc cagcggcccc cgcggggtcg cgaggcacag cagcggcaac tgcagaaaca   20100
cgctgaacag catcgtgggt ctgggggtgc agtccgtgaa gcgccgccga tgctactgaa   20160
tagcttagct aacggtgttg tatgtgtgta tgcgtcctat gtcaccgcca gaggagctgc   20220
tgagtcgccg ccgttcgcgc gcccaccgcc actaccaccg ccggtaccac tccagcgccc   20280
ctcaagatgg cgaccccatc gatgatgccg cagtggtcgt acatgcacat ctcgggccag   20340
gacgcctcgg agtacctgag ccccgggctg gtgcagttcg cccgcgccac cgacagctac   20400
ttcagcctga gtaacaagtt taggaacccc acggtggcgc ccacgcacga tgtgaccacc   20460
gaccggtccc agcgcctgac gctgcggttc atccccgtgg accgcgagga caccgcgtac   20520
tcttacaagg cgcggttcac cctggccgtg ggcgacaacc gcgtgctgga catggcctcc   20580
acctactttg acatccgcgg cgtgctggac aggggcccca ccttcaagcc ctactccggc   20640
accgcctaca actccctggc ccccaagggc gcccccaact cctgcgagtg ggagcaagag   20700
gagactcaga cagctgaaga ggcacaagac gaagaagaag atgaagctga agctgaggag   20760
gaaatgcctc aggaagagca agcacctgtc aaaagagactc atgtatatgc tcaggctccc   20820
ctttctggcg aaaaaattac taaagacggt ctgcagatag aacgacgc tacagctacc   20880
gaacaaaaac ctatttatgc agatcccaca ttccagccag aaccccaaat tggtgaatct   20940
cagtggaatg aggcagatgc ttcagttgcc ggcggtagag tgctgaagaa aactactccc   21000
atgaaaccct gttatggttc ctatgccagg cccacaaatg ccaatggagg tcagggtgta   21060
ttggtggaga aagacggtgg aaagatggaa agccaagtag atatgcaatt cttttcgact   21120
tctgaaaacg cccgtaacga ggctaacaac attcagccca aattggtgct gtacagcgag   21180
gatgtgcata tggagacccc agacacacac atttcttaca gcctgcaaa aagcgatgat   21240
aattcgaaag tcatgctggg tcagcagtcc atgcccaaca ggccaaatta catcggcttc   21300
agagacaact ttatcgggct catgtattac aacagcactg gcaacatggg ggtgctggca   21360
```

-continued

```
ggtcaggcct cacagttgaa tgcggtggtg gacttgcaag acagaaacac agaactgtcc   21420
taccagctct tgcttgattc catgggagac agaaccagat actttccat gtggaatcag    21480
gcggtggaca gttatgatcc agatgtcaga attattgaaa atcatggaac tgaagatgag   21540
ctgcccaact attgtttccc tctgggaggc atagggtaa ctgacactta ccaggccatt    21600
aagactaatg gcaatggcaa cggcggggc aataccactt ggaccaagga tgaaactttt    21660
gcagaccgca acgagatagg ggtgggaaac aatttcgcca tggagatcaa cctcagtgcc   21720
aacctgtgga ggaacttcct ctactccaac gtggccctgt acctgccaga caagcttaag   21780
tacaacccct ccaacgtgga aatctctgac aaccccaaca cctacgacta catgaacaag   21840
cgagtggtgg ccccggggct ggtggactgc tacatcaacc tgggcgcgcg ctggtccctg   21900
gactacatgg acaacgtcaa ccccttcaac caccaccgca acgcgggcct gcgctaccgc   21960
tccatgcttc tgggcaacgg gcgctacgtg cccttccaca tccaggtgcc ccagaagttc   22020
tttgccatca agaacctcct cctcctgccg ggctcctaca cctacgagtg gaacttcagg   22080
aaggatgtca acatggtcct ccagagctct ctgggtaacg acctcaggt cgacggggcc    22140
agcatcaagt tcgagagcat ctgcctctac gccaccttct tccccatggc ccacaacacg   22200
gcctccacgc tcgaggccat gctcaggaac gacaccaacg accagtcctt caacgactac   22260
ctctccgccg ccaacatgct ctaccccatc ccgccaacg ccaccaacgt tcccatctcc    22320
atccctcgc gcaactgggc ggccttccgc ggctgggcct tcacccgcct caagaccaag   22380
gagaccccct ccctgggctc gggtttcgac ccctactaca cctactcggg ctccataccc   22440
tacctggacg gaaccttcta cctcaaccac actttcaaga aggtctcggt cacccttcgac   22500
tcctcggtca gctggccggg caacgatcgc ctgctcaccc ccaacgagtt cgagatcaag   22560
cgctcggtcg acggggaggg ctacaacgtg gcccagtgca acatgaccaa ggactggttc   22620
ctcatccaaa tgctggccaa ctacaacatc ggctatcagg gcttctacat cccagagagc   22680
tacaaggaca ggatgtactc cttctttagg aacttccagc ccatgagccg gcaggtggtg   22740
gacgaaacca agtacaagga ctaccagcag gtgggcatca tccaccagca caacaactcg   22800
ggcttcgtgg gctacctcgc ccccaccatg cgcgagggac aggcctaccc cgccaacttc   22860
ccctacccgc tcattggcaa gaccgcggtc gacagcgtca cccagaaaaa gttcctctgc   22920
gaccgcaccc tctggcgcat ccccttctcc agcaacttca tgtccatggg tgcgctcacg   22980
gacctgggcc agaacctgct ctatgccaac tccgcccacg cgctcgacat gaccttcgag   23040
gtcgacccca tggacgagcc caccttctc tatgttctgt tcgaagtctt tgacgtggtc    23100
cgggtccacc agccgcaccg cggcgtcatc gagaccgtgt acctgcgcac gcccttctcg   23160
gccggcaacg ccaccaccta agaagcaag ccgccaccgc caccacctgc atgtcgtcgg    23220
gttccaccga gcaggagctc aaggccatcg tcagagacct gggatgcggg ccctattttt   23280
tgggcacctt cgacaaacgc ttcccggggct tcgtcgcccc gcacaagctg gcctgcgcca   23340
tcgtcaacac ggccggccgc gagaccgggg gcgtgcactg gctggccttc gcctggaacc   23400
cgcgctccaa acatgctac ctcttttgacc ccttcggatt ctcggaccag cggctcaagc    23460
agatctacca gttcgagtac gagggcctgc tgcgccgcag cgccatcgcc tcctcgcccg   23520
accgctgcgt caccctcgag aagtccaccc agaccgtgca ggggcccgac tcggccgcct   23580
gcggtctctt ctgctgcatg ttcctgcatg cctttgtgca ctggcccag agtcccatgg    23640
accgcaaccc caccatgaac ttgctgacgg ggatccccaa ctccatgctc cagagccccc   23700
aggtcgcgcc caccctgcgc cgcaaccagg agcggctcta cagcttcctg aacgccact   23760
```

```
cgccctactt ccgccgccac agcgcgcaga tcagggggc cacctctttc tgccgcatgc    23820
aagagatgca agggaaaatg caatgatgta cacagacact ttttcttttc tcaataaatg    23880
gcaactttat ttatacatgc tctctctcgg gtattcattt ccccaccacc caccacccgc    23940
cgccgccgta accatctgct gctggctttt tttttttttt ttaaaaatcg aaagggttct    24000
gccgggaatc gccgtgcgcc acgggcaggg acacgttgcg gaactggtag cgggtgcccc    24060
acttgaactc gggcaccacc atgcggggca agtcggggaa gttgtcggcc cacaggctgc    24120
gggtcagcac cagcgcgttc attaggtcgg gcgccgagat cttgaagtcg cagttggggc    24180
cgccgccctg cgcgcgcgag ttgcggtaca ccgggttgca acactggaac accagcagcg    24240
ccggataatt cacactggcc agcacgctcc ggtcggagat cagctcggcg tccaggtcct    24300
ccgcgttgct cagcgcgaac ggggtcagct tgggcacctg ccgccccagg aagggagcgt    24360
gccccggctt cgagttgcag tcgcagcgca gcgggatcag caggtgcccg cggccggact    24420
cggcgttggg gtacagcgcg cgcatgaagg cctccatctg gcggaaggcc atctgggcct    24480
tggcgccctc cgagaagaac atgccgcagg acttgcccga gaactggttc gcggggcagc    24540
tagcgtcgtg caggcagcag cgcgcgtcgg tgttggcgat ctgcaccacg ttgcgccccc    24600
accggttctt cacgattttg gccttggaag cctgctcctt cagcgcgcgc tgcccgttct    24660
cgctggtcac atccatctcg atcacgtgct ccttgttcac catgctgctg ccgtgcagac    24720
acttcagctc gccctccacc tcggtgcagc ggtgctgcca tagcgcgcag cccgtgggct    24780
cgaaatgctt gtaggtcacc tccgcgtagg actgcaggta ggcctgcagg aagcgcccca    24840
tcatggtcac gaaggtcttg ttgctgctga aggtcagctg cagcccgcgg tgctcctcgt    24900
tcagccaggc cttgcacacg gccgccagcg cctccacctg gtcgggcagc atcttgaagt    24960
tcagcttcag ctcattctcc acatggtact tgtccatcag cgcgcgcgca gcctccatgc    25020
ccttctccca ggccgacacc agcggcaggc tcaaggggtt caccaccgtc gcagccgccg    25080
ctgcgctttc gctttccgct ccgctgttct cttcttcctc ctcctcttct tcctcgccgc    25140
ccgcgcgcag cccccgcacc acgggtcgt cttcctgcag gcgccgcacc gagcgcttgc    25200
cgctcctgcc ctgcttgata cgcacgggcg ggttgctgaa gcctaccatc accagcgcgg    25260
cctcttcttg ctcgtcctcg ctgtccacta tgacctcggg ggaggggcgac ctcagaaccg    25320
tggcgcgctg cctcttctt tcctgggggg cgtttgccag ctccgcggcc gcggccgccg    25380
ccgaggtcga aggccgaggg ctgggcgtgc gcggcaccag cgcgtcctgc gagccgtcct    25440
cgtcctcgga ctcgaggcgg cagcgagccc gcttcttcgg gggcgcgcgg ggcggcggcg    25500
gcgggggcgg cggcgacgga gacggggacg agacatcgtc cagggtggga ggacggcggg    25560
ccgcgccgcg tccgcgctcg ggggtggttt cgcgctggtc ctcttcccga ctggccatct    25620
cccactgctc cttctcctat aggcagaaag agatcatgga gtctctcatg caagtcgaga    25680
aggaggagga cagcctaacc accaccgccc cctctgagcc ctccgccgcc gccgcggacg    25740
acgcgcccac caccaccgcc gccgccacca ccaccattac caccctaccc ggcgacgcag    25800
ccccgatcga gaaggaagtg ttgatcgagc aggacccggg ttttgtgagc gaagaggagg    25860
atgaggagga tgaaaaggag aaggataccg ccgcctcagt gccaaaagag gataaaaagc    25920
aagaccagga cgacgcagag acagatgagg cagcagtcgg gcgggggggac ggaaggcatg    25980
atgatgatga cggctaccta gacgtgggag acgacgtgct gcttaagcac ctgcaccgcc    26040
agtgcgtcat cgtctgcgac gcgctgcagg agcgctgcga agtgcccctg gacgtggcgg    26100
```

```
aggtcagccg cgcctacgag cggcacctct tcgcgccaca cgtgcccccc aagcgccggg    26160
agaacggcac ctgcgagccc aacccgcgcc tcaacttcta cccggtcttc gcggtacccg    26220
aggtgctggc cacctaccac atcttcttcc aaaactgcaa gatcccctc tcctgccgcg     26280 ccaaccgcac ccgcgccgac aagacgctgg ccctgcggca gggcgcccac atacctgata    26340
tcgcctctct ggaggaggtg cccaagatct tcgagggtct cggtcgcgac gagaaacggg    26400
cggcgaacgc tctgcaagga gacagcgaaa acgagagtca ctcggggtg ctggtggagc     26460 tcgagggcga caacgcgcgc ctggccgtgc tcaagcgcag catcgaagtc acccacttcg    26520 cctaccggc gctcaacctg cccccaagg tcatgagtgt ggtcatgagt gagctcatca      26580
tgcgccgcgc ccagcccctg gacgcggatg caaacttgca agagccctcc gaggaaggcc    26640
tgcccgcggt cagcgacgag cagctggcgc gctggctgga gacccgcgac ccgcccagc     26700 tggaggagcg gcgcaagctc atgatggccg cggtgctcgt caccgtggag ctcgagtgtc    26760
tgcagcgctt cttcgggac cccgagatgc agcgcaagct cgaggagacc ctgcactaca     26820
ccttccgcca gggctacgtg cgccaggcct gcaagatctc caacgtggag ctctgcaacc    26880
tggtctccta cctgggcatc ctgcacgaga accgcctcgg gcagaacgtc ctgcactcca    26940
ccctcaaagg ggaggcgcgc cgcgactacg tccgcgactg cgtctacctc ttcctctgct    27000
acacgtggca gacggccatg ggggtctggc agcagtgcct ggaggagcgc aacctcaagg    27060
agctggagaa gctcctccgg cgcgcccctca gggacctctg gacgggcttc aacgagcgct    27120
cggtggccgc cgcgctggcg gacatcatct tccccgagcg cctgctcaaa accctgcagc    27180
agggcctgcc cgacttcacc agccagagca tgctgcagaa cttcaggacc ttcatcctgg    27240
agcgctcggg catcctgccg gccacctgct gcgcgctgcc cagcgacttc gtgcccatca    27300
ggtacaggga gtgcccgccg ccgctctggg gccactgcta cctcttccag ctggccaact    27360
acctcgccta ccactcggat ctcatggaag acgtgagcgg cgagggcctg ctcgagtgcc    27420
actgccgctg caacctgtgc acgccccacc gctctctagt ctgcaatccg cagctgctca    27480
gcgagagtca gattatcggt accttcgagc tgcagggtcc ctcgcccgac gaaaagtccg    27540
cggctccggg gttgaaactc actccgggc tgtggacttc cgcctaccta cgcaaatttg     27600
tacctgaaga ctaccacgcc cacgagatca ggttttacga agaccaatcc cgcccgccca    27660
aggcggagct caccgcctgc gtcattaccc agggccacat cctgggccaa ttgcaagcca    27720
tcaacaaagc ccgccaagag ttcttgctga aaaagggtcg gggggtgtac ctggacccc     27780 agtccggcga ggagctaaac ccgctacccc cgccgccgcc ccagcagcgg gaccttgctt    27840
cccaggatgg caccagaaa gaagcagccg ccgccgccgc cagcatacat gcttctggag     27900
gaagaggagg actgggacag tcaggcagag gaggtttcgg acgaggacga ggaggaggag    27960
atgatggaag actgggagga ggacagccta gacgaggaag cttcagaggc cgaagaggtg    28020
gcagacgcaa caccatcacc ctcggccgca gcccccctcgc cggcgcccc gaaatcctcc    28080 gaccccagca gcagcgctat aacctccgct cctccgcgc cggcgcccac ccgcagcaga    28140
cccaaccgta gatgggacac tacaggaacc ggggtcggta agtccaagtg ccccccagcg    28200 ccgccccgc aacaggagca acagcagcag cagcggcgac agggctaccg ctcgtggcgc    28260
ggacacaaga acgccatagt cgcctgcttg caagactgcg ggggcaacat ctccttcgcc    28320
cgccgcttcc tgctcttcca ccacgggtg gcttttcccc gcaatgtcct gcattactac    28380
cgtcatctct acagcccta ctgcggcggc agcggcgacc cagagggagc ggcggcagca    28440
gcagcgccag ccacagcggc gaccacctag gaagacctcc gcgggcaaga cggcgggagc    28500
```

```
cgggagaccc gcggcggcgg cggtagcggc ggcggcgggc gcactgcgcc tctcgcccaa    28560
cgaacccctc tcgacccggg agctcagaca caggatcttc cccactctgt atgctatctt    28620
ccagcagagc agaggccagg aacaggagct caaaataaaa aacagatctc tgcgctccct    28680
cacccgcagc tgtctgtatc acaaaagcga agatcagctt cggcgcacgc tggaggacgc    28740
ggaggcactc ttcagcaaat actgcgcgct gactcttaag gactagccgc gcgcccttct    28800
cgaatttagg cgggagaaag actacgtcat cgccgaccgc cgcccagccc acccagccga    28860
catgagcaaa gagattccca cgccctacat gtggagctac cagccgcaga tgggactcgc    28920
ggcgggagcg gcccaagact actccacccg catgaactac atgagcgcgg ggccccacat    28980
gatctcacgg gttaatggga tccgcgccca gcgaaaccaa atactgctgg aacaggcggc    29040
cataaccgcc acacccgtc atgacctcaa tccccgaaat tggcccgccg ccctcgtgta    29100
ccaggaaacc ccctctgcca ccaccgtggt acttccgcgt gacacccagg ccgaagtcca    29160
gatgactaac tcaggggcgc agctcgcggg cggctttcgt cacggggtgc ggccgcaccg    29220
gccgggtata ttacacctgg cgatcagagg ccgaggtatt cagctcaacg acgagtcggt    29280
gagctcttcg ctcggtctcc gtccggacgg aaccttccag atcgccggat caggtcgctc    29340
ctcattcacg cctcgccagg cgtatctgac tctgcagacc tcctcctcgg agcctcgctc    29400
cggcggcatc ggcaccctcc agttcgtgga ggagttcgtg ccctcggtct acttcaaccc    29460
cttctcggga cctcccggac gctaccccga ccagttcatc ccgaactttg acgcggtgaa    29520
ggactcggcg gacggctacg actgaatgtc aagtgctgag gcagagagcg ttcgcctgaa    29580
acacctccag cactgccgcc gcttcgcctg cttgccgc agctccggtg agttctgcta    29640
ctttcagctg cccgaggagc ataccgaagg gccggcgcac ggcgtccgcc taaccaccca    29700
gggcgaggtt acctgtaccc ttatccggga gtttaccctc cgtcccctgc tagtggagcg    29760
ggagcggggt tcttgtgtca taactatcgc ctgcaactgc cctaaccctg gattacatca    29820
agatctttgt tgtcacctgt gcgctgagta taataaacgc tgagatcaga ctctactggg    29880
gctcctgtcg ccatcctgtg aacgccaccg tcttcaccca ccccgagcag ccccaggcga    29940
acctcacctg cggcctgcgt cggagggcca agaagtacct cacctggtac ttcaacggca    30000
cccccttgt ggtttacaac agcttcgacc aggacggagt tgccttgaga gacgaccttt    30060
ccggtctcag ctactccatt cacaagaaca ccacccctcca cctcttccct ccctacctgc    30120
cgggaaccta cgagtgcgtc accggccgct gcacccacct cctccgcctg atcgtaaacc    30180
agacctttcc gggaacacac ctcttcccca gaacaggagg tgagctcagg aaaccccctg    30240
gggcccaggg cggagactta ccttcgaccc ttgtggggtt aggattttt atcgccgggt    30300
tgctggctct cctgatcaaa gcttccttca gatttgttct ctccctttac ttttatgaac    30360
agctcaactt ctaataacgc taccttttct caggaatcga gtagtaactt ctcttccgaa    30420
atcgggctgg gtgtgctgct tactctgttg attttttttcc ttatcatact tagccttctg    30480
tgcctcaggc tcgccgcctg ctgcgcacat atctacatct acagccggtt gcttaactgc    30540
tggggtcgcc atccaagatg aacgggctc aggtgctatg tctgctggcc ctggtggcct    30600
gcagtgccgc cgtcaatttt gaggaacccg cttgcaatgt gactttcaag cctgagggcg    30660
cacattgcac cactctggtt aaatgtgtga cctctcatga aaaactgctc atcgcctaca    30720
aaaacaaaac aggccagatc gcagtctata gcgagtggct acccgagac cataataact    30780
actcagtcac cgtcttcgag ggtgcggagt ctaagaaatt cgattacacc tttcccttcg    30840
```

```
aggagatgtg tgatgcggtc atgtacctgt ccaaacagta caagctgtgg cccccccaccc   30900
ccaaggcgtg tgtggaaaac actgggtctt tctgctgtct ctctctggca atcactgtgc   30960
ttgctctaat ctgcacgctg ctatacatga gattcaggca gaggcgaatc tttatcgatg   31020
agaaaaaaat gccttgatcg ctaacaccgg ctttctgtct gcagaatgaa agcaatcacc   31080
tccctactaa tcagcaccac cctccttgcg attgcccatg ggttgacacg aatcgaagtg   31140
ccagtggggt ccaatgtcac catggtgggc ccgccggca attcctccct gatgtgggaa    31200
aaatatgtcc gtaatcaatg ggatcattac tgctctaatc gaatctgtat caagcccaga   31260
gccacctgcg acgggcaaaa tctaactttg attgatgtgc aaatgacgga tgctgggtac   31320
tattacgggc agcggggaga aatgattaat tactggcgac cccacaagga ctacatgctg   31380
catgtagtca aggcagtccc aactactacc accccacca ctaccactcc cactaccacc    31440
accccacca ctaccactag cactgctact accgctgccc gcaaagctat acccgcaaa     31500
agcaccatgc ttagcaccaa gccccattct cactcccacg ccggcgggcc caccggtgcg   31560
gcctcagaaa ccaccgagct ttgcttctgc caatgcacta cgccagcgc ccacgaactg    31620
ttcgacctgg agaatgagga cgatgaccag ctgagctccg cttgcccggt cccgctgccc   31680
gcagagccgg tcgccctgaa gcagctcggt gatccattta atgactctcc tgtttatccc   31740
tctcccgaat accctcccga ctctaccttc cacatcacgg gcaccaaaga ccccaacctc   31800
tccttctacc tgatgctgct gctctgtatc tctgtggtat cttccgcgct catgttactg   31860
ggcatgttct gctgcctcat ctgccgcaga aaagaaagt ctcgctctca gggccaacca    31920
ctgatgccct tccctaccc cccagatttt gcagataaca agatatgagc acgctgctga   31980
cactaaccgc tttactcgcc tgcgctctaa cccttgtcgc ttgcgaatcc agataccaca   32040
atgtcacagt tgtgacagga gaaaatgtta cattcaactc cacggccgac acccagtggt   32100
cgtggagtgg ccacggtagc tatgtataca tctgcaatag ctccacctcc cctagcatgt   32160
cctctcccaa gtaccactgc aatgacagcc tgttcaccct catcaacgcc tccacctcgg   32220
acaatggact ctatgtaggc tatgtgacac ccggtgggca gggaaagacc cacgcctaca   32280
acctgcaagt tcgccacccc tccaccaccg ccaccacctc tgccgcccct acccgcagca   32340
gcagcagcag cagcagcagc agcagcagca gcagcagcag attcctgact ttaatcctag   32400
ccagctcaac aaccaccgcc accgctgaga ccacccacag ctccgcgccc gaaaccaccc   32460
acacccacca cccagagacg accgcggcct ccagcgacca gatgtcggcc aacatcaccg   32520
cctcgggtct tgaacttgct tcaacccca ccccaaaacc agtggatgca gccgacgtct    32580
ccgccctcgt caatgactgg gcggggctgg gaatgtggtg gttcgccata ggcatgatgg   32640
cgctctgcct gcttctgctc tggctcatct gctgcctcaa ccgcaggcgg gccagaccca   32700
tctatagacc catcattgtt ctcaaccccg ctgatgatgg gatccataga ttggatggtc   32760
tgaaaaacct acttttctct tttacagtat gataaattga gacatgcctc gcattttcat   32820
gtacttgaca cttctcccac ttttctggg gtgttctacg ctggccgccg tctctccacct   32880
cgaggtagac tgcctcacac ccttcactgt ctacctgatt tacggattgg tcaccctcac   32940
tctcatctgc agcctaatca cagtagtcat cgccttcatc cagtgcattg actacatctg   33000
tgtgcgcctc gcatacctga gacaccaccc gcagtaccga gacaggaaca ttgcccaact   33060
cctaagactg ctctaatcat gcataagact gtgatctgcc tcctcatcct cctctccctg   33120
cccgctctcg tctcatgcca gcccaccaca aaacctccac gaaaaagaca tgcctcctgt   33180
cgcttgagcc aactgtggaa tattcccaaa tgctacaatg aaaagagcga gctttccgaa   33240
```

```
gcctggctat atgcggtcat gtgtgtcctt gtcttctgca gcacaatctt tgccctcatg   33300
atctaccccc actttgattt gggatggaat gcggtcgatg ccatgaatta ccctacctt    33360 cccgcgcccg atatgattcc actccgacag gttgtggtgc ccgtcgccct caatcaacgc   33420
cccccatccc ctacacccac tgaggtcagc tactttaatc taacaggcgg agatgactga   33480
cactctagat ctagaaatgg acggcatcgg caccgagcag cgtctcctac agaggcgcaa   33540
gcaggcggct gaacaagagc gcctcaatca ggagctccga gatctcatta acctgcacca   33600
gtgcaaaaaa ggcatctttt gcctggtcaa gcaggccgat gtcacctacg agaaaaccgg   33660
taacagccac cgcctcagct acaagctgcc cacccaacgc cagaagttgg tgctcatggt   33720
gggtcagaat cccatcaccg tcacccagca ctcggtggag accgaggggt gtctgcactc   33780
cccctgtcag ggtccggaag acctctgcac cctggtaaag accctgtgtg gtcttagaga   33840
tttaatcccc tttaactaat caaacactgg aatcaataaa agaatcact  tactttaaat   33900 cagtcagcag gtctctgtcc actttattca gcagcacctc cttcccctcc tcccaactct   33960
ggtactccaa acgcctcctg gcggcaaact tcctccacac cctgaaggga atgtcagatt   34020
cttgctcctg tccctccgca cccactatct tcatgttgtt gcagatgaag cgcgccaaaa   34080
cgtctgacga gaccttcaac cccgtgtacc cctatgacac ggaaaacggg cctccctccg   34140
ttcctttcct caccccctcc ttcgtgtccc ccgacggatt tcaagaaagc ccccagggg   34200 tcctgtctct gcgcctgtca gagccctgg  tcacttccca cggcatgctt gccctgaaaa   34260
tgggaaatgg cctctccctg gatgacgccg gcaacctcac ctctcaagat gtcaccaccg   34320 tcaccctcc cctcaaaaaa accaagacca acctcagcct ccagacctca gccccctga   34380 ccgttagctc tgggtccctc accgtcgcgg ccgccgctcc actggcggtg gccggcacct   34440
ctctcaccat gcaatctcag gccccttga cggtgcaaga tgcaaaactg ggtctggcca   34500
cccagggacc cctgaccgtg tctgaaggca aactcacctt gcagacatcg gctccactga   34560
cggccgccga cagcagcact ctcactgttg gcaccacacc gccaatcagt gtgagcagtg   34620
gaagtctagg cttagatatg gaagacccca tgtatactca cgatggaaaa ctggaatca   34680 gaattggtgg cccactgcaa gtagtagaca gcttgcacac actcactgta gttactggaa   34740
acggaataac tgtagctaac aatgcccttc aaactaaagt tgcgggtgcc ctgggttatg   34800
actcatctgg caatctagaa ttgcgagccg caggggtat  gcgaattaac acaggggtc   34860 aactcattct tgatgtggct tatccatttg atgctcagaa caatctcagc cttagactcg   34920
gccagggacc tttatatgtg aacaccaatc acaacctaga tttaaattgc aacagaggtc   34980
tgaccacaac caccagcagt aacacaacca acttgaaac  taaaatcgat tcgggcttag   35040
actataacgc caatggggct atcattgcta acttggcac  tgggttaacc tttgacaaca   35100
caggtgccat aactgtggga aacactgggg atgacaaact cactctgtgg actaccccag   35160
atccctctcc taactgcaga attcacgcag acaaagactg caagtttact ctagtcctga   35220
ctaagtgtgg aagtcaaatt ctggcctccg tcgccgccct ggcggtgtct ggaaacctat   35280
catcaatgac aggcactgtc tccagcgtta ccatctttct cagattcgat cagaatggag   35340
ttcttatgga aaattcctcg ctagacaagg agtactggaa cttcagaaat ggtaattcca   35400
ccaatgccac cccctacacc aatgcggttg ggttcatgcc caacctcagc gcctacccca   35460
aaacccagag tcaaactgca aaaaacaaca ttgtaagtga ggtttactta catgggaca   35520 aatctaaacc catgatcctt accattaccc ttaatggcac aaatgaatcc agtgaaacta   35580
```

```
gtcaggtgag tcactactcc atgtcattta catggtcgag ggacagtggg aaatatgcca    35640
ccgaaacctt tgccaccaac tcttttacct tctcctacat tgctgaacaa taaagaagca    35700
taacgctgct gttcatttgt aatcaagtgt tactttttta tttttcaatt acaacagaat    35760
cattcaagtc attctccatt tagcttaata gaccccagta gtgcaaagcc ccatactagc    35820
ttatttcagc aattgggaga agtactcgcc tacatggggg tagagtcata atcgtgcatc    35880
aggatagggc ggtggtgctg cagcagcgcg cgaataaact gctgccgccg ccgctccgtc    35940
ctgcaggaat acaacatggc agtggtctcc tcagcgatga ttcgcaccgc ccgcagcata    36000
aggcgccttg tcctccgggc acagcagcgc accctgatct cacttaaatc agcacagtaa    36060
ctgcagcaca gcaccacaat attgttcaaa atcccacagt gcaaggcgct gtatccaaag    36120
ctcatggcgg ggaccacaga acccacgtgg ccatcatacc acaagcgcag gtagattaag    36180
tggcgacccc tcataaacac gctggacata acattacct cttttggcat gttgtaattc    36240
accacctccc ggtaccatat aaacctctga ttaaacatgg cgccatccac caccatccta    36300
aaccagctgg ccaaaacctg cccgccggct atacactgca gggaaccggg actgaacaa    36360 tgacagtgga gagcccagga ctcgtaacca tggatcatca tgctcgtcat gatatcaatg    36420
ttggcacaac acaggcacac gtgcatacac ttcctcagga ttacaagctc ctcccgcgtt    36480
agaaccatat cccagggaac aacccattcc tgaatcagcg taaatcccac actgcaggga    36540
agacctcgca cgtaactcac gttgtgcatt gtcaaagtgt tacattcggg cagcagcgga    36600
tgatcctcca gtatggtagc gcgggtttct gtctcaaaag gaggtagacg atccctactg    36660
tacggagtgc gccgagacaa ccgagatcgt gttggtcgta gtgtcatgcc aaatggaacg    36720
ccggacgtag tcatatttcc tgaagtcttg gcgcgccaga cccgagtctt accaggaaaa    36780
ttttaaaaaa gattcctcaa cgcagcacca gcaccaacac ctgtcagtgt aaaatgccaa    36840
gcgccgagcg agtatatata ggaataaaaa gtgacgtaaa cggttaaagt ccagaaaacg    36900
cccagaaaaa ccgcacgcga acctacgccc gaaacgaaa gccaaaaaac agtgaacacg    36960 cccttcggc gtcaacttcc gctttcccac ggtacgtcac ttccgcatat agtaaaacta    37020
cgctacccaa catgcaagaa gccacgcccc aaaaacgtc acacctcccg gcccgccccg    37080
cgccgccgct cctccccgcc ccgccccgct ccgcccacct cattatcata ttggcttcaa    37140
tccaaaataa ggtatattat tgatgatg                                      37168
```

<210> SEQ ID NO 8
<211> LENGTH: 36397
<212> TYPE: DNA
<213> ORGANISM: Artificial Sequence
<220> FEATURE:
<223> OTHER INFORMATION: synthetic chimpanzee adenovirus serotype PanAd3
      with Ebola virus Sudan/Gulu codon optimized
      transmembrane envelope glycoprotein (GP) insert
      (PanAd3 GP Ebola S/G (PB/6611))
<220> FEATURE:
<221> NAME/KEY: CDS
<222> LOCATION: (1624)...(3654)
<223> OTHER INFORMATION: Ebola virus Sudan/Gulu codon optimized
      transmembrane envelope glycoprotein (GP) insert in PanAd3 GP Ebola
      S/G (PB/6611)
<220> FEATURE:
<221> NAME/KEY: CDS
<222> LOCATION: (14671)...(16425)
<223> OTHER INFORMATION: chimpanzee adenovirus serotype ChAd63 penton
<220> FEATURE:
<221> NAME/KEY: CDS
<222> LOCATION: (19516)...(22410)
<223> OTHER INFORMATION: chimpanzee adenovirus serotype ChAd63 hexon
<220> FEATURE:

<221> NAME/KEY: CDS
<222> LOCATION: (33294)...(34922)
<223> OTHER INFORMATION: chimpanzee adenovirus serotype ChAd63 fiber

<400> SEQUENCE: 8

```
catcatcaat aatatacctt attttggatt gaagccaata tgataatgag gtgggcggag      60
cggggcgggg cggggaggag cggcggcgcg gggcgggccg ggaggtgtgg cggaagttga     120
gtttgtaagt gtggcggatg tgacttgcta gcgccggatg tggtaaaagt gacgttttt     180
ggagtgcgac aacgcccacg ggaagtgaca ttttccccgc ggttttacc ggatgtcgta     240
gtgaatttgg gcgttaccaa gtaagatttg gccattttcg cgggaaaact gaaatgggga     300
agtgaaatct gattaatttc gcgttagtca taccgcgtaa tatttgccga gggccgaggg     360
actttgaccg attacgtgga ggaatcgccc aggtgttttt tgaggtgaat ttccgcgttc     420
cgggtcaaag tctccgtttt attattatag gtatacccat tgcatacgtt gtatccatat     480
cataatatgt acatttatat tggctcatgt ccaacattac cgccatgttg acattgatta     540
ttgactagtt attaatagta atcaattacg ggtcattag ttcatagccc atatatggag     600
ttccgcgtta cataacttac ggtaaatggc ccgcctggct gaccgcccaa cgaccccccgc    660
ccattgacgt caataatgac gtatgttccc atagtaacgc caatagggac tttccattga    720
cgtcaatggg tggagtattt acggtaaact gcccacttgg cagtacatca agtgtatcat    780
atgccaagta cgccccctat tgacgtcaat gacggtaaat ggcccgcctg gcattatgcc    840
cagtacatga ccttatggga ctttcctact tggcagtaca tctacgtatt agtcatcgct    900
attaccatgg tgatgcggtt ttggcagtac atcaatgggc gtggatagcg gtttgactca    960
cggggatttc caagtctcca ccccattgac gtcaatggga gtttgttttg gaaccaaaat   1020
caacgggact ttccaaaatg tcgtaacaac tccgccccat tgacgcaaat gggcggtagg   1080
cgtgtacggt gggaggtcta tataagcaga gctctcccta tcagtgatag agatctccct   1140
atcagtgata gagatcgtcg acgagctcgt ttagtgaacc gtcagatcgc ctggagacgc   1200
catccacgct gttttgacct ccatagaaga caccgggacc gatccagcct ccatcggctc   1260
gcatctctcc ttcacgcgcc cgccgcccta cctgaggccg ccatccacgc cggttgagtc   1320
gcgttctgcc gcctcccgcc tgtggtgcct cctgaactgc gtccgccgtc taggtaagtt   1380
taaagctcag gtcgagaccg ggcctttgtc cggcgctccc ttggagccta cctagactca   1440
gccggctctc cacgctttgc ctgaccctgc ttgctcaact ctagttaacg gtggagggca   1500
gtgtagtctg agcagtactc gttgctgccg cgcgcgccac cagacataat agctgacaga   1560
ctaacagact gttcctttcc atgggtcttt tctgcagtca ccgtcgtcga cgatatcgcc   1620
gccatgagg gcctgagcct gctgcagctg cccaggggaca agttcaggaa gagcagcttc   1680
ttcgtgtggg tgatcatcct gttccagaag gccttcagca tgcccctggg cgtggtgacc   1740
aacagcaccc tggaggtgac cgagatcgac cagctggtgt gcaaggacca cctggccagc   1800
accgaccagc tgaagagcgt gggcctgaac ctggagggca cgcgcgtgag caccgacatc   1860
cccagcgcca ccaagaggtg gggcttcagg agcggcgtgc ctcccaaggt ggtgagctac   1920
gaggccggcg agtgggccga gaactgctac aacctggaga tcaagaagcc cgacggcagc   1980
gagtgcctgc ctcctcctcc tgacggcgtg aggggcttcc ccaggtgcag gtacgtgcac   2040
aaggcccagg gcaccggccc ctgcccgggc gactacgcct tccacaagga cggcgccttc   2100
ttcctgtacg acaggctggc cagcaccgtg atctacaggg gcgtgaactt cgccgagggc   2160
gtgatcgcct tcctgatcct ggccaagccc aaggagacct tcctgcagag ccctccatc   2220
```

```
agggaggccg tgaactacac cgagaacacc agcagctact acgccaccag ctatctagag    2280
tacgagatcg agaacttcgg cgcccagcac agcaccaccc tgttcaagat cgacaacaac    2340
accttcgtga ggctggacag gccccacacc cctcagttcc tgttccagct gaacgacacc    2400
atccacctgc accagcagct gagcaacacc accggcaggc tgatctggac cctggacgcc    2460
aacatcaacg ccgacatcgg cgagtgggcc ttctgggaga caagaagaa cctgagcgag     2520
cagctgaggg gcgaggagct gagcttcgag gccctgagcc tgaacgagac cgaggacgac    2580
gacgccgcca gcagcaggat caccaagggc aggatcagcg acagggccac caggaagtac    2640
agcgacctgg tgcccaagaa cagccccggc atggtgcccc tgcacatccc cgagggcgag    2700
accaccctgc ccagccagaa cagcaccgag ggcaggaggg tgggcgtgaa cacccaggag    2760
accatcaccg agaccgccgc caccatcatc ggcaccaacg gcaaccacat gcagatcagc    2820
accatcggca tcaggcccag cagcagccag atccccagca gcagccccac caccgcccct    2880
agccccgagg cccagacccc caccacccac accagcggac ccagcgtgat ggccaccgag    2940
gagcccacca cccctcccgg cagcagcccc ggacccacca ccgaggcccc taccctgacc    3000
acccctgaga acatcaccac cgccgtgaag accgtgctgc cccaggagag caccagcaac    3060
ggcctgatca ccagcaccgt gaccggcatc ctgggcagcc tgggcctgag gaagaggagc    3120
aggaggcaga ccaacaccaa ggccaccggc aagtgcaacc ccaacctgca ctactggacc    3180
gcccaggagc agcacaacgc cgccggcatc gcctggattc cctacttcgg ccccggcgcc    3240
gagggcatct acaccgaggg cctgatgcac aaccagaacg ccctggtgtg cggcctgagg    3300
cagctggcca acgagaccac ccaggccctg cagctgttcc tgagggccac caccgagctg    3360
aggacctaca ccatcctgaa caggaaggcc atcgacttcc tgctgaggag gtggggcggc    3420
acctgcagga ttctgggccc cgactgctgc atcgagcccc acgactggac caagaacatc    3480
accgacaaga tcaaccagat catccacgac ttcatcgaca ccctctgcc caaccaggac    3540
aacgacgaca actggtggac cggctggcgg cagtggatac ctgccggcat cggcatcacc    3600
ggcatcatca tcgccatcat cgctctgctg tgcgtgtgca agctgctgtg ctgagaattc    3660
agatctgctg tgccttctag ttgccagcca tctgttgttt gcccctcccc cgtgccttcc    3720
ttgaccctgg aagtgccac tcccactgtc ctttcctaat aaaatgagga aattgcatcg    3780
cattgtctga gtaggtgtca ttctattctg ggggtgggg tggggcagga cagcaagggg    3840
gaggattggg aagacaatag caggcatgct ggggatgcgg tgggctctag atatcagcga    3900
tcgctgaggt gggtgagtgg gcgtggtctg ggggtgggaa gcaatatata agttgggggt    3960
cttagggtct ctgtgtctgt tttgcagagg gaccgccggc gccatgagcg ggagcagtag    4020
cagcaacgcc ttggatggca gcatcgtgag cccttatttg acgacgcgca tgccccactg    4080
ggccggggtg cgtcagaatg tgatgggctc cagcatcgac ggacgacccg tgctgcccgc    4140
aaattccgcc acgctgacct acgcgaccgt cgcggggacc ccgttggacg ccaccgccgc    4200
cgccgccgcc accgccgccg cctcggccgt gcgcagcctg ccacggact ttgcattctt    4260
gggacccttg gccaccgggg cggccgcccg tgccgccgtt cgcgatgaca agctgaccgc    4320
cctgctggcg cagttggatg cgcttacccg ggaactgggt gaccttccgc agcaggtcgt    4380
ggccctgcgc cagcaggtct ccgccctgca ggctagcggg aatgcttctc ctgcaaatgc    4440
cgtttaagat aaataaaacc agactctgtt gataaataaa accagactct gtttggatta    4500
aagaaaagta gcaagtgcat tgctctcttt atttcataat tttccgcgcg cgataggccc    4560
```

```
gagtccagcg ttctcggtcg ttgagggtgc ggtgtatctt ctccaggacg tggtagaggt    4620
ggctctggac gttgagatac atgggcatga gcccgtcccg ggggtggagg tagcaccact    4680
gcagagcttc atgctccggg gtggtgttgt agatgatcca gtcgtagcag gagcgctggg    4740
catggtgcct aaaaatgtcc ttaagcagca ggccgatggc caggggagg cccttggtgt      4800
aagtgtttac aaaacggttg agttgggaag ggtgcatgcg gggtgagatg atgtgcatct    4860
tagattgtat ttttagattg gcgatgtttc ctcccagatc ccttctggga ttcatgttgt    4920
ggaggaccac cagcacagta tatccggtgc acttgggaaa tttgtcatgc agcttagagg    4980
gaaatgcgtg gaagaacttg gagacgccct tgtggcctcc cagattctcc atgcattcgt    5040
ccatgatgat ggcaatgggc ccgcgggagg cggcctgggc aaagatgttt ctggggtcac    5100
tgacatcgta gttgtgttcc agggtgagat cgtcataggc cattttata aagcgcgggc      5160
ggagggtgcc cgactggggg atgatggttc cctcgggccc cggggcgtag ttgccttcgc    5220
agatctgcat ttcccaggcc ttaatctctg aggggggaat catatccact tgcggggcga    5280
tgaagaaaac ggtttccgga gccggggaga ttaactggga tgagagcagg tttctcagca    5340
gctgtgactt tccacagccg gtgggtccat aaataacacc tataaccggc tgcagctggt    5400
agttgagcga gctgcagctg ccgtcgtccc ggaggagggg ggccacctca ttgagcatgt    5460
cccggacgcg cttgttctcc tcgaccaggt ccgccagaag gcgctcgccg cccagggaca    5520
gcagctcttg caaggaagca aagttttca gcggtttgag gccgtccgcc gtgggcatgt      5580
ttttcagggt ctggccgagc agctccaggc ggtcccagag ctcggtgacg tgctctacgg    5640
catctctatc cagcatatct cctcgtttcg cgggttgggg cggctttcgc tgtagggcac    5700
caggcgatgg tcgtccagcg cggccagagt catgtccttc catgggcgca gggtcctcgt    5760
cagggtggtc tgggtcacgg tgaaggggtg cgccccgggc tgggcgctgg ccagggtgcg    5820
cttgagactg gtcctgctgg tgctgaagcg ctgccggtct tcgccctgcg cgtcggccag    5880
gtagcatttg accatggtgt cgtagtccag cccctccgcg gcgtgtccct tggcgcgcag    5940
cttgcccttg gaggtggcgc cgcacgcggg gcactgcagg ctcttgagcg cgtagagctt    6000
gggggcgagg aagaccgatt cggggagta ggcgtccgcg ccgcaggccc cgcacacggt      6060
ctcgcactcc accagccagg tgagctcggg gcgctcgggg tcaaaaacca ggtttccccc    6120
atgcttttg atgcgtttct tacctcgggt ctccatgagg cggtgtcccc gttcggtgac      6180
gaagaggctg tccgtgtctc cgtagaccga cttgaggggt ctgtcctcca gggggtccc      6240
tcggtcctct tcgtagagaa actcggacca ctctgagaca aaggcccgcg tccaggccag    6300
gacgaaggag gccaggtggg aggggtaccg gtcgttgtcc actagggggt ccaccttctc    6360
caaggtgtga agacacatgt cgccctcctc ggcgtccagg aaggtgattg gcttgtaggt    6420
gtaggccacg tgacccgggg ttccggacgg gggggtataa aaggggggtgg gggcgcgctc    6480
gtcctcactc tcttccgcat cgctgtctgc gagggccagc tgctggggtg agtattccct    6540
ctcgaaggcg ggcatgacct cagcgctgag gctgtcagtt tctaaaaacg aggaggattt    6600
gatgttcacc tgtcccgagc tgatgccttt gagggtgccc gcgtccatct ggtcagaaaa    6660
cacgatcttt ttattgtcca gcttggtggc gaacgacccg tagagggcgt ggagagcag     6720
cttggcgatg gagcgcaggg tctgattctt gtcccggtcg gcgcgctcct tggccgcgat    6780
gttgagctgc acgtactcgc gcgcgacgca gcgccactcg gggaagacgg tggtgcgctc    6840
gtcgggcacc aggcgcacgc gccagccgcg gttgtgcagg gtgacgaggt ccacgctggt    6900
ggcgacctcg ccgcgcaggc gctcgttggt ccagcagagg cgcccgccct tgcgcgagca    6960
```

```
gaaggggggc agggggtcga gttgggtttc gtccgggggg tccgcgtcca ccgtgaagac    7020 cccgggggcgc aggcgcgcgt cgaagtagtc gatcttgcat ccttgcaagt ccagcgcccg    7080
ctgccagtcg cgggcggcga gcgcgcgctc gtaggggttg agcggcgggc cccagggcat    7140
ggggtgggtg agcgcggagg cgtacatgcc gcagatgtca tagacgtaga ggggctcccg    7200
gaggatgccc aggtaggtgg ggtagcagcg gccgccgcgg atgctggcgc gcacgtagtc    7260
gtagagctcg tgcgaggggg cgaggaggtc ggggcccagg ttggtgcggg cggggcgctc    7320
cgcgcggaag acgatctgcc tgaagatggc atgcgagttg aagagatgg tggggcgctg    7380 gaagacgttg aagctggcgt cctgcaggcc gacggcgtcg cgcacgaagg aggcgtagga    7440
ctcgcgcagc ttgtgcacca gctcggcggt gacctgcacg tcgagcgcgc agtagtcgag    7500
ggtctcgcgg atgatgtcat acttagcctg ccccttcttt ttccacagct cgcggttgag    7560
gacgaactct tcgcggtctt tccagtactc ttggatcggg aaaccgtccg gctccgaacg    7620
gtaagagccc agcatgtaga actggttgac ggcctggtag cgcagcagc ccttctccac    7680 gggcagggcg taggcctgcg cggccttgcg gagcgaggtg tgggtcaggg cgaaggtgtc    7740
cctgaccatg accttgaggt actggtgttt gaagtcggag tcgtcgcagc cgccccgctc    7800
ccagagcgag aagtcggtgc gcttttggga gcggggttg ggcagcgcga aggtgacatc    7860
gttgtagagg atcttgcccg cgcgaggcat gaagttgcgg gtgatgcgga agggccccgg    7920
cacttccgag cggttgttga tgacctgggc ggcgagcacg atctcgtcga agccgttgat    7980
gttgtggccc acgatgtaga gttccaggaa gcggggccgg cccttgacgc tgggcagctt    8040
ctttagctct tcgtaggtga gctcctcggg cgaggcgagg ccgtgctcgg ccagggccca    8100
gtccgccagg tgcgggttgt ccgcgaggaa ggaccgccag aggtcgcggg ccaggagggt    8160
ctgcaggcgg tccctgaagg tcctgaactg gcggcctacg gccatctttt cggggtgac    8220 gcagtagaag gtgaggggggt cttgctgcca ggggtcccag tcgagctcca gggcgaggtc    8280
gcgcgcggcg gcgaccaggc gctcgtcgcc cccgaatttc atgaccagca tgaagggcac    8340
gagctgcttt ccgaaggcgc ccatccaagt gtaggtctct acatcgtagg tgacaaagag    8400
acgttccgtg cgaggatgcg agccgatcgg gaagaactgg atctcccgcc accagttgga    8460
ggagtggctg ttgatgtggt gaaagtagaa gtcccgtcgg cgggccgagc actcgtgctg    8520
gcttttgtaa aagcgagcgc agtactgcca gcgctgcacg ggctgtacct cttgcacgag    8580
atgcacctgc cgaccgcgga cgaggaagct gagtgggaat ctgagccccc cgcatggctc    8640
gcggcctggc tggtgctctt ctactttgga tgcgtggccg tcaccgtctg gctcctcgag    8700
gggtgttacg gtggagcgga tcaccacgcc gcgcgagccg caggtccaga tatcggcgcg    8760
cggcggtcgg agtttgatga cgacatcgcg cagctgggag ctgtccatgg tctggagctc    8820
ccgcggcggc ggcaggtcag ccgggagttc ttgcaggttt acctcgcaga acgggccag    8880 ggcgcggggc aggtccaggt ggtacttgaa ttcgagaggc gtgttggtgg cggcgtcgat    8940
ggcttgcagt atgccgcagc cccggggcgc gacgacggtg ccccgcgggg cggtgaagct    9000
cccgccgccg ctcctgctgt cgccgccggt ggcggggctt agaagcggtg ccgcggtcgg    9060
gcccccggag gtaggggggg ctccggtccc gcgggcaggg gcgcagcgg cacgtcggcg    9120 ccgcgcgcgg gcaggagctg gtgctgcgcc ggaggttgc tggcgaaggc gacgacgcgg    9180
cggttgatct cctggatctg gcgcctctgc gtgaagacga cgggtccggt gagcttgaac    9240
ctgaaagaga gttcgacaga atcaatctcg gtgtcattga ccgcgacctg gcgcaggatc    9300
```

```
tcctgcacgt cgcccgagtt gtcttggtag gcgatctcgg ccatgaactg ttcaatctct    9360
tcctcctgga ggtctccgcg tccggcgcgc tccacggtgg ccgccaggtc gttggagatg    9420
cgcgccatga gctgcgagaa ggcgttgagt ccgccctcgt tccacactcg gctgtagacc    9480
acgccgccct ggtcgtcgcg ggcgcgcatg accacctgcg cgaggttgag ttccacgtgg    9540
cgcgcaaaga cggcgtagtt gcgcaggcgc tggaagaggt agttgagggt ggtggcggtg    9600
tgctcggcca caaagaagta catgacccag cggcgcaacg tggattcgtt gatgtccccc    9660
aaggcctcca gtcgctccat ggcctcgtag aagtccacgg cgaagttgaa aaactgggag    9720
ttgcgcgccg acacggtcaa ctcctcctcc agaagacgga tgagctcggc gacggtgtcg    9780
cgcacctcgc gctcgaaggc tatgggaatc tcttcctccg ccagcatcac cacctcttcc    9840
tcttcttcct cctctggcac ttccatgatg gcttcctcct cttcggggggg tggcggcggg    9900 ggagggggcg ctcggcgccg gcggcggcgc accggggaggc ggtccacgaa gcgctcgatc    9960
atctccccgc ggcggcgacg catggtctcg gtgacggcgc ggccgttctc tcggggacgc    10020
agctggaaga cgccgccggt catctggtgc tgggcgggt ggccgtgggg cagcgagacc    10080
gcgctgacga tgcatcttaa caattgctgc gtaggtacgc cgccgaggga cctgagggag    10140
tccagatcca ccgatccga aaaccttccg aggaaggcat ctaaccagtc gcagtcgcaa    10200
ggtaggctga gcaccgtggc gggcggcggg gggtgggggg agtgtctggc ggaggtgctg    10260
ctgatgatgt aattgaagta ggcggtcttg acacggcgga tggtcgacag gagcaccatg    10320
tctttgggcc cggcctgctg gatgcggagg cggtcggcca tgccccaggc ttcgttctgg    10380
catctgcgca ggtcttttgta gtagtcttgc atgagccttt ccaccggcac ctcttctcct    10440
tcttcttctg acatctctgc tgcatctgcg gccctggggc gacggcgcgc gcccctgccc    10500
cccatgcgcg tcacccccgaa cccccctgagc ggctggagca gggccaggtc ggcgacgacg    10560
cgctcggcca ggatggcctg ctggacctgc gtgagggtgg tttggaagtc atccaagtcc    10620
acgaagcggt ggtaggcgcc cgtgttgatg gtgtaggtgc agttggccat gacgaccag    10680 ttgacggtct ggtggcccgg ttgcgtcatc tcggtgtacc tgaggcgcga gtaggcgcgc    10740
gagtcgaaga tgtagtcgtt gcaagtccgc accaggtact ggtagcccac caggaagtgc    10800
ggcggcggct ggcggtagag gggccagcgg agggtggcgg gggctccggg ggccaggtct    10860
tccagcatga ggcggtggta ttcgtagatg tacctggaca tccaggtgat gcccgcggcg    10920
gtggtggagg cgcgcgggaa gtcgcgcacc cggttccaga tgttgcgcag cggcagaaag    10980
tgctccatga taggcgtgct ctggccggtc aggcgcgcgc agtcgttgat actctagacc    11040
agggaaaacg aaagccggtc agcgggcact cttccgtggt ctggtggata aattcgcaag    11100
ggtatcatgg cggagggcct cggttcgagc cccgggcccg ggccggacgg tccgccatga    11160
tccacgcggt taccgcccgc gtgtcgaacc caggtggcga cgtcagacaa cggtggagtg    11220
ttccttttgg gtttttttcc aaattttct ggcggggcgc cgacgccgcc gcgtaagaga    11280
ctagagtgca aaagcgaaag cagtaagtgg ctcgctccct gtagcccgga ggatccttgc    11340
taagggttgc gttgcggcga accccggttc gagtctggct ctcgctgggc cgctcgggtc    11400
ggccggaacc gcggctaagg cgggattggc ctcccccctca ttaaagaccc cgcttgcgga    11460
ttcctccgga cacaggggac gagccccttt ttacttttgc ttttctcaga tgcatccggt    11520
gctgcggcag atgcgccccc cgcccagca gcagcagcag caacatcagc aagagcggca    11580
ccagcagcag cgggagtcat gcagggcccc ctcgcccacg ctcggcggtc cggcgacctc    11640
ggcgtccgcg gccgtgtctg gagccggcgg cggtgggctg gcggacgacc cggaggagcc    11700
```

```
cccgcggcgc agggccagac agtacctgga cctggaggag ggcgagggcc tggcgcgact   11760
gggggcgccg tcccccgagc gccacccgcg ggtgcagctg aagcgcgact cgcgcgaggc   11820
gtacgtgcct cggcagaacc tgttcagaga ccgcgcgggc gaggagcccg aggagatgcg   11880
ggaccgcagg ttcgccgcgg ggcgggagct cggcagggg ctgaaccggg agcggctgct   11940
gcgcgaggag gactttgagc ccgacgcgcg gacgggatc agccccgcgc gcgcgcacgt   12000
ggcggccgcc gacctggtga cggcgtacga gcagacggtg aaccaggaga tcaacttcca   12060
aaaaagcttc aacaaccacg tgcgcacgct ggtggcgcgc gaggaggtga ccatcggcct   12120
gatgcacctg tgggactttg tgagcgcgct ggagcagaac cccaacagca agcctctgac   12180
ggcgcagctg ttcctgatag tgcagcacag cagggacaac gaggcgttca gggacgcgct   12240
gctgaacatc accgagcccg agggtcggtg gctgctggac ctgattaaca tcttgcagag   12300
catagtggtg caggagcgca gcctgagcct ggccgacaag gtggcggcca tcaattactc   12360
gatgctcagt ctgggcaagt tttacgcgcg caagatctac cagacgccgt acgtgcccat   12420
agacaaggag gtgaagatcg acggcttcta catgcgcatg gcgctgaagg tgctgacccct   12480 gagcgacgac ctgggcgtgt accgcaacga gcgcatccac aaggccgtga gcgtgagccg   12540
gcggcgcgag ctgagcgacc gcgagctgat gcacagcctg cagcgggcgc tggcggggc   12600 cggcagcggc gacagggagg ccgagtccta cttcgaggcg ggggcggacc tgcgctgggt   12660
gcccagccgg agggccctgg aggccgcggg ggcccgccgc gaggactatg cagacgagga   12720
ggaggaggat gacgaggagt acgagctaga ggagggcgag tacctggact aaaccgcagg   12780
tggtgttttt ggtagatgca agacccgaac gtggtggacc cggcgctgcg ggcggctctg   12840
cagagccagc cgtccggcct taactctaca gacgactggc gacaggtcat ggaccgcatc   12900
atgtcgctga cggcgcgcaa tccggacgcg ttccggcagc agccgcaggc caacaggctc   12960
tccgccatct tggaggcggt ggtgcctgcg cgcgcgaacc ccacgcacga aaggtgctg   13020 gccatagtga acgcgctggc cgagaacagg gccatccgcc cggacgaggc cgggctggtg   13080
tacgacgcgc tgctgcagcg cgtggcccgc tacaacagcg gcaacgtgca gaccaacctg   13140
gaccggctgg tggggacgt gcgcgaggcg gtggcgcagc gggagcgcgc ggagcggcag   13200
ggaaacctgg gctccatggt ggcgctgaac gccttcctga gcacgcagcc ggccaacgtg   13260 ccgcggggc aggaggacta caccaacttt gtgagcgcgc tgcggctgat ggtgaccgag   13320
accccccaga gcgaggtgta ccagtcgggg ccggactact ttttccagac cagcagacag   13380
ggcctgcaga cggtgaacct gagccaggct ttcaagaacc tgcgggggct gtggggcgtg   13440
aaggcgccca ccggggaccg ggcgacggtg tccagcctgc tgacgcccaa ctcgcgcctg   13500
ctgctgctgc tgatcgcgcc gttcacggac agcggcagcg tgtcccggga gacctacctc   13560
gggcacctgc tgacgctgta ccgcgaggcc atcgggcaga cccaggtgga cgagcacacc   13620
ttccaggaga tcaccagcgt gagccgcgcg ctggggcagg aggacacggg cagcctggag   13680
gcgaccctga actacctgct gaccaaccgg cggcagaaga tcccctcgct gcatagtttg   13740
accaccgagg aggagcgcat cctgcgctac gtgcagcaga gcgtgagcct gaacctgatg   13800
cgcgacgggg tgacgcccag cgtggcgctg acatgaccg cgcgcaacat ggaaccggc   13860 atgtacgccg cgcatcggcc ttacatcaac cgcctgatgg actacttgca tcgcgcggcg   13920
gccgtgaacc ccgagtactt caccaacgcc atcctgaacc cgcactggct cccgccgccc   13980
gggttctaca gcggggcctt cgaggtcccc gaggccaacg acggcttcct gtgggacgac   14040
```

```
atggacgaca gcgtgttctc cccgcggccg caggcgctgg cggaggcgtc gctgctccgc    14100
ctccccaaga aagaagagag ccgccggccc agcagcgcgg cggcctctct gtccgagctg    14160
ggggcggcgg ccgcgcggcc cgggtccctg gggggcagcc cctttcccag tctggtgggg    14220
tctctgcaga gcgggcgcac cacccggccc cggctgctgg gcgaggacga gtacctgaac    14280
aactccctga tgcagccggt gcgggagaaa aacctgcccc ccgccttccc caacaacggg    14340
atagagagcc tggtagacaa gatgagcaga tggaagacct atgcgcagga gcacagggac    14400
tcgcccgtgc tccgtccgcc cacgcggcgc cagcgccacg accggcagcg ggggctggta    14460
tgggatgacg aggactccgc ggacgatagc agcgtgctgg acctgggggg gagcggcggt    14520
aacccgttcg cgcacctgcg cccccgcctg ggaggatgt ttcaataaga aaaatcaagc    14580
atgatgcaag gttttttaag cggataaata aaaaactcac caaggccatg gcgaccgagc    14640
gttgttggtt tcttgttgtg ttcccttagt atgcggcgcg cggcgatgta ccacgaggga    14700
cctcctccct cttatgagag cgtggtgggc gcggcggcgg cctctccctt tgcgtcgcag    14760
ctggagccgc cgtacgtgcc tccgcggtac ctgcggccta cgggggggaag aaacagcatc    14820 cgttactcgg agctggcgcc cctgtacgac accacccggg tgtacctggt ggacaacaag    14880
tcggcggacg tggcctccct gaactaccag aacgaccaca gcaatttttt gaccacggtc    14940
atccagaaca tgactacac cccgagcgag gccagcaccc agaccatcaa tctggatgac    15000
cggtcgcact ggggcggcga cctgaaaacc atcctgcaca ccaacatgcc caacgtgaac    15060
gagttcatgt tcaccaataa gttcaaggcg cgggtgatgg tgtcgcgttc gcacaccaag    15120
gacgaccggg tggagctgaa gtacgagtgg gtagagttcg agctgcccga gggcaactac    15180
tcggagacca tgaccataga cctgatgaac aacgcgatcg tggagcacta tctgaaagtg    15240
ggcaggcaga acggggtcct ggagagcgac atcggggtca agttcgacac caggaacttc    15300
cgcctggggc tggacccggt caccgggctg gtcatgcccg ggtctacac caacgaggcc    15360 ttccaccccg acatcatcct gctgcccggc tgcggggtgg acttcaccta cagccgcctg    15420
agcaacctgc tgggcatccg caagcggcag cccttccagg agggctttag gatcacctac    15480
gaggacctgg aggggggcaa catccccgcg ctcctggatg tggaggccta ccaggatagc    15540
ttgaaggaag aagaggcggg agagggcagc ggcggcggcg gcggcgccgg tcaggaggag    15600
ggcggggcct cctctgaggc ctctgcggac gccgccgctg ccgccgaggc ggaggcggcc    15660
gaccccgcga tggtggtaga ggaagagaag gatatgaatg acgaggcggt gcgcggcgac    15720
acctttgcca cccgggggga ggagaagaaa gcggaggccg aggccgcggc agaggaggcg    15780
gcagcggcgg cggcggcggc agtagaggcg gcggccgagg cggagaagcc ccccaaggag    15840
cccgtgatta aggccctgac cgaagatagc aagaagcgca gttacaacgt gctcaaggac    15900
agcaccaaca ccgcgtaccg cagctggtac ctggcctaca actacggcga cccggcgacg    15960
ggggtgcgct cctggaccct gctgtgtacg ccggacgtga cctgcggctc ggagcaggtg    16020
tactggtcgc tgcccgacat gatgcaagac cccgtgacct ccgctccac gcggcaggtc    16080 agcaacttcc cggtggtggg cgccgagctg ctgcccgtgc actccaagag cttctacaac    16140
gaccaggccg tctactccca gctcatccgc cagttcacct ctctgaccca cgtgttcaat    16200
cgctttcctg agaaccagat tctggcgcgc ccgcccgccc ccaccatcac caccgtcagt    16260
gaaaacgttc ctgctctcac agatcacggg acgctaccgc tgcgcaacag catcggagga    16320
gtccagcgag tgaccgtaac tgacgccaga cgccgcacct gtcctacgt ttacaaggcc    16380 ctgggcatag tctcgccgcg cgtcctttcc agccgcactt tttaagcatg tccatcctca    16440
```

```
tctcgcccag caataacacc ggctgggggcc tgctgcgcgc gcccagcaag atgtttggag    16500
gggcgaggaa gcgctccgac cagcaccccg tgcgcgtgcg cgggcactac cgcgccccct    16560
ggggcgcgca caaacgcggg cgcaccggca ccgcggggcg caccaccgtg gacgaagcca    16620
tcgactcggt ggtggagcag gcgcgcaact acacgcccgc ggtctccacc gtggacgcgg    16680
ctatcgagag cgtggtgcga ggcgcgcggc ggtacgccaa ggcgaagagc cgccggaggc    16740
gcgtggcccg ccgccaccgc cgtcgacccg gaagcgccgc caagcgcgcc gccgccgcct    16800
tgcttcgtcg ggccagacgc acgggccgcc gcgccgccat gagggccgcg cgccgcctgg    16860
ccgccggcat caccaccgtg gccccccgcg ccagaagacg cgcggccgct gccgccgccg    16920
cggccatcag cgacctggcc accaggcgcc ggggcaacgt gtactgggtg cgcgactcgg    16980
tgagcggcac gcgcgtgccc gtgcgcttcc gccccccgcg gacttgagag gagaggacag    17040
gaaaaagca tcaacaacac caccactgag tctcctgctg ttgtgtgtat cccagcggcg    17100
cgcgcgcaca cggcgacatg tccaagcgca aaatcaaaga agagatgctc caggtcgtcg    17160
cgccggaaat ctatgggccc ccgaagaagg aagagcagga tttcaagccc cgcaagataa    17220
agcgggtcaa aaagaaaaag aaagatgacg atgatgcga ggtggagttt ctgcgcgcca    17280
cggcgcccag gcgcccgctg cagtggaagg gtcggcgcgt aaagcgcgtt ctgcgccccg    17340
gcaccgcggt ggtcttcacg cccggcgagc gctccaccg cactttcaag cgcgtctatg    17400
acgaggtgta cggcgacgaa gacctgctgg agcaggccaa cgatcgctcc ggagagtttg    17460
cttacgggaa gcggcaccgg gcgatggaga aggacgaggt gctggcgctg ccgctggacc    17520
ggggcaaccc caccccagc ctgaagcccg tgaccctgca gcaggtgctg ccggccagcg    17580
cgccctccga gatgaagcgg ggcctgaagc gcgagggcgg cgacctggcg cccaccgtgc    17640
agctgatggt gcccaagcgg cagaggctgg aggacgtgct ggagaaaatg aaagtagacc    17700
ccggcctgca gccggacatc agggtccgcc ccatcaagca ggtggcgccg ggcctcggcg    17760
tgcagaccgt ggacgtggtc atccccaccg gcgcctcctc ttccagcgcc gccgccgcca    17820
ctagcaccgc ggacatggag acgcagacta gctccgccct cgccgccccc gcggccgccg    17880
ccgccgccac ctcctcggcg gaggtacaga cggaccctg gatgccgccg ccggcggccg    17940
cccctcgcg cgcacgccgc gggcgcagga agtacggcgc cgccagcgcg ctcatgcccg    18000
agtacgcctt gcatcttcc atcgcgccca ccccggcta ccgaggctac agctaccgcc    18060
cgcgaagagc caagggctcc acccgccgca gccgccgcgc cgccacctct acccgccgcc    18120
gcagtcgccg ccgccgccgg cagcccgcgc tggctccgat ctccgtgagg agagtggcgc    18180
gcaacgggga caccttggtg ctgcccaggg cgcgctacca ccccagcatc gtttaaaagc    18240
ctgttgtggt tcttgcagat atggccctca cttgccgcct ccgtttcccg gtgccgggat    18300
accgaggaag atcgcgccgt agaaggggta tggccggacg cggcctgagc ggaggcagcc    18360
gccgtgcgca ccgcggcga cgcgccacca gccgacgcat gcgcggcggg gtgctgcctc    18420
tgctgatccc cctgatcgcc gcggcgatcg gcgccgtgcc cgggatcgcc tccgtggcct    18480
tgcaggcgtc ccagaggcgt tgacacagac ttcttgcaag cttgcaaaaa tatggaaaaa    18540
atccccccaa taaaaagtc tagactctca cgctcgcttg gtcctgtgac tattttgtag    18600
aaaaaaagat ggaagacatc aactttgcgt cgctggcccc gcgtcacggc tcgcgcccgt    18660
tcctgggaca ctgaacgat atcggcacca gcaacatgag cggtggcgcc ttcagttggg    18720
gctctctgtg gagcggcatt aaaaatatcg gttctgccgt taagaattac ggctccaagg    18780
```

```
cctggaacag cagcacgggc cagatgttga gagacaagtt gaaagagcag aacttccagc   18840
agaaggtggt ggagggcctg gcctccggca tcaacgggt ggtggacctg gccaatcagg   18900
ccgtgcaaaa taagatcaac agcagactgg accccggcc gccggtggaa gagctgccgc   18960
cggcgctgga gacggtgtcc cccgatgggc ggggcgaaaa gcgcccgcgg cccgacaggg   19020
aagagaccac tctggtcacg cacaccgatg agccgccccc ctacgaggaa gctctgaagc   19080
aaggcttgcc caccactcgg cccatcgcgc ccatggccac cggggtggtg ggccgccaca   19140
cccccgccag gctggacctg cctcctcctc ctgtttcttc ttcggccgcc gatgcgcagc   19200
agcagaaggc ggcgctgccc ggtccgcccg cggccgcccc ccgtcccacc gccagtcgag   19260
cgccctgcg tcgcgcggcc agcggccccc gcggggtcgc gaggcacagc agcggcaact   19320
ggcagaacac gctgaacagc atcgtgggtc tgggggtgca gtccgtgaag cgccgccgat   19380
gctactgaat agcttagcta acggtgttgt atgtgtgtat gcgtcctatg tcaccgccag   19440
aggagctgct gagtcgccgc cgttcgcgcg cccaccgcca ctaccaccgc cggtaccact   19500
ccagcgcccc tcaagatggc gaccccatcg atgatgccgc agtggtcgta catgcacatc   19560
tcgggccagg acgcctcgga gtacctgagc cccgggctgg tgcagttcgc ccgcgccacc   19620
gacagctact tcagcctgag taacaagttt aggaaccccca cggtggcgcc cacgcacgat   19680
gtgaccaccg accggtccca gcgcctgacg ctgcggttca tccccgtgga ccgcgaggac   19740
accgcgtact cttacaaggc gcggttcacc ctggccgtgg gcgacaaccg cgtgctggac   19800
atggcctcca cctactttga catccgcggc gtgctggaca ggggcccac cttcaagccc   19860
tactccggca ccgcctacaa ctccctggcc cccaagggcg cccccaactc ctgcgagtgg   19920
gagcaagagg agactcagac agctgaagag gcacaagacg aagaagaaga tgaagctgaa   19980
gctgaggagg aaatgcctca ggaagagcaa gcacctgtca aaaagactca tgtatatgct   20040
caggctcccc tttctggcga aaaaattact aaagacggtc tgcagatagg aacggacgct   20100
acagctaccg aacaaaaacc tatttatgca gatcccacat tccagccaga accccaaatt   20160
ggtgaatctc agtggaatga ggcagatgct tcagttgccg gcggtagagt gctgaagaaa   20220
actactccca tgaaaccctg ttatggttcc tatgccaggc ccacaaatgc caatggaggt   20280
cagggtgtat tggtggagaa agacggtgga aagatggaaa gccaagtaga tatgcaattc   20340
ttttcgactt ctgaaaacgc ccgtaacgag gctaacaaca ttcagcccaa attggtgctg   20400
tacagcgagg atgtgcatat ggagacccca gacacacaca tttcttacaa gcctgcaaaa   20460
agcgatgata attcgaaagt catgctgggt cagcagtcca tgcccaacag gccaaattac   20520
atcggcttca gagacaactt tatcgggctc atgtattaca acagcactgg caacatgggg   20580
gtgctggcag gtcaggcctc acagttgaat gcgtggtgg acttgcaaga cagaaacaca   20640
gaactgtcct accagctctt gcttgattcc atggagacag aaccagata cttttccatg   20700
tggaatcagg cggtggacag ttatgatcca gatgtcagaa ttattgaaaa tcatggaact   20760
gaagatgagc tgcccaacta ttgtttccct ctggaggca tagggtaac tgacacttac   20820
caggccatta agactaatgg caatggcaac ggcgggggca ataccacttg gaccaaggat   20880
gaaacttttg cagaccgcaa cgagataggg gtgggaaaca atttcgccat ggagatcaac   20940
ctcagtgcca acctgtggag gaacttcctc tactccaacg tggccctgta cctgccagac   21000
aagcttaagt acaaccctc caacgtggaa atctctgaca accccaacac ctacgactac   21060
atgaacaagc gagtggtggc cccggggctg gtggactgct acatcaacct gggcgcgcgc   21120
tggtccctgg actacatgga caacgtcaac cccttcaacc accaccgcaa cgcgggcctg   21180
```

```
cgctaccgct ccatgcttct gggcaacggg cgctacgtgc ccttccacat ccaggtgccc   21240
cagaagttct ttgccatcaa gaacctcctc ctcctgccgg gctcctacac ctacgagtgg   21300
aacttcagga aggatgtcaa catggtcctc cagagctctc tgggtaacga cctcagggtc   21360
gacggggcca gcatcaagtt cgagagcatc tgcctctacg ccaccttctt ccccatggcc   21420
cacaacacgg cctccacgct cgaggccatg ctcaggaacg acaccaacga ccagtccttc   21480
aacgactacc tctccgccgc caacatgctc taccccatcc ccgccaacgc caccaacgtt   21540
cccatctcca tccctcgcg caactgggcg gccttccgcg gctgggcctt cacccgcctc   21600
aagaccaagg agaccccctc cctgggctcg ggtttcgacc cctactacac ctactcgggc   21660 tccatacctct acctggacgg aaccttctac ctcaaccaca ctttcaagaa ggtctcggtc   21720
accttcgact cctcggtcag ctggccgggc aacgatcgcc tgctcacccc caacgagttc   21780
gagatcaagc gctcggtcga cggggagggc tacaacgtgg cccagtgcaa catgaccaag   21840
gactggttcc tcatccaaat gctggccaac tacaacatcg gctatcaggg cttctacatc   21900
ccagagagct acaaggacag gatgtactcc ttctttagga acttccagcc catgagccgg   21960
caggtggtgg acgaaaccaa gtacaaggac taccagcagg tgggcatcat ccaccagcac   22020
aacaactcgg gcttcgtggg ctacctcgcc cccaccatgc gcgagggaca ggcctacccc   22080
gccaacttcc cctacccgct cattggcaag accgcggtcg acagcgtcac ccagaaaaag   22140
ttcctctgcg accgcaccct ctggcgcatc cccttctcca gcaacttcat gtccatgggt   22200
gcgctcacgg acctgggcca gaacctgctc tatgccaact ccgcccacgc gctcgacatg   22260
accttcgagg tcgaccccat ggacgagccc acccttctct atgttctgtt cgaagtcttt   22320
gacgtggtcc gggtccacca gccgcaccgc ggcgtcatcg agaccgtgta cctgcgcacg   22380
cccttctcgg ccggcaacgc caccacctaa agaagcaagc cgccaccgcc accacctgca   22440
tgtcgtcggg ttccaccgag caggagctca aggccatcgt cagagacctg ggatgcgggc   22500 cctattttt gggcaccttc gacaaacgct tcccgggctt cgtcgcccc cacaagctgg   22560 cctgcgccat cgtcaacacg gccggccgcg agaccggggg cgtgcactgg ctggccttcg   22620
cctggaaccc gcgctccaaa acatgctacc tctttgaccc cttcggattc tcggaccagc   22680
ggctcaagca gatctaccag ttcgagtacg agggcctgct cgccgcagc gccatcgcct   22740 cctcgcccga ccgctgcgtc accctcgaga agtccaccca accgtgcag gggcccgact   22800 cggccgcctg cggtctcttc tgctgcatgt tcctgcatgc cttttgtgcac tggccccaga   22860 gtcccatgga ccgcaacccc accatgaact tgctgacggg gatccccaac tccatgctcc   22920
agagccccca ggtcgcgccc accctgcgcc gcaaccagga gcggctctac agcttcctgg   22980
aacgccactc gccctacttc cgccgccaca gcgcgcagat caggggggcc acctcttct   23040 gccgcatgca agagatgcaa gggaaaatgc aatgatgtac acagacactt tttctttcct   23100
caataaatgg caactttatt tatacatgct ctctctcggg tattcatttc cccaccaccc   23160 accaccccgcc gccgccgtaa ccatctgctg ctggcttttt ttttttttttt taaaaatcga   23220 aagggttctg ccgggaatcg ccgtgcgcca cgggcaggga cacgttgcgg aactggtagc   23280
gggtgcccca cttgaactcg gcaccacca tgcggggcaa gtcggggaag ttgtcggccc   23340
acaggctgcg ggtcagcacc agcgcgttca ttaggtcggg cgccgagatc ttgaagtcgc   23400
agttggggcc gccgccctgc gcgcgcgagt tgcggtacac cggttgcaa cactggaaca   23460 ccagcagcgc cggataattc acactggcca gcacgctccg gtcggagatc agctcggcgt   23520
```

```
ccaggtcctc cgcgttgctc agcgcgaacg gggtcagctt gggcacctgc cgccccagga    23580
agggagcgtg ccccggcttc gagttgcagt cgcagcgcag cgggatcagc aggtgcccgc    23640
ggccggactc ggcgttgggg tacagcgcgc gcatgaaggc ctccatctgg cggaaggcca    23700
tctgggcctt ggcgccctcc gagaagaaca tgccgcagga cttgcccgag aactggttcg    23760
cggggcagct agcgtcgtgc aggcagcagc gcgcgtcggt gttggcgatc tgcaccacgt    23820
tgcgccccca ccggttcttc acgatttttgg ccttggaagc ctgctccttc agcgcgcgct    23880
gcccgttctc gctggtcaca tccatctcga tcacgtgctc cttgttcacc atgctgctgc    23940
cgtgcagaca cttcagctcg ccctccacct cggtgcagcg gtgctgccat agcgcgcagc    24000
ccgtgggctc gaaatgcttg taggtcacct ccgcgtagga ctgcaggtag gcctgcagga    24060
agcgccccat catggtcacg aaggtcttgt tgctgctgaa ggtcagctgc agcccgcggt    24120
gctcctcgtt cagccaggcc ttgcacacgg ccgccagcgc ctccacctgg tcgggcagca    24180
tcttgaagtt cagcttcagc tcattctcca catggtactt gtccatcagc gcgcgcgcag    24240
cctccatgcc cttctcccag gccgacacca gcggcaggct caaggggttc accaccgtcg    24300
cagccgccgc tgcgctttcg ctttccgctc cgctgttctc ttcttcctcc tcctcttctt    24360
cctcgccgcc cgcgcgcagc ccccgcacca cggggtcgtc ttcctgcagg cgccgcaccg    24420
agcgcttgcc gctcctgccc tgcttgatac gcacgggcgg gttgctgaag cctaccatca    24480
ccagcgcggc ctcttcttgc tcgtcctcgc tgtccactat gacctcgggg gagggcgacc    24540
tcagaaccgt ggcgcgctgc ctcttctttt tcctgggggc gtttgccagc tccgcggccg    24600
cggccgccgc cgaggtcgaa ggccgagggc tgggcgtgcg cggcaccagc gcgtcctgcg    24660
agccgtcctc gtcctcggac tcgaggcggc agcgagcccg cttcttcggg ggcgcgcggg    24720
gcggcggcgg cggggcggc ggcgacggag acggggacga acatcgtcc agggtgggag    24780 gacggcgggc cgcgccgcgt ccgcgctcgg gggtggtttc gcgctggtcc tcttcccgac    24840
tggccatctc ccactgctcc ttctcctata ggcagaaaga gatcatggag tctctcatgc    24900
aagtcgagaa ggaggaggac agcctaacca ccaccgcccc ctctgagccc tccgccgccg    24960
ccgcggacga cgcgcccacc accaccgccg ccgccaccac caccattacc accctacccg    25020
gcgacgcagc cccgatcgag aaggaagtgt tgatcgagca ggacccgggt tttgtgagcg    25080
aagaggagga tgaggaggat gaaaaggaga aggataccgc cgcctcagtg ccaaaagagg    25140
ataaaaagca agaccaggac gacgcagaga cagatgaggc agcagtcggg cgggggggacg    25200 gaaggcatga tgatgatgac ggctacctag acgtgggaga cgacgtgctg cttaagcacc    25260
tgcaccgcca gtgcgtcatc gtctgcgacg cgctgcagga gcgctgcgaa gtgcccctgg    25320
acgtggcgga ggtcagccgc gcctacgagc ggcacctctt cgcgccacac gtgccccca    25380 agcgccggga gaacggcacc tgcgagccca acccgcgcct caacttctac ccggtcttcg    25440
cggtacccga ggtgctggcc acctaccaca tcttcttcca aaactgcaag atcccctct    25500 cctgccgcgc caaccgcacc cgcgccgaca agacgctggc cctgcggcag ggcgcccaca    25560
tacctgatat cgcctctctg gaggaggtgc ccaagatctt cgagggtctc ggtcgcgacg    25620
agaaacgggc ggcgaacgct ctgcaaggag acagcgaaaa cgagagtcac tcggggggtgc    25680 tggtggagct cgagggcgac aacgcgcgcc tggccgtgct caagcgcagc atcgaagtca    25740 cccactcgc ctaccggcg ctcaacctgc ccccaaggt catgagtgtg gtcatgagtg    25800
agctcatcat gcgccgcgcc cagccctggg acgcggatgc aaacttgcaa gagccctccg    25860
aggaaggcct gcccgcggtc agcgacgagc agctggcgcg ctggctggag acccgcgacc    25920
```

```
ccgcccagct ggaggagcgg cgcaagctca tgatggccgc ggtgctcgtc accgtggagc   25980
tcgagtgtct gcagcgcttc ttcggggacc ccgagatgca gcgcaagctc gaggagaccc   26040
tgcactacac cttccgccag ggctacgtgc gccaggcctg caagatctcc aacgtggagc   26100
tctgcaacct ggtctcctac ctgggcatcc tgcacgagaa ccgcctcggg cagaacgtcc   26160
tgcactccac cctcaaaggg gaggcgcgcc gcgactacgt ccgcgactgc gtctacctct   26220
tcctctgcta cacgtggcag acggccatgg gggtctggca gcagtgcctg gaggagcgca   26280
acctcaagga gctggagaag ctcctccggc gcgccctcag ggacctctgg acgggcttca   26340
acgagcgctc ggtggccgcc gcgctggcgg acatcatctt ccccgagcgc ctgctcaaaa   26400
ccctgcagca gggcctgccc gacttcacca gccagagcat gctgcagaac ttcaggacct   26460
tcatcctgga gcgctcgggc atcctgccgg ccacctgctg cgcgctgccc agcgacttcg   26520
tgcccatcag gtacagggag tgcccgccgc cgctctgggg ccactgctac ctcttccagc   26580
tggccaacta cctcgcctac cactcggatc tcatggaaga cgtgagcggc gagggcctgc   26640
tcgagtgcca ctgccgctgc aacctgtgca cgccccaccg ctctctagtc tgcaatccgc   26700
agctgctcag cgagagtcag attatcggta ccttcgagct gcagggtccc tcgcccgacg   26760
aaaagtccgc ggctccgggg ttgaaactca ctccggggct gtggacttcc gcctacctac   26820
gcaaatttgt acctgaagac taccacgccc acgagatcag gttttacgaa gaccaatccc   26880
gcccgcccaa ggcggagctc accgcctgcg tcattaccca gggccacatc ctgggccaat   26940
tgcaagccat caacaaagcc cgccaagagt tcttgctgaa aaagggtcgg ggggtgtacc   27000
tggaccccca gtccggcgag gagctaaacc cgctaccccc gccgccgccc cagcagcggg   27060
accttgcttc ccaggatggc acccagaaag aagcagccgc cgccgccgcc agcatacatg   27120
cttctggagg aagaggagga ctgggacagt caggcagagg aggtttcgga cgaggacgag   27180
gaggaggaga tgatggaaga ctgggaggag gacagcctag acgaggaagc ttcagaggcc   27240
gaagaggtgg cagacgcaac accatcaccc tcggccgcag ccccctcgcc ggcgccccccg   27300 aaatcctccg accccagcag cagcgctata acctccgctc ctccggcgcc ggcgcccacc   27360
cgcagcagac ccaaccgtag atgggacact acaggaaccg gggtcggtaa gtccaagtgc   27420
cccccagcgc cgcccccgca acaggagcaa cagcagcagc agcggcgaca gggctaccgc   27480
tcgtggcgcg gacacaagaa cgccatagtc gcctgcttgc aagactgcgg gggcaacatc   27540
tccttcgccc gccgcttcct gctcttccac cacggggtgg cttttccccg caatgtcctg   27600
cattactacc gtcatctcta cagccctac tgcggcggca gcggcgaccc agagggagcg   27660
gcggcagcag cagcgccagc cacagcggcg accacctagg aagacctccg cgggcaagac   27720
ggcgggagcc gggagacccg cggcggcggc ggtagcggcg gcggcgggcg cactgcgcct   27780
ctcgcccaac gaacccctct cgacccggga gctcagacac aggatcttcc ccactctgta   27840
tgctatcttc cagcagagca gaggccagga acaggagctc aaaataaaaa acagatctct   27900
gcgctccctc acccgcagct gtctgtatca caaaagcgaa gatcagcttc ggcgcacgct   27960
ggaggacgcg gaggcactct tcagcaaata ctgcgcgctg actcttaagg actagccgcg   28020
cgcccttctc gaatttaggc gggagaaaga ctacgtcatc gccgaccgcc gcccagccca   28080
cccagccgac atgagcaaag agattcccac gccctacatg tggagctacc agccgcagat   28140
gggactcgcg gcgggagcgg cccaagacta ctccacccgc atgaactaca tgagcgcggg   28200
gccccacatg atctcacggg ttaatgggat ccgcgcccag cgaaaccaaa tactgctgga   28260
```

```
acaggcggcc ataaccgcca caccccgtca tgacctcaat ccccgaaatt ggcccgccgc   28320
cctcgtgtac caggaaaccc cctctgccac caccgtggta cttccgcgtg cacccaggc    28380 cgaagtccag atgactaact caggggcgca gctcgcgggc ggctttcgtc acggggtgcg   28440
gccgcaccgg ccgggtatat tacacctggc gatcagaggc cgaggtattc agctcaacga   28500
cgagtcggtg agctcttcgc tcggtctccg tccggacgga accttccaga tcgccggatc   28560
aggtcgctcc tcattcacgc ctcgccaggc gtatctgact ctgcagacct cctcctcgga   28620
gcctcgctcc ggcggcatcg gcaccctcca gttcgtggag gagttcgtgc cctcggtcta   28680
cttcaacccc ttctcgggac ctcccggacg ctaccccgac cagttcatcc gaactttga    28740 cgcggtgaag gactcggcgg acggctacga ctgaatgtca agtgctgagg cagagagcgt   28800
tcgcctgaaa cacctccagc actgccgccg cttcgcctgc tttgcccgca gctccggtga   28860
gttctgctac tttcagctgc ccgaggagca taccgaaggg ccggcgcacg gcgtccgcct   28920
aaccacccag ggcgaggtta cctgtaccct tatccgggag tttaccctcc gtccctgct    28980 agtggagcgg gagcggggtt cttgtgtcat aactatcgcc tgcaactgcc ctaaccctgg   29040
attacatcaa gatctttgtt gtcacctgtg cgctgagtat aataaacgct gagatcagac   29100
tctactgggg ctcctgtcgc catcctgtga acgccaccgt cttcacccac cccgagcagc   29160
cccaggcgaa cctcacctgc ggcctgcgtc ggagggccaa gaagtacctc acctggtact   29220
tcaacggcac ccccttttgtg gtttacaaca gcttcgacca ggacggagtt gccttgagag   29280
acgacctttc cggtctcagc tactccattc acaagaacac caccctccac ctcttccctc   29340
cctacctgcc gggaacctac gagtgcgtca ccggccgctg cacccacctc ctccgcctga   29400
tcgtaaacca gaccttccg ggaacacacc tcttccccag aacaggaggt gagctcagga   29460
aaccccctgg ggcccagggc ggagacttac cttcgaccct tgtggggtta ggatttttta   29520
tcgccgggtt gctggctctc ctgatcaaag cttccttcag atttgttctc tcccttact   29580 tttatgaaca gctcaacttc taataacgct accttttctc aggaatcgag tagtaacttc   29640
tcttccgaaa tcgggctggg tgtgctgctt actctgttga ttttttttcct tatcatactt   29700 agccttctgt gcctcaggct cgccgcctgc tgcgcacata tctacatcta cagccggttg   29760
cttaactgct ggggtcgcca tccaagatga acggggctca ggtgctatgt ctgctggccc   29820
tggtggcctg cagtgccgcc gtcaattttg aggaacccgc ttgcaatgtg actttcaagc   29880
ctgagggcgc acattgcacc actctggtta aatgtgtgac ctctcatgaa aaactgctca   29940
tcgcctacaa aaacaaaaca ggccagatcg cagtctatag cgagtggcta cccggagacc   30000
ataataacta ctcagtcacc gtcttcgagg gtgcggagtc taagaaattc gattacacct   30060 ttccccttcga ggagatgtgt gatgcggtca tgtacctgtc caaacagtac aagctgtggc   30120
cccccacccc caaggcgtgt gtggaaaaca ctgggtcttt ctgctgtctc tctctggcaa   30180
tcactgtgct tgctctaatc tgcacgctgc tatacatgag attcaggcag aggcgaatct   30240
ttatcgatga gaaaaaaatg ccttgatcgc taacaccggc tttctgtctg cagaatgaaa   30300
gcaatcacct ccctactaat cagcaccacc ctccttgcga ttgcccatgg gttgacacga   30360
atcgaagtgc cagtggggtc caatgtcacc atggtgggcc ccgccggcaa ttcctccctg   30420
atgtgggaaa aatatgtccg taatcaatgg gatcattact gctctaatcg aatctgtatc   30480
aagcccagag ccacctgcga cgggcaaaat ctaactttga ttgatgtgca aatgacggat   30540
gctgggtact attacgggca gcggggagaa atgattaatt actggcgacc ccacaaggac   30600
tacatgctgc atgtagtcaa ggcagtccca actactacca cccccaccac taccactccc   30660
```

```
actaccacca cccccaccac taccactagc actgctacta ccgctgcccg caaagctatt   30720
acccgcaaaa gcaccatgct tagcaccaag ccccattctc actcccacgc cggcgggccc   30780
accggtgcgg cctcagaaac caccgagctt tgcttctgcc aatgcactaa cgccagcgcc   30840
cacgaactgt tcgacctgga gaatgaggac gatgaccagc tgagctccgc ttgcccggtc   30900
ccgctgcccg cagagccggt cgccctgaag cagctcggtg atccatttaa tgactctcct   30960
gtttatccct ctcccgaata ccctcccgac tctaccttcc acatcacggg caccaaagac   31020
cccaacctct ccttctacct gatgctgctg ctctgtatct ctgtggtatc ttccgcgctc   31080
atgttactgg gcatgttctg ctgcctcatc tgccgcagaa aaagaaagtc tcgctctcag   31140
ggccaaccac tgatgcccct cccctacccc ccagattttg cagataacaa gatatgagca   31200
cgctgctgac actaaccgct ttactcgcct gcgctctaac ccttgtcgct tgcgaatcca   31260
gataccacaa tgtcacagtt gtgacaggag aaaatgttac attcaactcc acggccgaca   31320
cccagtggtc gtggagtggc cacggtagct atgtatacat ctgcaatagc tccacctccc   31380
ctagcatgtc ctctcccaag taccactgca atgacagcct gttcaccctc atcaacgcct   31440
ccacctcgga caatggactc tatgtaggct atgtgacacc cggtgggcag ggaaagaccc   31500
acgcctacaa cctgcaagtt cgccaccccct ccaccaccgc caccacctct gccgccccta   31560
cccgcagcag cagcagcagc agcagcagca gcagcagcag cagcagcaga ttcctgactt   31620
taatcctagc cagctcaaca accaccgcca ccgctgagac cacccacagc tccgcgcccg   31680
aaaccaccca cacccaccac ccagagacga ccgcggcctc cagcgaccag atgtcggcca   31740
acatcaccgc ctcgggtctt gaacttgctt caaccccccac cccaaaacca gtggatgcag   31800
ccgacgtctc cgccctcgtc aatgactggg cggggctggg aatgtggtgg ttcgccatag   31860
gcatgatggc gctctgcctg cttctgctct ggctcatctg ctgcctcaac cgcaggcggg   31920
ccagacccat ctatagaccc atcattgttc tcaaccccgc tgatgatggg atccatagat   31980
tggatggtct gaaaaaccta cttttctctt ttacagtatg ataaattgag acatgcctcg   32040
cattttcatg tacttgacac ttctcccact ttttctgggg tgttctacgc tggccgccgt   32100
ctctcacctc gaggtagact gcctcacacc cttcactgtc tacctgattt acggattggt   32160
caccctcact ctcatctgca gcctaatcac agtagtcatc gccttcatcc agtgcattga   32220
ctacatctgt gtgcgcctcg cataccgagg acaccacccg cagtaccgag acaggaacat   32280
tgcccaactc ctaagactgc tctaatcatg cataagactg tgatctgcct cctcatcctc   32340
ctctccctgc ccgctctcgt ctcatgccag cccaccacaa aacctccacg aaaaagacat   32400
gcctcctgtc gcttgagcca actgtggaat attcccaaat gctacaatga aaagagcgag   32460
cttttccgaag cctggctata tgcggtcatg tgtgtccttg tcttctgcag cacaatcttt   32520
gccctcatga tctacccccca ctttgatttg ggatggaatg cggtcgatgc catgaattac   32580
cctacctttc ccgcgcccga tatgattcca ctccgacagg ttgtggtgcc cgtcgccctc   32640
aatcaacgcc cccatccccc tacacccact gaggtcagct actttaatct aacaggcgga   32700
gatgactgac actctagatc tagaaatgga cggcatcggc accgagcagc gtctcctaca   32760
gaggcgcaag caggcggctg aacaagagcg cctcaatcag gagctccgag atctcattaa   32820
cctgcaccag tgcaaaaaag gcatctttttg cctggtcaag caggccgatg tcacctacga   32880
gaaaaccggt aacagccacc gcctcagcta caagctgccc acccaacgcc agaagttggt   32940
gctcatggtg ggtcagaatc ccatcaccgt cacccagcac tcggtggaga ccgaggggtg   33000
```

```
tctgcactcc ccctgtcagg gtccggaaga cctctgcacc ctggtaaaga ccctgtgtgg    33060
tcttagagat ttaatcccct ttaactaatc aaacactgga atcaataaaa agaatcactt    33120
actttaaatc agtcagcagg tctctgtcca ctttattcag cagcacctcc ttcccctcct    33180
cccaactctg gtactccaaa cgcctcctgg cggcaaactt cctccacacc ctgaagggaa    33240
tgtcagattc ttgctcctgt ccctccgcac ccactatctt catgttgttg cagatgaagc    33300
gcgccaaaac gtctgacgag accttcaacc ccgtgtaccc ctatgacacg aaaacgggc    33360 ctccctccgt tcctttcctc acccctccct tcgtgtcccc cgacggattt caagaaagcc    33420
ccccaggggt cctgtctctg cgcctgtcag agccctggt cacttcccac ggcatgcttg    33480
ccctgaaaat gggaaatggc ctctccctgg atgacgccgg caacctcacc tctcaagatg    33540
tcaccaccgt caccctcc ctcaaaaaaa ccaagaccaa cctcagcctc cagacctcag    33600
cccccctgac cgttagctct gggtccctca ccgtcgcggc cgccgctcca ctggcggtgg    33660
ccggcacctc tctcaccatg caatctcagg ccccccttgac ggtgcaagat gcaaaactgg    33720
gtctggccac ccagggaccc ctgaccgtgt ctgaaggcaa actcaccttg cagacatcgg    33780
ctccactgac ggccgccgac agcagcactc tcactgttgg caccacaccg ccaatcagtg    33840
tgagcagtgg aagtctaggc ttagatatgg aagaccccat gtatactcac gatggaaaac    33900
tgggaatcag aattggtggc ccactgcaag tagtagacag cttgcacaca ctcactgtag    33960
ttactggaaa cggaataact gtagctaaca atgcccttca aactaaagtt gcgggtgccc    34020
tgggttatga ctcatctggc aatctagaat tgcgagccgc agggggtatg cgaattaaca    34080
cagggggtca actcattctt gatgtggctt atccatttga tgctcagaac aatctcagcc    34140
ttagactcgg ccagggacct ttatatgtga acaccaatca caacctagat ttaaattgca    34200
acagaggtct gaccacaacc accagcagta acacaaccaa acttgaaact aaaatcgatt    34260
cgggcttaga ctataacgcc aatggggcta tcattgctaa acttggcact gggttaacct    34320
ttgacaacac aggtgccata actgtgggaa acactgggga tgacaaactc actctgtgga    34380
ctaccccaga tccctctcct aactgcagaa ttcacgcaga caaagactgc aagtttactc    34440
tagtcctgac taagtgtgga agtcaaattc tggcctccgt cgccgccctg cgggtgtctg    34500
gaaacctatc atcaatgaca ggcactgtct ccagcgttac catctttctc agattcgatc    34560
agaatggagt tcttatggaa aattcctcgc tagacaagga gtactggaac ttcagaaatg    34620
gtaattccac caatgccacc ccctacacca atgcggttgg gttcatgccc aacctcagcg    34680
cctaccccaa aacccagagt caaactgcaa aaaacaacat tgtaagtgag gtttacttac    34740
atggggacaa atctaaaccc atgatcctta ccattaccct taatggcaca aatgaatcca    34800
gtgaaactag tcaggtgagt cactactcca tgtcatttac atggtcgagg gacagtggga    34860
aatatgccac cgaaaccttt gccaccaact cttttacctt ctcctacatt gctgaacaat    34920
aaagaagcat aacgctgctg ttcatttgta atcaagtgtt actttttat ttttcaatta    34980 caacagaatc attcaagtca ttctccattt agcttaatag accccagtag tgcaaagccc    35040
catactagct tatttcagca attgggagaa gtactcgcct acatgggggt agagtcataa    35100
tcgtgcatca ggatagggcg gtggtgctgc agcagcgcgc gaataaactg ctgccgccgc    35160
cgctccgtcc tgcaggaata caacatggca gtggtctcct cagcgatgat tcgcaccgcc    35220
cgcagcataa ggcgccttgt cctcgggca cagcagcgca ccctgatctc acttaaatca    35280
gcacagtaac tgcagcacag caccacaata ttgttcaaaa tcccacagtg caaggcgctg    35340
tatccaaagc tcatggcggg gaccacagaa cccacgtggc catcatacca caagcgcagg    35400
```

```
tagattaagt ggcgacccct cataaacacg ctggacataa acattacctc ttttggcatg    35460
ttgtaattca ccacctcccg gtaccatata aacctctgat taaacatggc gccatccacc    35520
accatcctaa accagctggc caaaacctgc ccgccggcta tacactgcag ggaaccggga    35580
ctggaacaat gacagtggag agcccaggac tcgtaaccat ggatcatcat gctcgtcatg    35640
atatcaatgt tggcacaaca caggcacacg tgcatacact tcctcaggat tacaagctcc    35700
tcccgcgtta gaaccatatc ccagggaaca acccattcct gaatcagcgt aaatcccaca    35760
ctgcagggaa gacctcgcac gtaactcacg ttgtgcattg tcaaagtgtt acattcgggc    35820
agcagcggat gatcctccag tatggtagcg cgggtttctg tctcaaaagg aggtagacga    35880
tccctactgt acggagtgcg ccgagacaac cgagatcgtg ttggtcgtag tgtcatgcca    35940
aatggaacgc cggacgtagt catatttcct gaagtcttgg cgcgccagac ccgagtctta    36000
ccaggaaaat tttaaaaaag attcctcaac gcagcaccag caccaacacc tgtcagtgta    36060
aaatgccaag cgccgagcga gtatatatag gaataaaaag tgacgtaaac ggttaaagtc    36120
cagaaaacgc ccagaaaaac cgcacgcgaa cctacgcccc gaaacgaaag ccaaaaaaca    36180
gtgaacacgc cctttcggcg tcaacttccg ctttcccacg gtacgtcact tccgcatata    36240
gtaaaactac gctacccaac atgcaagaag ccacgcccca aaacacgtca cacctcccgg    36300
cccgccccgc gccgccgctc ctccccgccc cgccccgctc cgcccacctc attatcatat    36360
tggcttcaat ccaaaataag gtatattatt gatgatg                              36397

<210> SEQ ID NO 9
<211> LENGTH: 36445
<212> TYPE: DNA
<213> ORGANISM: Artificial Sequence
<220> FEATURE:
<223> OTHER INFORMATION: synthetic chimpanzee adenovirus serotype PanAd3
      with Marburg virus Angola codon optimized
      transmembrane envelope glycoprotein (GP) insert
      (PanAd3 GP Marburg (PB/6712))
<220> FEATURE:
<221> NAME/KEY: CDS
<222> LOCATION: (1656)...(3698)
<223> OTHER INFORMATION: Marburg virus Angola codon optimized
      transmembrane envelope glycoprotein (GP) insert in PanAd3 GP
      Marburg (PB/6712)
<220> FEATURE:
<221> NAME/KEY: CDS
<222> LOCATION: (14719)...(16473)
<223> OTHER INFORMATION: chimpanzee adenovirus serotype ChAd63 penton
<220> FEATURE:
<221> NAME/KEY: CDS
<222> LOCATION: (19564)...(22458)
<223> OTHER INFORMATION: chimpanzee adenovirus serotype ChAd63 hexon
<220> FEATURE:
<221> NAME/KEY: CDS
<222> LOCATION: (33342)...(34970)
<223> OTHER INFORMATION: chimpanzee adenovirus serotype ChAd63 fiber

<400> SEQUENCE: 9
catcatcaat aatataccct atttttggatt gaagccaata tgataatgag gtgggcggag       60
cggggcgggg cggggaggag cggcggcgcg gggcgggccg ggaggtgtgg cggaagttga      120
gtttgtaagt gtggcggatg tgacttgcta gcgccggatg tggtaaaagt gacgttttt      180 ggagtgcgac aacgcccacg ggaagtgaca ttttttccgc ggttttttacc ggatgtcgta     240 gtgaatttgg gcgttaccaa gtaagatttg gccattttcg cgggaaaact gaaatgggga     300
agtgaaatct gattaatttc gcgttagtca taccgcgtaa tatttgccga gggccgaggg     360
actttgaccg attacgtgga ggaatcgccc aggtgttttt tgaggtgaat ttccgcgttc     420
```

```
cgggtcaaag tctccgtttt attattatag gtatacccat tgcatacgtt gtatccatat      480
cataatatgt acatttatat tggctcatgt ccaacattac cgccatgttg acattgatta      540
ttgactagtt attaatagta atcaattacg gggtcattag ttcatagccc atatatggag      600
ttccgcgtta cataacttac ggtaaatggc ccgcctggct gaccgcccaa cgaccccgc       660 ccattgacgt caataatgac gtatgttccc atagtaacgc caatagggac tttccattga      720
cgtcaatggg tggagtattt acggtaaact gcccacttgg cagtacatca agtgtatcat      780
atgccaagta cgccccctat tgacgtcaat gacggtaaat ggcccgcctg gcattatgcc      840
cagtacatga ccttatggga ctttcctact tggcagtaca tctacgtatt agtcatcgct      900
attaccatgg tgatgcggtt ttggcagtac atcaatgggc gtggatagcg gtttgactca      960
cggggatttc caagtctcca ccccattgac gtcaatggga gtttgttttg gaaccaaaat     1020
caacgggact ttccaaaatg tcgtaacaac tccgccccat tgacgcaaat gggcggtagg     1080
cgtgtacggt gggaggtcta tataagcaga gctctcccta tcagtgatag agatctccct     1140
atcagtgata gagatcgtcg acgagctcgt ttagtgaacc gtcagatcgc ctggagacgc     1200
catccacgct gttttgacct ccatagaaga caccgggacc gatccagcct ccatcggctc     1260
gcatctctcc ttcacgcgcc cgccgcccta cctgaggccg ccatccacgc cggttgagtc     1320
gcgttctgcc gcctcccgcc tgtggtgcct cctgaactgc gtccgccgtc taggtaagtt     1380
taaagctcag gtcgagaccg ggcctttgtc cggcgctccc ttggagccta cctagactca     1440
gccggctctc cacgctttgc ctgacccctgc ttgctcaact ctagttaacg gtggagggca     1500
gtgtagtctg agcagtactc gttgctgccg cgcgcgccac cagacataat agctgacaga     1560
ctaacagact gttcctttcc atgggtcttt tctgcagtca ccgtcgtcga cacgtgtgat     1620
cagatatcgc ggccgctcta gagatatcgg ccgccatgaa gaccacctgc ctgctgatca     1680
gcctgatcct gatccagggc gtgaagaccc tgcccatcct ggagatcgcc agcaacatcc     1740
agccccagaa cgtggacagc gtgtgcagcg gcaccctgca gaagaccgag gacgtgcacc     1800
tgatgggctt caccctgagc ggccagaagg tggccgacag ccctctggag gccagcaaga     1860
ggtgggcctt cagggccggc gtgccccca agaacgtgga gtacaccgag ggcgaggagg     1920
ccaagacctg ctacaacatc agcgtgaccg accccagcgg caagagcctg ctgctggacc     1980
ctcccaccaa catcagggac tacctaagt gcaagaccat ccaccacatc cagggccaga     2040
accctcacgc ccagggcatc gccctgcacc tgtggggcgc cttcttcctg tacgacagga     2100
tcgccagcac caccatgtac agaggaaaag tgttcacaga gggaaacatc gctgctatga     2160
tcgtgaacaa gaccgtgcat aagatgatct tcagcagaca gggacaggga tatagacata     2220
tgaacctgac atccacaaac aagtactgga caagcagcaa cggaacacag acaaacgata     2280
caggatgttt tggaacactg caggaataca actccaccaa gaaccagaca tgtgccccta     2340
gcaagaagcc tctgcctctg cctacagctc atcctgaagt gaagctgaca tccacaagca     2400
cagatgccac aaagctgaac acaacagatc ctaatagcga cgacgaggat ctgacaacaa     2460
gcggatccgg atccggagaa caggaacctt atacaacaag cgacgctgct acaaaacagg     2520
gactgtcctc cacaatgcct cctacaccta gccctcagcc tagcacacct cagcagggag     2580
gcaacaacac aaaccattcc cagggagtgg tgacagaacc tggaaagaca aacacaacag     2640
cccagcctag catgcctcct cataacacaa caacaatcag cacaaacaac acctccaagc     2700
acaatctgag cacacctagc gtgcctattc agaatgccac caactacaac acacagtcca     2760
```

```
cagcccctga aaacgaacag acctccgccc cttccaaaac aaccctgctg cctacagaaa    2820
accctacaac agccaagagc acaaacagca caaagagccc tacaacaaca gtgcctaaca    2880
caacaaacaa gtatagcaca agccctagcc ctacacctaa ttccacagct cagcatctgg    2940
tgtattttag aagaaagaga acatcctgt ggagagaagg agatatgttc ccttttctgg     3000
atggactgat caacgctcct atcgattttg atcctgtgcc taacacaaag acaatctttg    3060
atgaaagcag cagcagcgga gcctccgccg aagaagatca gcatgcctcc cctaacatca    3120
gcctgacact gagctatttt cctaaggtga acgaaaacac agcccattcc ggagaaaacg    3180
aaaacgattg tgatgccgaa ctgagaatct ggagcgtgca ggaagatgat ctggccgccg    3240
gactgagctg gatcccttt tttgggcccg gaattgaagg actgtacacc gccggcctga     3300
tcaagaacca gaacacctg gtgtgcaggc tgaggaggct ggccaaccag accgccaaga    3360
gcctggagct gctgctgagg gtgaccaccg aggagaggac cttcagcctg atcaacaggc    3420
acgccatcga cttcctgctg gctaggtggg gcggcacctg caaggtgctg ggccccgact    3480
gctgcatcgg catcgaggac ctgagcagga acatcagcga gcagatcgac cagatcaaga    3540
aggacgagca gaaggagggc accggctggg gcctgggcgg caagtggtgg accagcgact    3600
ggggagtgct gacaaacctg gaatcctgc tgctgctgag cattgccgtg ctcattgctc       3660
tgtcctgtat ctgtagaatc tttaccaagt acatcggatg atagatccag atctgctgtg    3720
ccttctagtt gccagccatc tgttgtttgc ccctcccccg tgccttcctt gaccctggaa    3780
ggtgccactc ccactgtcct ttcctaataa aatgaggaaa ttgcatcgca ttgtctgagt    3840
aggtgtcatt ctattctggg gggtggggtg ggcaggaca gcaaggggga ggattgggaa      3900
gacaatagca ggcatgctgg ggatgcggtg ggctctagat atcagcgatc gctgaggtgg    3960
gtgagtgggc gtggtctggg ggtgggaagc aatatataag ttgggggtct tagggtctct    4020
gtgtctgttt tgcagaggga ccgccggcgc catgagcggg agcagtagca gcaacgcctt    4080
ggatggcagc atcgtgagcc cttatttgac gacgcgcatg ccccactggg ccggggtgcg    4140
tcagaatgtg atgggctcca gcatcgacgg acgacccgtg ctgcccgcaa attccgccac    4200
gctgacctac gcgaccgtcg cggggacccc gttggacgcc accgccgccg ccgccgccac    4260
cgccgccgcc tcggccgtgc gcagcctggc cacggacttt gcattcttgg gaccccttggc    4320 caccggggcg gccgcccgtg ccgccgttcg cgatgacaag ctgaccgccc tgctggcgca    4380
gttggatgcg cttacccggg aactgggtga cctttcgcag caggtcgtgg ccctgcgcca    4440
gcaggtctcc gccctgcagg ctagcgggaa tgcttctcct gcaaatgccg tttaagataa    4500
ataaaaccag actctgttga taaataaaac cagactctgt ttggattaaa gaaaagtagc    4560
aagtgcattg ctctctttat ttcataattt tccgcgcgcg ataggcccga gtccagcgtt    4620
ctcggtcgtt gagggtgcgg tgtatcttct ccaggacgtg gtagaggtgg ctctggacgt    4680
tgagatacat gggcatgagc ccgtcccggg ggtggaggta gcaccactgc agagcttcat    4740
gctccggggt ggtgttgtag atgatccagt cgtagcagga gcgctgggca tggtgcctaa    4800
aaatgtcctt aagcagcagg ccgatggcca ggggaggcc cttggtgtaa gtgtttacaa     4860
aacggttgag ttgggaaggg tgcatgcggg gtgagatgat gtgcatctta gattgtattt    4920
ttagattggc gatgtttcct cccagatccc ttctgggatt catgttgtgg aggaccacca    4980
gcacagtata tccggtgcac ttgggaaatt tgtcatgcag cttagaggga aatgcgtgga    5040
agaacttgga gacgccttg tggcctccca gattctccat gcattcgtcc atgatgatcg      5100
caatgggccc gcgggaggcg gcctgggcaa agatgtttct ggggtcactg acatcgtagt    5160
```

```
tgtgttccag ggtgagatcg tcataggcca tttttataaa gcgcgggcgg agggtgcccg    5220
actgggggat gatggttccc tcgggccccg gggcgtagtt gccttcgcag atctgcattt    5280
cccaggcctt aatctctgag gggggaatca tatccacttg cggggcgatg aagaaaacgg    5340
tttccggagc cggggagatt aactgggatg agagcaggtt tctcagcagc tgtgactttc    5400
cacagccggt gggtccataa ataacaccta taaccggctg cagctggtag ttgagcgagc    5460
tgcagctgcc gtcgtcccgg aggagggggg ccacctcatt gagcatgtcc cggacgcgct    5520
tgttctcctc gaccaggtcc gccagaaggc gctcgccgcc cagggacagc agctcttgca    5580
aggaagcaaa gttttcagc ggtttgaggc cgtccgccgt gggcatgttt tcagggtct     5640 ggccgagcag ctccaggcgg tcccagagct cggtgacgtg ctctacggca tctctatcca    5700
gcatatctcc tcgtttcgcg ggttgggcg gctttcgctg tagggcacca ggcgatggtc     5760
gtccagcgcg gccagagtca tgtccttcca tgggcgcagg gtcctcgtca gggtggtctg    5820
ggtcacggtg aaggggtgcg ccccgggctg ggcgctggcc agggtgcgct tgagactggt    5880
cctgctggtg ctgaagcgct gccggtcttc gccctgcgcg tcggccaggt agcatttgac    5940
catggtgtcg tagtccagcc cctccgcggc gtgtcccttg gcgcgcagct tgcccttgga    6000
ggtggcgccg cacgcggggc actgcaggct cttgagcgcg tagagcttgg gggcgaggaa    6060
gaccgattcg ggggagtagg cgtccgcgcc gcaggcccg cacacggtct cgcactccac     6120
cagccaggtg agctcgggc gctcggggtc aaaaaccagg tttcccccat gctttttgat     6180
gcgtttctta cctcgggtct ccatgaggcg gtgtccccgt tcggtgacga agaggctgtc    6240
cgtgtctccg tagaccgact tgaggggtct gtcctccagg ggggtccctc ggtcctcttc    6300
gtagagaaac tcggaccact ctgagacaaa ggcccgcgtc caggccagga cgaaggaggc    6360
caggtgggag gggtaccggt cgttgtccac taggggtcc accttctcca aggtgtgaag     6420
acacatgtcg ccctcctcgg cgtccaggaa ggtgattggc ttgtaggtgt aggccacgtg    6480
acccggggtt ccggacgggg gggtataaaa ggggtgggg gcgcgctcgt cctcactctc     6540
ttccgcatcg ctgtctgcga gggccagctg ctgggggtgag tattccctct cgaaggcggg    6600
catgacctca gcgctgaggc tgtcagtttc taaaaacgag gaggatttga tgttcacctg    6660
tcccgagctg atgcctttga gggtgcccgc gtccatctgg tcagaaaaca cgatctttt     6720 attgtccagc ttggtggcga acgacccgta gagggcgttg gagagcagct tggcgatgga    6780
gcgcagggtc tgattcttgt cccggtcggc gcgctccttg gccgcgatgt tgagctgcac    6840
gtactcgcgc gcgacgcagc gccactcggg gaagacggtg gtgcgctcgt cgggcaccag    6900
gcgcacgcgc cagccgcggt tgtgcagggt gacgaggtcc acgctggtgg cgacctcgcc    6960
gcgcaggcgc tcgttggtcc agcagaggcg cccgcccttg cgcgagcaga aggggggcag    7020
ggggtcgagt tgggtttcgt ccgggggtc cgcgtccacc gtgaagaccc cggggcgcag     7080
gcgcgcgtcg aagtagtcga tcttgcatcc ttgcaagtcc agcgcccgct gccagtcgcg    7140
ggcggcgagc gcgcgctcgt aggggttgag cggcgggccc cagggcatgg ggtgggtgag    7200
cgcggaggcg tacatgccgc agatgtcata gacgtagagg ggctcccgga ggatgcccag    7260
gtaggtgggg tagcagcggc cgccgcggat gctggcgcgc acgtagtcgt agagctcgtg    7320
cgagggggcg aggaggtcgg ggccccaggtt ggtgcgggcg gggcgctccg cgcggaagac    7380
gatctgcctg aagatggcat gcgagttgga agagatggtg gggcgctgga agacgttgaa    7440
gctggcgtcc tgcaggccga cggcgtcgcg cacgaaggag gcgtaggact cgcgcagctt    7500
```

```
gtgcaccagc tcggcggtga cctgcacgtc gagcgcgcag tagtcgaggg tctcgcggat    7560
gatgtcatac ttagcctgcc ccttctttt ccacagctcg cggttgagga cgaactcttc    7620
gcggtctttc cagtactctt ggatcgggaa accgtccggc tccgaacggt aagagcccag    7680
catgtagaac tggttgacgg cctggtaggc gcagcagccc ttctccacgg gcagggcgta    7740
ggcctgcgcg gccttgcgga gcgaggtgtg ggtcagggcg aaggtgtccc tgaccatgac    7800
cttgaggtac tggtgtttga agtcggagtc gtcgcagccg ccccgctccc agagcgagaa    7860
gtcggtgcgc ttttggagc gggggttggg cagcgcgaag gtgacatcgt tgtagaggat    7920
cttgcccgcg cgaggcatga agttgcgggt gatgcggaag ggccccggca cttccgagcg    7980
gttgttgatg acctgggcgg cgagcacgat ctcgtcgaag ccgttgatgt tgtggcccac    8040
gatgtagagt tccaggaagc ggggccggcc cttgacgctg ggcagcttct ttagctcttc    8100
gtaggtgagc tcctcgggcg aggcgaggcc gtgctcggcc agggcccagt ccgccaggtg    8160
cgggttgtcc gcgaggaagg accgccagag gtcgcgggcc aggagggtct gcaggcggtc    8220
cctgaaggtc ctgaactggc ggcctacggg catcttttcg ggggtgacgc agtagaaggt    8280 gaggggtct tgctgccagg ggtcccagtc gagctccagg gcgaggtcgc gcgcggcggc    8340
gaccaggcgc tcgtcgcccc cgaatttcat gaccagcatg aagggcacga gctgctttcc    8400
gaaggcgccc atccaagtgt aggtctctac atcgtaggtg acaaagagac gttccgtgcg    8460
aggatgcgag ccgatcggga agaactggat ctcccgccac cagttggagg agtggctgtt    8520
gatgtggtga agtagaagt cccgtcggcg ggccgagcac tcgtgctggc ttttgtaaaa    8580
gcgagcgcag tactggcagc gctgcacggg ctgtacctct tgcacgagat gcacctgccg    8640
accgcggacg aggaagctga gtgggaatct gagccccccg catggctcgc ggcctggctg    8700
gtgctcttct actttggatg cgtggccgtc accgtctggc tcctcgaggg gtgttacggt    8760
ggagcggatc accacgccgc gcgagccgca ggtccagata tcggcgcgcg gcggtcggag    8820
tttgatgacg acatcgcgca gctgggagct gtccatggtc tggagctccc gcggcggcgg    8880
caggtcagcc gggagttctt gcaggtttac ctcgcagaga cgggccaggg cgcggggcag    8940
gtccaggtgg tacttgaatt cgagaggcgt gttggtggcg gcgtcgatgg cttgcagtat    9000
gccgcagccc cggggcgcga cgacggtgcc ccgcggggcg gtgaagctcc gccgccgct    9060 cctgctgtcg ccgccggtgg cggggcttag aagcggtgcc gcggtcgggc ccccggaggt    9120 aggggggct ccggtcccgc gggcagggc ggcagcggca cgtcggcgcc gcgcgcgggc    9180
aggagctggt gctgcgcccg gaggttgctg gcgaaggcga cgacgcggcg gttgatctcc    9240
tggatctggc gcctctgcgt gaagacgacg ggtccggtga gcttgaacct gaaagagagt    9300
tcgacagaat caatctcggt gtcattgacc gcgacctggc gcaggatctc ctgcacgtcg    9360
cccgagttgt cttggtaggc gatctcggcc atgaactgtt caatctcttc ctcctggagg    9420
tctccgcgtc cggcgcgctc cacggtggcc gccaggtcgt tggagatgcg cgccatgagc    9480
tgcgagaagg cgttgagtcc gccctcgttc cacactcggc tgtagaccac gccgccctgg    9540
tcgtcgcggg cgcgcatgac cacctgcgcg aggttgagtt ccacgtggcg cgcaaagacg    9600
gcgtagttgc gcaggcgctg gaagaggtag ttgagggtgg tggcggtgtg ctcggccaca    9660
aagaagtaca tgacccagcg gcgcaacgtg gattcgttga tgtcccccaa ggcctccagt    9720
cgctccatgg cctcgtagaa gtccacggcg aagttgaaaa actgggagtt gcgcgccgac    9780
acggtcaact cctcctccag aagacggatg agctcggcga cggtgtcgcg cacctcgcgc    9840
tcgaaggcta tgggaatctc ttcctccgcc agcatcacca cctcttcctc ttcttcctcc    9900
```

```
tctggcactt ccatgatggc ttcctcctct tcgggggggtg gcggcggggg aggggcgct    9960
cggcgccggc ggcggcgcac cgggaggcgg tccacgaagc gctcgatcat ctccccgcgg   10020
cggcgacgca tggtctcggt gacggcgcgg ccgttctctc ggggacgcag ctggaagacg   10080
ccgccggtca tctggtgctg gggcgggtgg ccgtggggca gcgagaccgc gctgacgatg   10140
catcttaaca attgctgcgt aggtacgccg ccgagggacc tgagggagtc cagatccacc   10200
ggatccgaaa acctttcgag gaaggcatct aaccagtcgc agtcgcaagg taggctgagc   10260
accgtggcgg gcggcggggg gtgggggag tgtctggcgg aggtgctgct gatgatgtaa    10320
ttgaagtagg cggtcttgac acggcggatg gtcgacagga gcaccatgtc tttgggcccg   10380
gcctgctgga tgcggaggcg gtcggccatg ccccaggctt cgttctggca tctgcgcagg   10440
tctttgtagt agtcttgcat gagcctttcc accggcacct cttctccttc ttcttctgac   10500
atctctgctg catctgcggc cctggggcga cggcgcgcgc ccctgccccc catgcgcgtc   10560
accccgaacc ccctgagcgg ctggagcagg gccaggtcgg cgacgacgcg ctcggccagg   10620
atggcctgct ggacctgcgt gagggtggtt tggaagtcat ccaagtccac gaagcggtgg   10680
taggcgcccg tgttgatggt gtaggtgcag ttggccatga cggaccagtt gacggtctgg   10740
tggcccggtt gcgtcatctc ggtgtacctg aggcgcgagt aggcgcgcga gtcgaagatg   10800
tagtcgttgc aagtccgcac caggtactgg tagcccacca ggaagtgcgg cggcggctgg   10860
cggtagaggg gccagcggag ggtggcgggg gctccggggg ccaggtcttc cagcatgagg   10920
cggtggtatt cgtagatgta cctggacatc caggtgatgc ccgcggcggt ggtggaggcg   10980
cgcgggaagt cgcgcacccg gttccagatg ttgcgcagcg gcagaaagtg ctccatggta   11040
ggcgtgctct ggccggtcag gcgcgcgcag tcgttgatac tctagaccag ggaaaacgaa   11100
agccggtcag cgggcactct tccgtggtct ggtggataaa ttcgcaaggg tatcatggcg   11160
gagggcctcg gttcgagccc cgggcccggg ccggacggtc cgccatgatc cacgcggtta   11220
ccgcccgcgt gtcgaaccca ggtggcgacg tcagacaacg gtggagtgtt ccttttgggt   11280
tttttttccaa attttttctgg ccgggcgccg acgccgccgc gtaagagact agagtgcaaa   11340
agcgaaagca gtaagtggct cgctccctgt agcccggagg atccttgcta agggttgcgt   11400
tgcggcgaac cccggttcga gtctggctct cgctgggccg ctcgggtcgg ccggaaccgc   11460
ggctaaggcg ggattggcct ccccctcatt aaagaccccg cttgcggatt cctccggaca   11520
caggggacga gccccttttt acttttgctt ttctcagatg catccggtgc tgcggcagat   11580
gcgcccccg cccccagcagc agcagcagca acatcagcaa gagcggcacc agcagcagcg   11640
ggagtcatgc agggccccct cgcccacgct cggcggtccg gcgacctcgg cgtccgcggc   11700
cgtgtctgga gccggcggcg gtgggctggc ggacgacccg gaggagcccc cgcggcgcag   11760
ggccagacag tacctggacc tggaggaggg cgagggcctg gcgcgactgg gggcgccgtc   11820
ccccgagcgc cacccgcggg tgcagctgaa gcgcgactcg cgcgaggcgt acgtgcctcg   11880
gcagaacctg ttcagagacc gcgcgggcga ggagcccgag gagatgcggg accgcaggtt   11940
cgccgcgggg cgggagctgc ggcaggggct gaaccgggag cggctgctgc gcgaggagga   12000
ctttgagccc gacgcgcgga cggggatcag ccccgcgcgc gcgcacgtgg cggccgccga   12060
cctggtgacg gcgtacgagc agacggtgaa ccaggagatc aacttccaaa aaagcttcaa   12120
caaccacgtg cgcacgctgg tggcgcgcga ggaggtgacc atcggcctga tgcacctgtg   12180
ggactttgtg agcgcgctgg agcagaaccc caacagcaag cctctgacgg cgcagctgtt   12240
```

```
cctgatagtg cagcacagca gggacaacga ggcgttcagg gacgcgctgc tgaacatcac   12300
cgagcccgag ggtcggtggc tgctggacct gattaacatc ttgcagagca tagtggtgca   12360
ggagcgcagc ctgagcctgg ccgacaaggt ggcggccatc aattactcga tgctcagtct   12420
gggcaagttt tacgcgcgca agatctacca gacgccgtac gtgcccatag acaaggaggt   12480
gaagatcgac ggcttctaca tgcgcatggc gctgaaggtg ctgaccctga gcgacgacct   12540
gggcgtgtac cgcaacgagc gcatccacaa ggccgtgagc gtgagccggc ggcgcgagct   12600
gagcgaccgc gagctgatgc acagcctgca gcgggcgctg gcggggccg gcagcggcga    12660 cagggaggcc gagtcctact tcgaggcggg ggcggacctg cgctgggtgc ccagccggag   12720
ggccctggag gccgcggggg cccgccgcga ggactatgca gacgaggagg aggaggatga   12780
cgaggagtac gagctagagg agggcgagta cctggactaa accgcaggtg gtgttttttgg  12840 tagatgcaag acccgaacgt ggtggacccg gcgctgcggg cggctctgca gagccagccg   12900
tccggcctta actctacaga cgactggcga caggtcatgg accgcatcat gtcgctgacg   12960
gcgcgcaatc cggacgcgtt ccggcagcag ccgcaggcca acaggctctc cgccatcttg   13020
gaggcggtgg tgcctgcgcg cgcgaacccc acgcacgaga aggtgctggc catagtgaac   13080
gcgctggccg agaacagggc catccgcccg gacgaggccg ggctggtgta cgacgcgctg   13140
ctgcagcgcg tggcccgcta caacagcggc aacgtgcaga ccaacctgga ccggctggtg   13200
ggggacgtgc gcgaggcggt ggcgcagcgg gagcgcgcgg agcggcaggg aaacctgggc   13260
tccatggtgg cgctgaacgc cttcctgagc acgcagccgg ccaacgtgcc gcggggcag    13320 gaggactaca ccaactttgt gagcgcgctg cggctgatgg tgaccgagac cccccagagc   13380
gaggtgtacc agtcggggcc ggactacttt ttccagacca gcagacaggg cctgcagacg   13440
gtgaacctga gccaggcttt caagaacctg cggggggctgt ggggcgtgaa ggcgcccacc   13500
ggggaccggg cgacggtgtc cagcctgctg acgcccaact cgcgcctgct gctgctgctg   13560
atcgcgccgt tcacggacag cggcagcgtg tcccgggaga cctacctcgg gcacctgctg   13620
acgctgtacc gcgaggccat cggcagacc caggtggacg agcacacctt ccaggagatc    13680
accagcgtga gccgcgcgct ggggcaggag gacacgggca gcctggaggc gaccctgaac   13740
tacctgctga ccaaccggcg gcagaagatc ccctcgctgc atagtttgac caccgaggag   13800
gagcgcatcc tgcgctacgt gcagcagagc gtgagcctga acctgatgcg cgacggggtg   13860
acgcccagcg tggcgctgga catgaccgcg cgcaacatgg aaccgggcat gtacgccgcg   13920
catcggcctt acatcaaccg cctgatggac tacttgcatc gcgcggcggc cgtgaacccc   13980
gagtacttca ccaacgccat cctgaacccg cactggctcc cgccgccggg gttctacagc   14040
gggggcttcg aggtccccga ggccaacgac ggcttcctgt gggacgacat ggacgacagc   14100
gtgttctccc cgcggccgca ggcgctggcg gaggcgtcgc tgctccgcct ccccaagaaa   14160
gaagagagcc gccggcccag cagcgcgcg gcctctctgt ccgagctggg ggcggcggcc    14220
gcgcggcccg ggtccctggg gggcagcccc tttcccagtc tggtgggtc tctgcagagc     14280 gggcgcacca cccggcccg gctgctgggc gaggacgagt acctgaacaa ctccctgatg   14340
cagccggtgc gggagaaaaa cctgcccccc gccttcccca caacgggat agagagcctg    14400 gtagacaaga tgagcagatg gaagacctat gcgcaggagc acagggactc gcccgtgctc   14460
cgtccgccca cgcggcgcca gcgccacgac cggcagcggg ggctggtatg ggatgacgag   14520
gactccgcgc acgatagcag cgtgctggac ctggggggga gcgcggtaa cccgttcgcg    14580 cacctgcgcc cccgcctggg gaggatgttt caataagaaa aatcaagcat gatgcaaggt   14640
```

```
tttttaagcg gataaataaa aaactcacca aggccatggc gaccgagcgt tgttggtttc   14700
ttgttgtgtt cccttagtat gcggcgcgcg gcgatgtacc acgagggacc tcctccctct   14760
tatgagagcg tggtgggcgc ggcggcggcc tctcccttg cgtcgcagct ggagccgccg   14820
tacgtgcctc cgcggtacct gcggcctacg gggggaagaa acagcatccg ttactcggag   14880
ctggcgcccc tgtacgacac cacccgggtg tacctggtgg acaacaagtc ggcggacgtg   14940
gcctccctga actaccagaa cgaccacagc aattttttga ccacggtcat ccagaacaat   15000
gactacaccc cgagcgaggc cagcacccag accatcaatc tggatgaccg gtcgcactgg   15060
ggcggcgacc tgaaaaccat cctgcacacc aacatgccca acgtgaacga gttcatgttc   15120
accaataagt tcaaggcgcg ggtgatggtg tcgcgttcgc acaccaagga cgaccgggtg   15180
gagctgaagt acgagtgggt agagttcgag ctgcccgagg gcaactactc ggagaccatg   15240
accatagacc tgatgaacaa cgcgatcgtg gagcactatc tgaaagtggg caggcagaac   15300
ggggtcctgg agagcgacat cggggtcaag ttcgacacca ggaacttccg cctggggctg   15360
gacccggtca ccgggctggt catgcccggg gtctacacca acgaggcctt ccaccccgac   15420
atcatcctgc tgcccggctg cggggtggac ttcacctaca gccgcctgag caacctgctg   15480
ggcatccgca agcggcagcc cttccaggag ggctttagga tcacctacga ggacctggag   15540
gggggcaaca tccccgcgct cctggatgtg gaggcctacc aggatagctt gaaggaagaa   15600
gaggcgggag agggcagcgg cggcggcggc ggcgccggtc aggaggaggg cggggcctcc   15660
tctgaggcct ctgcggacgc cgccgctgcc gccgaggcgg aggcggccga ccccgcgatg   15720
gtggtagagg aagagaagga tatgaatgac gaggcggtgc gcggcgacac ctttgccacc   15780
cgggggggagg agaagaaagc ggaggccgag gccgcggcag aggaggcggc agcggcggcg   15840
gcggcggcag tagaggcggc ggccgaggcg gagaagcccc ccaaggagcc cgtgattaag   15900
gccctgaccg aagatagcaa gaagcgcagt tacaacgtgc tcaaggacag caccaacacc   15960
gcgtaccgca gctggtacct ggcctacaac tacgcgacc cggcgacggg ggtgcgctcc   16020
tggaccctgc tgtgtacgcc ggacgtgacc tgcggctcgg agcaggtgta ctggtcgctg   16080
cccgacatga tgcaagaccc cgtgaccttc cgctccacgc ggcaggtcag caacttcccg   16140
gtggtgggcg ccgagctgct gcccgtgcac tccaagagct tctacaacga ccaggccgtc   16200
tactcccagc tcatccgcca gttcacctct ctgacccacg tgttcaatcg ctttcctgag   16260
aaccagattc tggcgcgccc gcccgccccc accatcacca ccgtcagtga aaacgttcct   16320
gctctcacag atcacgggac gctaccgctg cgcaacagca tcggaggagt ccagcgagtg   16380
accgtaactg acgccagacg ccgcacctgt ccctacgttt acaaggccct gggcatagtc   16440
tcgccgcgcg tcctttccag ccgcactttt taagcatgtc catcctcatc tcgcccagca   16500
ataacaccgg ctgggggcctg ctgcgcgcgc ccagcaagat gtttggaggg gcgaggaagc   16560
gctccgacca gcacccgtg cgcgtgcgcg ggcactaccg cgcccctgg ggcgcgcaca   16620
aacgcgggcg caccggcacc gcggggcgca ccaccgtgga cgaagccatc gactcggtgg   16680
tggagcaggc gcgcaactac acgcccgcg tctccaccgt ggacgcggct atcgagagcg   16740
tggtgcgagg cgcgcggcgg tacgccaagg cgaagagccg ccggaggcgc gtggcccgcc   16800
gccaccgccg tcgacccgga agcgccgcca gcgcgccgc cgccgccttg cttcgtcggg   16860
ccagacgcac gggccgccgc gccgccatga gggccgcgcg ccgcctggcc gccggcatca   16920
ccaccgtggc ccccgcgcc agaagacgcg cggccgctgc cgccgccgcg gccatcagcg   16980
```

```
acctggccac caggcgccgg ggcaacgtgt actgggtgcg cgactcggtg agcggcacgc   17040
gcgtgcccgt gcgcttccgc cccccgcgga cttgagagga gaggacagga aaaaagcatc   17100
aacaacacca ccactgagtc tcctgctgtt gtgtgtatcc cagcggcgcg cgcgcacacg   17160
gcgacatgtc caagcgcaaa atcaaagaag agatgctcca ggtcgtcgcg ccggaaatct   17220
atgggccccc gaagaaggaa gagcaggatt tcaagcgccg caagataaag cgggtcaaaa   17280
agaaaaagaa agatgacgat gatggcgagg tggagtttct gcgcgccacg cgcccaggc    17340 gcccgctgca gtggaagggt cggcgcgtaa agcgcgttct gcgccccggc accgcggtgg   17400
tcttcacgcc cggcgagcgc tccacccgca ctttcaagcg cgtctatgac gaggtgtacg   17460
gcgacgaaga cctgctggag caggccaacg atcgctccgg agagtttgct tacgggaagc   17520
ggcaccgggc gatggagaag gacgaggtgc tggcgctgcc gctggaccgg gcaaccccca   17580
cccccagcct gaagcccgtg accctgcagc aggtgctgcc ggccagcgcg ccctccgaga   17640
tgaagcgggg cctgaagcgc gagggcggcg acctggcgcc caccgtgcag ctgatggtgc   17700
ccaagcggca gaggctggag gacgtgctgg agaaaatgaa agtagacccc ggcctgcagc   17760
cggacatcag ggtccgcccc atcaagcagg tggcgccggg cctcggcgtg cagaccgtgg   17820
acgtggtcat ccccaccggc gcctcctctt ccagcgccgc cgccgccact agcaccgcgg   17880
acatggagac gcagactagc tccgccctcg ccgcccccgc ggccgccgcc gccgccacct   17940
cctcggcgga ggtacagacg gacccctgga tgccgccgcc ggcggccgcc cctcgcgcg    18000 cacgccgcgg gcgcaggaag tacggcgccg ccagcgcgct catgcccgag tacgccttgc   18060
atccttccat cgcgcccacc cccggctacc gaggctacag ctaccgcccg cgaagagcca   18120
agggctccac ccgccgcagc cgccgcgccg ccacctctac ccgccgccgc agtcgccgcc   18180
gccgccggca gccgcgctg gctccgatct ccgtgaggag agtggcgcgc aacggggaca    18240
ccttggtgct gcccagggcg cgctaccacc ccagcatcgt ttaaaagcct gttgtggttc   18300
ttgcagatat ggccctcact tgccgcctcc gtttcccggt gccgggatac cgaggaagat   18360
cgcgccgtag aagggggtatg gccggacgcg gcctgagcgg aggcagccgc cgtgcgcacc   18420
ggcggcgacg cgccaccagc cgacgcatgc gcggcggggt gctgcctctg ctgatccccc   18480
tgatcgccgc ggcgatcggc gccgtgcccg ggatcgcctc cgtggccttg caggcgtccc   18540
agaggcgttg acacagactt cttgcaagct tgcaaaaata tggaaaaaat ccccccaata   18600
aaaaagtcta gactctcacg ctcgcttggt cctgtgacta ttttgtagaa aaaagatgg    18660 aagacatcaa ctttgcgtcg ctggccccgc gtcacggctc gcgccgttc ctgggacact    18720 ggaacgatat cggcaccagc aacatgagcg gtggcgcctt cagttggggc tctctgtgga   18780
gcggcattaa aaatatcggt tctgccgtta agaattacgg ctccaaggcc tggaacagca   18840
gcacgggcca gatgttgaga gacaagttga aagagcagaa cttccagcag aaggtggtgg   18900
agggcctggc ctccggcatc aacgggtgg tggacctggc caatcaggcc gtgcaaaata    18960
agatcaacag cagactggac ccccggccgc cggtggaaga gctgccgccg gcgctggaga   19020
cggtgtcccc cgatgggcgg ggcgaaaagc gcccgcggcc cgacagggaa gagaccactc   19080
tggtcacgca caccgatgag ccgccccct acgaggaagc tctgaagcaa ggcttgccca    19140
ccactcggcc catcgcgccc atggccaccg gggtggtggg ccgccacacc cccgccaggc   19200
tggacctgcc tcctcctcct gtttcttctt cggccgccga tgcgcagcag cagaaggcgg   19260
cgctgccccg tccgccgcg gccgccccc gtcccaccgc cagtcgagcg ccctgcgtc     19320 gcgcggccag cggcccccgc ggggtcgcga ggcacagcag cggcaactgg cagaacacgc   19380
```

```
tgaacagcat cgtgggtctg ggggtgcagt ccgtgaagcg ccgccgatgc tactgaatag   19440
cttagctaac ggtgttgtat gtgtgtatgc gtcctatgtc accgccagag gagctgctga   19500
gtcgccgccg ttcgcgcgcc caccgccact accaccgccg gtaccactcc agcgcccctc   19560
aagatggcga ccccatcgat gatgccgcag tggtcgtaca tgcacatctc gggccaggac   19620
gcctcggagt acctgagccc cgggctggtg cagttcgccc gcgccaccga cagctacttc   19680
agcctgagta caagtttag gaaccccacg gtggcgccca cgcacgatgt gaccaccgac   19740
cggtcccagc gcctgacgct gcggttcatc cccgtggacc gcgaggacac cgcgtactct   19800
tacaaggcgc ggttcaccct ggccgtgggc gacaaccgcg tgctggacat ggcctccacc   19860
tactttgaca tccgcggcgt gctggacagg ggccccacct tcaagcccta ctccggcacc   19920
gcctacaact ccctggcccc caagggcgcc cccaactcct gcgagtggga gcaagaggag   19980
actcagacag ctgaagaggc acaagacgaa gaagaagatg aagctgaagc tgaggaggaa   20040
atgcctcagg aagagcaagc acctgtcaaa aagactcatg tatatgctca ggctccccctt  20100 tctggcgaaa aaattactaa agacggtctg cagataggaa cggacgctac agctaccgaa   20160
caaaaaccta tttatgcaga tcccacattc cagccagaac cccaaattgg tgaatctcag   20220
tggaatgagg cagatgcttc agttgccggc ggtagagtgc tgaagaaaac tactcccatg   20280
aaaccctgtt atggttccta tgccaggccc acaaatgcca atggaggtca gggtgtattg   20340
gtggagaaag acggtggaaa gatggaaagc caagtagata tgcaattctt ttcgacttct   20400
gaaaacgccc gtaacgaggc taacaacatt cagcccaaat tggtgctgta cagcgaggat   20460
gtgcatatgg agaccccaga cacacacatt tcttacaagc ctgcaaaaag cgatgataat   20520
tcgaaagtca tgctgggtca gcagtccatg cccaacaggc caaattacat cggcttcaga   20580 gacaaccttta tcgggctcat gtattacaac agcactggca catgggggt gctggcaggt   20640 caggcctcac agttgaatgc ggtggtggac ttgcaagaca gaaacacaga actgtcctac   20700
cagctcttgc ttgattccat gggagacaga accagatact tttccatgtg gaatcaggcg   20760
gtggacagtt atgatccaga tgtcagaatt attgaaaatc atggaactga agatgagctg   20820
cccaactatt gtttccctct gggaggcata ggggtaactg acacttacca ggccattaag   20880
actaatggca atggcaacgg cggggggcaat accacttgga ccaaggatga aactttttgca 20940 gaccgcaacg agataggggt gggaaacaat ttcgccatgg agatcaacct cagtgccaac   21000
ctgtggagga acttcctcta ctccaacgtg gccctgtacc tgccagacaa gcttaagtac   21060
aacccctcca acgtggaaat ctctgacaac cccaacacct acgactacat gaacaagcga   21120
gtggtggccc cggggctggt ggactgctac atcaacctgg gcgcgcgctg gtccctggac   21180
tacatggaca acgtcaaccc cttcaaccac caccgcaacg cgggcctgcg ctaccgctcc   21240
atgcttctgg gcaacgggcg ctacgtgccc ttccacatcc aggtgcccca gaagttcttt   21300
gccatcaaga acctcctcct cctgccgggc tcctacacct acgagtggaa cttcaggaag   21360
gatgtcaaca tggtcctcca gagctctctg ggtaacgacc tcagggtcga cggggccagc   21420
atcaagttcg agagcatctg cctctacgcc accttcttcc ccatggccca caacacggcc   21480
tccacgctcg aggccatgct caggaacgac accaacgacc agtccttcaa cgactacctc   21540
tccgccgcca acatgctcta ccccatcccc gccaacgcca ccaacgttcc catctccatc   21600
ccctcgcgca actgggcggc cttcgcggc tgggccttca cccgcctcaa gaccaaggag   21660
accccctccc tgggctcggg tttcgacccc tactacacct actcgggctc catacccta   21720
```

```
ctggacggaa ccttctacct caaccacact ttcaagaagg tctcggtcac cttcgactcc   21780
tcggtcagct ggccgggcaa cgatcgcctg ctcaccccca acgagttcga gatcaagcgc   21840
tcggtcgacg gggagggcta caacgtggcc cagtgcaaca tgaccaagga ctggttcctc   21900
atccaaatgc tggccaacta caacatcggc tatcagggct tctacatccc agagagctac   21960
aaggacagga tgtactcctt ctttaggaac ttccagccca tgagccggca ggtggtggac   22020
gaaaccaagt acaaggacta ccagcaggtg ggcatcatcc accagcacaa caactcgggc   22080
ttcgtgggct acctcgcccc caccatgcgc gagggacagg cctacccgc caacttcccc   22140 tacccgctca ttggcaagac cgcggtcgac agcgtcaccc agaaaaagtt cctctgcgac   22200
cgcaccctct ggcgcatccc cttctccagc aacttcatgt ccatgggtgc gctcacggac   22260
ctgggccaga acctgctcta tgccaactcc gcccacgcgc tcgacatgac cttcgaggtc   22320 gacccccatgg acgagcccac ccttctctat gttctgttcg aagtctttga cgtggtccgg   22380
gtccaccagc cgcaccgcgg cgtcatcgag accgtgtacc tgcgcacgcc cttctcggcc   22440
ggcaacgcca ccacctaaag aagcaagccg ccaccgccac cacctgcatg tcgtcgggtt   22500
ccaccgagca ggagctcaag gccatcgtca gagacctggg atgcgggccc tattttttgg   22560
gcaccttcga caaacgcttc ccgggcttcg tcgccccgca caagctggcc tgcgccatcg   22620
tcaacacggc cggccgcgag accggggcg tgcactggct ggccttcgcc tggaacccgc   22680
gctccaaaac atgctacctc tttgacccct tcggattctc ggaccagcgg ctcaagcaga   22740
tctaccagtt cgagtacgag ggcctgctgc gccgcagcgc catcgcctcc tcgcccgacc   22800
gctgcgtcac cctcgagaag tccacccaga ccgtgcaggg gcccgactcg gccgcctgcg   22860
gtctcttctg ctgcatgttc ctgcatgcct ttgtgcactg gccccagagt cccatggacc   22920
gcaaccccac catgaacttg ctgacgggga tccccaactc catgctccag agcccccagg   22980
tcgcgcccac cctgcgccgc aaccaggagc ggctctacag cttcctggaa cgccactcgc   23040
cctacttccg ccgccacagc gcgcagatca ggggggccac ctctttctgc cgcatgcaag   23100
agatgcaagg gaaaatgcaa tgatgtacac agacactttt tcttttctca ataaatggca   23160
actttattta tacatgctct ctctcgggta ttcatttccc caccacccac cacccgccgc   23220
cgccgtaacc atctgctgct ggcttttttt tttttttttta aaaatcgaaa gggttctgcc   23280
gggaatcgcc gtgcgccacg ggcagggaca cgttgcggaa ctggtagcgg gtgccccact   23340
tgaactcggg caccaccatg cggggcaagt cggggaagtt gtcggcccac aggctgcggg   23400
tcagcaccag cgcgttcatt aggtcggcg ccgagatctt gaagtcgcag ttggggccgc   23460
cgccctgcgc gcgcgagttg cggtacaccg ggttgcaaca ctggaacacc agcagcgccg   23520
gataattcac actggccagc acgctccggt cggagatcag ctcggcgtcc aggtcctccg   23580
cgttgctcag cgcgaacggg gtcagcttgg gcacctgccg ccccaggaag ggagcgtgcc   23640
ccggcttcga gttgcagtcg cagcgcagcg ggatcagcag gtgcccgcgg ccggactcgg   23700
cgttggggta cagcgcgcgc atgaaggcct ccatctggcg gaaggccatc tgggccttgg   23760
cgccctccga gaagaacatg ccgcaggact tgcccgagaa ctggttcgcg gggcagctag   23820
cgtcgtgcag gcagcagcgc gcgtcggtgt tggcgatctg caccacgttg cgcccccacc   23880
ggttcttcac gattttggcc ttggaagcct gctccttcag cgcgcgctgc ccgttctcgc   23940
tggtcacatc catctcgatc acgtgctcct tgttcaccat gctgctgccg tgcagacact   24000
tcagctcgcc ctccacctcg gtgcagcggt gctgccatag cgcgcagccc gtgggctcga   24060
aatgcttgta ggtcaccctcc gcgtaggact gcaggtaggc ctgcaggaag cgccccatca   24120
```

-continued

```
tggtcacgaa ggtcttgttg ctgctgaagg tcagctgcag cccgcggtgc tcctcgttca   24180
gccaggcctt gcacacggcc gccagcgcct ccacctggtc gggcagcatc ttgaagttca   24240
gcttcagctc attctccaca tggtacttgt ccatcagcgc gcgcgcagcc tccatgccct   24300
tctcccaggc cgacaccagc ggcaggctca aggggttcac caccgtcgca gccgccgctg   24360
cgctttcgct ttccgctccg ctgttctctt cttcctcctc ctcttcttcc tcgccgcccg   24420
cgcgcagccc ccgcaccacg gggtcgtctt cctgcaggcg ccgcaccgag cgcttgccgc   24480
tcctgccctg cttgatacgc acgggcgggt tgctgaagcc taccatcacc agcgcggcct   24540
cttcttgctc gtcctcgctg tccactatga cctcggggga gggcgacctc agaaccgtgg   24600
cgcgctgcct cttcttttc ctgggggcgt ttgccagctc cgcggccgcg gccgccgccg   24660
aggtcgaagg ccgagggctg ggcgtgcgcg gcaccagcgc gtcctgcgag ccgtcctcgt   24720
cctcggactc gaggcggcag cgagcccgct tcttcggggg cgcgcggggc ggcggcggcg   24780
ggggcggcgg cgacggagac ggggacgaga catcgtccag ggtgggagga cggcgggccg   24840
cgccgcgtcc gcgctcgggg gtggtttcgc gctggtcctc ttcccgactg gccatctccc   24900
actgctcctt ctcctatagg cagaaagaga tcatggagtc tctcatgcaa gtcgagaagg   24960
aggaggacag cctaaccacc accgccccct ctgagccctc cgccgccgcc gcggacgacg   25020
cgcccaccac caccgccgcc gccaccacca ccattaccac cctacccggc gacgcagccc   25080
cgatcgagaa ggaagtgttg atcgagcagg acccgggttt tgtgagcgaa gaggaggatg   25140
aggaggatga aaaggagaag gataccgccg cctcagtgcc aaaagaggat aaaaagcaag   25200
accaggacga cgcagagaca gatgaggcag cagtcgggcg gggggacgga aggcatgatg   25260
atgatgacgg ctacctagac gtgggagacg acgtgctgct taagcacctg caccgccagt   25320
gcgtcatcgt ctgcgacgcg ctgcaggagc gctgcgaagt gccctggac gtggcggagg   25380
tcagccgcgc ctacgagcgg cacctcttcg cgccacacgt gccccccaag cgccgggaga   25440
acggcacctg cgagcccaac ccgcgcctca acttctaccc ggtcttcgcg gtacccgagg   25500
tgctggccac ctaccacatc ttcttccaaa actgcaagat ccccctctcc tgccgcgcca   25560
accgcacccg cgccgacaag acgctggccc tgcggcaggg cgcccacata cctgatatcg   25620
cctctctgga ggaggtgccc aagatcttcg agggtctcgg tcgcgacgag aaacgggcgg   25680
cgaacgctct gcaaggagac agcgaaaacg agagtcactc gggggtgctg gtggagctcg   25740
agggcgacaa cgcgcgcctg gccgtgctca agcgcagcat cgaagtcacc cacttcgcct   25800
acccggcgct caacctgccc cccaaggtca tgagtgtggt catgagtgag ctcatcatgc   25860
gccgcgccca gccctggac gcggatgcaa acttgcaaga gccctccgag aaggcctgc    25920
ccgcggtcag cgacgagcag ctggcgcgct ggctggagac ccgcgacccc gccagctgg    25980
aggagcggcg caagctcatg atggccgcgg tgctcgtcac cgtggagctc gagtgtctgc   26040
agcgcttctt cggggacccc gagatgcagc gcaagctcga ggagaccctg cactacacct   26100
tccgccaggg ctacgtgcgc caggcctgca agatctccaa cgtggagctc tgcaacctgg   26160
tctcctacct gggcatcctg cacgagaacc gcctcgggca gaacgtcctg cactccaccc   26220
tcaaagggga ggcgcgccgc gactacgtcc gcgactgcgt ctacctcttc ctctgctaca   26280
cgtggcagac ggccatgggg gtctggcagc agtgcctgga ggagcgcaac ctcaaggagc   26340
tggagaagct cctccggcgc gccctcaggg acctctggac gggcttcaac gagcgctcgg   26400
tggccgccgc gctggcggac atcatcttcc ccgagcgcct gctcaaaacc ctgcagcagg   26460
```

```
gcctgcccga cttcaccagc cagagcatgc tgcagaactt caggaccttc atcctggagc  26520
gctcgggcat cctgccggcc acctgctgcg cgctgcccag cgacttcgtg cccatcaggt  26580
acagggagtg cccgccgccg ctctggggcc actgctacct cttccagctg gccaactacc  26640
tcgcctacca ctcggatctc atggaagacg tgagcggcga gggcctgctc gagtgccact  26700
gccgctgcaa cctgtgcacg ccccaccgct ctctagtctg caatccgcag ctgctcagcg  26760
agagtcagat tatcggtacc ttcgagctgc agggtccctc gcccgacgaa aagtccgcgg  26820
ctccggggtt gaaactcact ccggggctgt ggacttccgc ctacctacgc aaatttgtac  26880
ctgaagacta ccacgcccac gagatcaggt tttacgaaga ccaatcccgc ccgcccaagg  26940
cggagctcac cgcctgcgtc attacccagg gccacatcct gggccaattg caagccatca  27000
acaaagcccg ccaagagttc ttgctgaaaa agggtcgggg ggtgtacctg gaccccagt   27060
ccggcgagga gctaaacccg ctaccccgc cgccgcccca gcagcgggac cttgcttccc   27120
aggatggcac ccagaaagaa gcagccgccg ccgccgccag catacatgct tctggaggaa  27180
gaggaggact gggacagtca ggcagaggag gtttcggacg aggacgagga ggaggagatg  27240
atggaagact gggaggagga cagcctagac gaggaagctt cagaggccga agaggtggca  27300
gacgcaacac catcaccctc ggccgcagcc ccctcgccgg cgccccgaa atcctccgac   27360
cccagcagca gcgctataac ctccgctcct ccggcgccgg cgcccacccg cagcagaccc  27420
aaccgtagat gggacactac aggaaccggg gtcggtaagt ccaagtgccc cccagcgccg  27480
ccccgcaac aggagcaaca gcagcagcag cggcgacagg gctaccgctc gtggcgcgga  27540
cacaagaacg ccatagtcgc ctgcttgcaa gactgcgggg gcaacatctc cttcgcccgc  27600
cgcttcctgc tcttccacca cggggtggct tttccccgca atgtcctgca ttactaccgt  27660
catctctaca gccctactg cggcggcagc ggcgacccag agggagcggc ggcagcagca   27720
gcgccagcca cagcggcgac cacctaggaa gacctccgcg ggcaagacgg cgggagccgg  27780
gagaccgcg gcggcggcgg tagcggcggc ggcgggcgca ctgcgcctct cgcccaacga   27840
acccctctcg acccgggagc tcagacacag gatcttcccc actctgtatg ctatcttcca  27900
gcagagcaga ggccaggaac aggagctcaa aataaaaaac agatctctgc gctccctcac  27960
ccgcagctgt ctgtatcaca aaagcgaaga tcagcttcgg cgcacgctgg aggacgcgga  28020
ggcactcttc agcaaatact gcgcgctgac tcttaaggac tagccgcgcg ccttctcga   28080
atttaggcgg gagaaagact acgtcatcgc cgaccgccgc ccagcccacc cagccgacat  28140
gagcaaagag attcccacgc cctacatgtg gagctaccag ccgcagatgg gactcgcggc  28200
gggagcggcc caagactact ccacccgcat gaactacatg agcgcggggc cccacatgat  28260
ctcacgggtt aatgggatcc gcgcccagcg aaaccaaata ctgctggaac aggcggccat  28320
aaccgccaca ccccgtcatg acctcaatcc ccgaaattgg cccgccgccc tcgtgtacca  28380
ggaaaccccc tctgccacca ccgtggtact tccgcgtgac acccaggccg aagtccagat  28440
gactaactca ggggcgcagc tcgcgggcgg ctttcgtcac ggggtgcggc cgcaccggcc  28500
gggtatatta cacctggcga tcagaggccg aggtattcag ctcaacgacg agtcggtgag  28560
ctcttcgctc ggtctccgtc cggacggaac cttccagatc gccggatcag gtcgctcctc  28620
attcacgcct cgccaggcgt atctgactct gcagacctcc tcctcggagc ctcgctccgg  28680
cggcatcggc accctccagt tcgtggagga gttcgtgccc tcggtctact tcaacccctt  28740
ctcgggacct cccggacgct accccgacca gttcatcccg aactttgacg cggtgaagga  28800
ctcggcggac ggctacgact gaatgtcaag tgctgaggca gagagcgttc gcctgaaaca  28860
```

```
cctccagcac tgccgccgct tcgcctgctt tgcccgcagc tccggtgagt tctgctactt   28920
tcagctgccc gaggagcata ccgaagggcc ggcgcacggc gtccgcctaa ccacccaggg   28980
cgaggttacc tgtacccttta tccgggagtt taccctccgt ccctgctag tggagcggga   29040 gcggggttct tgtgtcataa ctatcgcctg caactgccct aaccctggat acatcaaga   29100 tctttgttgt cacctgtgcg ctgagtataa taaacgctga gatcagactc tactggggct   29160
cctgtcgcca tcctgtgaac gccaccgtct tcacccaccc cgagcagccc caggcgaacc   29220
tcacctgcgg cctgcgtcgg agggccaaga agtacctcac ctggtacttc aacggcaccc   29280
cctttgtggt ttacaacagc ttcgaccagg acggagttgc cttgagagac gaccctttccg   29340 gtctcagcta ctccattcac aagaacacca ccctccacct cttccctccc tacctgccgg   29400
gaacctacga gtgcgtcacc ggccgctgca cccacctcct ccgcctgatc gtaaaccaga   29460
cctttccggg aacacacctc ttccccagaa caggaggtga gctcaggaaa cccctgggg   29520 cccagggcg agacttacct tcgacccttg tggggttagg attttttatc gccgggttgc   29580
tggctctcct gatcaaagct tccttcagat ttgttctctc cctttacttt tatgaacagc   29640
tcaacttcta ataacgctac cttttctcag gaatcgagta gtaacttctc ttccgaaatc   29700
gggctgggtg tgctgcttac tctgttgatt ttttttcctta tcatacttag ccttctgtgc   29760
ctcaggctcg ccgcctgctg cgcacatatc tacatctaca gccggttgct taactgctgg   29820
ggtcgccatc caagatgaac ggggctcagg tgctatgtct gctggccctg gtggcctgca   29880
gtgccgccgt caattttgag gaacccgctt gcaatgtgac tttcaagcct gagggcgcac   29940
attgcaccac tctggttaaa tgtgtgacct ctcatgaaaa actgctcatc gcctacaaaa   30000
acaaaacagg ccagatcgca gtctatagcg agtggctacc cggagaccat aataactact   30060
cagtcaccgt cttcgagggt gcggagtcta agaaattcga ttacacctttt cccttcgagg   30120 agatgtgtga tgcggtcatg tacctgtcca aacagtacaa gctgtggccc cccacccca   30180 aggcgtgtgt ggaaaacact gggtctttct gctgtctctc tctggcaatc actgtgcttg   30240
ctctaatctg cacgctgcta tacatgagat tcaggcagag gcgaatcttt atcgatgaga   30300
aaaaaatgcc ttgatcgcta acaccggctt tctgtctgca gaatgaaagc aatcacctcc   30360
ctactaatca gcaccaccct ccttgcgatt gcccatgggt tgacacgaat cgaagtgcca   30420
gtggggtcca atgtcaccat ggtgggcccc gccggcaatt cctccctgat gtgggaaaaa   30480
tatgtccgta atcaatggga tcattactgc tctaatcgaa tctgtatcaa gcccagagcc   30540
acctgcgacg ggcaaaatct aactttgatt gatgtgcaaa tgacggatgc tgggtactat   30600
tacgggcagc ggggagaaat gattaattac tggcgacccc acaaggacta catgctgcat   30660
gtagtcaagg cagtcccaac tactaccacc cccaccacta ccactccac taccaccacc   30720 cccaccacta ccactagcac tgctactacc gctgcccgca aagctattac ccgcaaaagc   30780
accatgctta gcaccaagcc ccattctcac tcccacgccg gcgggcccac cggtgcggcc   30840
tcagaaacca ccgagctttg cttctgccaa tgcactaacg ccagcgccca cgaactgttc   30900
gacctggaga atgaggacga tgaccagctg agctccgctt gcccggtccc gctgcccgca   30960
gagccggtcg ccctgaagca gctcggtgat ccatttaatg actctcctgt ttatccctct   31020
cccgaatacc ctcccgactc taccttccac atcacgggca ccaaagaccc caacctctcc   31080
ttctacctga tgctgctgct ctgtatctct gtggtatctt ccgcgctcat gttactgggc   31140
atgttctgct gcctcatctg ccgcagaaaa agaaagtctc gctctcaggg ccaaccactg   31200
```

```
atgcccttcc cctacccccc agattttgca gataacaaga tatgagcacg ctgctgacac   31260
taaccgcttt actcgcctgc gctctaaccc ttgtcgcttg cgaatccaga taccacaatg   31320
tcacagttgt gacaggagaa aatgttacat tcaactccac ggccgacacc cagtggtcgt   31380
ggagtggcca cggtagctat gtatacatct gcaatagctc cacctcccct agcatgtcct   31440
ctcccaagta ccactgcaat gacagcctgt tcaccctcat caacgcctcc acctcggaca   31500
atggactcta tgtaggctat gtgacacccg gtgggcaggg aaagacccac gcctacaacc   31560
tgcaagttcg ccaccctcc accaccgcca ccacctctgc cgccctacc cgcagcagca   31620
gcagcagcag cagcagcagc agcagcagca gcagcagatt cctgacttta atcctagcca   31680
gctcaacaac caccgccacc gctgagacca cccacagctc cgcgcccgaa accacccaca   31740
cccaccaccc agagacgacc gcggcctcca gcgaccagat gtcggccaac atcaccgcct   31800
cgggtcttga acttgcttca accccaccc caaaaccagt ggatgcagcc gacgtctccg   31860
ccctcgtcaa tgactgggcg gggctgggaa tgtggtggtt cgccataggc atgatggcgc   31920
tctgcctgct tctgctctgg ctcatctgct gcctcaaccg caggcgggcc agacccatct   31980
atagacccat cattgttctc aaccccgctg atgatgggat ccatagattg gatggtctga   32040
aaaacctact tttctctttt acagtatgat aaattgagac atgcctcgca ttttcatgta   32100
cttgacactt ctcccacttt ttctggggtg ttctacgctg ccgccgtct ctcacctcga   32160
ggtagactgc ctcacaccct tcactgtcta cctgatttac ggattggtca ccctcactct   32220
catctgcagc ctaatcacag tagtcatcgc cttcatccag tgcattgact acatctgtgt   32280
gcgcctcgca tacctgagac accacccgca gtaccgagac aggaacattg cccaactcct   32340
aagactgctc taatcatgca taagactgtg atctgcctcc tcatcctcct ctccctgccc   32400
gctctcgtct catgccagcc caccacaaaa cctccacgaa aaagacatgc ctcctgtcgc   32460
ttgagccaac tgtggaatat tcccaaatgc tacaatgaaa agagcgagct ttccgaagcc   32520
tggctatatg cggtcatgtg tgtccttgtc ttctgcagca caatctttgc cctcatgatc   32580
taccccact ttgatttggg atggaatgcg gtcgatgcca tgaattaccc tacctttccc   32640
gcgcccgata tgattccact ccgacaggtt gtggtgcccg tcgccctcaa tcaacgcccc   32700
ccatcccta cacccactga ggtcagctac tttaatctaa caggcggaga tgactgacac   32760
tctagatcta gaaatggacg gcatcggcac cgagcagcgt ctcctacaga ggcgcaagca   32820
ggcggctgaa caagagcgcc tcaatcagga gctccgagat ctcattaacc tgcaccagtg   32880
caaaaaaggc atcttttgcc tggtcaagca ggccgatgtc acctacgaga aaaccggtaa   32940
cagccaccgc ctcagctaca agctgcccac ccaacgccag aagttggtgc tcatggtggg   33000
tcagaatccc atcaccgtca cccagcactc ggtggagacc gaggggtgtc tgcactcccc   33060
ctgtcagggt ccggaagacc tctgcaccct ggtaaagacc ctgtgtggtc ttagagattt   33120
aatcccttt aactaatcaa acactggaat caataaaaag aatcacttac tttaaatcag   33180
tcagcaggtc tctgtccact ttattcagca gcacctcctt cccctcctcc caactctggt   33240
actccaaacg cctcctggcg gcaaacttcc tccacaccct gaagggaatg tcagattctt   33300
gctcctgtcc ctccgcaccc actatcttca tgttgttgca gatgaagcgc gccaaaacgt   33360
ctgacgagac cttcaacccc gtgtacccct atgacacgga aaacgggcct ccctccgttc   33420
ctttcctcac ccctcccttc gtgtccccg acggatttca agaaagcccc caggggtcc   33480
tgtctctgcg cctgtcagag cccctggtca cttcccacgg catgcttgcc ctgaaaatgg   33540
gaaatggcct ctccctggat gacgccggca acctcacctc tcaagatgtc accaccgtca   33600
```

```
cccctcccct caaaaaaacc aagaccaacc tcagcctcca gacctcagcc cccctgaccg   33660
ttagctctgg gtccctcacc gtcgcggccg ccgctccact ggcggtggcc ggcacctctc   33720
tcaccatgca atctcaggcc cccttgacgg tgcaagatgc aaaactgggt ctggccaccc   33780
agggacccct gaccgtgtct gaaggcaaac tcaccttgca gacatcggct ccactgacgg   33840
ccgccgacag cagcactctc actgttggca ccacaccgcc aatcagtgtg agcagtggaa   33900
gtctaggctt agatatggaa gaccccatgt atactcacga tggaaaactg ggaatcagaa   33960
ttggtggccc actgcaagta gtagacagct tgcacacact cactgtagtt actggaaacg   34020
gaataactgt agctaacaat gcccttcaaa ctaaagttgc gggtgccctg ggttatgact   34080
catctggcaa tctagaattg cgagccgcag ggggtatgcg aattaacaca ggggggtcaac  34140 tcattcttga tgtggcttat ccatttgatg ctcagaacaa tctcagcctt agactcggcc   34200
agggaccttt atatgtgaac accaatcaca acctagattt aaattgcaac agaggtctga   34260
ccacaaccac cagcagtaac acaaccaaac ttgaaactaa aatcgattcg ggcttagact   34320
ataacgccaa tggggctatc attgctaaac ttggcactgg gttaacccttt gacaacacag   34380 gtgccataac tgtgggaaac actggggatg acaaactcac tctgtggact accccagatc   34440
cctctcctaa ctgcagaatt cacgcagaca aagactgcaa gtttactcta gtcctgacta   34500
agtgtggaag tcaaattctg gcctccgtcg ccgccctggc ggtgtctgga aacctatcat   34560
caatgacagg cactgtctcc agcgttacca tctttctcag attcgatcag aatggagttc   34620
ttatggaaaa ttcctcgcta gacaaggagt actggaactt cagaaatggt aattccacca   34680
atgccacccc ctacaccaat gcggttgggt tcatgcccaa cctcagcgcc tacccccaaaa  34740 cccagagtca aactgcaaaa aacaacattg taagtgaggt ttacttacat ggggacaaat   34800
ctaaacccat gatccttacc attacccctta atggcacaaa tgaatccagt gaaactagtc   34860
aggtgagtca ctactccatg tcatttacat ggtcgaggga cagtgggaaa tatgccaccg   34920
aaacctttgc caccaactct tttaccttct cctacattgc tgaacaataa agaagcataa   34980
cgctgctgtt catttgtaat caagtgttac ttttttattt ttcaattaca acagaatcat   35040
tcaagtcatt ctccatttag cttaatagac cccagtagtg caaagcccca tactagctta   35100
tttcagcaat tgggagaagt actcgcctac atgggggtag agtcataatc gtgcatcagg   35160 ataggcggt ggtgctgcag cagcgcgcga ataaactgct gccgccgccg ctccgtcctg    35220
caggaataca acatggcagt ggtctcctca gcgatgattc gcaccgcccg cagcataagg   35280
cgccttgtcc tccgggcaca gcagcgcacc ctgatctcac ttaaatcagc acagtaactg   35340
cagcacagca ccacaatatt gttcaaaatc ccacagtgca aggcgctgta tccaaagctc   35400
atggcgggga ccacagaacc cacgtggcca tcataccaca agcgcaggta gattaagtgg   35460 cgaccctca taaacacgct ggacataaac attacctctt ttggcatgtt gtaattcacc    35520 acctccggt accatataaa cctctgatta aacatggcgc catccaccac catcctaaac   35580
cagctggcca aaacctgccc gccggctata cactgcaggg aaccgggact ggaacaatga   35640
cagtggagag cccaggactc gtaaccatgg atcatcatgc tcgtcatgat atcaatgttg   35700
gcacaacaca ggcacacgtg catacacttc ctcaggatta caagctcctc ccgcgttaga   35760
accatatccc agggaacaac ccattcctga atcagcgtaa atcccacact gcagggaaga   35820
cctcgcacgt aactcacgtt gtgcattgtc aaagtgttac attcgggcag cagcggatga   35880
tcctccagta tggtagcgcg ggtttctgtc tcaaaaggag gtagacgatc cctactgtac   35940
```

-continued

| | |
|---|---|
| ggagtgcgcc gagacaaccg agatcgtgtt ggtcgtagtg tcatgccaaa tggaacgccg | 36000 |
| gacgtagtca tatttcctga agtcttggcg cgccagaccc gagtcttacc aggaaaattt | 36060 |
| taaaaaagat tcctcaacgc agcaccagca ccaacacctg tcagtgtaaa atgccaagcg | 36120 |
| ccgagcgagt atatatagga ataaaaagtg acgtaaacgg ttaaagtcca gaaaacgccc | 36180 |
| agaaaaaccg cacgcgaacc tacgccccga aacgaaagcc aaaaaacagt gaacacgccc | 36240 |
| tttcggcgtc aacttccgct ttcccacggt acgtcacttc cgcatatagt aaaactacgc | 36300 |
| tacccaacat gcaagaagcc acgccccaaa acacgtcaca cctcccggcc cgccccgcgc | 36360 |
| cgccgctcct ccccgccccg ccccgctccg cccacctcat tatcatattg gcttcaatcc | 36420 |
| aaaataaggt atattattga tgatg | 36445 |

<210> SEQ ID NO 10
<211> LENGTH: 2302
<212> TYPE: DNA
<213> ORGANISM: Ebola virus
<220> FEATURE:
<223> OTHER INFORMATION: Ebola virus Zaire wild type transmembrane
      envelope glycoprotein (GP) (EBOV GP Zaire wild type)

<400> SEQUENCE: 10

| | |
|---|---|
| cgtcgtcgac acgtgtgatc agatatcgcg gccgctctag accaggccct ggatcgatcc | 60 |
| aacaacacaa tgggcgttac aggaatattg cagttacctc gtgatcgatt caagaggaca | 120 |
| tcattctttc tttgggtaat tatccttttc caaagaacat tttccatccc acttggagtc | 180 |
| atccacaata gcacattaca ggttagtgat gtcgacaaac tagtttgtcg tgacaaactg | 240 |
| tcatccacaa atcaattgag atcagttgga ctgaatctcg aagggaatgg agtggcaact | 300 |
| gacgtgccat ctgcaactaa agatgggggc ttcaggtccg gtgtcccacc aaaggtggtc | 360 |
| aattatgaag ctggtgaatg ggctgaaaac tgctacaatc ttgaaatcaa aaaacctgac | 420 |
| gggagtgagt gtctaccagc agcgccagac gggattcggg gcttcccccg gtgccggtat | 480 |
| gtgcacaaag tatcaggaac gggaccgtgt gccggagact tgccttccha taagagggt | 540 |
| gctttcttcc tgtatgatcg acttgcttcc acagttatct accgaggaac gactttcgct | 600 |
| gaaggtgtcg ttgcatttct gatactgccc caagctaaga aggacttctt cagctcacac | 660 |
| cccttgagag agccggtcaa tgcaacggag gacccgtcta gtggctacta ttctaccaca | 720 |
| attagatatc aggctaccgg ttttggaacc aatgagacag agtacttgtt cgaggttgac | 780 |
| aatttgacct acgtccaact tgaatcaaga ttcacaccac agtttctgct ccagctgaat | 840 |
| gagacaatat atacaagtgg gaaaaggagc aataccacgg gaaaactaat ttggaaggtc | 900 |
| aaccccgaaa ttgatacaac aatcggggag tgggccttct gggaaactaa aaaaaacctc | 960 |
| actagaaaaa ttcgcagtga agagttgtct ttcacagttg tatcaaacgg agccaaaaac | 1020 |
| atcagtggtc agagtccggc gcgaacttct tccgacccag ggaccaacac aacaactgaa | 1080 |
| gaccacaaaa tcatggcttc agaaaaattc ctctgcaatgg ttcaagtgca cagtcaagga | 1140 |
| agggaagctg cagtgtcgca tctaacaacc cttgccacaa tctccacgag tccccaatcc | 1200 |
| ctcacaacca aaccaggtcc ggacaacagc acccataata cacccgtgta taaacttgac | 1260 |
| atctctgagg caactcaagt tgaacaacat caccgcagaa cagacaacga cagcacagcc | 1320 |
| tccgacactc cctctgccac gaccgcagcc ggaccccaa agcagagaa caccaacacg | 1380 |
| agcaagagca ctgacttcct ggaccccgcc accacaacaa gtcccaaaa ccacagcgag | 1440 |
| accgctggca caacaacaca tcatcaccaa gataccggag aagagagtgc cagcagcggg | 1500 |

| | |
|---|---|
| aagctaggct taattaccaa tactattgct ggagtcgcag gactgatcac aggcgggaga | 1560 |
| agaactcgaa gagaagcaat tgtcaatgct caacccaaat gcaaccctaa tttacattac | 1620 |
| tggactactc aggatgaagg tgctgcaatc ggactggcct ggataccata tttcgggcca | 1680 |
| gcagccgagg gaatttacat agaggggcta atgcacaatc aagatggttt aatctgtggg | 1740 |
| ttgagacagc tggccaacga gacgactcaa gctcttcaac tgttcctgag agccacaact | 1800 |
| gagctacgca ccttttcaat cctcaaccgt aaggcaattg atttcttgct gcagcgatgg | 1860 |
| ggcggcacat gccacattct gggaccggac tgctgtatcg aaccacatga ttggaccaag | 1920 |
| aacataacag acaaaattga tcagattatt catgattttg ttgataaaac ccttccggac | 1980 |
| caggggcaca atgacaattg gtggacagga tggagacaat ggataccggc aggtattgga | 2040 |
| gttacaggcg ttgtaattgc agttatcgct ttattctgta tatgcaaatt tgtcttttag | 2100 |
| tttttcttca gattgcttca tggaaaagct cagcctcaaa tcaatgaaac caggatttaa | 2160 |
| ttatatggat tacttgaatc taagattact tgacaaatga taatataata cactggagct | 2220 |
| ttaaacatag ccaatgtgat tctaactcct ttaaactcac agttaatcat aaacaaggtt | 2280 |
| tgaggtaccg agctcgaatt ga | 2302 |

<210> SEQ ID NO 11
<211> LENGTH: 2031
<212> TYPE: DNA
<213> ORGANISM: Artificial Sequence
<220> FEATURE:
<223> OTHER INFORMATION: synthetic Ebola virus Sudan/Gulu codon
      optimized transmembrane envelope glycoprotein (GP) (EBOV GP
      Sudan/Gulu codon optimized)

<400> SEQUENCE: 11

| | |
|---|---|
| atggagggcc tgagcctgct gcagctgccc agggacaagt tcaggaagag cagcttcttc | 60 |
| gtgtgggtga tcatcctgtt ccagaaggcc ttcagcatgc ccctgggcgt ggtgaccaac | 120 |
| agcaccctgg aggtgaccga gatcgaccag ctggtgtgca aggaccacct ggccagcacc | 180 |
| gaccagctga agagcgtggg cctgaacctg gagggcagcg gcgtgagcac cgacatcccc | 240 |
| agcgccacca gaggtggggg cttcaggagc ggcgtgcctc ccaaggtggt gagctacgag | 300 |
| gccggcgagt gggccgagaa ctgctacaac ctggagatca agaagcccga cggcagcgag | 360 |
| tgcctgcctc ctcctcctga cggcgtgagg ggcttcccca ggtgcaggta cgtgcacaag | 420 |
| gcccagggca ccggcccctg ccccggcgac tacgccttcc acaaggacgg cgccttcttc | 480 |
| ctgtacgaca ggctggccag caccgtgatc tacaggggcg tgaacttcgc cgagggcgtg | 540 |
| atcgccttcc tgatcctggc caagcccaag gagaccttcc tgcagagccc tcccatcagg | 600 |
| gaggccgtga actacaccga gaacaccagc agctactacg ccaccagcta tctagagtac | 660 |
| gagatcgaga acttcggcgc ccagcacagc accaccctgt tcaagatcga caacaacacc | 720 |
| ttcgtgaggc tggacaggcc ccacacccct cagttcctgt tccagctgaa cgacaccatc | 780 |
| cacctgcacc agcagctgag caacaccacc ggcaggctga tctggaccct ggacgccaac | 840 |
| atcaacgccg acatcggcga gtgggccttc tgggagaaca agaagaacct gagcgagcag | 900 |
| ctgaggggcg aggagctgag cttcgaggcc ctgagcctga cgagaccga ggacgacgac | 960 |
| gccgccagca gcaggatcac caagggcagg atcagcgaca gggccaccag gaagtacagc | 1020 |
| gacctggtgc ccaagaacag cccccggcat gtgcccctgc acatccccga gggcgagacc | 1080 |
| accctgccca gccagaacag caccgagggc aggagggtgg cgtgaacac ccaggagacc | 1140 |
| atcaccgaga ccgccgccac catcatcggc accaacggca accacatgca gatcagcacc | 1200 |

```
atcggcatca ggcccagcag cagccagatc cccagcagca gccccaccac cgcccctagc    1260
cccgaggccc agaccccac  cacccacacc agcggaccca gcgtgatggc caccgaggag    1320
cccaccaccc ctcccggcag cagccccgga cccaccaccg aggcccctac cctgaccacc    1380
cctgagaaca tcaccaccgc cgtgaagacc gtgctgcccc aggagagcac cagcaacggc    1440
ctgatcacca gcaccgtgac cggcatcctg ggcagcctgg gcctgaggaa gaggagcagg    1500
aggcagacca caccaaggc  caccggcaag tgcaaccca  acctgcacta ctggaccgcc    1560
caggagcagc acaacgccgc cggcatcgcc tggattccct acttcggccc cggcgccgag    1620
ggcatctaca ccgagggcct gatgcacaac agaacgccc  tggtgtgcgg cctgaggcag    1680
ctggccaacg agaccaccca ggccctgcag ctgttcctga gggccaccac cgagctgagg    1740
acctacacca tcctgaacag gaaggccatc gacttcctgc tgaggaggtg gggcggcacc    1800
tgcaggattc tgggccccga ctgctgcatc gagccccacg actggaccaa gaacatcacc    1860
gacaagatca accagatcat ccacgacttc atcgacaacc ctctgcccaa ccaggacaac    1920
gacgacaact ggtggaccgg ctggcggcag tggatacctg ccggcatcgg catcaccggc    1980
atcatcatcg ccatcatcgc tctgctgtgc gtgtgcaagc tgctgtgctg a              2031
```

<210> SEQ ID NO 12
<211> LENGTH: 2043
<212> TYPE: DNA
<213> ORGANISM: Artificial Sequence
<220> FEATURE:
<223> OTHER INFORMATION: synthetic Marburg virus Angola codon optimized
      transmembrane envelope glycoprotein (GP) (Marburg
      virus Angola codon optimized)

<400> SEQUENCE: 12

```
atgaagacca cctgcctgct gatcagcctg atcctgatcc agggcgtgaa gaccctgccc      60
atcctggaga tcgccagcaa catccagccc cagaacgtgg acagcgtgtg cagcggcacc     120
ctgcagaaga ccgaggacgt gcacctgatg ggcttcaccc tgagcggcca aaggtggcc      180 gacagccctc tggaggccag caagaggtgg gccttcaggg ccggcgtgcc ccccaagaac     240
gtggagtaca ccgagggcga ggaggccaag acctgctaca acatcagcgt gaccgacccc     300
agcggcaaga gcctgctgct ggaccctccc accaacatca gggactaccc taagtgcaag     360
accatccacc acatccaggg ccagaaccct cacgcccagg catcgccct  gcacctgtgg     420 ggcgccttct tcctgtacga caggatcgcc agcaccacca tgtacagagg aaaagtgttc     480
acagagggaa acatcgctgc tatgatcgtg aacaagaccg tgcataagat gatcttcagc     540
agacagggac agggatatag acatatgaac ctgacatcca caaacaagta ctggacaagc     600
agcaacggaa cacagacaaa cgatacagga tgtttggaa  cactgcagga atacaactcc     660
accaagaacc agacatgtgc ccctagcaag aagcctctgc ctctgcctac agctcatcct     720
gaagtgaagc tgacatccac aagcacagat gccacaaagc tgaacacaac agatcctaat    780
agcgacgacg aggatctgac aacaagcgga tccggatccg agaacaggga accttataca     840
acaagcgacg ctgctacaaa cagggactg  tcctccacaa tgcctcctac acctagccct     900
cagcctagca cacctcagca gggaggcaac aacacaaacc attcccaggg agtggtgaca     960
gaacctggaa agacaaacac aacagcccag cctagcatgc ctcctcataa cacaacaaca    1020
atcagcacaa caacacctc  caagcacaat ctgagcacac tagcgtgcc tattcagaat    1080 gccaccaact acaacacaca gtccacagcc cctgaaaacg aacagacctc cgccccttcc    1140
```

| | |
|---|---|
| aaaacaaccc tgctgcctac agaaaaccct acaacagcca gagcacaaa cagcacaaag | 1200 |
| agccctacaa caacagtgcc taacacaaca aacaagtata gcacaagccc tagccctaca | 1260 |
| cctaattcca cagctcagca tctggtgtat tttagaagaa agagaaacat cctgtggaga | 1320 |
| gaaggagata tgttcccttt tctggatgga ctgatcaacg ctcctatcga ttttgatcct | 1380 |
| gtgcctaaca caaagacaat cttttgatgaa agcagcagca gcggagcctc cgccgaagaa | 1440 |
| gatcagcatg cctcccctaa catcagcctg acactgagct atttcctaa ggtgaacgaa | 1500 |
| aacacagccc attccggaga aaacgaaaac gattgtgatg ccgaactgag aatctggagc | 1560 |
| gtgcaggaag atgatctggc cgccggactg agctggatcc cttttttggg gcccggaatt | 1620 |
| gaaggactgt acaccgccgg cctgatcaag aaccagaaca acctggtgtg caggctgagg | 1680 |
| aggctggcca ccagaccgc caagagcctg gagctgctgc tgagggtgac caccgaggag | 1740 |
| aggaccttca gcctgatcaa caggcacgcc atcgacttcc tgctggctag gtggggcggc | 1800 |
| acctgcaagg tgctgggccc cgactgctgc atcggcatcg aggacctgag caggaacatc | 1860 |
| agcgagcaga tcgaccagat caagaaggac gagcagaagg agggcaccgg ctggggcctg | 1920 |
| ggcggcaagt ggtggaccag cgactgggga gtgctgacaa acctgggaat cctgctgctg | 1980 |
| ctgagcattg ccgtgctcat tgctctgtcc tgtatctgta gaatctttac caagtacatc | 2040 |
| gga | 2043 |

<210> SEQ ID NO 13
<211> LENGTH: 2028
<212> TYPE: DNA
<213> ORGANISM: Ebola virus
<220> FEATURE:
<223> OTHER INFORMATION: Ebola virus Sudan/Gulu wild type transmembrane
envelope glycoprotein (GP) (EBOV GP Sudan/Gulu
wild type)

<400> SEQUENCE: 13

| | |
|---|---|
| atgggggggtc ttagcctact ccaattgccc agggacaaat ttcggaaaag ctctttcttt | 60 |
| gtttgggtca tcatcttatt ccaaaaggcc ttttccatgc ctttgggtgt tgtgactaac | 120 |
| agcactttag aagtaacaga gattgaccag ctagtctgca aggatcatct tgcatctact | 180 |
| gaccagctga atcagttgg tctcaacctc gaggggagcg gagtatctac tgatatccca | 240 |
| tctgcaacaa agcgttgggg cttcagatct ggtgttcctc caaggtggt cagctatgaa | 300 |
| gcgggagaat gggctgaaaa tgctacaat cttgaaataa agaagccgga cgggagcgaa | 360 |
| tgcttaccc caccgccaga tgtgtcaga ggctttccaa ggtgccgcta tgttcacaaa | 420 |
| gcccaaggaa ccgggccctg cccaggtgac tacgcctttc acaaggatgg agctttcttc | 480 |
| ctctatgaca ggctggcttc aactgtaatt tacagaggag tcaattttgc tgagggggta | 540 |
| attgcattct tgatattggc taaaccaaaa gaaacgttcc ttcagtcacc ccccattcga | 600 |
| gaggcagtaa actacactga aaatacatca agttattatg ccacatccta cttggagtat | 660 |
| gaaatcgaaa attttggtgc tcaacactcc acgaccctt tcaaaattga caataatact | 720 |
| tttgttcgtc tggacaggc ccacacgcct cagttccttt tccagctgaa tgataccatt | 780 |
| caccttcacc aacagttgag taatacaact gggagactaa tttggacact agatgctaat | 840 |
| atcaatgctg atattggtga atgggcttt tgggaaaata aaaaaaatct ctccgaacaa | 900 |
| ctacgtggag aagagctgtc ttttgaagct ttatcgctca acgagacaga agacgatgat | 960 |
| gcggcatcgt cgagaattac aaagggaaga atctccgacc gggccaccag gaagtattcg | 1020 |
| gacctggttc caaagaattc ccctgggatg gttccattgc atacccaga aggggaaaca | 1080 |

-continued

```
acattgccgt ctcagaattc gacagaaggt cgaagagtag gtgtgaacac tcaggagacc    1140
attacagaga cagctgcaac aattataggc actaacggca accatatgca gatctccacc    1200
atcgggataa gaccgagctc cagccaaatc ccgagttcct caccgaccac ggcaccaagc    1260
cctgaggctc agaccccccac aacccacaca tcaggtccat cagtgatggc caccgaggaa    1320
ccaacaacac caccgggaag ctcccccggc caacaacag aagcacccac tctcaccacc    1380
ccagaaaata taacaacagc ggttaaaact gtcctgccac aggagtccac aagcaacggt    1440
ctaataactt caacagtaac agggattctt gggagtcttg ggcttcgaaa acgcagcaga    1500
agacaaacta acaccaaagc cacgggtaag tgcaatccca acttacacta ctggactgca    1560
caagaacaac ataatgctgc tgggattgcc tggatcccgt actttggacc gggtgcggaa    1620
ggcatataca ctgaaggcct gatgcataac caaaatgcct tagtctgtgg acttaggcaa    1680
cttgcaaatg aaacaactca agctctgcag cttttcttaa gagccacaac ggagctgcgg    1740
acatatacca tactcaatag gaaggccata gatttccttc tgcgacgatg gggcgggaca    1800
tgcaggatcc tgggaccaga ttgttgcatt gagccacatg attggacaaa aacatcact    1860 gataaaatca accaaatcat ccatgatttc atcgacaacc ccttacctaa tcaggataat    1920
gatgataatt ggtggacggg ctggagacag tggatccctg caggaatagg cattactgga    1980
attattattg caattattgc tcttctttgc gtttgcaagc tgctttgc              2028
```

<210> SEQ ID NO 14
<211> LENGTH: 2031
<212> TYPE: DNA
<213> ORGANISM: Artificial Sequence
<220> FEATURE:
<223> OTHER INFORMATION: synthetic Ebola virus Zaire codon optimized
      transmembrane envelope glycoprotein (GP) (EBOV GP
      Zaire codon optimized)

<400> SEQUENCE: 14

```
atgggcgtga ccggcatcct gcagctgccc agggacaggt tcaagaggac cagcttcttc     60
ctgtgggtga tcatcctgtt ccagaggacc ttcagcatcc ccctgggcgt gatccacaac    120
agcaccctgc aggtgagcga cgtggacaag ctggtgtgca gggacaagct gagcagcacc    180
aaccagctga gagcgtgggg cctgaacctg gagggcaacg gcgtggccac cgacgtgccc    240
agcgccacca gaggtggggg cttcaggagc ggcgtgcctc ccaaggtggt gaactacgag    300
gccggcgagt gggccgagaa ctgctacaac ctggagatca agaagcccga cggcagcgag    360
tgcctgcccg ccgcccctga cggcatcagg ggcttcccca ggtgcaggta cgtgcacaag    420
gtgagcggca ccggcccctg cgccggcgac ttcgccttcc acaaggaggg cgccttcttc    480
ctgtacgaca ggctggccag caccgtgatc tacaggggca ccaccttcgc cgagggcgtg    540
gtggccttcc tgatcctgcc ccaggccaag aaggacttct tcagcagcca cctctgagg    600 gagcccgtga cgccaccga ggaccccagc agcggctact acagcaccac catcaggtac    660
caggccaccg gcttcggcac caacgagacc gagtacctgt tcgaggtgga caacctgacc    720
tacgtgcagc tggagtctag attcacccct cagttcctgc tgcagctgaa cgagaccatc    780
tacaccagcg gcaagaggag caacaccacc ggcaagctga tctggaaggt gaaccccgag    840
atcgacacca ccatcggcga gtgggccttc tgggagacca agaagaacct gaccaggaag    900
atcaggagcg aggagctgag cttcaccgtc gtgagcaacg ggccaagaa catcagcggc    960 cagagccccg ccaggaccag cagcgacccc ggcaccaaca ccaccaccga ggaccacaag    1020
```

-continued

```
atcatggcca gcgagaacag cagcgccatg gtgcaggtgc acagccaggg cagggaggcc    1080
gccgtgagcc acctgaccac cctggccacc atcagcacca gccctcagtc tttaaccacc    1140
aagcccggcc ccgacaacag cacccacaac acccctgtgt acaagctgga catcagcgag    1200
gccacccagg tggagcagca ccacaggagg accgacaacg acagcaccgc cagcgacacc    1260
ccttccgcca ccaccgccgc cggccctccg aaggccgaga acaccaacac cagcaagagc    1320
accgactttc tggatcccgc caccaccacc agccctcaga accacagcga gaccgccggc    1380
aacaacaaca cccaccacca ggacaccggc gaggagagcg ccagcagcgg caagctgggc    1440
ctgatcacca acaccatcgc cggcgtggcc ggcctgatca ccggcggcag gaggaccagg    1500
agggaggcca tcgtgaacgc ccagcccaag tgcaacccca acctgcacta ctggaccacc    1560
caggacgagg gcgccgccat cggcctggcc tggattccct acttcggccc cgccgccgag    1620
ggcatctaca tcgagggcct gatgcacaac caggacggcc tgatctgcgg cctgaggcag    1680
ctggccaacg agaccaccca ggccctgcag ctgttcctga gggccaccac cgagctgagg    1740
accttcagca tcctgaacag gaaggccatc gacttcctgc tgcagaggtg gggcggcacc    1800
tgccacatcc tgggccccga ctgctgcatc gagcccacg actggaccaa gaacatcacc    1860
gacaagatcg accagatcat ccacgacttc gtggacaaga ccctgccaga ccagggcgac    1920
aacgacaact ggtggaccgg ctggcggcag tggatacctg ccggcatcgg cgtgaccggc    1980
gtggtgatcg ccgtgatcgc tctgttctgc atctgcaagt tcgtgttctg a             2031
```

CHIMPANZEE ADENOVIRAL VECTOR-BASED FILOVIRUS VACCINES

CROSS-REFERENCES TO RELATED APPLICATIONS

This application is a Divisional Application of U.S. application Ser. No. 13/641,655, filed Jan. 2, 2013, which is a U.S. National Phase Application of PCT/US2011/032682, filed Apr. 15, 2011 which claims the benefit of U.S. Provisional Patent Application No. 61/325,166, filed Apr. 16, 2010 each of which are incorporated herein by reference in their entirety.

REFERENCE TO SEQUENCE LISTING

This application includes a Sequence Listing as a text file named "77867-591100US-854933 SEQLIST.txt" created Oct. 15, 2012, and containing 387,507 bytes. The material contained in this text file is incorporated by reference in its entirety for all purposes.

FIELD OF THE INVENTION

This invention relates generally to viral vaccines and, more particularly, to filovirus vaccines based on chimpanzee adenoviral vectors.

BACKGROUND OF THE INVENTION

The Ebola viruses, and the genetically-related Marburg virus, viruses of the Filoviridae family, are associated with outbreaks of highly lethal hemorrhagic fever in humans and primates in North America, Europe, and Africa (Peters, C. J. et al. in: *Fields Virology*, eds. Fields, B. N. et al. 1161-1176, Philadelphia, Lippincott-Raven, 1996; Peters, C. J. et al. 1994 *Semin Virol* 5:147-154). Ebola viruses are negative-stranded RNA viruses comprised of five subtypes, including those described in the Zaire, Sudan, Reston, Ivory Coast and Bundibugyo episodes (Sanchez, A. et al. 1996 *PNAS USA* 93:3602-3607). The Ebola virus, was first recognized during an outbreak in 1976 in the Ebola River valley of Zaire (currently the Democratic Republic of the Congo), Africa. Mortality rates vary between different species, spanning from approximately 35 to 90% for the most virulent ones, Zaire and Sudan. The development of effective vaccines and/or drugs is a high priority. The Ebola (EBOV) and Marburg (MARV) viruses have also been categorized as priority class A pathogens due to their virulence, ease of dissemination, lack of effective countermeasures to prevent or treat them, and their potential to cause public panic and social disruption.

Although several subtypes have been defined, the genetic organization of Ebola viruses is similar, each containing seven linearly arrayed genes. Among the viral proteins, the envelope glycoprotein exists in two alternative forms, a 50-70 kilodalton (kDa) secreted protein of unknown function encoded by the viral genome and a 130 kDa transmembrane glycoprotein generated by RNA editing that mediates viral entry (Peters, C. J. et al. in: *Fields Virology*, eds. Fields, B. N. et al. 1161-1176, Philadelphia, Lippincott-Raven, 1996; Sanchez, A. et al. 1996 *PNAS USA* 93:3602-3607). Other structural gene products include the nucleoprotein (NP), matrix proteins VP24 and VP40, presumed nonstructural proteins VP30 and VP35, and the viral polymerase (reviewed in Peters, C. J. et al. in: *Fields Virology*, eds. Fields, B. N. et al. 1161-1176, Philadelphia, Lippincott-Raven, 1996). Although spontaneous variation of its RNA sequence does occur in nature, there appears to be less nucleotide polymorphism within Ebola subtypes than among other RNA viruses (Sanchez, A. et al. 1996 *PNAS USA* 93:3602-3607), suggesting that immunization may be useful in protecting against this disease. Previous attempts to elicit protective immune responses against Ebola virus using traditional active and passive immunization approaches have, however, not succeeded in primates (Peters, C. J. et al. in: *Fields Virology*, eds. Fields, B. N. et al. 1161-1176, Philadelphia, Lippincott-Raven, 1996; Clegg, J. C. S. et al. 1997 *New Generation Vaccines*, eds.: Levine, M. M. et al. 749-765, New York, N.Y. Marcel Dekker, Inc.; Jahrling, P. B. et al. 1996 *Arch Virol Suppl* 11:135-140).

Replication-defective adenovirus vectors (rAd) are powerful inducers of cellular immune responses and have therefore come to serve as useful vectors for gene-based vaccines, particularly for lentiviruses and filoviruses, as well as other nonviral pathogens (Shiver, et al., (2002) *Nature* 415(6869): 331-5; (Hill, et al., *Hum Vaccin* 6(1): 78-83.; Sullivan, et al., (2000) *Nature* 408(6812): 605-9; Sullivan et al., (2003) *Nature* 424(6949): 681-4; Sullivan, et al., (2006) *PLoS Med* 3(6): e177; Radosevic, et al., (2007); Santra, et al., (2009) *Vaccine* 27(42): 5837-45. Adenovirus-based vaccines have several advantages as human vaccines since they can be produced to high titers under GMP conditions and have proven to be safe and immunogenic in humans (Asmuth, et al., *J Infect Dis* 201(1): 132-41; Kibuuka, et al., *J Infect Dis* 201(4): 600-7; Koup, et al., *PLoS One* 5(2): e9015.; Catanzaro, et al., (2006) *J Infect Dis* 194(12): 1638-49; Harro, et al., (2009) *Clin Vaccine Immunol* 16(9): 1285-92). While most of the initial vaccine work was conducted using rAd5 due to its significant potency in eliciting broad antibody and CD8+ T cell responses, pre-existing immunity to rAd5 in humans may limit efficacy (Catanzaro, (2006); Cheng, et al., (2007) *PLoS Pathog* 3(2): e25.; McCoy, et al., (2007) *J Virol* 81(12): 6594-604.; Buchbinder, et al., (2008) *Lancet* 372 (9653): 1881-93). This property might restrict the use of rAd5 in clinical applications for many vaccines that are currently in development including Ebola virus (EBOV) and Marburg virus (MARV).

To circumvent the issue of pre-existing immunity to rAd5, several alternative vectors are currently under investigation. These include adenoviral vectors derived from rare human serotypes and vectors derived from other animals such as chimpanzees (Vogels, et al., (2003) *J Virol* 77(15): 8263-71; Abbink, et al., (2007) *J Virol* 81: 4654-63; Santra, (2009) *Vaccine* 27(42): 5837-45). Chimpanzee adenoviral vectors are also described in WO 2010/086189, WO 2005/071093 and WO 98/10087.

It would thus be desirable to provide a vaccine to elicit an immune response against a filovirus or disease caused by infection with filovirus using improved adenoviral vectors. It would further be desirable to provide methods of making and using said vaccine. The present invention addresses these and other needs.

BRIEF SUMMARY OF THE INVENTION

This invention provides vaccines for inducing an immune response and protection against filovirus infection for use as a preventative vaccine in humans. In particular, the invention provides chimpanzee adenoviral vectors (adenoviral vectors derived from chimpanzees) expressing filovirus proteins. For example, these vaccines include chimpanzee adenovirus serotypes ChAd3, ChAd63, PanAd3, PanAd1, PanAd2, or ChAd83 expressing filovirus envelope glycoprotein (GP), including different strains of Ebolavirus (EBOV) or Marburg (MARV). Exemplary Chimp Adenoviral Ebola and Marburg sequences are provided in SEQ ID NOs:1-9.

DEFINITIONS

An "adenovirus capsid protein" refers to a protein on the capsid of an adenovirus (e.g., chimpanzee adenovirus) that is involved in determining the serotype and/or tropism of a particular adenovirus. Adenoviral capsid proteins typically include the fiber, penton and/or hexon proteins. As used herein an "adenovirus capsid protein" may be, for example, a chimeric capsid protein that includes capsid protein sequences from two adenoviral iolates.

The terms "adjuvant" and "immune stimulant" are used interchangeably herein, and are defined as one or more substances that cause stimulation of the immune system. In this context, an adjuvant is used to enhance an immune response to the adenovirus vectors of the invention.

The term "corresponding to", when applied to positions of amino acid residues in sequences, means corresponding positions in a plurality of sequences when the sequences are optimally aligned.

The terms "identical" or percent "identity," in the context of two or more nucleic acids or polypeptide sequences, (e.g., adenovirus capsid proteins of the invention and polynucleotides that encode them) refer to two or more sequences or subsequences that are the same or have a specified percentage of amino acid residues or nucleotides that are the same, when compared and aligned for maximum correspondence, as measured using one of the following sequence comparison algorithms or by visual inspection. Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

An "isolated" nucleic acid molecule or adenovirus vector is a nucleic acid molecule (e.g., DNA or RNA) or virus, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

"Operably linked" indicates that two or more DNA segments are joined together such that they function in concert for their intended purposes. For example, coding sequences are operably linked to promoter in the correct reading frame such that transcription initiates in the promoter and proceeds through the coding segment(s) to the terminator.

A "polynucleotide" is a single- or double-stranded polymer of deoxyribonucleotide or ribonucleotide bases typically read from the 5' to the 3' end. Polynucleotides include RNA and DNA, and may be isolated from natural sources, synthesized in vitro, or prepared from a combination of natural and synthetic molecules. When the term is applied to double-stranded molecules it is used to denote overall length and will be understood to be equivalent to the term "base pairs".

A "polypeptide" is a polymer of amino acid residues joined by peptide bonds, whether produced naturally or synthetically. Polypeptides of less than about 50 amino acid residues are commonly referred to as "oligopeptides".

The term "promoter" is used herein for its art-recognized meaning to denote a portion of a gene containing DNA sequences that provide for the binding of RNA polymerase and initiation of transcription of an operably linked coding sequence. Promoter sequences are typically found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The phrase "substantially identical," in the context of two nucleic acids or polypeptides of the invention (e.g., adenovirus capsid proteins or filovirus antigens), refers to two or more sequences or subsequences that have at least 60%, 65%, 70%, 75%, 80%, 85%, 90%, and 95% nucleotide or amino acid residue identity, when compared and aligned for maximum correspondence, as measured using one of the following sequence comparison algorithms or by visual inspection. In some embodiments, the substantial identity exists over a region of the sequences that is at least about 50 residues, at least about 100 residues, or at least about 150 residues in length. In one embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990)*J Mol. Biol.* 215: 403-410 and Altschuel et al. (1977) *Nucleic Acids Res.* 25: 3389-3402, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=-4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, less than about 0.01, or less than about 0.001.

A further indication that two nucleic acid sequences or polypeptides of the invention are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

BRIEF DESCRIPTION OF THE DRAWINGS

FIGS. 1A-1B Transgene expression by rAd5, ChAd63 and ChAd3 vectors. FIG. 1A is a schematic of the genomic features of rAd vector. FIG. 1B shows Ebola GP expression in HEK 293 cells. The cells were transduced with rAd5, ChAd63 or ChAd3 vectors at 0, or $10^1$ to $10^3$ vp/cell as indicated. The cell lysates were harvested at 20 hours post transduction and subjected to SDS-PAGE and Western blot analysis.

FIGS. 2A and 2B show % IFN-γ-producing CD4+ and CD8+ T cells, respectively. FIG. 2C shows detection of IgG by ELISA Serum IgG (sera were diluted at 1:1000). *p<0.05; ***p<0.001.

FIGS. 3A and 3B show % IFN-γ-producing CD4+ and CD8+ T cells, FIG. 3C shows Serum IgG (serum was diluted at 1:1000). *p<0.05; ***p<0.001.

FIGS. 4A and 4B show % IFN-γ-producing CD4+ and CD8+ T cells, respectively. FIG. 4C shows Serum IgG (sera were diluted at 1:1000). *p<0.05; **p<0.01.

FIGS. 6A-6B ChAd3 Ebola GP (Zaire) single immunization generates antigen-specific CD4+ and CD8+ T cell responses. Cynomolgus macaques were immunized with rAd5 or ChAd3 encoding EBOV-GP at a dose of $10^{11}$ vp intramuscularly. Blood cells were collected 4 weeks post immunization to detect cellular immune responses by intracellular cytokine staining after stimulation with EBOV-GP peptides. FIG. 6A shows % cytokine-producing CD4+ T cells, FIG. 6B shows % cytokine-producing CD8+ T cells.

FIG. 7. ChAd3 Ebola GP (Zaire) single immunization protects nonhuman primates against infectious challenge with a lethal dose of EBOV-Zaire. Cynomolgus macaques were immunized with rAd5 or ChAd3 encoding EBOV-GP at a dose of $10^{11}$ vp intramuscularly. Subjects were challenged with 1000 PFU of EBOV-Zaire by the intramuscular route at 5 weeks after vaccination. *Additional 10 historical controls performed with the same vaccine and infectious virus challenge stock have yielded the same survival result, **More than 50 historical controls with the same infectious challenge stock have yielded the same survival result.

FIGS. 9A-9B A single immunization with $10^{10}$ vp of rAdC3 Ebola (Zaire) elicits antigen-specific CD4+ and CD8+ T cell responses. Cynomolgus macaques were vaccinated with rAdC3 or rAd5 encoding EBOV-GP at a dose of $10^{10}$ vp intramuscularly. Blood cells were collected 4 weeks post immunization to detect cellular immune responses by intracellular cytokine staining after stimulation with EBOV-GP peptides. FIG. 9A shows % cytokine producing CD4+ T cells, FIG. 9B shows % cytokine producing CD8+ T cells.

FIG. 10. A single immunization with $10^{10}$ vp of rAdC3 Ebola (Zaire) protects nonhuman primates against infectious challenge with a lethal dose of EBOV-Zaire. Cynomolgus macaques were vaccinated with rAdC3 or rAd5 encoding EBOV-GP at a dose of $10^{10}$ vp intramuscularly. Subjects were challenged with 1000 PFU of EBOV-Zaire by the intramuscular route at 5 weeks post vaccination. *Additional 10 historical controls that received the same vaccine and infectious virus challenge stock have yielded the same survival result. **More than 50 historical controls injected with the same infectious challenge stock have yielded the same survival result.

FIG. 11A shows CD4 cellular immune responses in PBMC. FIG. 11B shows CD8 cellular immune responses in PMBC and FIG. 11C shows humoral responses (IgG) to EBOV-GP. Each were measured at three week post immunization by ICS and ELISA, respectively. Zh: humanized EBOV-GP; Z: non-humanized EBOV-GP; *: $p<0.05$; : $p<0.01$; *: $p<0.001$.

FIG. 12A shows CD4 cellular immune responses in PBMC and FIG. 12B shows CD8 cellular immune responses in PBMC. FIG. 12C shows humoral responses (IgG) to EBOV-GP. Each were measured at week 5 by ICS and ELISA, respectively. 5: rAd5; C3: rChAd3; C63: rChAd63; *: $p<0.05$; : $p<0.01$; *: $p<0.001$.

FIG. 13A shows CD4 cellular immune responses in PBMC and FIG. 13B shows CD8 cellular immune responses in PBMC. FIG. 13C shows humoral responses (IgG) to EBOV-GP. Each were measured at week 6 by ICS and ELISA, respectively. 5: rAd5; C3: rChAd3; C63: rChAd63; *: $p<0.05$; : $p<0.01$; *: $p<0.001$.

DETAILED DESCRIPTION

Figure 2A:
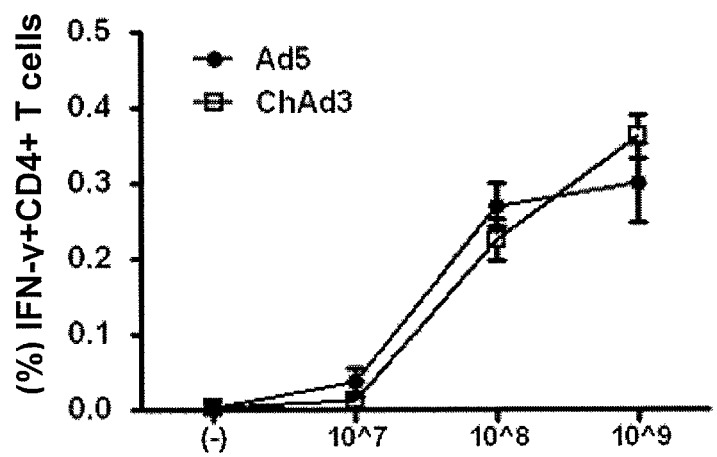
FIGS. 2A-2C ChAd3 Ebola GP (Zaire) single immunization generated comparable CD4+ T cell and IgG responses to rAd5. The mice were immunized with rAd5 Ebola (Zaire) or ChAd3 Ebola (Zaire) at $10^7$, $10^8$ and $10^9$ vp intramuscularly. The spleens and sera were harvested 3 weeks post immunization to detect cellular immune responses by ICS (intracellular cytokine staining) and IgG by ELISA.
Figure 2B:
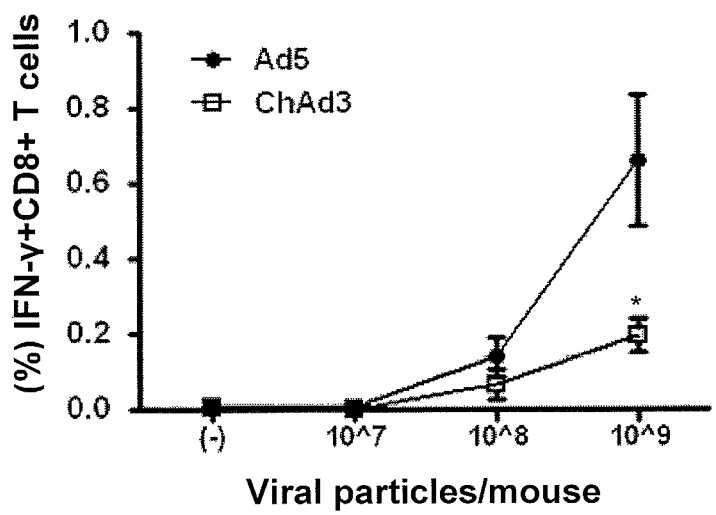
Figure 2C:
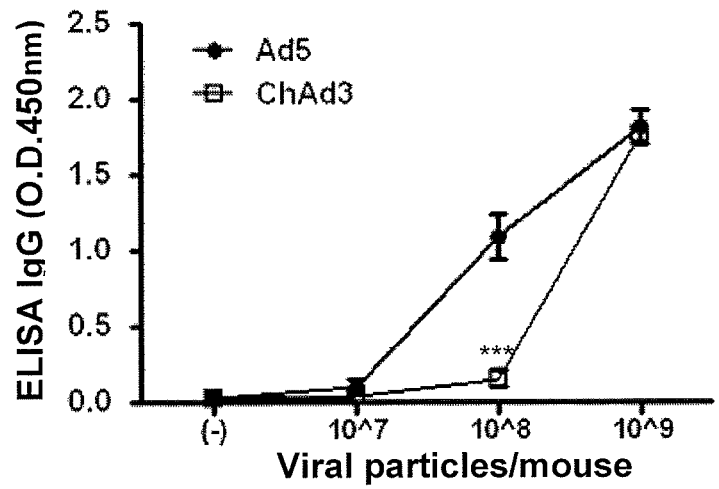
Figure 3A:
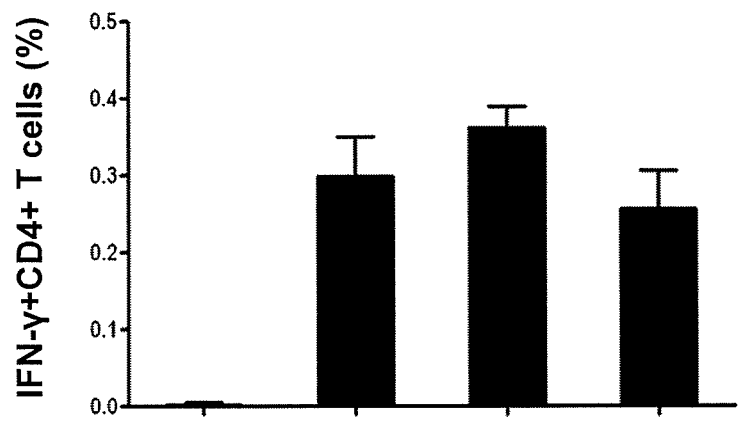
FIGS. 3A-3C ChAd3 Ebola (Zaire) single immunization generated stronger cellular and humoral responses than ChAd63. Mice were immunized with rAd5, ChAd3 or ChAd63 at $10^9$ vp intramuscularly. Spleens and serum were harvested 3 weeks post immunization to detect cellular immune responses by ICS and IgG response by ELISA.
Figure 3B:
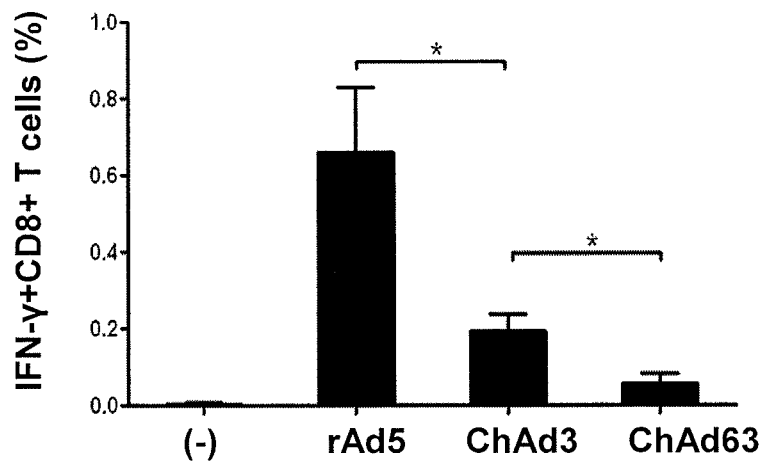
Figure 3C:
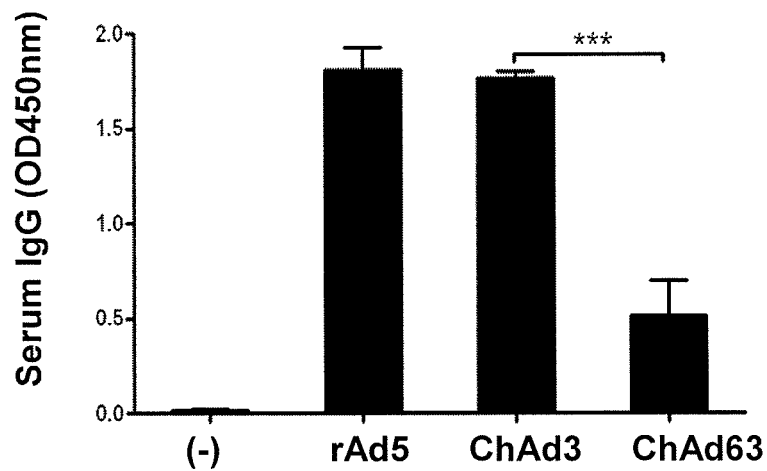
Figure 4A:
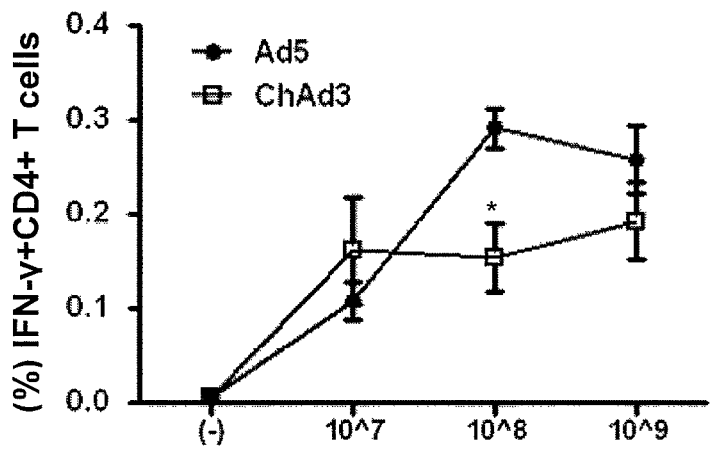
FIGS. 4A-4C ChAd3 Ebola (S/G) single immunization generated comparable cellular and humoral responses to rAd5. Mice were immunized with rAd5 Ebola (S/G) or ChAd3 Ebola (S/G) at 107, 108 and 109 vp intramuscularly. Spleens and sera were harvested 3 weeks post immunization to detect cellular immune responses by ICS and IgG by ELISA.
Figure 4B:
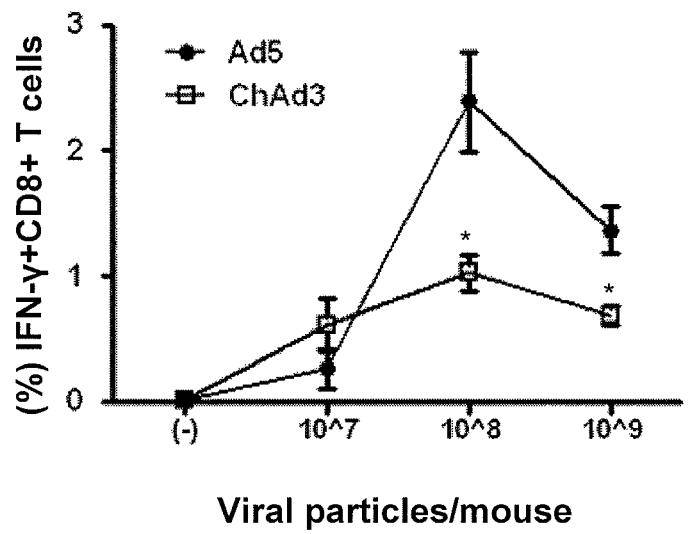
Figure 4C:
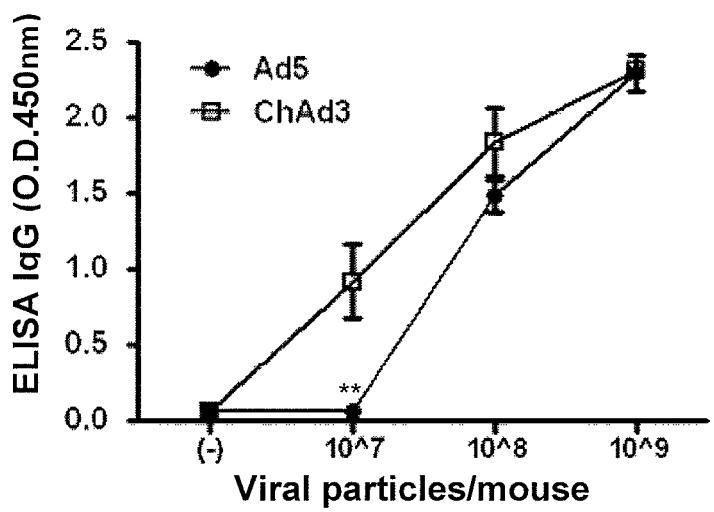
Figure 5:
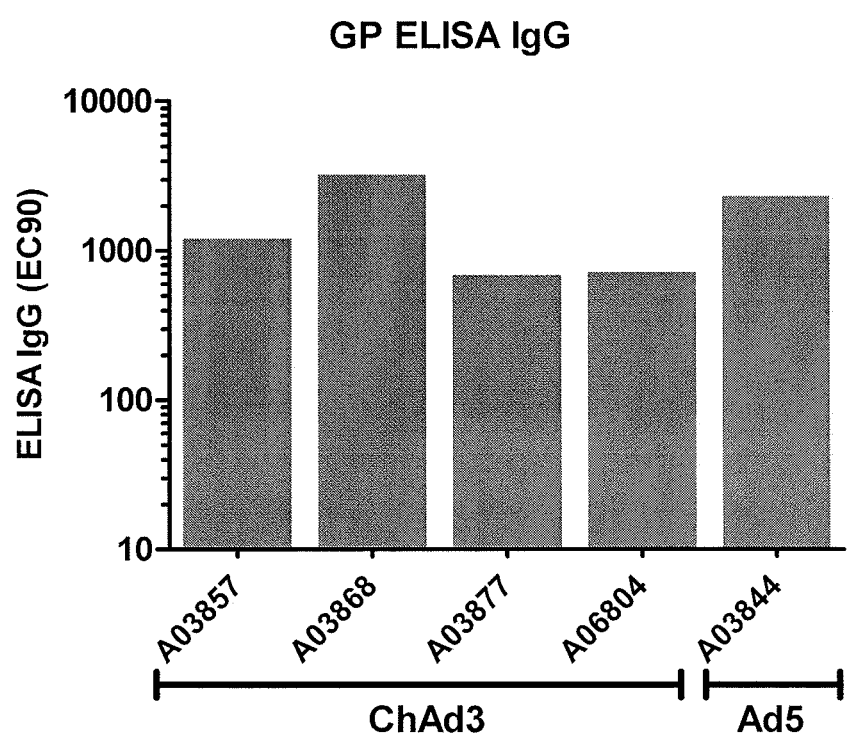
FIG. 5. ChAd3 Ebola (Zaire) single immunization generates antigen-specific antibody responses. Cynomolgus macaques were immunized with rAd5 or ChAd3 encoding EBOV-GP at a dose of 1011 vp intramuscularly. Serum was collected 4 weeks post immunization to detect IgG response by ELISA against EBOV GP.

The present invention also relates to chimpanzee adenovirus vectors which include the nucleic acid molecules of the present invention, host cells which are genetically engineered with the recombinant vectors, the production of filovirus polypeptides or fragments thereof by recombinant techniques and these chimpanzee adenovirus vectors for use in inducing an immune response.

The present invention also relates to pharmaceutical compositions (also referred to as immunogenic compositions) comprising the chimpanzee vectors described above, and a pharmaceutically acceptable diluent, carrier, or excipient carrier as well as to such compositions for use in inducing an immune response. Additionally the compositions may also contain an aqueous medium or a water containing suspension, often mixed with other constituents in order to increase the activity and/or the shelf life. These constituents may be salt, pH buffers, stabilizers (such as skimmed milk or casein hydrolysate), emulsifiers, and preservatives. An adjuvant may be included in the pharmaceutical composition to augment the immune response to the viral antigen expressed from the recombinant virus.

Filovirus Antigens

The nucleic acid molecules of the invention may encode structural gene products of any filovirus species. There are five species of Ebola viruses, Zaire (type species, also referred to herein as ZEBOV), Sudan (also referred to herein as SEBOV), Reston, Bundibugyo, and Ivory Coast. There is a single species of Marburg virus (also referred to herein as MARV).

The particular antigen expressed in the vectors of the invention is not a critical aspect of the present invention. The adenoviral vectors of the invention can be used to express proteins comprising an antigenic determinant of a wide variety of filovirus antigens. In a typical embodiment, the vectors of the invention include nucleic acid encoding the transmembrane form of the viral glycoprotein (GP). In other embodiments, the vectors of the invention may encode the secreted form of the viral glycoprotein (SGP), or the viral nucleoprotein (NP).

One of skill will recognize that the nucleic acid molecules encoding the filovirus antigenic protein may be modified, e.g., the nucleic acid molecules set forth herein may be mutated, as long as the modified expressed protein elicits an immune response against a pathogen or disease. Thus, as used herein, the term "filovirus antigenic protein" refers to a protein that comprises at least one antigenic determinant of a filovirus protein described above. The term encompasses filovirus antigens (i.e., gene products of a filovirus), as well as recombinant proteins that comprise one or more filovirus antigenic determinants.

In some embodiments, the protein may be mutated so that it is less toxic to cells (see e.g., WO2006/037038). The present invention also includes vaccines comprising a combination of nucleic acid molecules. For example, and without limitation, nucleic acid molecules encoding GP, SGP and NP of the Zaire, Sudan and Ivory Coast Ebola strains may be combined in any combination, in one vaccine composition.

Adenoviral Vectors

As noted above, exposure to certain adenoviruses has resulted in immune responses against certain adenoviral serotypes, which can affect efficacy of adenoviral vaccines. The present invention provides adenoviral vectors comprising capsid proteins from chimpanzee adenoviruses.

Thus, the vectors of the invention comprise a chimpanzee adenovirus capsid protein (e.g., a fiber, penton or hexon protein). One of skill will recognize that it is not necessary that an entire chimpanzee capsid protein be used in the vectors of the invention. Thus, chimeric capsid proteins that include at least a part of a chimpanzee capsid protein can be used in the vectors of the invention. The vectors of the invention may also comprise capsid proteins in which the fiber, penton, and hexon proteins are each derived from a different serotype, so long as at least one capsid protein is derived from a chimpanzee adenovirus. For example, the fiber protein can be derived from PanAd3, the penton from ChAd3, and the hexon from ChAd63. In other embodiments, the fiber, penton and hexon proteins can be those provided in SEQ ID NOS:1-9.

In certain embodiments the recombinant adenovirus vector of the invention is derived mainly or entirely from a chimpanzee adenovirus. Exemplary chimpanzee adenoviruses are known in the art and include, for example, ChAd3 and ChAd63 (described in WO 2005/071093), and PanAd3, PanAd1, PanAd2, and ChAd83 (described in WO 2010/086189). ChAd 3, ChAd63, and ChAd83 were isolated from the common chimpanzee (Pan troglodytes) and PanAd3, PanAd1, PanAd2 were isolated from the bonobo or pygmy chimpanzee (Pan paniscus).

In some embodiments, the adenovirus is replication deficient, e.g. because it contains a deletion in the E1 region of the genome. This allows propagation of such adenoviruses in well known complementing cell lines that express the E1 genes, such as for example 293 cells, PER.C6 cells, and the like. In certain embodiments, the adenovirus is a chimpanzee adenovirus, with a deletion in the E1 and E3 region into which an expression cassette encoding the antigen has been cloned. The construction of chimpanzee adenovirus comprising heterologous sequences encoding antigens is described in WO 2005/071093 and WO 2010/086189.

Typically, a vector of the invention is produced using a nucleic acid comprising the entire recombinant adenoviral genome (e.g., a plasmid, cosmid, or baculovirus vector). Thus, the invention also provides isolated nucleic acid molecules that encode the adenoviral vectors of the invention. The nucleic acid molecules of the invention may be in the form of RNA or in the form of DNA obtained by cloning or produced synthetically. The DNA may be double-stranded or single-stranded.

The adenovirus vectors of the invention are typically replication defective. In these embodiments, the virus is rendered replication-defective by deletion or inactivation of regions critical to replication of the virus, such as the E1 region. The regions can be substantially deleted or inactivated by, for example, inserting the gene of interest (usually linked to a promoter). In some embodiments, the vectors of the invention may contain deletions in other regions, such as the E2, E3 or E4 regions or insertions of heterologous genes linked to a promoter. For E2- and/or E4-mutated adenoviruses, generally E2- and/or E4-complementing cell lines are used to generate recombinant adenoviruses. Mutations in the E3 region of the adenovirus need not be complemented by the cell line, since E3 is not required for replication.

A packaging cell line is typically used to produce sufficient amount of adenovirus vectors of the invention. A packaging cell is a cell that comprises those genes that have been deleted or inactivated in a replication-defective vector, thus allowing the virus to replicate in the cell. Suitable cell lines include, for example, PER.C6, 911, 293, and E1 A549.

As noted above, a wide variety of filovirus antigenic proteins can be expressed in the vectors of the invention. If required, the heterologous gene encoding the filovirus antigenic protein can be codon-optimized to ensure proper expression in the treated host (e.g., human). Thus, codon-optimized antigens are also referred to as humanized antigens. In some embodiments, the viral GP, SGP or NP protein is codon-optimized. For example, codon-optimized antigens include those of SEQ ID NOS: 11, 12, and 14. Codon-optimization is a technology widely applied in the art. Typically, the heterologous gene is cloned into the E1 and/or the E3 region of the adenoviral genome.

The heterologous filovirus gene may be under the control of (i.e., operably linked to) an adenovirus-derived promoter (e.g., the Major Late Promoter) or may be under the control of a heterologous promoter. Examples of suitable heterologous promoters include the CMV promoter and the RSV promoter. In some embodiments, the promoter is located upstream of the heterologous gene of interest within an expression cassette.

As noted above, the adenovirus vectors of the invention can comprise a wide variety of filovirus antigens known to those of skill in the art.

Immunogenic Compositions

Purified or partially purified adenovirus vectors of the invention may be formulated as a vaccine (also referred to as an "immunogenic composition") according to methods well known in the art. Such compositions may include adjuvants to enhance immune responses. The optimal ratios of each component in the formulation may be determined by techniques well known to those skilled in the art.

The preparation and use of immunogenic compositions are well known to those of skill in the art. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

The compositions are suitable for single administrations or a series of administrations. When given as a series, inoculations subsequent to the initial (priming) administration are given to boost the immune response and are typically referred to as booster inoculations. The compositions of the invention can be used as a boosting composition primed by antigen using any of a variety of different priming compositions, or as the priming composition. Thus, one aspect of the present invention provides a method of priming and/or boosting an immune response to an antigen in an individual. For example, in some embodiments, a priming administration of one adenoviral vector of the invention is followed by a booster inoculation of the second adenoviral vector.

The timing of the administration of boosting compositions is well within the skill in the art. Boosting compositions are generally administered weeks or months after administration of the priming composition, for example, about 2-3 weeks or 4 weeks, or 8 weeks, or 16 weeks, or 20 weeks, or 24 weeks, or 28 weeks, or 32 weeks or one to two years. Methods of accelerated vaccination by administering a single dose of a recombinant adenovirus are described for example in U.S. Pat. No. 7,635,485.

The compositions of the invention may comprise other filovirus antigens or the priming or boosting inoculations may comprise other antigens. The other antigens used in combination with the adenovirus vectors of the invention are not critical to the invention and may be, for example, filovirus antigens, nucleic acids expressing them, virus like particles (VLPs), or prior art viral vectors. Such viral vectors include, for example, other adenoviral vectors, vaccinia virus vectors, avipox vectors such as fowlpox or canarypox, herpes virus vectors, vesicular stomatitis virus vectors, or alphavirus vectors. One of skill will recognize that the immunogenic compositions of the invention may comprise multiple antigens and vectors.

The antigens in the respective priming and boosting compositions (however many boosting compositions are employed) need not be identical, but should share antigenic determinants.

In some embodiments, heterologous prime-boost approaches can be used, for example, priming with Pan3-EBOV and boosting with ChAd3EBOV, priming with ChAd3EBOV and boosting with rLCMV (recombinant lymphocytic choriomeningitis virus), or priming with ChAd63EBOV and boosting with rLCMV. The rLCMV can be constructed as described in Flatz, L. et al., Nature Medicine, 16:339-345, 2010, except that the sequence encoding the antigenic protein is a sequence encoding a filovirus GP protein of the invention. In other embodiments, the boost can be rMVA (modified vaccinia virus Ankara) encoding an Ebola GP protein. Preparation and use of rMVA vectors is known and described for example in Ourmanov et al. *J. Virol.* 83:5388-5400, 2009 and Martinon et al. *Vaccine* 26:532-545, 2008. The vaccines of the invention can be used to generate protection against all human EBOV threats including Bundibugyo and Ivory Coast in a single vaccine. Finally, the vaccines against EBOV and MARV may also be mixed into a single inoculation in order to provide protection against both filoviruses simultaneously. In "prime and boost" immunization regimes, the immune response induced by administration of a priming composition is boosted by administration of a boosting composition. Effective boosting can be achieved using replication-defective adenovirus vectors, following priming with any of a variety of different types of priming compositions, as described for example in U.S. Pat. No. 7,094,598, which is incorporated herein by reference.

As noted above, the immunogenic compositions of the invention may comprise adjuvants. Adjuvants suitable for co-administration in accordance with the present invention should be ones that are potentially safe, well tolerated and effective in people including QS-21, Detox-PC, MPL-SE, MoGM-CSF, TiterMax-G, CRL-1005, GERBU, TERamide, PSC97B, Adjumer, PG-026, GSK-I, GcMAF, B-alethine, MPC-026, Adjuvax, CpG ODN, Betafectin, Alum, and MF59.

Other adjuvants that may be administered include lectins, growth factors, cytokines and lymphokines such as alpha-interferon, gamma interferon, platelet derived growth factor (PDGF), granulocyte-colony stimulating factor (gCSF), granulocyte macrophage colony stimulating factor (gMCSF), tumor necrosis factor (TNF), epidermal growth factor (EGF), IL-I, IL-2, IL-4, IL-6, IL-8, IL-10, and IL-12 or encoding nucleic acids therefore.

As noted above, the compositions of the invention may comprise a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g., oral, intravenous, cutaneous or subcutaneous, intramucosal (e.g., gut), intranasal, intramuscular, or intraperitoneal routes. Adiminstration is typically intramuscular.

Intramuscular administration of the immunogenic compositions may be achieved by using a needle to inject a suspension of the adenovirus vector. An alternative is the use of a needless injection device to administer the composition (using, e.g., Biojector™) or a freeze-dried powder containing the vaccine.

For intravenous, cutaneous or subcutaneous injection, or injection at the site of affliction, the adenovirus vector will be in the form of a parenterally acceptable aqueous solution which is pyrogen-free and has suitable pH, isotonicity and stability. Those of skill in the art are well able to prepare suitable solutions using, for example, isotonic vehicles such as Sodium Chloride Injection, Ringer's Injection, or Lactated Ringer's Injection. Preservatives, stabilizers, buffers, antioxidants and/or other additives may be included, as required. A slow-release formulation may also be employed.

Typically, administration will have a prophylactic aim to generate an immune response against a filovirus antigen before infection or development of symptoms. Diseases and disorders that may be treated or prevented in accordance with the present invention include those in which an immune response may play a protective or therapeutic role. In other embodiments, the adenovirus vectors can be administered for post-exposure prophylactics.

The immunogenic compositions containing the adenovirus vectors are administered to a subject, giving rise to an anti-filovirus immune response in the subject. An amount of a composition sufficient to induce a detectable immune response is defined to be an "immunologically effective dose." As shown below, the immunogenic compositions of the invention induce a humoral as well as a cell-mediated immune response. In a typical embodiment the immune response is a protective immune response.

The actual amount administered, and rate and time-course of administration, will depend on the nature and severity of what is being treated. Prescription of treatment, e.g., decisions on dosage etc., is within the responsibility of general practitioners and other medical doctors, or in a veterinary context a veterinarian, and typically takes account of the disorder to be treated, the condition of the individual patient, the site of delivery, the method of administration and other factors known to practitioners. Examples of the techniques and protocols mentioned above can be found in *Remington's Pharmaceutical Sciences,* 16th edition, Osol, A. ed., 1980.

Following production of adenovirus vectors and optional formulation of such particles into compositions, the adenovirus vectors may be administered to an individual, particularly human or other primate. Administration may be to humans, or another mammal, e.g., mouse, rat, hamster, guinea pig, rabbit, sheep, goat, pig, horse, cow, donkey, monkey, dog or cal. Delivery to a non-human mammal need not be for a therapeutic purpose, but may be for use in an experimental context, for instance in investigation of mechanisms of immune responses to the adenovirus vector.

In one exemplary regimen, the adenovirus vector is administered (e.g., intramuscularly) in the range of from about 100 μl to about 10 ml of saline solution containing concentrations of from about $10^4$ to $10^{12}$ virus particles/ml. Typically, the adenovirus vector is administered in an amount of about $10^9$ to about $10^{12}$ viral particles (vp) to a human subject during one administration. For example, the adenovirus vector can be administered in an amount of about $10^9$, $10^{10}$, $10^{11}$, or $10^{12}$ vp per administration. In some embodiments, the dose administered is from about $10^{10}$ to about $10^{12}$ vp. An initial vaccination can be followed by a boost as described above. The composition may, if desired, be presented in a kit, pack or dispenser, which may contain one or more unit dosage forms containing the active ingredient. The kit, for example, may comprise metal or plastic foil, such as a blister pack. The kit, pack, or dispenser may be accompanied by instructions for administration.

The present invention also provides kits for enhancing the immunity of a host to a pathogen. These kits may include any one ore more vaccines according to the present invention in combination with a composition for delivering the vaccine to a host and/or a device, such as a syringe, for delivering the vaccine to a host.

The vaccine according to the invention is administered as a pre-exposure (or post-exposure) single dose in a manner compatible with the dosage formulation, and in such amount as will be prophylactively effective. Immunity is defined as the induction of a significant level of protection after vaccination compared to an unvaccinated human or other host.

The vaccine of the present invention, i.e., the recombinant virus, may be administered to a host, such as a human subject, via any pharmaceutically acceptable routes of administration. The routes of administration include, but are not limited to, intramuscular, intratracheal, subcutaneous, intranasal, intradermal, rectal, oral and parental route of administration. Routes of administration may be combined, if desired, or adjusted depending upon the type of the pathogenic virus to be immunized against and the desired body site of protection.

Doses or effective amounts of the recombinant virus may depend on factors such as the condition, the selected viral antigen, the age, weight and health of the host, and may vary among hosts. The appropriate titer of the recombinant virus of the present invention to be administered to an individual is the titer that can modulate an immune response against the viral antigen and elicits antibodies against the pathogenic virus from which the antigen is derived. An effective titer can be determined using an assay for determining the activity of immunoeffector cells following administration of the vaccine to the individual or by monitoring the effectiveness of the therapy using well known in vivo diagnostic assays.

The chimp Ad vectors of the invention can be used as single inoculations to provide either immediate (e.g., 2-4 weeks) or long-term (e.g., one year) immune protection.

Nucleic Acid Molecules

As indicated herein, nucleic acid molecules of the present invention may be in the form of RNA or in the form of DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand. By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Nucleic acid molecules of the present invention include DNA molecules comprising an open reading frame (ORF) encoding a modified or wild-type filovirus or adenovirus structural gene product; and DNA molecules which comprise a sequence substantially different from those described above but which, due to the degeneracy of the genetic code, still encode an ORF of a filovirus structural gene product. Of course, the genetic code is well known in the art.

The present invention is further directed to fragments of the nucleic acid molecules described herein. By a fragment of a nucleic acid molecule having the nucleotide sequence of an ORF encoding a wild-type filovirus or adenovirus structural gene product is intended fragments at least about 15 nt., at least about 20 nt., at least about 30 nt., or at least about 40 nt. in length. Of course, larger fragments 50, 100, 150, 200, 250, 300, 350, 400, 450, or 500 nt. in length are also intended according to the present invention as are fragments corresponding to most, if not all, of the nucleotide sequence of the ORF encoding a wild-type filovirus or adenovirus structural gene product. By a fragment at least 20 nt. in length, for example, is intended fragments which include 20 or more contiguous bases from the nucleotide sequence of the ORF of a wild-type filovirus or adenovirus structural gene product.

In another aspect, the invention provides a nucleic acid molecule comprising a polynucleotide which hybridizes under stringent hybridization conditions to a portion of the polynucleotide in a nucleic acid molecule of the invention described above. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt.), at least about 20 nt., at least about 30 nt., or about 30-70 nt. of the reference polynucleotide.

By a portion of a polynucleotide of "at least 20 nt. in length," for example, is intended 20 or more contiguous nucleotides from the nucleotide sequence of the reference polynucleotide. Of course, a polynucleotide which hybridizes only to a poly A sequence or a complementary stretch of T (or U) residues, would not be included in a polynucleotide of the invention used to hybridize to a portion of a nucleic acid of the invention, since such a polynucleotide would hybridize to any nucleic acid molecule containing a poly A stretch or the complement thereof (e.g., practically any double-stranded cDNA clone).

As indicated herein, nucleic acid molecules of the present invention which encode a filovirus structural gene product may include, but are not limited to those encoding the amino acid sequence of the full-length polypeptide, by itself, the coding sequence for the full-length polypeptide and additional sequences, such as those encoding a leader or secretory sequence, such as a pre-, or pro- or prepro-protein sequence, the coding sequence of the full-length polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example, ribosome binding and stability of mRNA; and additional coding sequence which codes for additional amino acids, such as those which provide additional functionalities.

The present invention further relates to variants of the nucleic acid molecules of the present invention, which encode portions, analogs or derivatives of the filovirus or adenovirus structural gene product. Variants may occur naturally, such as a natural allelic variant. By an "allelic variant" is intended one of several alternate forms of a gene occupying a given locus on a genome of an organism. (*Genes II*, Lewin, B., ed., John Wiley & Sons, 1985 New York). Non-naturally occurring variants may be produced using art-known mutagenesis techniques.

Such variants include those produced by nucleotide substitutions, deletions or additions, which may involve one or more nucleotides. The variants may be altered in coding regions, non-coding regions, or both. Alterations in the coding regions may produce conservative or non-conservative amino acid substitutions, deletions or additions. In some embodiments, the variations are silent substitutions, additions and deletions, which do not alter the properties and activities of the filovirus or adenovirus structural gene product or portions thereof. In some embodiments the variants are conservative substitutions.

Further embodiments of the invention include nucleic acid molecules comprising a polynucleotide having a nucleotide sequence at least 95% identical, or at least 96%, 97%, 98% or 99% identical to a nucleotide sequence encoding a polypeptide having the amino acid sequence of a wild-type filovirus or adenovirus structural gene product or fragment thereof or a nucleotide sequence complementary thereto.

By a polynucleotide having a nucleotide sequence at least, for example, 95% "identical" to a reference nucleotide sequence encoding a filovirus or adenovirus structural gene product is intended that the nucleotide sequence of the polynucleotide is identical to the reference sequence except that the polynucleotide sequence may include up to five point mutations per each 100 nucleotides of the reference nucleotide sequence encoding the virus structural gene product. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to the reference nucleotide sequence can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, 1981 *Advances in Applied Mathematics* 2:482-489, to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

Of course, due to the degeneracy of the genetic code, one of ordinary skill in the art will immediately recognize that a large number of the nucleic acid molecules having a sequence at least 95%, 96%, 97%, 98%, or 99% identical to a nucleic acid sequence shown herein in the Sequence Listing will encode a polypeptide of the invention. In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having the desired activity. This is because the skilled artisan is fully aware of amino acid substitutions that are either less likely or not likely to significantly affect protein function (e.g., replacing one aliphatic amino acid with a second aliphatic amino acid).

For example, guidance concerning how to make phenotypically silent amino acid substitutions is provided in Bowie, J. U. et al. 1990 *Science* 247:1306-1310, wherein the authors indicate that proteins are surprisingly tolerant of amino acid substitutions.

Polypeptides and Fragments

The invention further provides filovirus and adenovirus polypeptides having the amino acid sequence encoded by an open reading frame (ORF) of a wild-type or modified filovirus or adenovirus structural gene, or a peptide or polypeptide comprising a portion thereof.

It will be recognized in the art that some amino acid sequences of the filovirus polypeptides can be varied without significant effect on the structure or function of the protein. If such differences in sequence are contemplated, it should be remembered that there will be critical areas on the protein which determine activity.

Thus, the invention further includes variations of the filovirus or adenovirus polypeptides which show substantial antigenic or other relevant biological activity. Such mutants include deletions, insertions, inversions, repeats, and type substitutions. As indicated, guidance concerning which amino acid changes are likely to be phenotypically silent can be found in Bowie, J. U. et al. 1990 *Science* 247:1306-1310.

Thus, the fragment, derivative or analog of the polypeptide of the invention may be (i) one in which one or more of the amino acid residues are substituted with a conserved or non-conserved amino acid residue and such substituted amino acid residue may or may not be one encoded by the genetic code, or (ii) one in which one or more of the amino acid residues include a substituent group, or (iii) one in which additional amino acids are fused to the mature polypeptide. Such fragments, derivatives and analogs are deemed to be within the scope of those skilled in the art from the teachings herein.

Of course, the number of amino acid substitutions a skilled artisan would make depends on many factors, including those described above. Generally speaking, the number of amino acid substitutions for any given filovirus or adenovirus polypeptide will not be more than 50, 40, 30, 20, 10, 5 or 3.

Amino acids in the filovirus or adenovirus polypeptides of the present invention that are essential for the desired function can be identified by methods known in the art, such as site-directed mutagenesis or alanine-scanning mutagenesis (Cunningham & Wells 1989 *Science* 244:1081-1085). The latter procedure introduces single alanine mutations at every residue in the molecule. The resulting mutant molecules are then tested for biological activity such as changes in immunological character.

The polypeptides of the present invention are conveniently provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell or a native source. For example, a recombinantly produced version of the filovirus or adenovirus polypeptide can be substantially purified by the one-step method described in Smith and Johnson 1988 *Gene* 67:31-40.

The polypeptides of the present invention include a polypeptide comprising a polypeptide having the amino acid sequence of a wild-type filovirus structural gene product or portion thereof or encoded by a nucleic acid sequence shown herein in the Sequence Listing; as well as polypeptides which are at least 95% identical, or at least 96%, 97%, 98%, or 99% identical to those described above.

By a polypeptide having an amino acid sequence at least, for example, 95% "identical" to a reference amino acid sequence of an filovirus or adenovirus polypeptide is intended that the amino acid sequence of the polypeptide is identical to the reference sequence except that the polypeptide sequence may include up to five amino acid alterations per each 100 amino acids of the reference amino acid of the filovirus or adenovirus polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 95%, 96%, 97%, 98%, or 99% identical to a reference amino acid sequence can be determined conventionally using known computer programs such as the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

EXAMPLES

The following examples are offered to illustrate, but not to limit the claimed invention.

Example 1

This example shows that humoral and cellular responses generated by ChAdC3 Ebola (S/G) and ChAdC3 Ebola (Zaire) were comparable to those generated by rAd 5Ebola (S/G) and rAd5 Ebola (Zaire) respectively.

Immunization of cynomologous macaques with ChAdC3 Ebola (Zaire) produced antigen-specific antibody and Cd4+ and Cd8+ T cell responses. Protection against infection with a lethal dose of EBOV-Zaire was also demonstrated, as 4 macaques survived the challenge after immunization with ChAdC3 Ebola (Zaire) (see FIGS. 1-7).

Example 2

This example shows that a single immunization with rChAdC3 Ebola (Zaire) elicited humoral and cellular immune responses comparable to those generated by rAd5 Ebola (Zaire).

Figure 8:
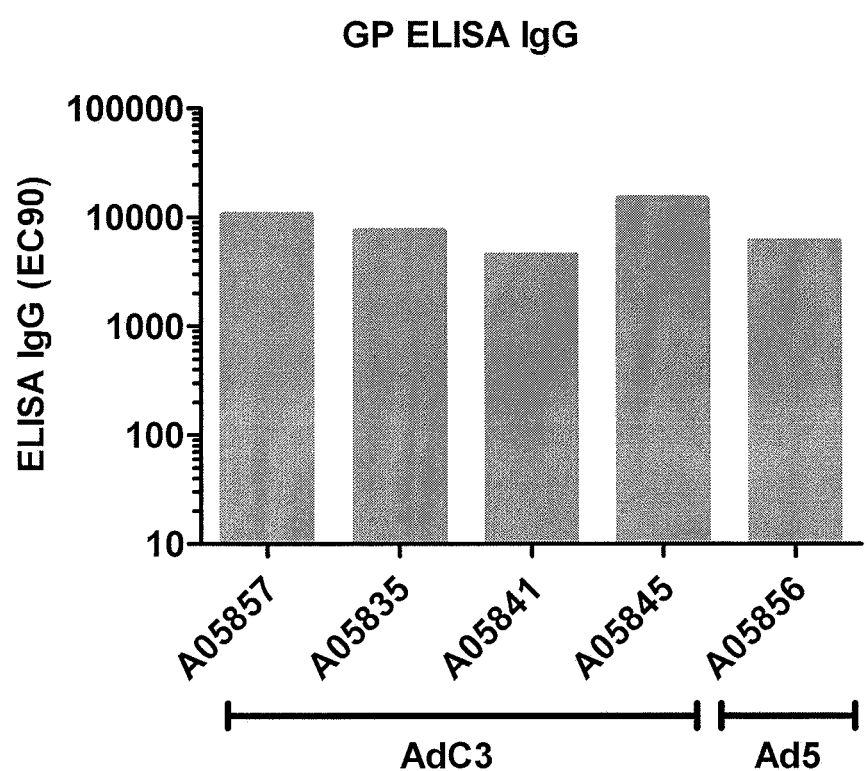
FIG. 8. A single immunization with $10^{10}$ vp of rAdC3 Ebola (Zaire) elicits antigen-specific Antibody responses. Cynomolgus macaques were vaccinated with rAdC3 or rAd5 encoding EBOV-GP at a dose of $10^{10}$ vp intramuscularly. Serum was collected at 4 weeks post Immunization to detect IgG responses against EBOV GP by ELISA.

Immunization of cynomologous macaques with rChAdC3 Ebola (Zaire) produced antigen-specific antibody and Cd4+ and Cd8+ T cell responses. Protection against infection with a lethal dose of EBOV-Zaire was also demonstrated, as 4 out of 4 macaques survived the challenge after immunization with rChAdC3 Ebola (Zaire) (see FIGS. 8-10).

Example 3

This example shows that a single immunization with adenoviral vectors encoding humanized Ebola glycoprotein (EBOV-GP) induced stronger cellular and humoral responses in mice than adenoviral vectors encoding non-humanized EBOV-GP.

Figure 11A:
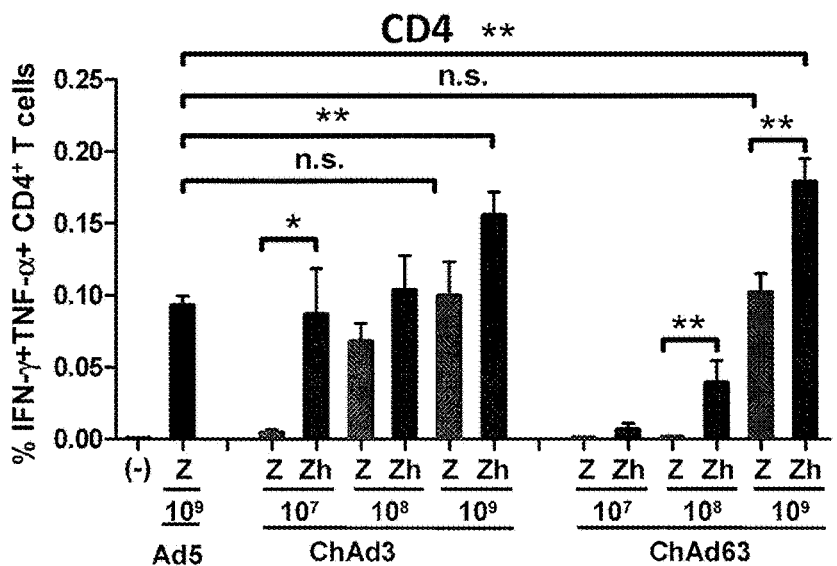
FIGS. 11A-11C rChAd vectors encoding humanized EBOV-GP or non-humanized EBOV-GP elicited potent immune responses in mice. Five 6-8 weeks female Balb/C mice in each group were immunized with rAd EBOV-GP at indicated $10^7$ or $10^8$ or $10^9$ viral particles through intramuscular injection.
Figure 11B:
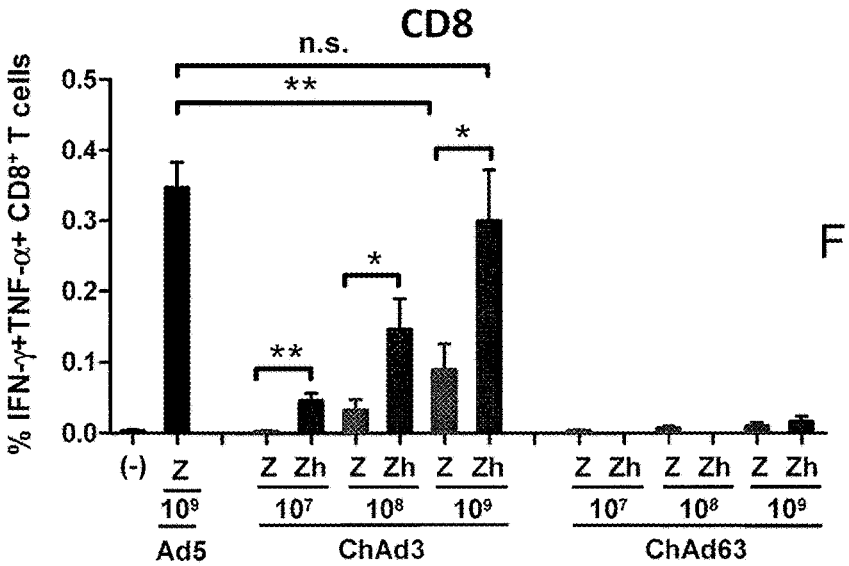
Figure 11C:
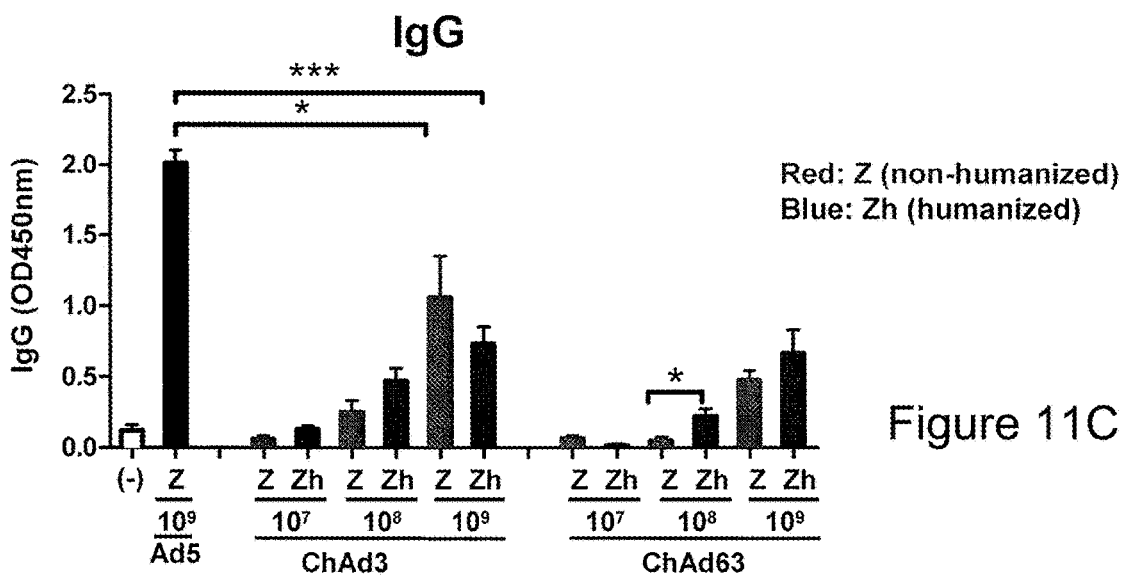

Groups of female Balb/C mice were immunized with rAd EBOV-GP (Z) at a dose of $10^7$, $10^8$, and $10^9$ viral particles via intramuscular injection. Cellular immune responses (Cd4+ and Cd8+ T cell responses) in PBMC and humoral responses (IgG) to EBOV-GP were measured at three weeks post immunization by ICS (intracellular cytokine staining) and ELISA, respectively. As shown in FIG. 11, immunization with adenoviral vectors rChAd3 and rChAd63 encoding EBOV-GP (Zh) codon optimized for expression in humans produced significantly higher percentages of CD4+ T cells that express cytokines IFN-γ and TNF-α than the same vectors encoding non-humanized (wild-type) EBOV-GP (Z) (SEQ ID NO:10), and these responses were significantly greater than the response due to rAd5 at $10^9$ viral particles.

Immunization with rChAd3 encoding humanized EBOV-GP produced significantly higher percentages of CD8+ T cells that express cytokines IFN-γ and TNF-α than the same vector encoding non-humanized EBOV-GP, and the percentage of cytokine positive cells was comparable, although not significantly different, to the percentage of cytokine positive CD8+ T cells produced by rAd5 at $10^9$ viral particles (see FIG. 11). There was no significant difference in the CD8+ response produced by rChAd63 encoding humanized and non-humanized EBOV-GP.

Immunization with rChAd63 encoding humanized EBOV-GP produced significantly higher IgG when compared to the same vector encoding non-humanized EBOV-GP at $10^8$ viral particles. There was no significant difference in the IgG response by rChAd3 encoding humanized and non-humanized EBOV-GP. Further, the IgG response by rChAd3 and rChAd63 encoding humanized and non-humanized EBOV-GP was significantly lower than response generated by Ad5 (see FIG. 11).

Example 4

This example shows that a prime/boost regimen using adenoviral vectors encoding EBOV-GP generated potent immune responses in mice.

Groups of female Balb/C mice were immunized with $10^8$ and $10^9$ rAd EBOV-GP (Z) viral particles via intramuscular injection at week 0 and boosted at week 3. Cellular and humoral immune responses were measured as described above at week 5.

Figure 12A:
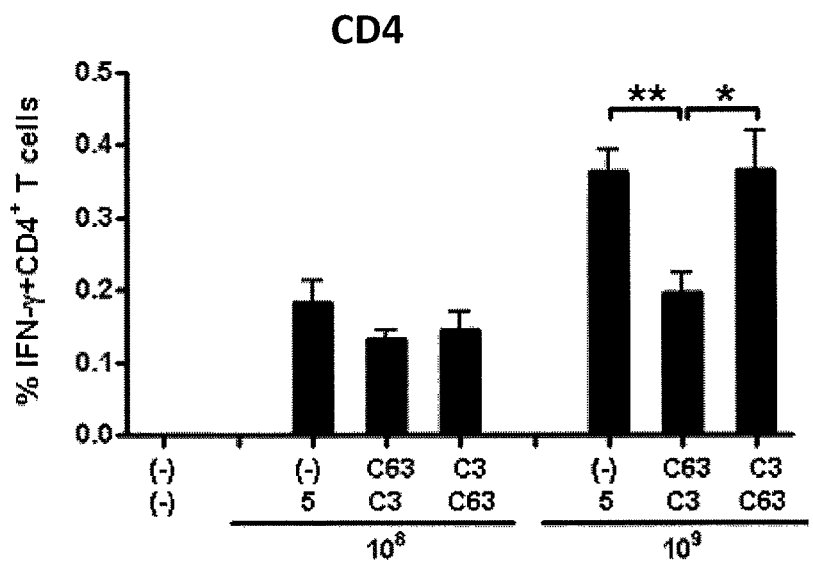
FIGS. 12A-12C rChAd prime and boost regimen generated potent immune responses in mice. Five 6-8 weeks female Balb/C mice in each group were immunized with rAd EBOV-GP at week 0 and boosted at week 3, at $10^8$ or $10^9$ viral particles as indicated through intramuscular injection.
Figure 12B:
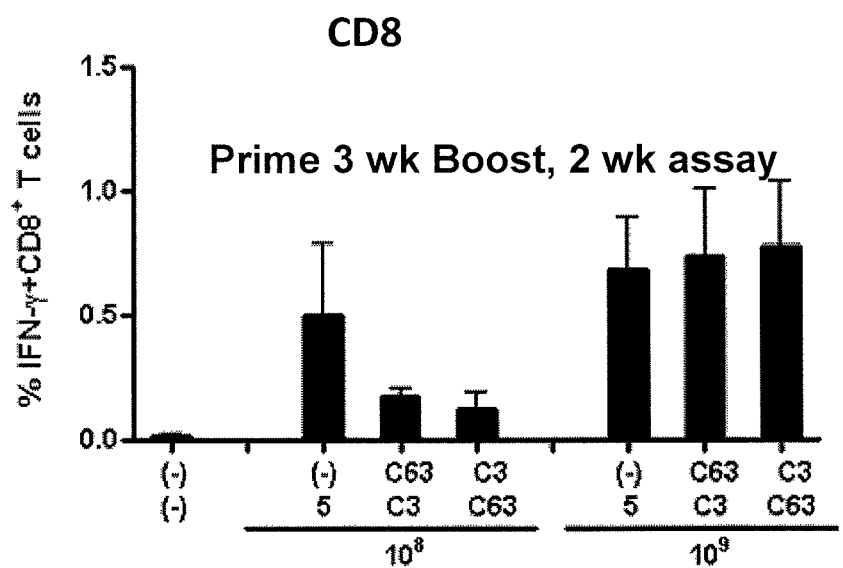
Figure 12C:
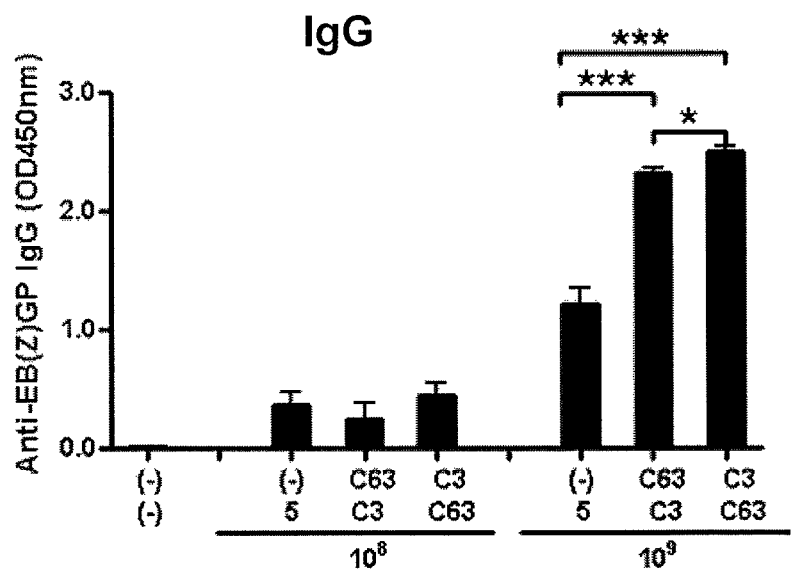

As shown in FIG. 12, prime with $10^9$ particles of rChAd3 and boost with $10^9$ particles of rChAd63 generated similar CD4+ and CD8+ responses as a single immunization at 3 weeks with rAd5. Likewise, prime with $10^9$ particles of rChAd63 and boost with $10^9$ particles of rChAd3 generated a similar CD8+ response as a single immunization at 3 weeks with rAd5, whereas this regimen produced a significantly lower CD4+ response.

Prime with $10^9$ particles of rChAd3 and boost with $10^9$ particles of rChAd63 generated a significantly higher IgG response than a single rAd5 immunization at 3 weeks.

Similarly, prime with $10^9$ particles of rChAd63 and boost with $10^9$ particles of rChAd3 generated a significantly higher IgG response than a single rAd5 immunization at 3 weeks.

Figure 13A:
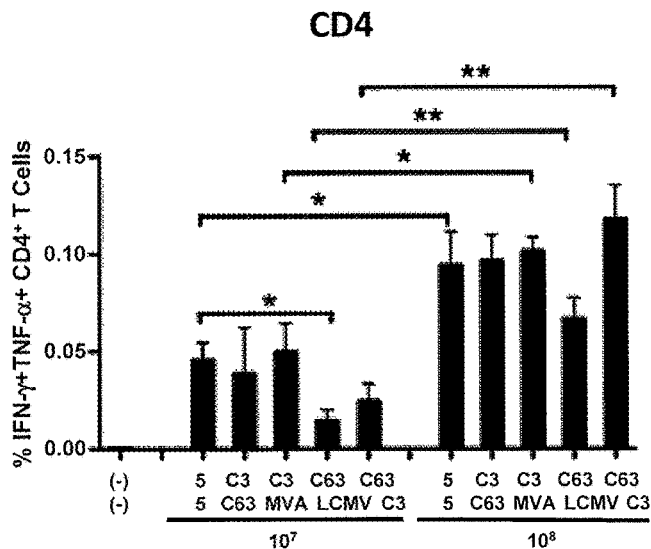
FIGS. 13A-13C rAd, rMVA and rLCMV vectors used in prime and boost regimen generated potent immune responses in mice. Five 6-8 weeks female Balb/C mice in each group were immunized with vectors encoding EBOV-GP at week 0 and boosted at week 4. rAd vectors were dosed at $10^7$ or $10^8$ viral particles as indicated, and MVA vectors at $10^5$ pfu, LCMV at $10^6$ pfu, through intramuscular injection
Figure 13B:
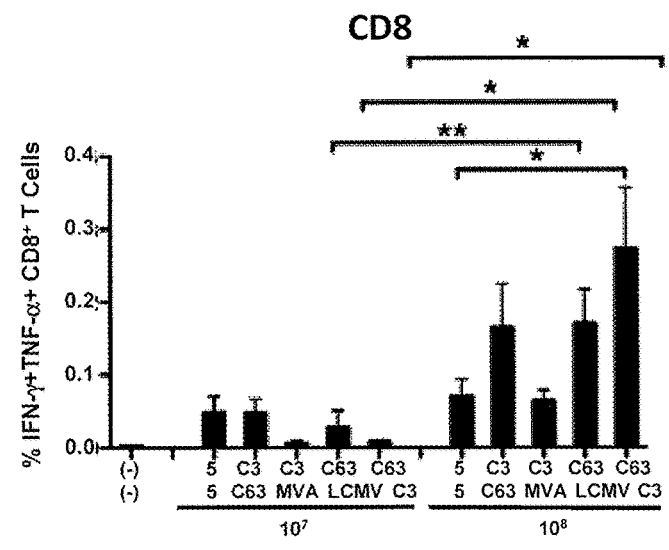
Figure 13C:
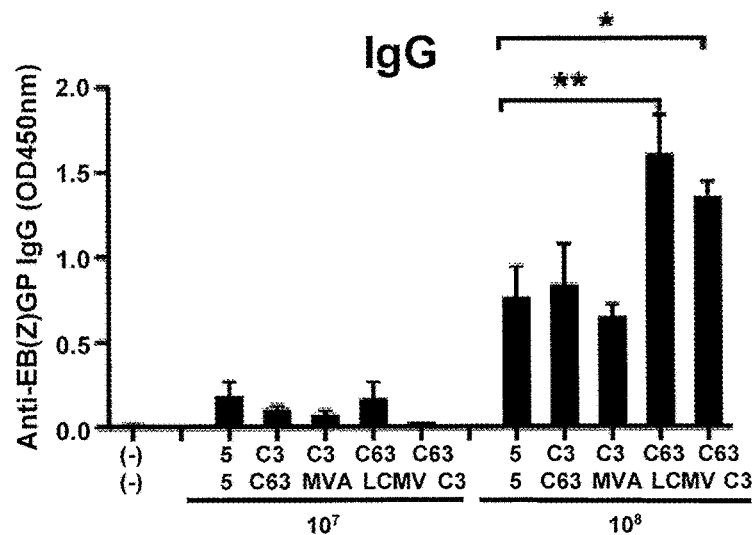

As shown in FIG. 13, prime with $10^8$ particles of rChAd63 and boost with $10^8$ particles of rChAd3 induced higher CD8+ and IgG responses than prime and boost with rAd5. The LCMV and MVA vectors were prepared as described above.

In summary, the above examples demonstrate that rChAd3 consistently generated comparable immune responses as rAd5 for single administration. Further, prime and boost with rChAd3/rChAd63, ChAd63/ChAd3, and ChAd3/LCMV are useful candidates for a combination regimen.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An isolated nucleic acid molecule, wherein the isolated nucleic acid molecule comprises a sequence selected from the group consisting of SEQ ID NO:1, SEQ ID NO:2 and SEQ ID NO:3.

2. The isolated nucleic acid molecule of claim 1, comprising an expression cassette comprising a CMV promoter operably linked to a polynucleotide sequence encoding a filovirus antigenic protein.

3. The isolated nucleic acid molecule of claim 1, which comprises a sequence identical to SEQ ID NO:1.

4. The isolated nucleic acid molecule of claim 1, which comprises a sequence identical to SEQ ID NO:2.

5. The isolated nucleic acid molecule of claim 1, which comprises a sequence identical to SEQ ID NO:3.

6. The isolated nucleic acid molecule of claim 3, further comprising a promoter operably linked to said nucleic acid molecule.

7. The isolated nucleic acid molecule of claim 4, further comprising a promoter operably linked to said nucleic acid molecule.

8. The isolated nucleic acid molecule of claim 5, further comprising a promoter operably linked to said nucleic acid molecule.

9. A composition, comprising:
the isolated nucleic acid molecule of claim 3; and
a pharmaceutically acceptable carrier.

10. A composition, comprising:
the isolated nucleic acid molecule of claim 4; and
a pharmaceutically acceptable carrier.

11. A composition, comprising:
the isolated nucleic acid molecule of claim 5; and
a pharmaceutically acceptable carrier.

12. The isolated nucleic acid molecule of claim 6, wherein the promoter is a CMV promoter.

13. The isolated nucleic acid molecule of claim 7, wherein the promoter is a CMV promoter.

14. The isolated nucleic acid molecule of claim 8, wherein the promoter is a CMV promoter.

15. A composition, comprising:
the isolated nucleic acid of claim 1 contained in a viral particle and a pharmaceutically acceptable carrier.

16. A composition, comprising:
the isolated nucleic acid molecule of claim 1; and
a pharmaceutically acceptable carrier.

* * * * *